(12) United States Patent
Darout et al.

(10) Patent No.: US 9,227,956 B2
(45) Date of Patent: Jan. 5, 2016

(54) SUBSTITUTED AMIDE COMPOUNDS

(71) Applicant: Pfizer Inc., New York, NY (US)

(72) Inventors: Etzer Darout, Cambridge, MA (US); Robert Dullea, Groton, MA (US); Julie Jia Li Hawkins, Weston, CT (US); Allyn T. Londregan, Barrington, RI (US); Paula M. Loria, Killingworth, CT (US); Bruce Maguire, Chester, CT (US); Kim F. McClure, Mystic, CT (US); Donna N. Petersen, Salem, CT (US); David W. Piotrowski, Waterford, CT (US)

(73) Assignee: Pfizer Inc., New York, NY (US)

( * ) Notice: Subject to any disclaimer, the term of this patent is extended or adjusted under 35 U.S.C. 154(b) by 66 days.

(21) Appl. No.: 14/253,084

(22) Filed: Apr. 15, 2014

(65) Prior Publication Data

US 2014/0315928 A1    Oct. 23, 2014

Related U.S. Application Data

(60) Provisional application No. 61/812,864, filed on Apr. 17, 2013, provisional application No. 61/880,336, filed on Sep. 20, 2013, provisional application No. 61/898,667, filed on Nov. 1, 2013.

(51) Int. Cl.
| | |
|---|---|
| *C07D 401/14* | (2006.01) |
| *A61K 31/519* | (2006.01) |
| *A61K 45/06* | (2006.01) |
| *C07D 413/14* | (2006.01) |
| *A61K 31/437* | (2006.01) |
| *A61K 31/4709* | (2006.01) |
| *A61K 31/4545* | (2006.01) |
| *C07D 487/04* | (2006.01) |
| *C07D 471/04* | (2006.01) |

(52) U.S. Cl.
CPC ............ *C07D 401/14* (2013.01); *A61K 31/519* (2013.01); *A61K 45/06* (2013.01); *C07D 413/14* (2013.01); *C07D 471/04* (2013.01); *C07D 487/04* (2013.01)

(58) Field of Classification Search
None
See application file for complete search history.

(56) References Cited

U.S. PATENT DOCUMENTS

| | | | |
|---|---|---|---|
| 5,461,060 A | 10/1995 | Miyasaka et al. |
| 6,107,040 A | 8/2000 | Shuman |
| 6,197,947 B1 | 3/2001 | Hemmati-Brivanlou et al. |
| 6,558,906 B2 | 5/2003 | Obokata et al. |
| 7,553,819 B2 | 6/2009 | Bundle et al. |
| 8,198,255 B2 | 6/2012 | Houchen et al. |
| 8,283,115 B1 | 10/2012 | Friesen et al. |
| 8,283,116 B1 | 10/2012 | Bhattacharyya et al. |
| 8,329,667 B2 | 12/2012 | Christiano |
| 2002/0127702 A1 | 9/2002 | Bernstein et al. |
| 2003/0032158 A1 | 2/2003 | Peltz et al. |
| 2003/0087852 A1 | 5/2003 | DeBenedetti et al. |
| 2003/0119017 A1 | 6/2003 | McSwiggen |
| 2004/0224912 A1 | 11/2004 | Dobie et al. |
| 2005/0019808 A1 | 1/2005 | Palmenberg et al. |
| 2005/0164970 A1 | 7/2005 | Li |
| 2005/0282849 A1 | 12/2005 | Moon et al. |
| 2006/0035212 A1 | 2/2006 | Balakireva |
| 2006/0110397 A1 | 5/2006 | Kim |
| 2007/0105764 A1 | 5/2007 | Cosson et al. |
| 2007/0281992 A1 | 12/2007 | Batts et al. |
| 2008/0008697 A1 | 1/2008 | Mintier et al. |
| 2008/0039415 A1 | 2/2008 | Stewart et al. |
| 2008/0081791 A1 | 4/2008 | Huang et al. |
| 2008/0260854 A1 | 10/2008 | Walker et al. |
| 2009/0170793 A1 | 7/2009 | Gaur |
| 2009/0238862 A1 | 9/2009 | Chen |
| 2010/0158858 A1 | 6/2010 | Cao et al. |
| 2010/0215634 A1 | 8/2010 | Tennenbaum et al. |
| 2011/0039911 A1 | 2/2011 | Pe'ery et al. |
| 2011/0040077 A1 | 2/2011 | Inoue et al. |
| 2011/0065772 A1 | 3/2011 | Khachigian |
| 2011/0143998 A1 | 6/2011 | Llano-Sotelo et al. |
| 2011/0230451 A1 | 9/2011 | Lorsch et al. |
| 2011/0269754 A1 | 11/2011 | Liu et al. |
| 2012/0220647 A1 | 8/2012 | Choy et al. |
| 2013/0079382 A1 | 3/2013 | Smith |
| 2013/0109739 A1 | 5/2013 | Goregaoker et al. |
| 2013/0123330 A1 | 5/2013 | Lu et al. |
| 2013/0225618 A1 | 8/2013 | Shibuya et al. |

(Continued)

FOREIGN PATENT DOCUMENTS

| | | |
|---|---|---|
| CA | 2227508 | 10/1999 |
| CN | 1523113 | 8/2004 |

(Continued)

OTHER PUBLICATIONS

Chemical Abstract Registry No. 1319428-50-6, indexed in the Registry File on STN CAS Online Aug. 18, 2011.*

(Continued)

*Primary Examiner* — Michael Barker
*Assistant Examiner* — Po-Chih Chen
(74) *Attorney, Agent, or Firm* — A. Dean Olson

(57) ABSTRACT

The present invention is directed at substituted amide compounds, pharmaceutical compositions containing such compounds and the use of such compounds to reduce plasma lipid levels, such as LDL-cholesterol and triglycerides and accordingly to treat diseases which are exacerbated by high levels of LDL-cholesterol and triglycerides, such as atherosclerosis and cardiovascular diseases, in mammals, including humans.

30 Claims, 10 Drawing Sheets

(56) References Cited

U.S. PATENT DOCUMENTS

| | | |
|---|---|---|
| 2013/0225657 A1 | 8/2013 | Rice et al. |
| 2013/0296401 A1 | 11/2013 | Graham et al. |

FOREIGN PATENT DOCUMENTS

| | | |
|---|---|---|
| CN | 1924014 | 3/2007 |
| CN | 1974759 | 6/2007 |
| CN | 101054577 | 10/2007 |
| CN | 101380477 | 3/2009 |
| CN | 101485885 | 7/2009 |
| CN | 101643731 | 2/2010 |
| CN | 101869715 | 10/2010 |
| CN | 101897982 | 12/2010 |
| CN | 101948834 | 1/2011 |
| CN | 102168085 | 8/2011 |
| CN | 102453713 | 5/2012 |
| CN | 102533768 | 7/2012 |
| CN | 103421792 | 12/2013 |
| DE | 19937350 | 2/2001 |
| DE | 10200410 | 7/2003 |
| EP | 140308 | 5/1985 |
| EP | 0747386 | 12/1996 |
| EP | 1188769 | 3/2002 |
| EP | 1471152 | 10/2004 |
| EP | 1566202 | 8/2005 |
| EP | 2014769 | 1/2009 |
| EP | 2221063 | 8/2010 |
| EP | 2338485 | 6/2011 |
| EP | 2390327 | 11/2011 |
| EP | 2023939 | 6/2012 |
| EP | 2471548 | 7/2012 |
| EP | 2578574 | 4/2013 |
| FR | 2909668 | 6/2008 |
| JP | 7165598 | 6/1995 |
| JP | 2002095483 | 4/2002 |
| JP | 2004059471 | 2/2004 |
| JP | 2004300048 | 10/2004 |
| JP | 2006141305 | 6/2006 |
| JP | 2007028932 | 2/2007 |
| JP | 2009209050 | 9/2009 |
| JP | 2009227619 | 10/2009 |
| JP | 2009227620 | 10/2009 |
| JP | 2009235044 | 10/2009 |
| JP | 2010215571 | 9/2010 |
| JP | 2011001326 | 1/2011 |
| JP | 2011155914 | 8/2011 |
| JP | 2011184392 | 9/2011 |
| JP | 2011190209 | 9/2011 |
| JP | 2012039911 | 3/2012 |
| KR | 20060020139 | 3/2006 |
| KR | 20090020244 | 2/2009 |
| KR | 20090061727 | 6/2009 |
| KR | 20100115157 | 10/2010 |
| KR | 20110028981 | 3/2011 |
| KR | 20120032317 | 4/2012 |
| KR | 20130051605 | 5/2013 |
| KR | 20130088690 | 8/2013 |
| RU | 2240125 | 11/2004 |
| WO | 94/10301 | 5/1994 |
| WO | 96/11211 | 4/1996 |
| WO | 97/33623 | 9/1997 |
| WO | 99/15648 | 4/1999 |
| WO | 99/62941 | 12/1999 |
| WO | 00/20432 | 4/2000 |
| WO | 01/23584 | 4/2001 |
| WO | 01/72765 | 10/2001 |
| WO | 01/90371 | 11/2001 |
| WO | 01/98468 | 12/2001 |
| WO | 2002/010374 | 2/2002 |
| WO | 02/46383 | 6/2002 |
| WO | 02/053103 | 7/2002 |
| WO | 02/72538 | 9/2002 |
| WO | 03/044166 | 5/2003 |
| WO | 03/084478 | 10/2003 |
| WO | 2004/003134 | 1/2004 |
| WO | 2004/047872 | 6/2004 |
| WO | 2004/055210 | 7/2004 |
| WO | 2004/078940 | 9/2004 |
| WO | 2005/007150 | 1/2005 |
| WO | 2005/012283 | 2/2005 |
| WO | 2005/014815 | 2/2005 |
| WO | 2005/010038 | 3/2005 |
| WO | 2005/059135 | 6/2005 |
| WO | 2005/080355 | 9/2005 |
| WO | 2005/116210 | 12/2005 |
| WO | 2005/116236 | 12/2005 |
| WO | 2006/058088 | 1/2006 |
| WO | 2006/021817 | 3/2006 |
| WO | 2006/023544 | 3/2006 |
| WO | 2006/044716 | 4/2006 |
| WO | 2006/047687 | 5/2006 |
| WO | 2006/062369 | 6/2006 |
| WO | 2006/077112 | 7/2006 |
| WO | 2006/078942 | 7/2006 |
| WO | 2006/086345 | 8/2006 |
| WO | 2006/133099 | 12/2006 |
| WO | 2006/133561 | 12/2006 |
| WO | 2007/024991 | 3/2007 |
| WO | 2007/044468 | 4/2007 |
| WO | 2007/056227 | 5/2007 |
| WO | 2007/079224 | 7/2007 |
| WO | 2007/109674 | 9/2007 |
| WO | 2007/117121 | 10/2007 |
| WO | 2007/123896 | 11/2007 |
| WO | 2007/128121 | 11/2007 |
| WO | 2007/145458 | 12/2007 |
| WO | 2008/050329 | 5/2008 |
| WO | 2008/059491 | 5/2008 |
| WO | 2008/064304 | 5/2008 |
| WO | 2008/066776 | 6/2008 |
| WO | 2008/087278 | 7/2008 |
| WO | 2008/109005 | 9/2008 |
| WO | 2008/109871 | 9/2008 |
| WO | 2008/110624 | 9/2008 |
| WO | 2008/118386 | 10/2008 |
| WO | 2008/127193 | 10/2008 |
| WO | 2008/127714 | 10/2008 |
| WO | 2008/151428 | 12/2008 |
| WO | 2008/154482 | 12/2008 |
| WO | 2009/002873 | 12/2008 |
| WO | 2009/003211 | 1/2009 |
| WO | 2009/013621 | 1/2009 |
| WO | 2009/023025 | 2/2009 |
| WO | 2009/026218 | 2/2009 |
| WO | 2009/066757 | 5/2009 |
| WO | 2009/072649 | 6/2009 |
| WO | 2009/111073 | 9/2009 |
| WO | 2009/118567 | 10/2009 |
| WO | 2009/143633 | 12/2009 |
| WO | 2009/147009 | 12/2009 |
| WO | 2009/151539 | 12/2009 |
| WO | 2010/038043 | 4/2010 |
| WO | 2010/038965 | 4/2010 |
| WO | 2010/053606 | 5/2010 |
| WO | 2010/075469 | 7/2010 |
| WO | 2010/076935 | 7/2010 |
| WO | 2010/078517 | 7/2010 |
| WO | 2010/080248 | 7/2010 |
| WO | 2010/083338 | 7/2010 |
| WO | 2010/095879 | 8/2010 |
| WO | 2010/130447 | 11/2010 |
| WO | 2010/138820 | 12/2010 |
| WO | 2011/003018 | 1/2011 |
| WO | 2011/006000 | 1/2011 |
| WO | 2011/030946 | 3/2011 |
| WO | 2011/051961 | 5/2011 |
| WO | 2011/090307 | 7/2011 |
| WO | 2011/152508 | 12/2011 |
| WO | 2011/163612 | 12/2011 |
| WO | 2011/163619 | 12/2011 |
| WO | 2012/014993 | 2/2012 |
| WO | 2012/015775 | 2/2012 |
| WO | 2012/016139 | 2/2012 |

(56) References Cited

FOREIGN PATENT DOCUMENTS

| WO | 2012/046681 | 4/2012 |
|---|---|---|
| WO | 2012/055362 | 5/2012 |
| WO | 2012/174126 | 12/2012 |
| WO | 2013/012835 | 1/2013 |
| WO | 2013/039969 | 3/2013 |
| WO | 2013/059610 | 4/2013 |
| WO | 2013/097873 | 7/2013 |
| WO | 2013/103842 | 7/2013 |
| WO | 2013/132509 | 9/2013 |
| WO | 2013/137371 | 9/2013 |
| WO | 2013/154766 | 10/2013 |
| WO | 2014/001988 | 1/2014 |
| WO | 2014/047437 | 3/2014 |

OTHER PUBLICATIONS

Seidah, "PCSK9 as Therapeutic target of dyslipidemia", Expert Opinion on Therapeutic Targets, vol. 13(1), pp. 19-28 (2009).

Medda, et al., "Novel cambinol analogs as sirtuin inhibitors: Synthesis, biological evaluation, and rationalization of activity", J. Med. Chem., vol. 52(9), pp. 2673-2682 (2009).

El-Ziaty, et al., "Antibacterial Activities of New (E) 2-Cyano-3-(3',4'-dimethoxyphenyl)-2-propenoylamide Derivatives", Synthetic Communications, vol. 37(22), pp. 4043-4057 (2007).

Lorente, et al., "Synthetic and Conformational Studies on 5,6-Substituted Dihydro-2-Thiouracils", Heterocycles, vol. 38(5), pp. 1077-1088 (1994).

Skulnick, et al., "Pyrimidinones. 3. N-Substituted 6-Phenylpyrimidones and Pyrimidinediones with Diuretic/Hypotensive and Anti-inflammatory Activity", Journal of Medicinal Chemistry, vol. 29(8), pp. 1499-1504 (1986).

Ramiz, et al., "Synthesis and antiviral activity of new substituted pyrimidine glycosides", Journal of Heterocyclic Chemistry, vol. 48(5), pp. 1028-1038 (2011).

Al-Awadi, et al., "A direct synthetic approach to uracil anhydrothionucleoside derivatives" Carbohydrate Research, vol. 344(17), pp. 2322-2328 (2009).

Assy, et al., "New Synthesis of Some Pyrimidines", Polish Journal of Chemistry, vol. 69(7), pp. 1018-1021 (1995).

Elghandour, et al., "A Facile Synthesis of Substituted Perhydro-1,3-thiazin-4-ones and 2-Thioxoperhydro-4-pyrimidinones", Liebigs Annalen der Chemie, vol. 1988, Issue 10, pp. 983-987 (1988).

Dzurilla, et al., "A New Method for Preparation of 1-(4-Substituted Phenyl)-6-Phenyl-2-Thiouracils via Cyclization of N-(4-Substituted Phenyl)-N'-3-Phenylpropenoylthioureas and Dimroth Rearrangement of 2-(4-Substituted Phenylimino)-6-Phenyl-5,6-Dihydro-4H-1,3-Thiazin-4-Ones", Collection of Czechoslovak Chemical Communications, vol. 52(9), pp. 2260-2265 (1987).

Hafez, et al., "A New, Convenient Synthesis of 1,6-Diaryl-2-thioxoperhydro-4-pyrimidnones: Reaction of 3-Phenyl-2-propenoyl Isothiocyanate With Heteroaromatic Amines", Liebigs Annalen der Chemie, vol. 1987, Issue 1, pp. 65-67 (1987).

Ito, et al., "Arrest Peptides: Cis-Acting Modulators of Translation", Annual Review of Biochemistry, vol. 82, pp. 171-202 (2013).

Cruz-Vera, et al. "Nascent polypeptide sequences that influence ribosome function", Current Opinion in Microbiology, vol. 14(2), pp. 160-166 (2011).

Dever, et al., "The Elongation, Termination, and Recycling Phases of Translation in Eukaryotes", Cold Spring Harbor Perspectives in Biology 2012; 4:a013706.

Lee, et al, Global mapping of translation initiation sites in mammalian cells at single-nucleotide resolution, PNAS, vol. 109(37), pp. E2424-E2432 (2012).

Blagden, et al., "The biological and therapeutic relevance of mRAN translation in cancer", Nature, vol. 8, pp. 280-291 (2011).

Boyce, et al., "A Selective Inhibitor of eIF2a Dephosphorylation Protects Cells from ER Stress", Science, vol. 307, pp. 935-939 (2005).

Crunkhorn, "Targeting translation in autism", Nature Reviews Drug Discovery, published online Dec. 14, 2012; doi:10.1038/nrd3915.

Diaz-Guerra, et al., "Translation Controlled mRNAs: New Drug Targets in Infectious Diseases?", Infectious Disorders—Drug Targets, vol. 8, pp. 252-261 (2008).

Graff, et al., "Therapeutic suppression of translation initiation factor eIF4E expression reduces tumor growth without toxicity", The Journal of Clinical Investigation, vol. 117(9), pp. 2638-2648 (2007).

Low, et al., "Second-generation derivatives of the eukaryotic translation initiation inhibitor pateamine a trageting eIF4A as potential anticancer agents", Bioorganic & Medicinal Chemistry, vol. 22, pp. 116-125 (2014).

Malina, "Emerging Therapeutics Targeting mRNA Translation", Cold Spring Harb Perspect Biol, doi: 10.1101/cshperspect.a012377.

Meric, et al., "Translation Initiation in Cancer: A Novel Target for Therapy", Molecular Cancer Therapeutics, vol. 1, pp. 971-979 (2002).

Moreira, et al., "Thalidomide Experts Its Inhibitory Action on Tumor Necrosis Factor a by Enhancing mRNA Degradation", J. Exp. Med., vol. 177, pp. 1675-1680 (1993).

Ortiz-Zapater, et al., "Key contribution of CPEB4-mediated translational control to cancer progression", Nature Medicine, vol. 18(1), pp. 83-91 (2012).

Rogers, et al., "Alzheimer's Disease Drug Discovery Targeted to the APP mRNA 5'Untranslated Region", Journal of Molecular Neuroscience, vol. 19, pp. 77-82 (2002).

Shaw, et al., Phenserine regulates translation of B-amyloid precursor protein mRNA by putative interleukin-1 responsive element, a target for drug development, PNAS, vol. 98(13), pp. 7605-7610 (2001).

Terada, et al., "Rapamycin selectively inhibits translation of mRNAs encoding elongation factors and ribosomal proteins", PNAS, vol. 91, pp. 11477-11481 (1994).

Wilson, "Less is More for Leaderless mRNA Translation", Molecular Cell, vol. 33, pp. 141-142 (2009).

Altman, et al., "Acute myeloid leukemia: potential for new therapeutic approaches targeting mRNA translation pathways", Int. J. Hematol. Oncol., vol. 2(3), pp. 243-250 (2013).

Hershey, et al., "Principles of Translational Control: An Overview", Cold Spring Harbor Perspectives in Biology, 2012; 4:a011528.

Roux, et al., "Regulation of mRNA Translation by Signaling Pathways", Cold Spring Harbor Perspectives in Biology, 2012; 4:a012252.

Li, et al., "Recent Patents on PCSK9: A New Target for Treating Hypercholesterolemia", Recent Patents on DNA & Gene Sequences, vol. 3, pp. 201-212 (2009).

Ingolia, et al., "Genome-Wide Analysis in Vivo of Translation with Nucleotide Resolution Using Ribosome Profiling", Science, vol. 324(5924), pp. 218-223 (2009).

Pelletier, et al., "Therapeutic Opportunities in Translation, Translational Control in Biology and Medicine", Chapter 30, pp. 855-895 (2007) (Cold Spring Harbor Laboratory Press 978-087969767-9).

"Fenofibrate", downloaded from http://en.wikipedia.org on Aug. 21, 2014. Page last modified on Aug. 1, 2014.

"Berberine", downloaded from http://en.wikipedia.org on Aug. 21, 2014. Page last modified on Aug. 13, 2014.

* cited by examiner

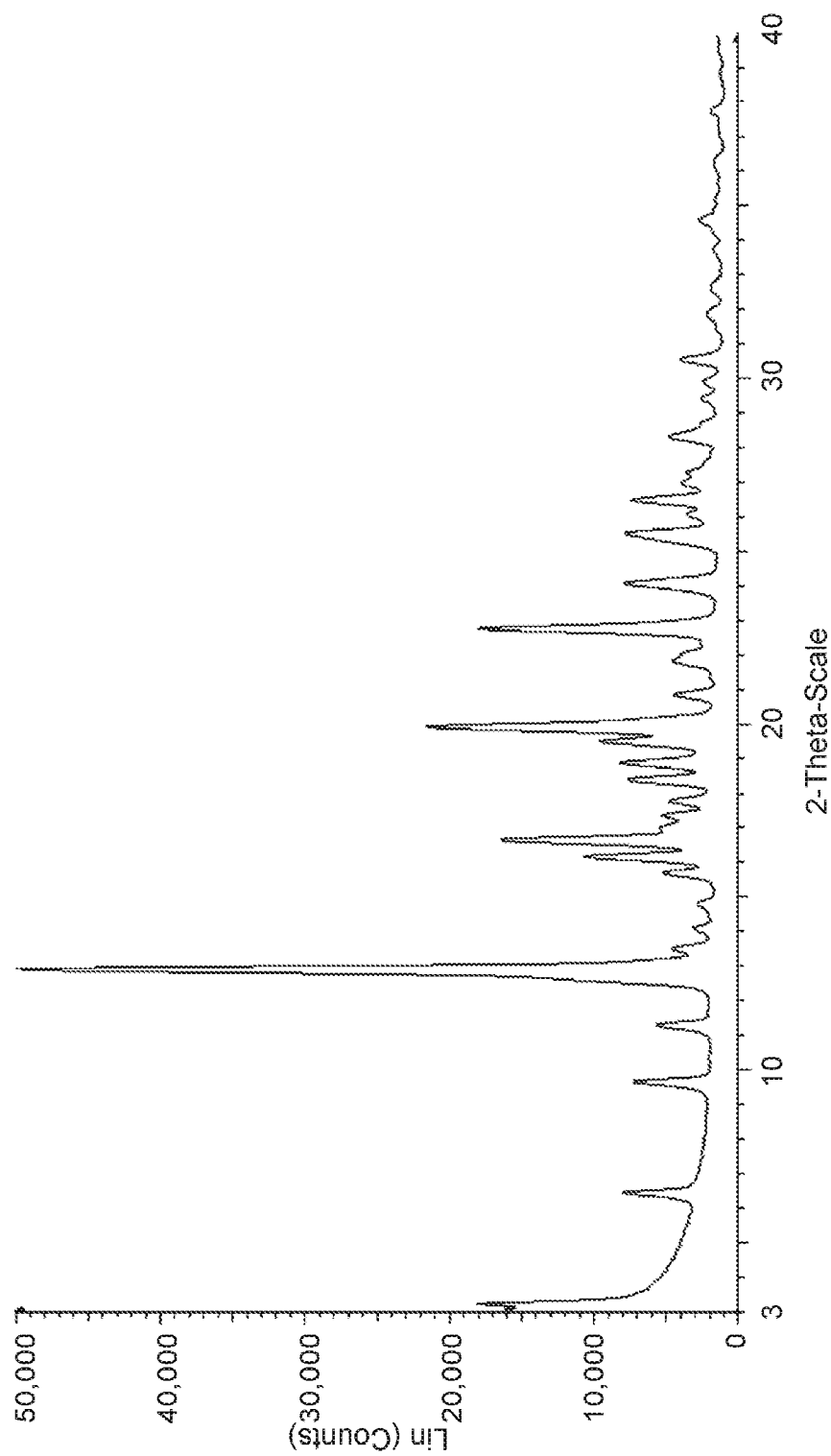

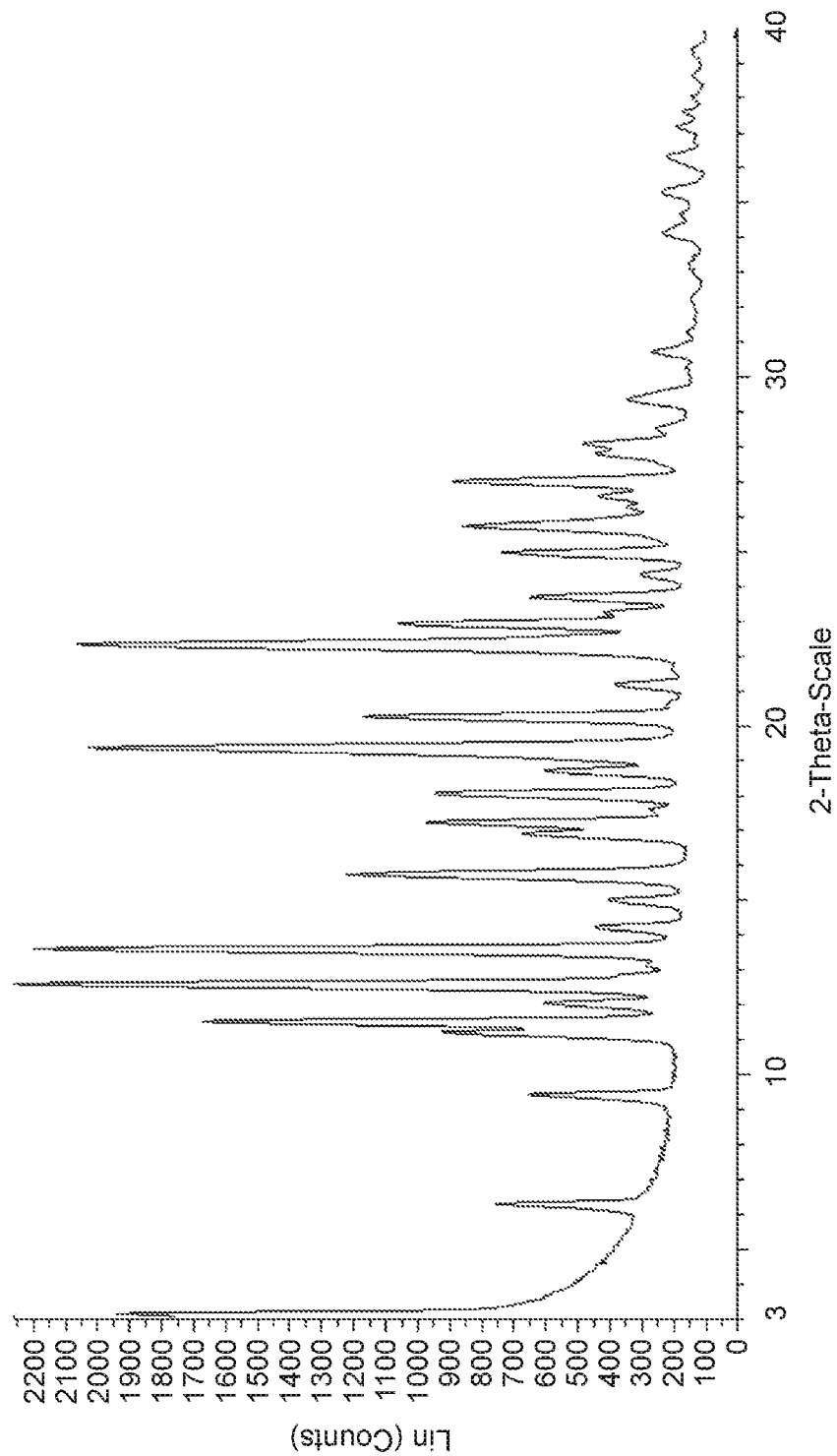

SUBSTITUTED AMIDE COMPOUNDS

CROSS-REFERENCE TO RELATED APPLICATION

This application claims the benefit of priority of U.S. provisional Patent Application Ser. No. 61/812,864, filed Apr. 17, 2013; U.S. provisional Patent Application Ser. No. 61/880,336, filed Sep. 20, 2013 and U.S. provisional Patent Application Ser. No. 61/898,667 filed Nov. 1, 2013, which are incorporated herein by reference in their entirety for all purposes.

BACKGROUND OF INVENTION

The present invention relates to substituted amide compounds, pharmaceutical compositions containing such compounds and the use of such compounds to treat cardiovascular disease including atherosclerosis, hyperlipidemia, hypercholesterolemia, and hypertriglyceridemia in mammals, including humans.

Atherosclerosis, a disease of the arteries, is recognized to be the leading cause of death in the United States and Western Europe. The pathological sequence leading to atherosclerosis and occlusive heart disease is well known. The earliest stage in this sequence is the formation of "fatty streaks" in the carotid, coronary and cerebral arteries and in the aorta. These lesions are yellow in color due to the presence of lipid deposits found principally within smooth-muscle cells and in macrophages of the intima layer of the arteries and aorta. Further, it is postulated that most of the cholesterol found within the fatty streaks, in turn, gives rise to development of the "fibrous plaque," which consists of accumulated intimal smooth muscle cells laden with lipid and surrounded by extra-cellular lipid, collagen, elastin and proteoglycans. These cells plus matrix form a fibrous cap that covers a deeper deposit of cell debris and more extracellular lipid. The lipid is primarily free and esterified cholesterol. The fibrous plaque forms slowly, and is likely in time to become calcified and necrotic, advancing to the "complicated lesion," which accounts for the arterial occlusion and tendency toward mural thrombosis and arterial muscle spasm that characterize advanced atherosclerosis.

Epidemiological evidence has firmly established hyperlipidemia as a primary risk factor in causing cardiovascular disease (CVD) due to atherosclerosis. In recent years, leaders of the medical profession have placed renewed emphasis on lowering plasma cholesterol levels, and low density lipoprotein cholesterol in particular, as an essential step in prevention of CVD. The upper limits of "normal" are now known to be significantly lower than heretofore appreciated. As a result, large segments of Western populations are now realized to be at particularly high risk. Additional independent risk factors include glucose intolerance, left ventricular hypertrophy, hypertension, and being of the male sex. Cardiovascular disease is especially prevalent among diabetic subjects, at least in part because of the existence of multiple independent risk factors in this population. Successful treatment of hyperlipidemia in the general population, and in diabetic subjects in particular, is therefore of exceptional medical importance.

While there are a variety of anti-atherosclerosis compounds, cardiovascular disease is still a leading cause of death and accordingly, there is a continuing need and a continuing search in this field of art for alternative therapies.

SUMMARY OF THE INVENTION

The present invention is directed to compounds of Formula I

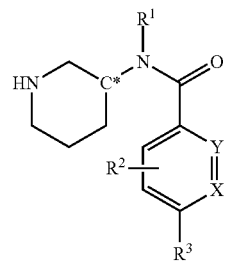

Formula I or a pharmaceutically acceptable salt thereof wherein
$R^1$ is pyrid-2-yl, isoquinolin-1-yl or 1H-pyrrolo[2,3-c]pyridin-7-yl;
$R^1$ is optionally mono- or di-substituted with chloro or ($C_1$-$C_4$)alkyl;
X and Y are independently either N or C(H), provided that at least one of X or Y is C(H);
$R^2$ is H, fluoro, hydroxyl or methyl;
$R^3$ is

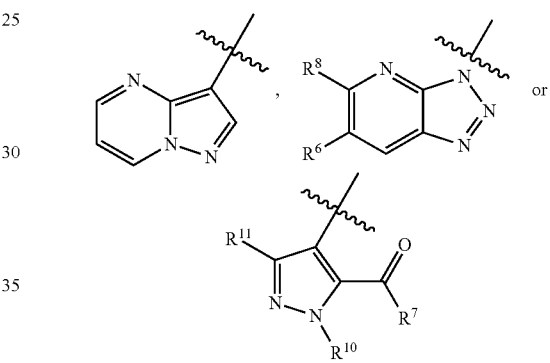

wherein $R^6$ and $R^8$ are each independently H, methyl, halo or ($C_1$-$C_4$)alkyloxy, provided that only one of $R^6$ and $R^8$ is halo;
wherein $R^{10}$ and $R^{11}$ are each independently H, ($C_1$-$C_4$)alkyl or ($C_3$-$C_5$)cycloalkyl; and
wherein $R^7$ is hydroxyl, ($C_1$-$C_4$)alkyloxy, ($C_1$-$C_4$)alkoxycarbonyloxy($C_1$-$C_4$)alkyloxy, or ($C_1$-$C_4$)alkylcarbonyloxy($C_1$-$C_4$)alkoxy.

The present application is also directed to methods for treating dyslipidemia, hypercholesterolemia (including heterozygous and homozygous familial hypercholesterolemia), hypertriglyceridemia, hyperlipidemia, hypoalphalipoproteinemia, metabolic syndrome, diabetic complications, atherosclerosis, stroke, vascular dimensia, chronic kidney disease, coronary heart disease, coronary artery disease, retinopathy, inflammation, thrombosis, peripheral vascular disease or congestive heart failure in a mammal by administering to a mammal in need of such treatment a therapeutically effective amount of a compound of Formula I or a pharmaceutically acceptable salt of said compound.

The present application also is directed to pharmaceutical compositions which comprise a therapeutically effective amount of a compound of Formula I, or a pharmaceutically acceptable salt of said compound and a pharmaceutically acceptable carrier, vehicle or diluent.

In addition, the present application is directed to pharmaceutical combination compositions comprising: a therapeutically effective amount of a composition comprising a first compound, said first compound being a compound of Formula I or a pharmaceutically acceptable salt of said compound;

a second compound, said second compound being a lipid modulating agent; and a pharmaceutically acceptable carrier, vehicle or diluent.

Examples of lipid modulating agents include a lipase inhibitor, an HMG-CoA reductase inhibitor, an HMG-CoA synthase inhibitor, an HMG-CoA reductase gene expression inhibitor, an HMG-CoA synthase gene expression inhibitor, an MTP/Apo B secretion inhibitor, a CETP inhibitor, a bile acid absorption inhibitor, a cholesterol absorption inhibitor, a cholesterol synthesis inhibitor, a squalene synthetase inhibitor, a squalene epoxidase inhibitor, a squalene cyclase inhibitor, a combined squalene epoxidase/squalene cyclase inhibitor, a fibrate, niacin, a combination of niacin and lovastatin, an ion-exchange resin, an antioxidant, an ACAT inhibitor and a bile acid sequestrant.

Another aspect of this invention is directed to a method of treating dyslipidemia by administering to a patient in need thereof a therapeutically effective amount of a compound that selectively inhibits the translation of PCSK9 mRNA to PCSK9 protein. Preferably the compound is administered by oral administration.

The present invention is also directed to compounds of Formula II

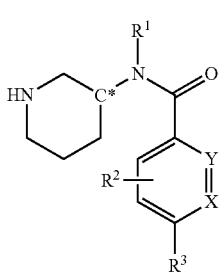

Formula II or a pharmaceutically acceptable salt thereof wherein $R^1$ is pyrid-2-yl, isoquinolin-1-yl or 1H-pyrrolo[2,3-c]pyridin-7-yl;

$R^1$ is optionally mono- or di-substituted with chloro or $(C_1-C_4)$alkyl;

X and Y are independently either N or C(H), provided that at least one of X or Y is C(H);

$R^2$ is H, fluoro, hydroxyl or methyl;

$R^3$ is

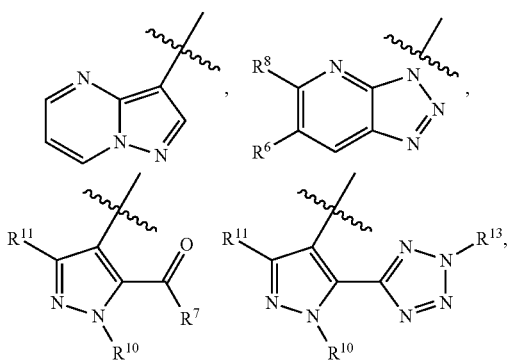

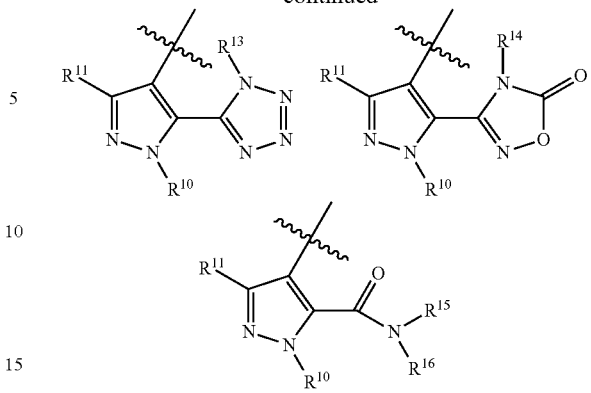

wherein $R^6$ and $R^8$ are each independently H, methyl, halo or $(C_1-C_4)$alkyloxy, provided that only one of $R^6$ and $R^8$ is halo;

wherein $R^{10}$ and $R^{11}$ are each independently H, $(C_1-C_4)$alkyl or $(C_3-C_5)$cycloalkyl; wherein $R^7$ is hydroxyl, $(C_1-C_4)$alkyloxy, $(C_1-C_4)$alkoxycarbonyloxy $(C_1-C_4)$alkyloxy, or $(C_1-C_4)$alkylcarbonyloxy$(C_1-C_4)$ alkoxy;

$R^{13}$ is H, $(C_1-C_4)$alkyl, $(C_1-C_4)$alkylcarbonyloxy$(C_1-C_4)$ alkyl or $(C_1-C_4)$alkoxycarbonyloxy$(C_1-C_4)$alkyl;

$R^{14}$ is H, $(C_1-C_4)$alkyl, $(C_1-C_4)$alkylcarbonyloxy$(C_1-C_4)$ alkyl or $(C_1-C_4)$alkoxycarbonyloxy$(C_1-C_4)$alkyl;

$R^{15}$ is hydroxyl, tetrazolyl, $(C_1-C_2)$alkylsulfonyl or trifluoromethylsulfonyl, and $R^{16}$ is H, $(C_1-C_4)$alkyl, $(C_1-C_4)$alkylcarbonyloxy$(C_1-C_4)$ alkyl or $(C_1-C_4)$alkoxycarbonyloxy$(C_1-C_4)$alkyl.

The present application is also directed to methods for treating dyslipidemia, hypercholesterolemia (including heterozygous and homozygous familial hypercholesterolemia), hypertriglyceridemia, hyperlipidemia, hypoalphalipoproteinemia, metabolic syndrome, diabetic complications, atherosclerosis, stroke, vascular dimensia, chronic kidney disease, coronary heart disease, coronary artery disease, retinopathy, inflammation, thrombosis, peripheral vascular disease or congestive heart failure in a mammal by administering to a mammal in need of such treatment a therapeutically effective amount of a compound of Formula II or a pharmaceutically acceptable salt of said compound.

The present application also is directed to pharmaceutical compositions which comprise a therapeutically effective amount of a compound of Formula II, or a pharmaceutically acceptable salt of said compound and a pharmaceutically acceptable carrier, vehicle or diluent.

In addition, the present application is directed to pharmaceutical combination compositions comprising: a therapeutically effective amount of a composition comprising a first compound, said first compound being a compound of Formula II or a pharmaceutically acceptable salt of said compound;

a second compound, said second compound being a lipid modulating agent; and a pharmaceutically acceptable carrier, vehicle or diluent.

It is to be understood that both the foregoing general description and the following detailed description are exemplary and explanatory only and are not restrictive of the invention, as claimed.

BRIEF DESCRIPTION OF THE FIGURES

FIG. 8. is an X-ray crystal structure (ORTEP drawing) of Preparation 23a.

FIG. 9. is a characteristic x-ray powder diffraction pattern showing a crystalline form of Example 30 (Vertical Axis: Intensity (CPS); Horizontal Axis: Two theta (degrees)).

FIG. 10. is a characteristic x-ray powder diffraction pattern showing a crystalline form of Example 31 (Vertical Axis: Intensity (CPS); Horizontal Axis: Two theta (degrees)).

DETAILED DESCRIPTION OF THE INVENTION

Figure 1:
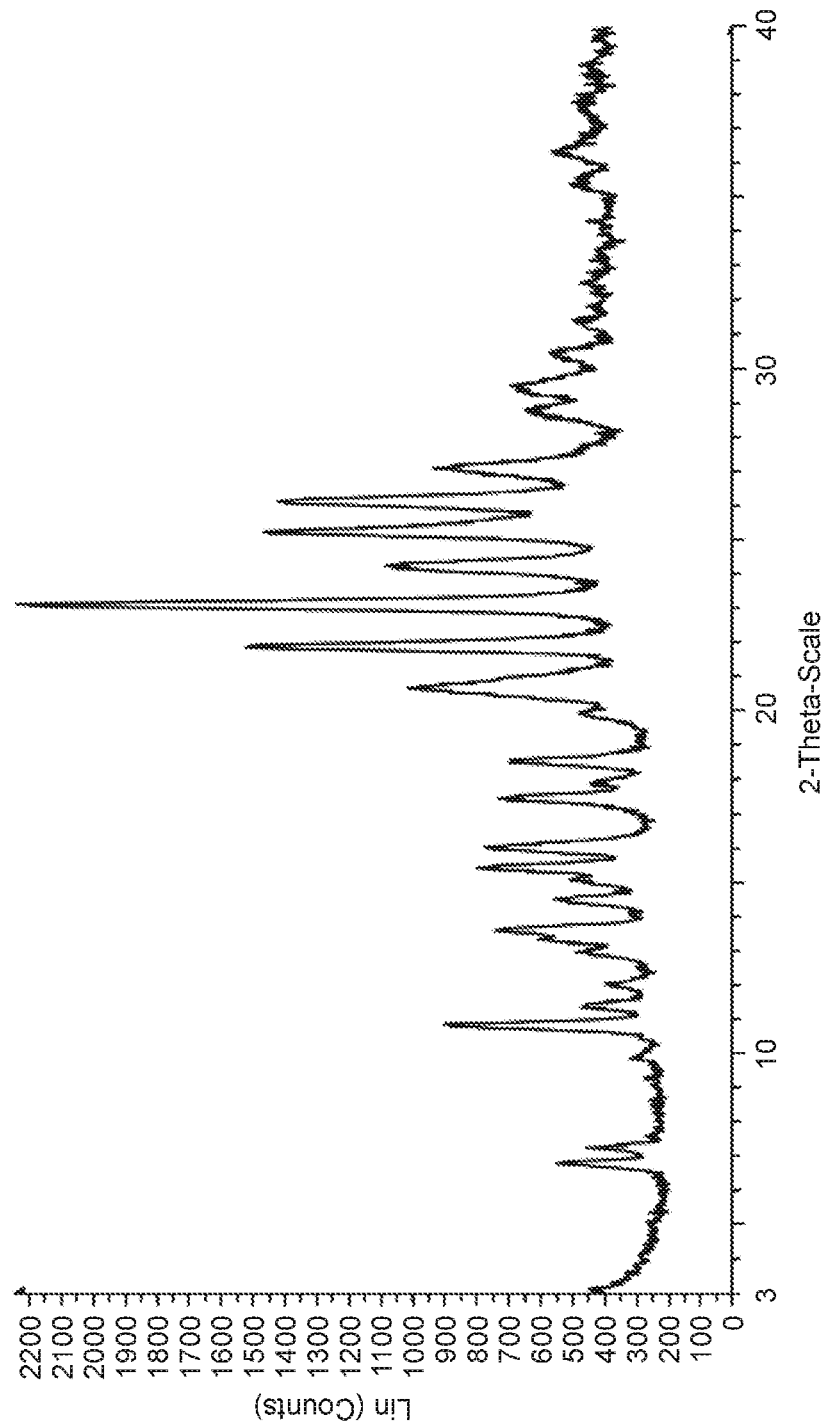
FIG. 1 is a characteristic X-ray powder diffraction pattern showing a crystalline form of Example 2 (Vertical Axis: Intensity (CPS); Horizontal Axis: Two theta (degrees)).

The present invention may be understood more readily by reference to the following detailed description of exemplary embodiments of the invention and the examples included therein.

References to Compounds of Formula I or the like are herein defined to also include Compounds of Formula II.

Before the present compounds, compositions and methods are disclosed and described, it is to be understood that this invention is not limited to specific synthetic methods of making the compounds that may of course vary. It is also to be understood that the terminology used herein is for the purpose of describing particular embodiments only and is not intended to be limiting.

A preferred group of compounds, designated the A Group, contains those compounds having the Formula I as shown above wherein:

$R^1$ is pyrid-2-yl and the piperidinyl C* is (R).

A group of compounds which is preferred among the A Group of compounds designated the B Group, contains those compounds wherein:

X and Y are both C(H), $R^2$ is H and $R^1$ is optionally mono-substituted with chloro or methyl.

A group of compounds which is preferred among the B Group of compounds designated the C Group, contains those compounds wherein $R^3$ is

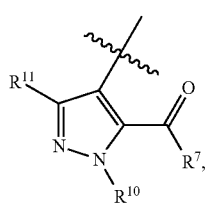

$R^7$ is hydroxyl, $(C_1-C_2)$alkyloxy or

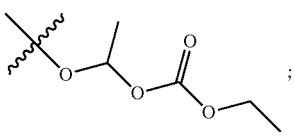 [SMILES: *OC(C)OC(=O)OCC]

;

$R^{10}$ is methyl; and $R^{11}$ is H.

A group of compounds which is preferred among the B Group of compounds designated the D Group, contains those compounds wherein $R^3$ is

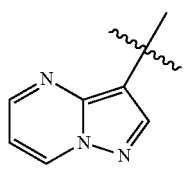

A group of compounds which is preferred among the B Group of compounds designated the E Group, contains those compounds wherein $R^3$ is

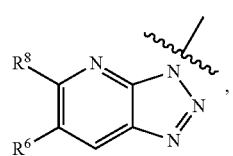

$R^6$ is H or methyl and $R^8$ is H.

A preferred group of compounds, designated the F Group, contains those compounds having the Formula I as shown above wherein:

$R^1$ isoquinolin-1-yl; and the piperidinyl C* is (R).

A group of compounds which is preferred among the F Group of compounds designated the G Group, contains those compounds wherein X and Y are both C(H), $R^2$ is H, hydroxyl, or methyl and $R^1$ is optionally mono-substituted with chloro or methyl.

A group of compounds which is preferred among the G Group of compounds designated the H Group, contains those compounds wherein $R^3$ is

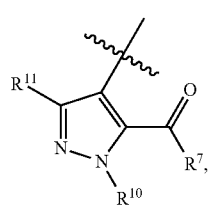

$R^7$ is hydroxyl, $(C_1-C_2)$alkyloxy or

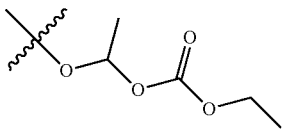 [SMILES: *OC(C)OC(=O)OCC]

$R^{10}$ is methyl; and
$R^{11}$ is H.

A group of compounds which is preferred among the G Group of compounds designated the I Group, contains those compounds wherein
$R^3$ is

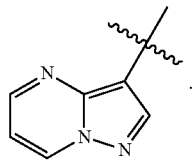 [SMILES: *c1cnn2cccnc12]

A group of compounds which is preferred among the G Group of compounds designated the J Group, contains those compounds wherein
$R^3$ is

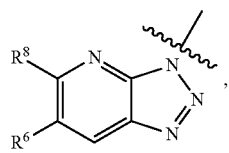

$R^6$ is H or methyl and $R^8$ is H.

A preferred group of compounds, designated the K Group, contains those compounds having the Formula I as shown above wherein:
$R^1$ is 1H-pyrrolo[2,3-c]pyridin-7-yl and the piperidinyl C* is (R).

A group of compounds which is preferred among the K Group of compounds designated the L Group, contains those compounds wherein
wherein X and Y are both C(H), $R^2$ is H, hydroxyl, or methyl and $R^1$ is optionally mono-substituted with chloro or methyl.

A group of compounds which is preferred among the L Group of compounds designated the M Group, contains those compounds wherein $R^3$ is

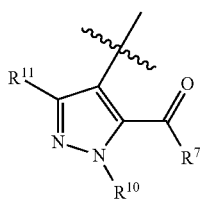

$R^7$ is hydroxyl, $(C_1-C_2)$alkyloxy or

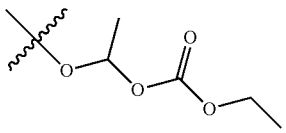 [SMILES: *OC(C)OC(=O)OCC]

$R^{10}$ is methyl; and
$R^{11}$ is H.

A group of compounds which is preferred among the L Group of compounds designated the N Group, contains those compounds wherein
$R^3$ is

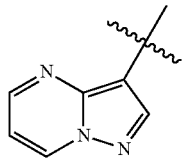

A group of compounds which is preferred among the L Group of compounds designated the O Group, contains those compounds wherein
$R^3$ is

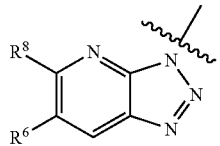

and $R^6$ is H or methyl and $R^8$ is H.

A preferred group of compounds, designated the P Group, contains the following compounds
N-(3-methylpyridin-2-yl)-N-[(3R)-piperidin-3-yl]-4-(pyrazolo[1,5-a]pyrimidin-3-yl)benzamide;
N-(3-chloropyridin-2-yl)-N-[(3R)-piperidin-3-yl]-4-(pyrazolo[1,5-a]pyrimidin-3-yl)benzamide;
N-(3-chloropyridin-2-yl)-4-(6-methyl-3H-[1,2,3]triazolo[4,5-b]pyridin-3-yl)-N-[(3R)-piperidin-3-yl]benzamide;
4-(4-{isoquinolin-1-yl[(3R)-piperidin-3-yl]carbamoyl}phenyl)-1-methyl-1H-pyrazole-5-carboxylic acid;
N-(3-chloropyridin-2-yl)-N-[(3R)-piperidin-3-yl]-5-(3H-[1,2,3]triazolo[4,5-b]pyridin-3-yl)pyridine-2-carboxamide;
ethyl 4-(4-{(3-chloropyridin-2-yl)[(3R)-piperidin-3-yl]carbamoyl}phenyl)-1-methyl-1H-pyrazole-5-carboxylate;
4-(4-{(3-chloropyridin-2-yl)[(3R)-piperidin-3-yl]carbamoyl}phenyl)-1-methyl-1H-pyrazole-5-carboxylic acid;
4-(4-{(3-chloropyridin-2-yl)[piperidin-3-yl]carbamoyl}phenyl)-1-methyl-1H-pyrazole-5-carboxylic acid;
1-[(ethoxycarbonyl)oxy]ethyl 4-(4-{(3-chloropyridin-2-yl)[piperidin-3-yl]carbamoyl}phenyl)-1-methyl-1H-pyrazole-5-carboxylate;
1-[(ethoxycarbonyl)oxy]ethyl 4-(4-{(3-chloropyridin-2-yl)[(3R)-piperidin-3-yl]carbamoyl}phenyl)-1-methyl-1H-pyrazole-5-carboxylate;
(1R)-1-[(ethoxycarbonyl)oxy]ethyl 4-(4-{(3-chloropyridin-2-yl)[(3R)-piperidin-3-yl]carbamoyl}phenyl)-1-methyl-1H-pyrazole-5-carboxylate;

(1S)-1-[(ethoxycarbonyl)oxy]ethyl 4-(4-{(3-chloropyridin-2-yl)[(3R)-piperidin-3-yl]carbamoyl}phenyl)-1-methyl-1H-pyrazole-5-carboxylate; or N-(3-chloropyridin-2-yl)-N-[(3R)-piperidin-3-yl]-4-(3H-[1,2,3]triazolo[4,5-b]pyridin-3-yl)benzamide; or a pharmaceutically acceptable salt of any of said compounds.

A preferred group of compounds, designated the Q Group, contains the following compounds:

N-(3-chloropyridin-2-yl)-5-(6-methyl-3H-[1,2,3]triazolo[4,5-b]pyridin-3-yl)-N-[(3R)-piperidin-3-yl]pyridine-2-carboxamide;

methyl 4-(4-{(3-chloropyridin-2-yl)[(3R)-piperidin-3-yl]carbamoyl}phenyl)-1-methyl-1H-pyrazole-5-carboxylate;

1-[(ethoxycarbonyl)oxy]ethyl 4-(4-{isoquinolin-1-yl[(3R)-piperidin-3-yl]carbamoyl}phenyl)-1-methyl-1H-pyrazole-5-carboxylate;

1-methyl-4-(4-{(1-methyl-1H-pyrrolo[2,3-c]pyridin-7-yl)[(3R)-piperidin-3-yl]carbamoyl}phenyl)-1H-pyrazole-5-carboxylic acid;

methyl 1-methyl-4-(4-{(3-methylpyridin-2-yl)[(3R)-piperidin-3-yl]carbamoyl}phenyl)-1H-pyrazole-5-carboxylate; or 1-[(ethoxycarbonyl)oxy]ethyl 1-methyl-4-(4-{(1-methyl-1H-pyrrolo[2,3-c]pyridin-7-yl)[(3R)-piperidin-3-yl]carbamoyl}phenyl)-1H-pyrazole-5-carboxylate; or a pharmaceutically acceptable salt of any of said compounds.

A preferred group of compounds designated the R Group, contains those compounds having the Formula II as shown above wherein $R^1$ is pyrid-2-yl optionally mono-substituted with chloro or methyl; the piperidinyl C* is the R configuration; X and Y are both C(H);

$R^2$ is H;

$R^3$ is

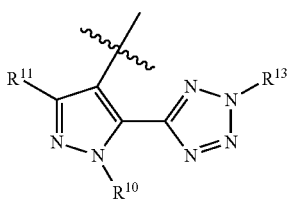

$R^{10}$ is methyl;

$R^{11}$ is H; and $R^{13}$ is $(C_1-C_4)$alkylcarbonyloxy$(C_1-C_4)$alkyl.

A preferred group of compounds designated the S Group, contains those compounds having the Formula II as shown above wherein $R^1$ is pyrid-2-yl optionally mono-substituted with chloro or methyl; the piperidinyl C* is the R configuration; X and Y are both C(H);

$R^2$ is H; and $R^3$ is

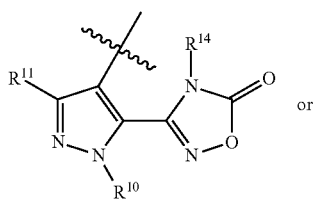

or

-continued

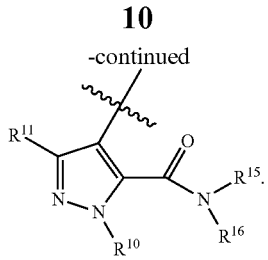

A preferred group of compounds, designated the T Group, contains the following compounds:

4-(4-{(3-chloropyridin-2-yl)[(3R)-piperidin-3-yl]carbamoyl}phenyl)-1-methyl-N-[(trifluoromethyl)sulfonyl]-1H-pyrazole-5-carboxamide;

N-(3-chloropyridin-2-yl)-4-[1-methyl-5-(2H-tetrazol-5-yl)-1H-pyrazol-4-yl]-N-[(3R)-piperidin-3-yl]benzamide;

1-methyl-4-(4-{(3-methylpyridin-2-yl)[(3R)-piperidin-3-yl]carbamoyl}phenyl)-N-(methylsulfonyl)-1H-pyrazole-5-carboxamide;

N-(3-methylpyridin-2-yl)-4-[1-methyl-5-(2H-tetrazol-5-yl)-1H-pyrazol-4-yl]-N-[(3R)-piperidin-3-yl]benzamide; or ethyl 1-[{[1-methyl-4-(4-{(3-methylpyridin-2-yl)[(3R)-piperidin-3-yl]carbamoyl}phenyl)-1H-pyrazol-5-yl]carbonyl}(methylsulfonyl)amino]ethyl carbonate;

or a pharmaceutically acceptable salt of any of said compounds.

A preferred group of compounds, designated the U Group, contains the following compounds:

ethyl 1-{5-[1-methyl-4-(4-{(3-methylpyridin-2-yl)[(3R)-piperidin-3-yl]carbamoyl}phenyl)-1H-pyrazol-5-yl]-1H-tetrazol-1-yl}ethyl carbonate;

ethyl (1S)-1-{5-[1-methyl-4-(4-{(3-methylpyridin-2-yl)[(3R)-piperidin-3-yl]carbamoyl}phenyl)-1H-pyrazol-5-yl]-2H-tetrazol-2-yl}ethyl carbonate; or ethyl (1R)-1-{5-[1-methyl-4-(4-{(3-methylpyridin-2-yl)[(3R)-piperidin-3-yl]carbamoyl}phenyl)-1H-pyrazol-5-yl]-2H-tetrazol-2-yl}ethyl carbonate;

A preferred group of compounds, designated the V Group, contains the following compounds:

(1-{5-[1-methyl-4-(4-{(3-methylpyridin-2-yl)[(3R)-piperidin-3-yl]carbamoyl}phenyl)-1H-pyrazol-5-yl]-2H-tetrazol-2-yl}ethyl 2-methylpropanoate (Diastereomer B; Example 51)

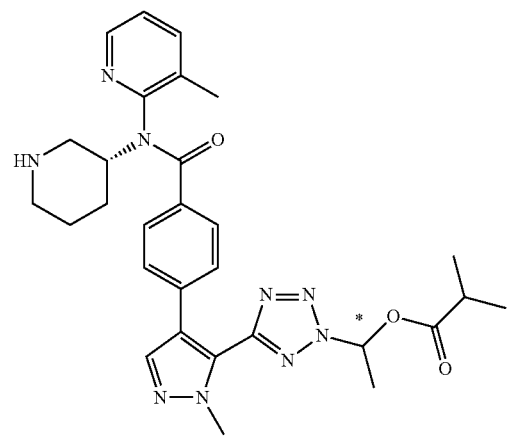 [SMILES: Cc1cccnc1N(C(=O)c1ccc(-c2cnn(C)c2-c2nnn(C(C)OC(=O)C(C)C)n2)cc1)[C@@H]1CCCNC1]

2-methyl-1-{5-[1-methyl-4-(4-{(3-methylpyridin-2-yl)[(3R)-piperidin-3-yl]carbamoyl}phenyl)-1H-pyrazol-5-yl]-2H-tetrazol-2-yl}propyl 2-methylpropanoate (Diastereomer B; Example 55)

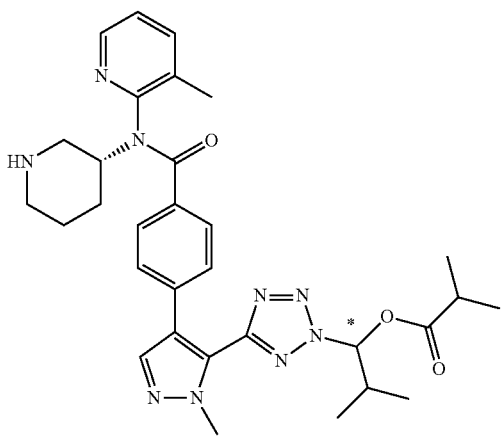 [SMILES: Cc1cccnc1N(C(=O)c1ccc(-c2cnn(C)c2-c2nnn(C(OC(=O)C(C)C)C(C)C)n2)cc1)[C@@H]1CCCNC1]

or a pharmaceutically acceptable salt of any of said compounds.

A preferred group of compounds, designated the W Group, contains the following compounds:
(1-{5-[1-methyl-4-(4-{(3-methylpyridin-2-yl)[(3R)-piperidin-3-yl]carbamoyl}phenyl)-1H-pyrazol-5-yl]-2H-tetrazol-2-yl}ethyl 2-methylpropanoate; or
2-methyl-1-{5-[1-methyl-4-(4-{(3-methylpyridin-2-yl)[(3R)-piperidin-3-yl]carbamoyl}phenyl)-1H-pyrazol-5-yl]-2H-tetrazol-2-yl}propyl 2-methylpropanoate;
or a pharmaceutically acceptable salt of any of said compounds.

Another preferred group of compounds is each of the compounds in the P and Q groups taken individually.

Another preferred group of compounds is each of the compounds in the T and U groups taken individually.

Another preferred group of compounds is each of the compounds in the V and W groups taken individually.

It is also preferred that each of those compounds taken individually is a pharmaceutically acceptable salt, and especially preferred that each taken individually is an acid addition salt thereof.

In one preferred embodiment of the pharmaceutical combination compositions, methods and kits of the present invention, the second compound is an HMG-CoA reductase inhibitor or a CETP inhibitor, such as rosuvastatin, rivastatin, pitavastatin, lovastatin, simvastatin, pravastatin, fluvastatin, atorvastatin or cerivastatin or a prodrug of said compound or a pharmaceutically acceptable salt of said compound or prodrug. It is especially preferred that the second compound is atorvastatin hemi-calcium.

Pharmaceutically acceptable salts of the compounds of Formula I include the acid addition and base salts thereof. Suitable acid addition salts are formed from acids which form non-toxic salts. Examples include the acetate, adipate, aspartate, benzoate, besylate, bicarbonate/carbonate, bisulphate/sulphate, borate, camsylate, citrate, cyclamate, edisylate, esylate, formate, fumarate, gluceptate, gluconate, glucuronate, hexafluorophosphate, hibenzate, hydrochloride/chloride, hydrobromide/bromide, hydroiodide/iodide, isethionate, lactate, malate, maleate, malonate, mesylate, methylsulphate, naphthylate, 2-napsylate, nicotinate, nitrate, orotate, oxalate, palmitate, pamoate, phosphate/hydrogen phosphate/dihydrogen phosphate, pyroglutamate, saccharate, stearate, succinate, tannate, tartrate, tosylate, trifluoroacetate and xinofoate salts.

Suitable base salts are formed from bases which form non-toxic salts. Examples include the aluminium, arginine, calcium, choline, diethylamine, glycine, lysine, magnesium, meglumine, olamine, potassium, sodium, trimethamine and zinc salts. Hemisalts of acids and bases may also be formed, for example, hemisulphate and hemicalcium salts. For a review on suitable salts, see *Handbook of Pharmaceutical Salts: Properties, Selection, and Use* by Stahl and Wermuth (Wiley-VCH, 2002).

The compounds of the invention may exist in both unsolvated and solvated forms. The term 'solvate' is used herein to describe a molecular complex comprising the compound of the invention and one or more pharmaceutically acceptable solvent molecules, for example, ethanol. Such solvent molecules are those commonly used in the pharmaceutical art, which are known to be innocuous to the recipient, e.g., water, ethanol, and the like. Other solvents may be used as intermediate solvates in the preparation of more desirable solvates, such as methanol, methyl t-butyl ether, ethyl acetate, methyl acetate, (S)-propylene glycol, (R)-propylene glycol, 1,4-butyne-diol, and the like. The term 'hydrate' is employed when said solvent is water. Pharmaceutically acceptable solvates include hydrates and other solvates wherein the solvent of crystallization may be isotopically substituted, e.g. $D_2O$, $d_6$-acetone, $d_6$-DMSO. The term "hydrate" refers to the complex where the solvent molecule is water. The solvates and/or hydrates preferably exist in crystalline form.

The compounds of the invention may also exist as complexes such as clathrates, drug-host inclusion complexes wherein, in contrast to the aforementioned solvates, the drug and host are present in stoichiometric or non-stoichiometric amounts. Also included are complexes of the drug containing two or more organic and/or inorganic components which may be in stoichiometric or non-stoichiometric amounts. The resulting complexes may be ionised, partially ionised, or non-ionised. For a review of such complexes, see J Pharm Sci, 64 (8), 1269-1288 by Haleblian (August 1975).

The compounds of the invention include compounds of Formula I as hereinbefore defined, polymorphs, and isomers thereof (including optical, geometric and tautomeric isomers including compounds exhibiting more than one type of isomerism, and mixtures of one or more thereof) and isotopically-labelled compounds of Formula I. Thus, the compounds of the present invention can exist in the form of various stereoisomers, R and S isomers, depending upon the presence of asymmetric carbon atoms. Herein, they may be referred to as the "R configuration" or "S configuration" or the like. The present invention encompasses both the individual isomers and mixtures thereof, including racemic and diastereomeric mixtures.

Compounds of Formula I containing an asymmetric carbon atom can exist as two or more stereoisomers. Alpha and Beta refer to the orientation of a substituent with reference to the plane of the ring. Beta is above the plane of the ring and Alpha is below the plane of the ring.

Where a compound of Formula I contains an alkenyl or alkenylene group or a cycloalkyl group, geometric cis/trans (or Z/E) isomers are possible. Thus, compounds of the invention exist as cis or trans configurations and as mixtures thereof. The term "cis" refers to the orientation of two substituents with reference to each other and the plane of the ring (either both "up" or both "down"). Analogously, the term "trans" refers to the orientation of two substituents with reference to each other and the plane of the ring (the substituents being on opposite sides of the ring).

Where the compound contains, for example, a keto or oxime group or an aromatic moiety, tautomeric isomerism ('tautomerism') can occur. An example of tautomerism within the scope of the claimed compounds is when $R^3$ is the pyrazol below and $R^{10}$ is hydrogen.

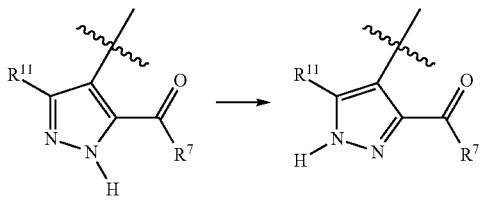

The present invention includes all pharmaceutically acceptable isotopically-labelled compounds of Formula I wherein one or more atoms are replaced by atoms having the same atomic number, but an atomic mass or mass number different from the atomic mass or mass number usually found in nature.

Examples of isotopes suitable for inclusion in the compounds of the invention include isotopes of hydrogen, such as $^2H$ and $^3H$, carbon, such as $^{11}C$, $^{13}C$ and $^{14}C$, chlorine, such as $^{36}Cl$, fluorine, such as $^{18}F$, iodine, such as $^{123}I$ and $^{125}I$, nitrogen, such as $^{13}N$ and $^{15}N$, oxygen, such as $^{15}O$, $^{17}O$ and $^{18}O$, phosphorus, such as $^{32}P$, and sulphur, such as $^{35}S$.

Certain isotopically-labelled compounds of Formula (I), for example, those incorporating a radioactive isotope, are useful in drug and/or substrate tissue distribution studies. The radioactive isotopes tritium, i.e. $^3H$, and carbon-14, i.e. $^{14}C$, are particularly useful for this purpose in view of their ease of incorporation and ready means of detection.

Substitution with heavier isotopes such as deuterium, i.e. $^2H$, may afford certain therapeutic advantages resulting from greater metabolic stability, for example, increased in vivo half-life or reduced dosage requirements, and hence may be preferred in some circumstances.

Substitution with positron emitting isotopes, such as $^{11}C$, $^{18}F$, $^{15}O$ and $^{13}N$, can be useful in Positron Emission Tomography (PET) studies for examining substrate receptor occupancy.

References herein to "treat", "treating", "treatment" and the like include curative, palliative and prophylactic treatment.

As used herein, the expressions "reaction-inert solvent" and "inert solvent" refer to a solvent or a mixture thereof which does not interact with starting materials, reagents, intermediates or products in a manner which adversely affects the yield of the desired product.

By "pharmaceutically acceptable" is meant the carrier, vehicle, or diluent and/or salt must be compatible with the other ingredients of the formulation, and not deleterious to the recipient thereof.

The term "pharmaceutically effective amount", as used herein, refers to an amount of the compound of Formula I (or a combination agent or a Formula I compound in combination with a combination agent) sufficient to treat, prevent onset of or delay or diminish the symptoms and physiological manifestations of the indications described herein.

The term "room temperature or ambient temperature" means a temperature between 18 to 25° C., "HPLC" refers to high pressure liquid chromatography, "MPLC" refers to medium pressure liquid chromatography, "TLC" refers to thin layer chromatography, "MS" refers to mass spectrum or mass spectroscopy or mass spectrometry, "NMR" refers to nuclear magnetic resonance spectroscopy, "DCM" refers to dichloromethane, "DMSO" refers to dimethyl sulfoxide, "DME" refers to dimethoxyethane, "EtOAc" refers to ethyl acetate, "MeOH" refers to methanol, "Ph" refers to the phenyl group, "Pr" refers to propyl, "trityl" refers to the triphenylmethyl group, "ACN" refers to acetonitrile, "DEAD" refers to diethylazodicarboxylate, and "DIAD" refers to diisopropylazodicarboxylate.

It is to be understood that if a carbocyclic or heterocyclic moiety may be bonded or otherwise attached to a designated substrate through differing ring atoms without denoting a specific point of attachment, then all possible points are intended, whether through a carbon atom or, for example, a trivalent nitrogen atom. For example, the term "pyridyl" means 2-, 3-, or 4-pyridyl, the term "thienyl" means 2-, or 3-thienyl, and so forth. In general the compounds of this invention can be made by processes which include processes analogous to those known in the chemical arts, particularly in light of the description contained herein.

The term "coronary artery disease", as used herein, is selected, but not limited to, the group consisting of atherosclerotic plaque (e.g., prevention, regression, stablilization), vulnerable plaque (e.g., prevention, regression, stabilization), vulnerable plaque area (reduction), arterial calcification (e.g., calcific aortic stenosis), increased coronary artery calcium score, dysfunctional vascular reactivity, vasodilation disorders, coronary artery spasm, first myocardial infarction, myocardia re-infarction, ischemic cardiomyopathy, stent restenosis, PTCA restenosis, arterial restenosis, coronary bypass graft restenosis, vascular bypass restenosis, decreased exercise treadmill time, angina pectoris/chest pain, unstable angina pectoris, exertional dyspnea, decreased exercise capacity, ischemia (reduce time to), silent ischemia (reduce time to), increased severity and frequency of ischemic symptoms, reperfusion after thrombolytic therapy for acute myocardial infarction.

The term "hypertension", as used herein, is selected, but not limited to, the group consisting of lipid disorders with hypertension, systolic hypertension and diastolic hypertension.

The term "peripheral vascular disease", as used herein, is selected, but not limited to, the group consisting of peripheral vascular disease and claudication.

The term "diabetes", as used herein, refers to any of a number of diabetogenic states including type I diabetes, type II diabetes, Syndrome X, Metabolic syndrome, lipid disorders associated with insulin resistance, impaired glucose tolerance, non-insulin dependent diabetes, microvascular diabetic complications, reduced nerve conduction velocity, reduced or loss of vision, diabetic retinopathy, increased risk of amputation, decreased kidney function, kidney failure, insulin resistance syndrome, pluri-metabolic syndrome, central adiposity (visceral)(upper body), diabetic dyslipidemia, decreased insulin sensitization, diabetic retinopathy/neuropathy, diabetic nephropathy/micro and macro angiopathy and micro/macro albuminuria, diabetic cardiomyopathy, diabetic gastroparesis, obesity, increased hemoglobin glycoslation (including HbA1C), improved glucose control, impaired renal function (dialysis, endstage) and hepatic function (mild, moderate, severe).

"Metabolic syndrome," also known as "Syndrome X," refers to a common clinical disorder that is defined as the presence of increased insulin concentrations in association with other disorders including viceral obesity, hyperlipidemia, dyslipidemia, hyperglycemia, hypertension, and potentially hyperuricemis and renal dysfunction.

The carbon atom content of various hydrocarbon-containing moieties is indicated by a prefix designating the minimum and maximum number of carbon atoms in the moiety, i.e., the prefix $C_i$-$C_j$ indicates a moiety of the integer "i" to the integer "j" carbon atoms, inclusive. Thus, for example, $C_1$-$C_3$ alkyl refers to alkyl of one to three carbon atoms, inclusive, or methyl, ethyl, propyl and isopropyl, and all isomeric forms and straight and branched forms thereof.

By "halo" or "halogen" is meant chloro, bromo, iodo, or fluoro.

By "alkyl" is meant straight chain saturated hydrocarbon or branched chain saturated hydrocarbon. Exemplary of such alkyl groups (assuming the designated length encompasses the particular example) are methyl, ethyl, propyl, isopropyl, butyl, sec-butyl, tertiary butyl, pentyl, isopentyl, neopentyl, tertiary pentyl, 1-methylbutyl, 2-methylbutyl, 3-methylbutyl, hexyl, isohexyl, heptyl and octyl. This term also includes a saturated hydrocarbon (straight chain or branched) wherein a hydrogen atom is removed from each of the terminal carbons.

"Alkenyl" referred to herein may be linear or branched, and they may also be cyclic (e.g. cyclobutenyl, cyclopentenyl, cyclohexenyl) or bicyclic or contain cyclic groups. They contain 1-3 carbon-carbon double bonds, which can be cis or trans.

By "alkoxy" is meant straight chain saturated alkyl or branched chain saturated alkyl bonded through an oxy. Exemplary of such alkoxy groups (assuming the designated length encompasses the particular example) are methoxy, ethoxy, propoxy, isopropoxy, butoxy, isobutoxy, tertiary butoxy, pentoxy, isopentoxy, neopentoxy, tertiary pentoxy, hexoxy, isohexoxy, heptoxy and octoxy.

Certain processes for the manufacture of the compounds of this invention are provided as further features of the invention and are illustrated by the following exemplary reaction schemes. Those skilled in the art will appreciate that other synthetic routes may be used to synthesize the inventive compounds. For a more detailed description of the individual reaction steps, see the Examples section below. Although specific starting materials and reagents are depicted in the schemes and discussed below, other starting materials and reagents can be easily substituted to provide a variety of derivatives and/or reaction conditions. In addition, many of the compounds prepared by the methods described below can be further modified in light of this disclosure using conventional chemistry well known to those skilled in the art. In particular, it is noted that the compounds prepared according to these Schemes may be modified further to provide new Examples within the scope of this invention. In addition, it will be evident from the detailed descriptions given in the Experimental section that the modes of preparation employed extend further than the general procedures described herein.

The starting materials are generally available from commercial sources such as Aldrich Chemicals (Milwaukee, Wis.) or are readily prepared using methods known to those skilled in the art (e.g., prepared by methods generally described in Louis F. Fieser and Mary Fieser, *Reagents for Organic Synthesis*, v. 1-19, Wiley, New York (1967-1999 ed.), or *Beilsteins Handbuch der organischen Chemie*, 4, Aufl. ed. Springer-Verlag, Berlin, including supplements (also available via the Beilstein online database).

As an initial note, in the preparation of compounds of the present invention, it is noted that some of the preparation methods useful for the preparation of the compounds described herein may require protection of remote functionality (e.g., primary amine, secondary amine, carboxyl in intermediates). The need for such protection will vary depending on the nature of the remote functionality and the conditions of the preparative methods and can be readily determined by one of ordinary skill in the art. The use of such protection/deprotection methods is also within the ordinary skill in the art. For a general description of protecting groups and their use, see T. W. Greene, *Protective Groups in Organic Synthesis*, John Wiley & Sons, New York, 1991.

For example, in the reaction schemes below, certain compounds contain primary amines or carboxylic acid functionalities, which may interfere with reactions at other sites of the molecule if left unprotected. Accordingly, such functionalities may be protected by an appropriate protecting group, which may be removed in a subsequent step. Suitable protecting groups for amine and carboxylic acid protection include those protecting groups commonly used in peptide synthesis (such as N-t-butoxycarbonyl, benzyloxycarbonyl, and 9-fluorenylmethylenoxycarbonyl for amines and lower alkyl or benzyl esters for carboxylic acids) which are generally not chemically reactive under the reaction conditions described and can typically be removed without chemically altering other functionality in the compound.

The schemes below, while depicting racemic mixtures, can be used to synthesize individual enantiomers by starting with the appropriate chiral starting materials.

Reaction Scheme I below, illustrates methodologies for preparing the compounds of Formula I, where in $R^2$, X and Y are as defined above, $R^1$ is isoquinolin-1-yl and $R^3$ is substituted triazolopyridine or pyrazolopyrimidine. In general, these compounds are prepared by the addition of an acyl chloride or activated aryl carboxylic to produce the corresponding Formula 3 compounds, followed by incorporation of an isoquinolinyl heterocycle. Formula I compounds are prepared by further modification of the Formula 6 compounds via metal-catalyzed aryl coupling reactions followed by cleavage of t-butoxycarbonyl (BOC) group from the resulting in the Formula 9 compounds

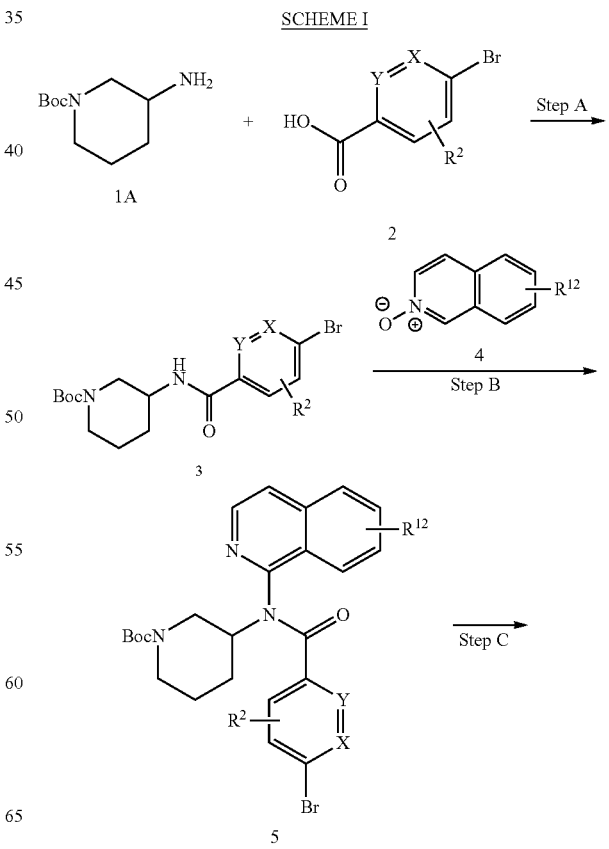

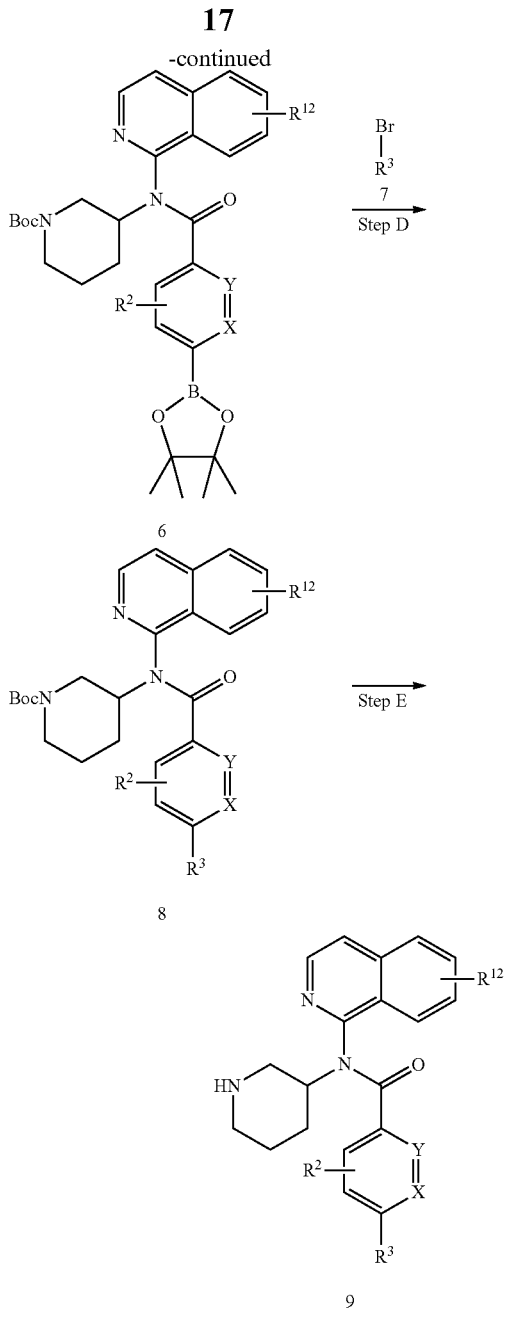

skilled in the chemical arts. The activating agent is used in equimolar amounts or in slight excess in solvents such as a N,N-dimethylformamide (DMF) or tetrahydrofuran (THF) with or without additives such as triethylamine, 1,8-diazabicycloundec-7-ene, or diisopropylethylamine. This reaction may be run at temperatures ranging from 0° C. to 50° C., depending on the choice of conditions for about 0.5 hours to about 18 hours. Alternative activating agents include those that can activate the carboxylic acid to an acyl chloride such as phosphorous trichloride, phosphorus oxychloride ($POCl_3$), thionyl chloride or oxalyl chloride. Alternative activating agents can also include dehydrating agents such as N,N-dicyclohexylcarbodiimide (DCC), or benzotriazol-1-yloxytris(dimethylamino)-phosphonium hexafluorophosphate (BOP).

In Step B, an isoquinoline substituent is added to the Formula 3 amide via the isoquinoline N-oxide Formula 4 compound, to provide the Formula 5 compound (Bilodeau, Mark T. et al, Org. Lett., 2002, 3127-3129, Londregan, Allyn et al Org. Lett., 2011, 1840-1843). The reaction preferably proceeds with an activating agent such as oxalyl chloride, benzotriazol-1-yloxy-tris(dimethylamino)-phosphonium hexafluorophosphate (BOP), bromo-tris-pyrrolidino phosphoniumhexafluorophosphate (PyBrOP), or suitable substitute in solvents such as dichloromethane, 1,4-dioxane, tetrahydrofuran (THF), acetonitrile, and DMF at a temperature of about 0° C. to about 50° C. for about 0.5 hours to about 24 hours. In addition, Step B is carried out in the presence of additives such as diisopropylethylamine, triethylamine, 2,6-lutidine or similar bases.

Step C is preferably carried out with a suitable boronate source, such as pinacol boronate in the presence of a palladium compound (e.g. tris(dibenzylideneacetone)dipalladium ($Pd_2(dba)_3$), 1,1-bis(diphenylphosphino)ferrocene]dichloropalladium(II) ($PdCl_2(dppf)_2$), tetrakis(triphenylphosphine) palladium ($Pd(PPh_3)_4$) or other suitable catalysts. The reaction proceeds at a temperature of about 23° C. to about 180° C. for about 1 hour to about 24 hours. Exemplary solvents for Step C are methanol, ethanol, water, acetonitrile, N,N-dimethylformamide (DMF), 1,4-dioxane, and tetrahydrofuran (THF). Step C is carried out in the presence of a base such as potassium acetate (KOAc), cesium carbonate ($Cs_2CO_3$), sodium hydroxide, (NaOH), potassium hydroxide (KOH), potassium or sodium carbonate and sodium bicarbonate ($K_2CO_3$, $Na_2CO_3$, $NaHCO_3$).

Step D incorporates $R^3$ via a cross-coupling reaction of a Formula 6 boronate ester and a Formula 7 bromide via reaction conditions similar to those used in Step C. The $R^3$ substituent is selected to provide the desired Formula I compound $R^3$ substituent as defined above or the $R^3$ substituent can be modified after addition by procedures known in the chemical art to obtain an alternative $R^3$ substituent (as defined above).

The t-butoxycarbonyl (BOC) is cleaved in Step E with acids such as hydrochloric acid (HCl), trifluoroacetic acid (TFA), p-toluene sulfonic acid in aqueous or non-aqueous (e.g. dichloromethane, tetrahydrofuran, ethyl acetate, toluene) conditions at a temperature of about 0° C. to about 50° C. for about 0.5 hours to about 18 hours. Those skilled in the art will recognize that a variety of other conditions may be used to cleave the t-butoxycarbonyl (BOC) group. In Scheme I, $R^{12}$ is optionally mono- or di-chloro or ($C_1$-$C_4$)alkyl The Formula IA starting material in Reaction Scheme I, tert-butyl 3-aminopiperidine-1-carboxylate, can be obtained from commercial sources. In step A, the Formula IA amine and the Formula 2 carboxylic acid are allowed to react with an activating agent such as carbonyldiimidazole (CDI) (Lopez-Rodriguez, Maria L. et al, Bioorg. Med. Chem. 2004, 12, 5181-5184) to produce the Formula 3 amide derivatives. In the Formula 3 compound, $R^2$ can be represented by the same substituent as is desired in the final product or can be modified after addition by procedures known in the art to obtain the desired substituent. The Formula 2 carboxylic acid can either be obtained from commercial sources or synthesized by those

SCHEME II

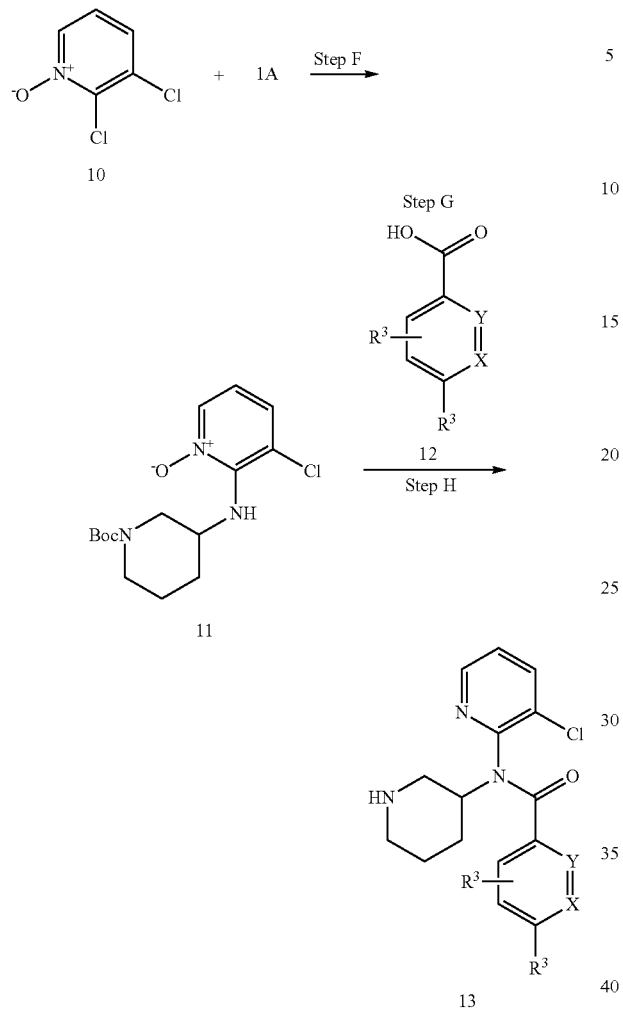

SCHEME III

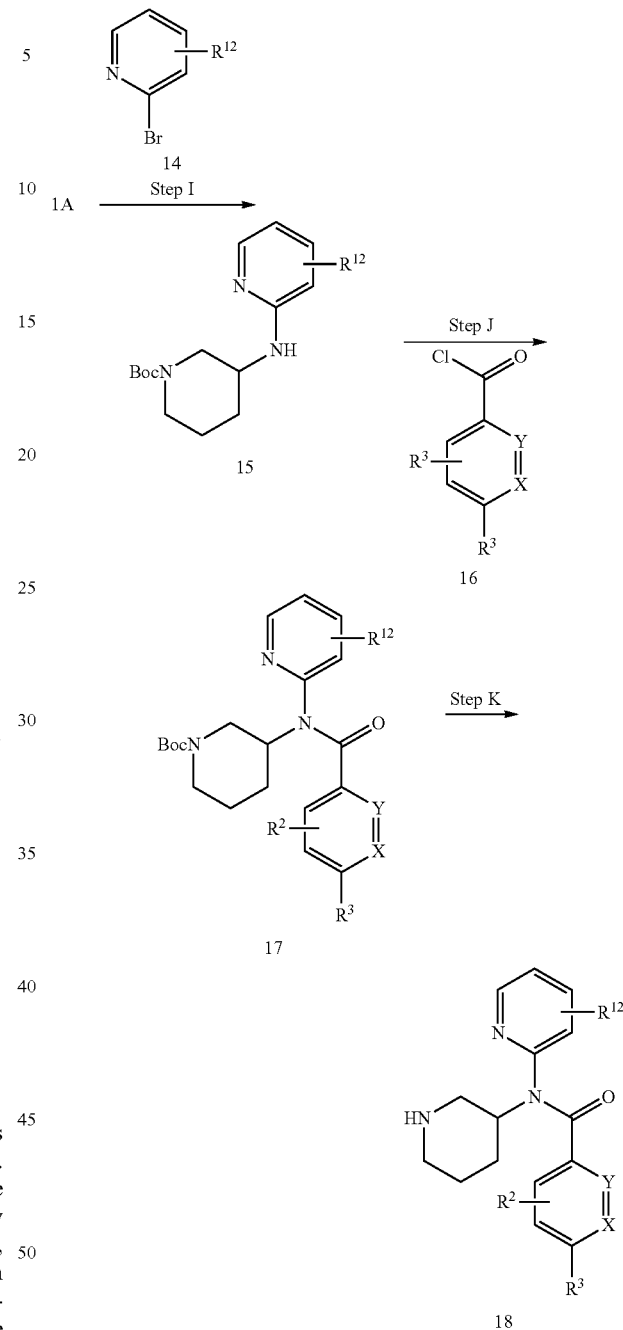

Compounds of Formula I, wherein $R^2$, $R^3$, X and Y are as defined above, are prepared as depicted in Scheme II above. In Step F, the Formula 1A amine and Formula 10 N-oxide (readily obtained from commercial sources) are preferably reacted in the presence of a base such diisopropylethylamine, triethylamine (optionally with an additive such as cesium fluoride), potassium acetate, cesium carbonate, or other carbonate sources in solvents such as dimethylsulfoxide (DMSO), acetonitrile, or isopropanol at a temperature of about 20° C. to about 160° C. for about 1 hour to about 24 hours resulting in the Formula 11 N-oxide. In Step G, the reaction between the Formula 12 carboxylic acid and Formula 11 N-oxide is carried out in an analogous manner to Step B. The Formula 12 acid $R^2$ and $R^3$ substituents are selected to provide the desired Formula I substituents, or the $R^2$ and $R^3$ substituents can be modified after addition by procedures known in the chemical art to obtain alternative Formula I $R^2$ and $R^3$ substituents. Step G includes a one pot reduction of the Formula 11 N-oxide, followed by cleavage (Step H) of the t-butoxycarbonyl group (BOC) in a manner analogous to Step E.

Alternatively Formula I compounds wherein $R^2$, $R^3$, X and Y are as defined above and $R^{12}$ is optionally mono- or di-chloro or $(C_1-C_4)$alkyl are prepared according to Scheme III above. Step I is preferably carried out with a Formula 1A amine and a Formula 14 aryl bromide in the presence of a palladium catalyst, or precatalyst and ligand (e.g. 2-(dimethylaminomethyl)ferrocen-1-yl-palladium(II) chloride dinorbornylphosphine, palladium acetate $(Pd(OAc)_2)$, Brettphos, PEPPSI™, Josiphos, BINAP) or other suitable catalysts. The reaction proceeds at a temperature of about 90°

C. to about 150° C. for about 1 hour to about 24 hours in solvents such as methanol, ethanol, water, acetonitrile, N,N-dimethylformamide (DMF), 1,4-dioxane, and THF. Exemplary bases for this reaction are potassium t-butoxide (KOt-Bu) and cesium carbonate ($Cs_2OC_3$). In Step J the Formula 17 compound is synthesized by deprotonation of the Formula 15 protected amine with a strong base such as methylmagnesium chloride (MeMgCl), n-butyllithium (n-BuLi), lithium N,N-diisopropylamine, lithium hexamethyldisililazide (LiHMDS) or other similar bases in solvents such THF, 1,4-dioxane, or 1,2-dimethoxyethane (DME) at a temperature of about −78° C. to about 23° C. for about 1 hour to about 4 hours. Addition of the Formula 16 acyl chloride at a temperature of about −10° C. to about 23° C. for about 1 hour to about 18 hours yields the Formula 17 compound. The Formula 16 acyl chloride is commercially available or synthesized using methods known to those skilled in the chemical arts. The Formula 16 compound $R^2$ and $R^3$ substituents are selected to provide the desired Formula I substituents, or the $R^2$ and $R^3$ substituents can be modified after addition by procedures known in the chemical art to obtain alternative Formula I $R^2$ and $R^3$ substituents. Step K includes cleavage of the t-butoxycarbonyl (BOC) group in a manner analogous to Steps E and H.

SCHEME IV

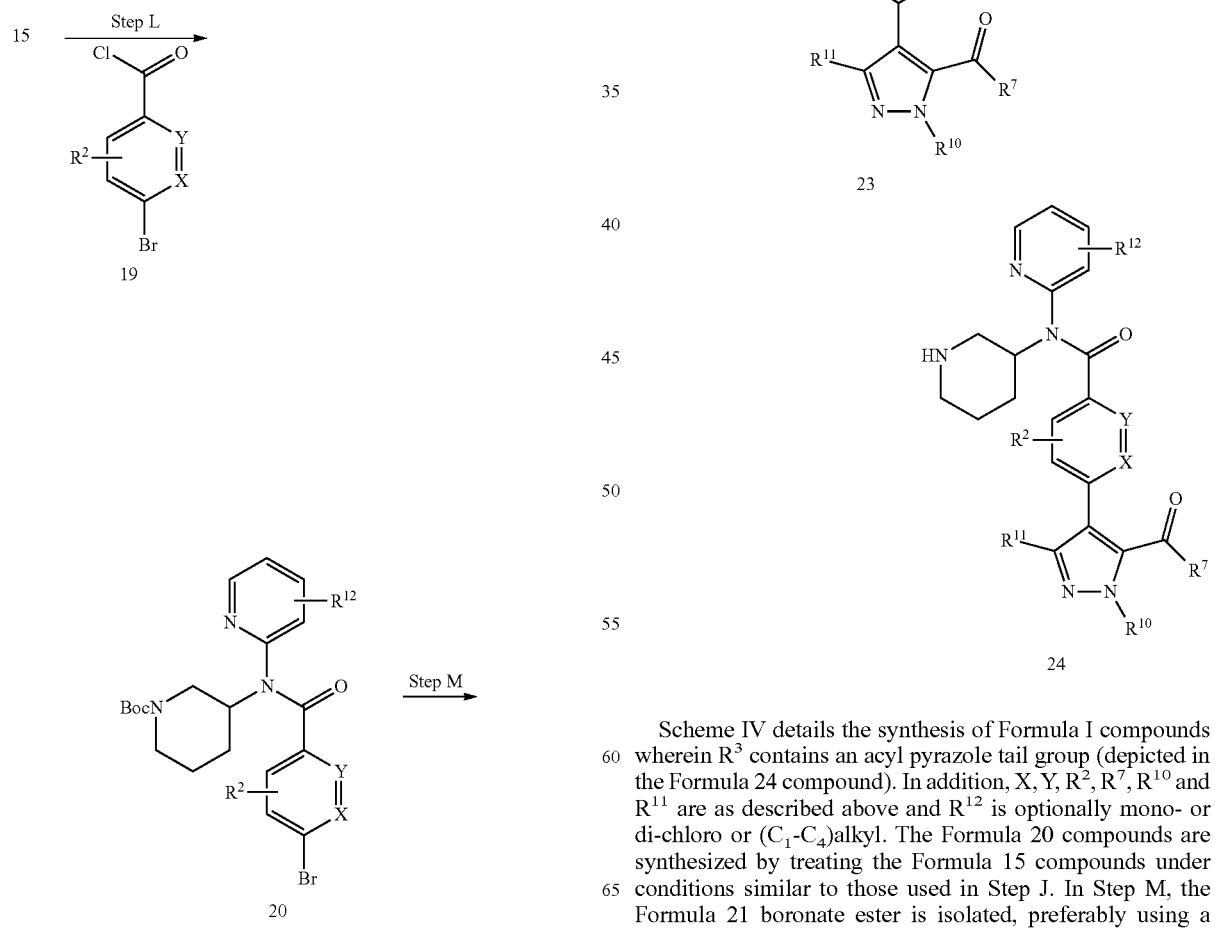

Scheme IV details the synthesis of Formula I compounds wherein $R^3$ contains an acyl pyrazole tail group (depicted in the Formula 24 compound). In addition, X, Y, $R^2$, $R^7$, $R^{10}$ and $R^{11}$ are as described above and $R^{12}$ is optionally mono- or di-chloro or ($C_1$-$C_4$)alkyl. The Formula 20 compounds are synthesized by treating the Formula 15 compounds under conditions similar to those used in Step J. In Step M, the Formula 21 boronate ester is isolated, preferably using a palladium-catalyzed cross-coupling reaction analogous to that described in Step C or Step D above. In Step N the Formula 23 acyl pyrazole is prepared through a cross-coupling reaction of the Formula 21 compound and the Formula 22 acyl pyrazole under conditions similar to those used in Steps C, D, or M. The Formula 22 acyl pyrazole $R^2$, $R^7$, $R^{10}$, and $R^{11}$ substituents are selected to provide the desired Formula I substituents, or the $R^2$, $R^7$, $R^{10}$, and $R^{11}$ substituents can be modified after addition by procedures known in the chemical art to obtain alternative desired Formula I $R^2$, $R^7$, $R^{10}$, and $R^{11}$ substituents. The Formula 24 compound is prepared by cleaving the t-butoxycarbonyl group in Step O in a manner analogous to Steps E, H, and K above.

Similarly, according to Scheme V below, in Step P the Formula 26 compounds can be prepared via cross-coupling of Formula 6 compounds and Formula 22 compounds using methods analogous to that described in C, D or M above, followed by cleavage of the t-butoxycarbonyl (BOC) group in a manner analogous to Steps E, H and K.

SCHEME V

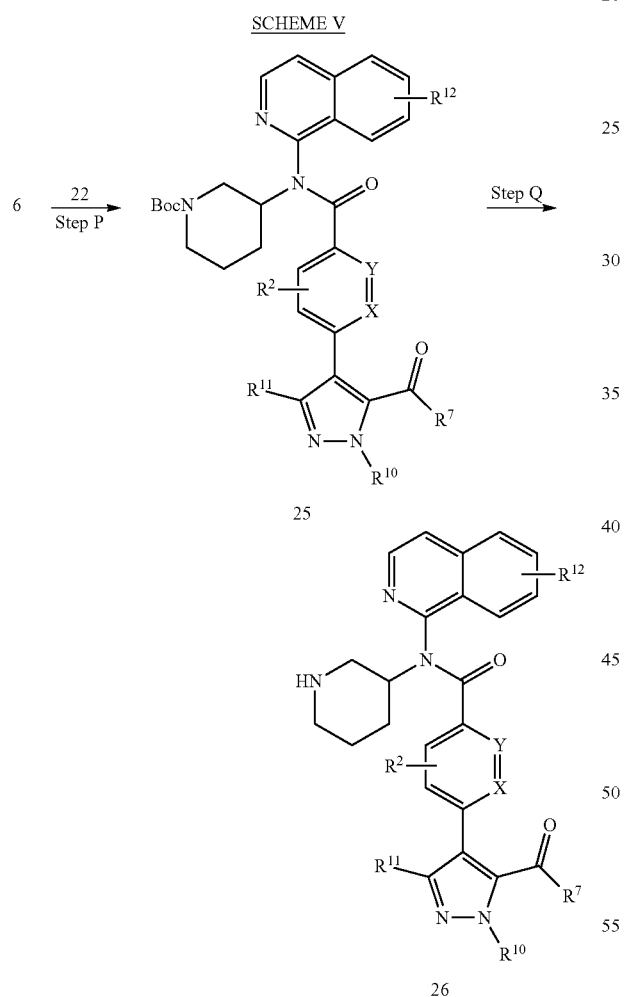

Formula I compounds wherein $R^2$, $R^3$, $R^{12}$, X and Y are as described above, $R^1$ is azaindol-7-yl, are prepared from the Formula 29 protected compound in Scheme VI. The Formula 27 compound can be purchased from commercial sources or synthesized from methods known to those skilled in the chemical arts. In Step R, the Formula 28 compound is prepared by treatment of the Formula 27 compound with a base such as sodium hydride (NaH), sodium (NaOH), potassium hydroxide (KOH), or potassium carbonate, optionally with an additive such as tetrabutyammonium bromide, in solvents such as N,N-dimethylformamide (DMF), dimethylsulfoxide (DMSO), or tetrahydrofuran (THF), followed by addition of methyl iodide at a temperature of about 0° C. to about 50° C. for about 1 hour to about 18 hours. In Step S, the Formula 29 compound is obtained via a cross-coupling reaction of the Formula 28 compound and the Formula 1 compound in an analogous manner to Step I. The Formula 29 compound can be further modified in a manner analogous to the modification of the Formula 15 compound in Scheme 3 to obtain compounds of Formula I wherein $R^1$ is azaindol-7-yl and $R^{12}$ is optionally mono- or di-chloro or ($C_1$-$C_4$)alkyl.

SCHEME VI

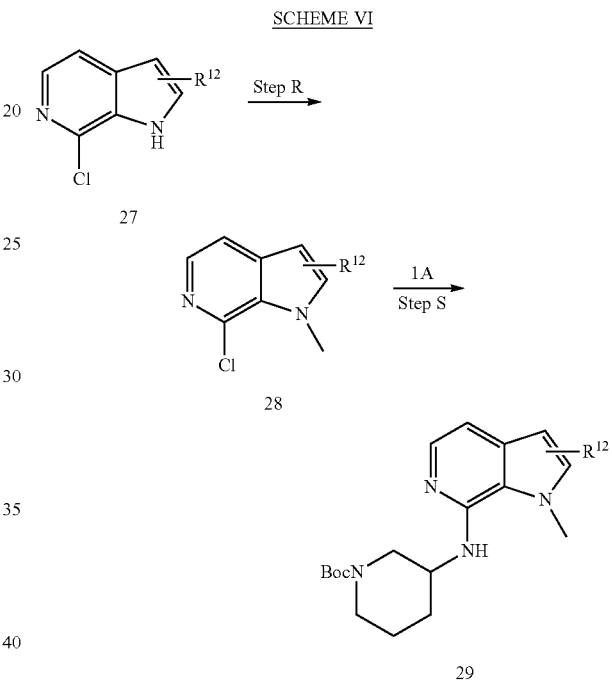

Reaction Scheme VII, below, illustrates methodologies for preparing the compounds of Formula II, wherein $R^2$, $R^{10}$, $R^{11}$, $R^{12}$, $R^{15}$, $R^{16}$, X and Y are as defined above. In general, these compounds can be prepared beginning with compounds described in Scheme IV (e.g., compound 23, 24). Formula 31 compounds can be prepared by modification of compound 30 in Scheme VII, where $R^7$ is methoxy (OMe) or ethoxy (OEt), via based catalyzed amidation reactions using bases such as sodium ethoxide, sodium methoxide, and potassium hydroxide. Reactions are typically performed at temperatures ranging from about 0° C. to about 23° C., Step T (Lauder et al, *J. Am. Chem. Soc.* 39, 659-68; St. Maurice et al, *Biochem.* 43, 2524-2532).

Alternatively, compound 30 (Scheme VII, where $R^7$ is hydroxyl) can be treated with an activating agent in the presence of an amine, or treated with an activating agent followed by addition of the amine to yield compounds of Formula 31. Similar to Scheme I Step A, activating agents such as carbonyldiimidazole (CDI) (Lopez-Rodriguez, Maria L. et al, *Bioorg. Med. Chem.* 2004, 12, 5181-5184) can be used in equimolar amounts or in slight excess in solvents such as N,N-dimethylformamide (DMF), dichloromethane (DCM), or tetrahydrofuran (THF) with or without additives such as triethylamine, 1,8-diazabicycloundec-7-ene, or diisopropylethylamine. This reaction may be run at temperatures ranging from about 0° C. to about 50° C., depending on the choice of conditions for about 0.5 hours to about 18 hours. Alternative activating agents include phosphorous trichloride, phosphorus oxychloride (POCl$_3$), thionyl chloride or oxalyl chloride. In addition, dehydrating agents such as N,N-dicyclohexylcarbodiimide (DCC), or benzotriazol-1-yloxytris(dimethylamino)-phosphonium hexafluorophosphate (BOP) can be used to activate compound 30.

SCHEME VII

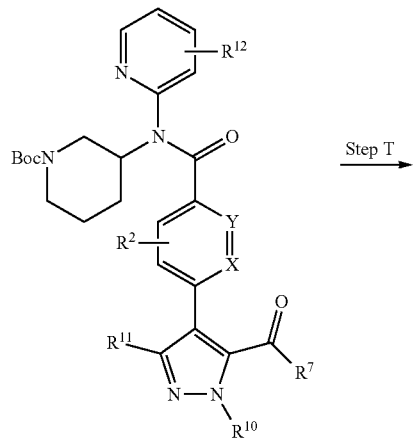

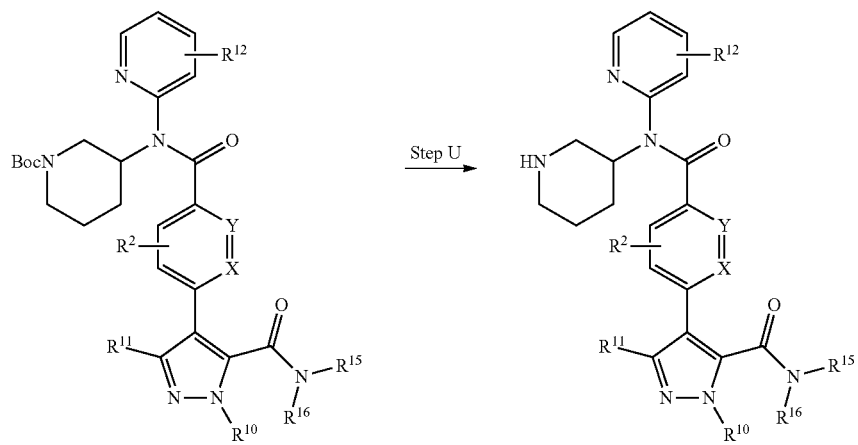

-continued

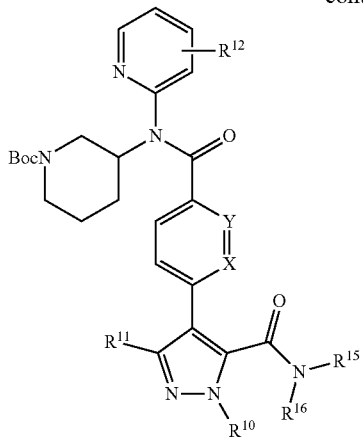

33

In Step U, the t-butoxycarbonyl (BOO) is cleaved with acids such as hydrochloric acid (HCl), trifluoracetic acid (TFA), p-toluene sulfonic acid in aqueous or non-aqueous (e.g. dichloromethane, tetrahydrofuran, ethyl acetate or toluene) conditions at a temperature of about 0° C. to about 50° C. for about 0.5 hours to about 18 hours to give the Formula II compound (32) derivatives with $R^{15}$ and $R^{16}$ as described above. Formula 31 compounds can be further derivatized when either $R^{15}$ or $R^{16}$ is hydrogen in Step V from methods known to those skilled in the chemical arts. Typical conditions involve the use of an alkyl chloride with a base such as triethylamine or diisopropylethylamine, optionally with an additive such as tetrabutyammonium bromide, in solvents such as N,N-dimethylformamide (DMF), toluene or dichloromethane (DCM) at a temperature of about 0° C. to about 50° C. for about 1 hour to about 18 hours. As in step U, the t-butoxycarbonyl group is removed to give the Formula II compound (32) derivatives with $R^{15}$ and $R^{16}$ as described above.

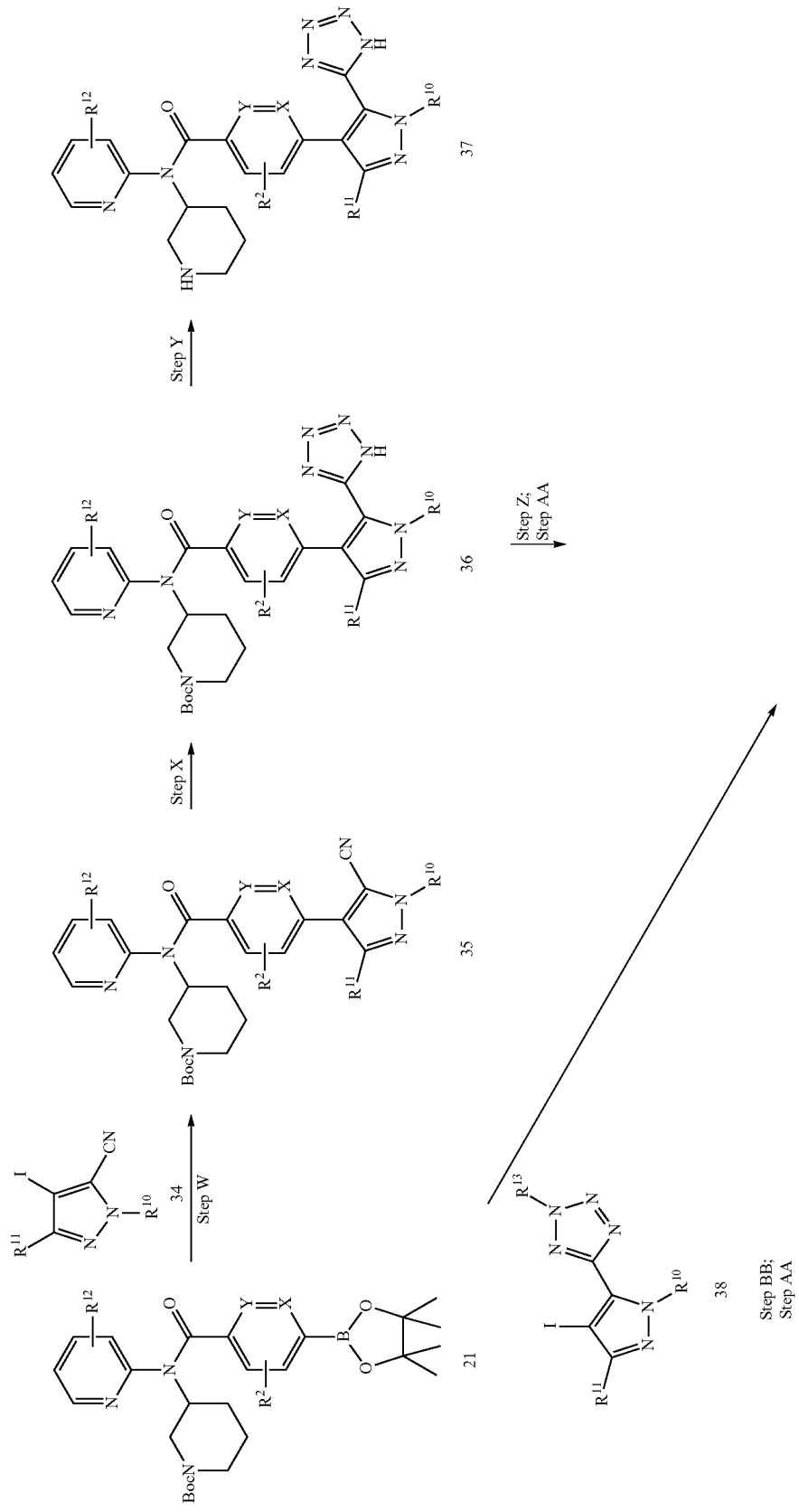

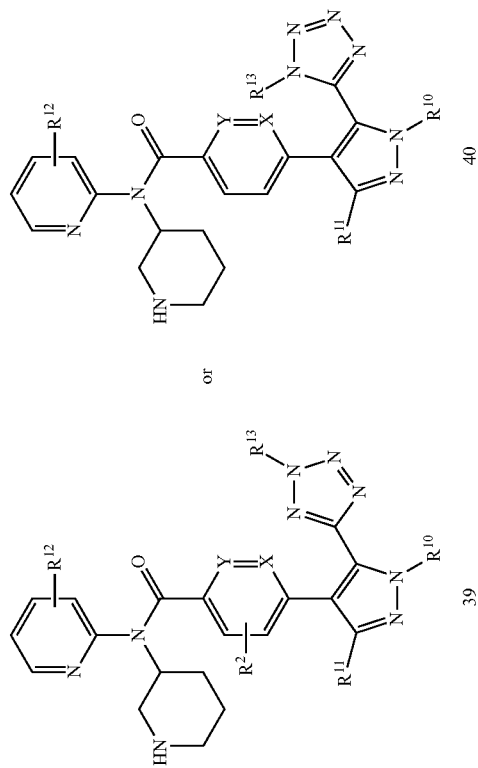

Formula II compounds can also be prepared according to Scheme VIII. In Step W, Formula 21 boronate (Scheme IV) and a Formula 34 pyrazole are combined via a cross-coupling reaction under conditions similar to those used in Steps C, D (Scheme I), or M (Scheme IV). The Formula 35 cyano-pyrazole $R^2$, $R^{10}$, $R^{11}$, and $R^{12}$ substituents are selected to provide the desired Formula II substituents, or the $R^2$, $R^{10}$, $R^{11}$, and $R^{12}$ substituents can be modified after addition by procedures known in the chemical art to obtain alternative desired Formula II $R^2$, $R^{10}$, $R^{11}$, and $R^{12}$ substituents.

In Step X, the Formula 35 cyano-pyrazole is converted to a tetrazole derivative by procedures known in the chemical arts. Conditions for this transformation include but are not limited to the reaction of a cyano derivative with an inorganic, organometallic, or organosilicon azide source with or without a lewis or Brønsted acid (Roh et al, *Eur. J. Org. Chem.* 2012, 6101-6118 and pertinent references therein). In Step Y, compounds of Formula 36 are subjected to acidic conditions, as described in Scheme VII Step U, to remove the t-butoxycarbonyl (BOC) group and provide Formula II compounds where $R^{13}$ is H. Alternatively, compounds of Formula 36 can be further derivatized in Step Z, similar to conditions used in Scheme VII step V, followed by cleavage of the t-butoxycarbonyl group to give Formula II compounds with $R^{13}$ as described above. In Step Z, reactions of the Formula 36 compound with alkylating agents produce the two regioisomers of Formula 39 and 40 shown in Scheme VIII. These regioisomers can be used as a single pharmaceutical ingredient or used as two separate and distinct pharmaceutical ingredients.

In Step AA, the t-butoxycarbonyl group is than removed as in Scheme VII Step U to provide compounds of Formula II as described above. Compounds of Formula 39 and 40 can also be prepared by reacting compounds of Formula 21 with Formula 38 compounds in Step BB, using conditions similar to those in Step W, followed by Step AA to provide the two regioiosmers of Formula 39 and 40.

In another embodiment of the claim, Formula II compounds can be prepared via the sequence shown in Scheme IX. The Formula 40 compound can be prepared by first reacting the Formula 35 compound in Step CC with hydroxylamine, or an appropriate hydroxylamine salt, in solvents such as water, ethanol, or methanol to produce a hydroxyamidine derivative. Reactions are typically run at a temperature between about 23° C. and about 100° C. Alternatively, reactions can be run with hydroxylamine or an appropriate hydroxylamine salt in the presence of an alkaline base such as sodium methoxide, sodium, ethoxide, or potassium hydroxide in a solvent such as methanol, ethanol, or water at a temperature between about 0° C. and about 100° C.

In Step DD, the hydroxyamidine derivative from Step CC is treated with carbonyldiimidazole (CDI) (Charton, J. et al, *Tetrahedron Lett.,* 2007, 1479-1483) or another carbonyl source such as phosgene, ethyl chloroformate in solvents such as a toluene, tetrahydrofuran (THF), or 1,4-dioxane. Reactions such as these are typically performed in the presence of bases such as triethylamine, 1,8-diazabicycloundec-7-ene, or diisopropylethylamine at temperatures ranging from about 0° C. to about 120° C., depending on the choice of conditions for about 0.5 hours to about 18 hours.

SCHEME IX

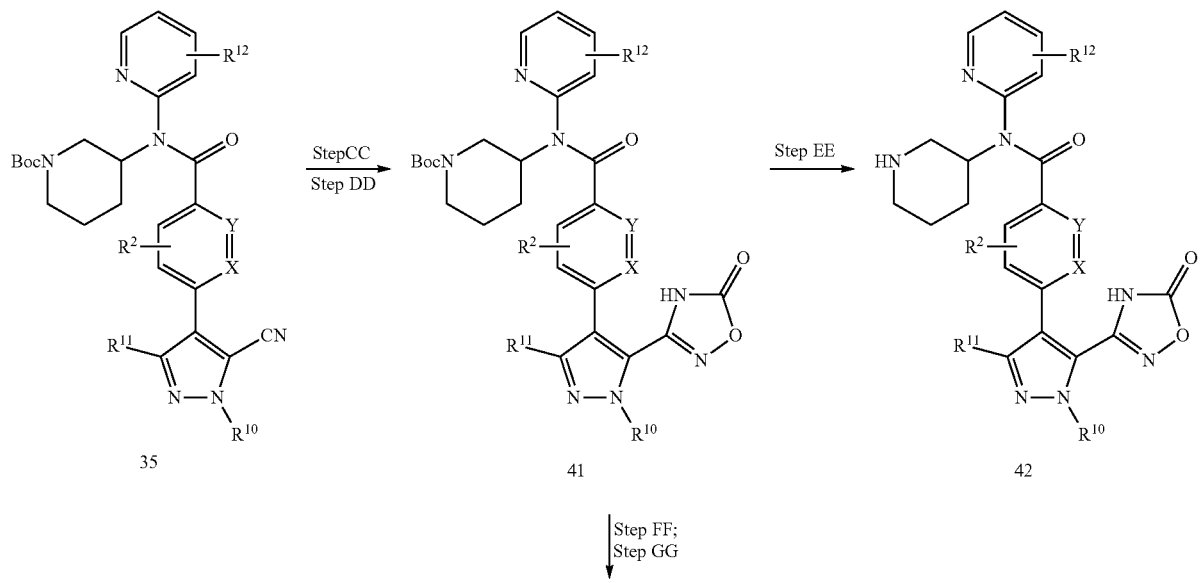

-continued

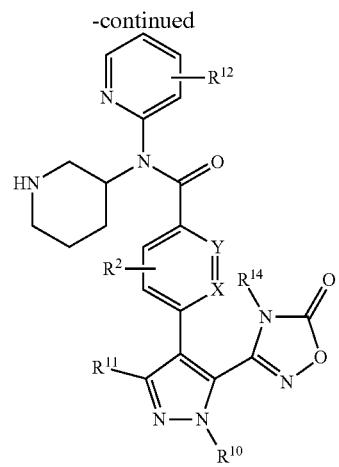

43

In Step EE, Formula 41 compounds can be subjected to acidic conditions as previously described to remove the t-butoxycarbonyl (BOO) and provide Formula II compounds where $R^{14}$ is H. Alternatively, compounds of Formula 41 can be further derivatized in Step FF, as in Scheme VII Step V and Scheme VIII Step Z, followed by cleavage of the t-butoxycarbonyl group via Step GG to give Formula II compounds with $R^{14}$ as described above.

After the reaction is completed, the desired Formula I compound, exemplified in the above schemes as Formula 9, 13, 18, and 24 compounds, may be recovered and isolated as known in the art. It may be recovered by evaporation and/or extraction as is known in the art. It may optionally be purified by chromatography, recrystallization, distillation, or other techniques known in the art.

As previously mentioned and readily apparent to one skilled in the art, many of the substituents represented by $R^2$, $R^3$, $R^7$, $R^{10}$, and $R^{11}$ and the optional substituents on $R^1$ may be manipulated after the Formula I core is produced. For example, a sulfonyl moiety may be generated by oxidizing a thioether. Such variations are well known to those skilled in the art and should be considered part of the invention.

The Formula I compounds of this invention may also be used in conjunction with other pharmaceutical agents (e.g., LDL-cholesterol lowering agents, triglyceride lowering agents) for the treatment of the disease/conditions described herein. For example, they may be used in combination with lipid modulating agents, antidiabetic agents and cardiovascular agents.

Lipid modulating agents may be used as a combination agent in conjunction with the Formula I compounds. Any HMG-CoA reductase inhibitor may be used in the combination aspect of this invention. The conversion of 3-hydroxy-3-methylglutaryl-coenzyme A (HMG-CoA) to mevalonate is an early and rate-limiting step in the cholesterol biosynthetic pathway. This step is catalyzed by the enzyme HMG-CoA reductase. Statins inhibit HMG-CoA reductase from catalyzing this conversion. The following paragraphs describe exemplary statins.

The term HMG-CoA reductase inhibitor refers to compounds which inhibit the bioconversion of hydroxymethylglutaryl-coenzyme A to mevalonic acid catalyzed by the enzyme HMG-CoA reductase. Such inhibition is readily determined by those skilled in the art according to standard assays (e.g., Meth. Enzymol. 1981; 71:455-509 and references cited therein). A variety of these compounds are described and referenced below however other HMG-CoA reductase inhibitors will be known to those skilled in the art. U.S. Pat. No. 4,231,938 (the disclosure of which is hereby incorporated by reference) discloses certain compounds isolated after cultivation of a microorganism belonging to the genus *Aspergillus*, such as lovastatin. Also, U.S. Pat. No. 4,444,784 (the disclosure of which is hereby incorporated by reference) discloses synthetic derivatives of the aforementioned compounds, such as simvastatin. Also, U.S. Pat. No. 4,739,073 (the disclosure of which is incorporated by reference) discloses certain substituted indoles, such as fluvastatin. Also, U.S. Pat. No. 4,346,227 (the disclosure of which is incorporated by reference) discloses ML-236B derivatives, such as pravastatin. Also, EP-491226A (the disclosure of which is incorporated by reference) discloses certain pyridyldihydroxyheptenoic acids, such as cerivastatin. In addition, U.S. Pat. No. 5,273,995 (the disclosure of which is incorporated by reference) discloses certain 6-[2-(substituted-pyrrol-1-yl)alkyl]pyran-2-ones such as atorvastatin and any pharmaceutically acceptable form thereof (i.e. LIPITOR®). Additional HMG-CoA reductase inhibitors include rosuvastatin and pitavastatin.

Atorvastatin calcium (i.e., atorvastatin hemicalcium), disclosed in U.S. Pat. No. 5,273,995, which is incorporated herein by reference, is currently sold as Lipitor®.

Statins also include such compounds as rosuvastatin disclosed in U.S. RE37,314 E, pitivastatin disclosed in EP 304063 B1 and U.S. Pat. No. 5,011,930, simvastatin, disclosed in U.S. Pat. No. 4,444,784, which is incorporated herein by reference; pravastatin, disclosed in U.S. Pat. No. 4,346,227 which is incorporated herein by reference; cerivastatin, disclosed in U.S. Pat. No. 5,502,199, which is incorporated herein by reference; mevastatin, disclosed in U.S. Pat. No. 3,983,140, which is incorporated herein by reference; velostatin, disclosed in U.S. Pat. No. 4,448,784 and U.S. Pat. No. 4,450,171, both of which are incorporated herein by reference; fluvastatin, disclosed in U.S. Pat. No. 4,739,073, which is incorporated herein by reference; compactin, disclosed in U.S. Pat. No. 4,804,770, which is incorporated herein by reference; lovastatin, disclosed in U.S. Pat. No. 4,231,938, which is incorporated herein by reference; dalvastatin, disclosed in European Patent Application Publication No. 738510 A2; fluindostatin, disclosed in European Patent Application Publication No. 363934 A1; and dihydrocompactin, disclosed in U.S. Pat. No. 4,450,171, which is incorporated herein by reference.

Any HMG-CoA synthase inhibitor may be used in the combination aspect of this invention. The term HMG-CoA synthase inhibitor refers to compounds which inhibit the biosynthesis of hydroxymethylglutaryl-coenzyme A from acetyl-coenzyme A and acetoacetyl-coenzyme A, catalyzed by the enzyme HMG-CoA synthase. Such inhibition is readily determined by those skilled in the art according to standard assays (Meth Enzymol. 1975; 35:155-160: Meth. Enzymol. 1985; 110:19-26 and references cited therein). A variety of these compounds are described and referenced below, however other HMG-CoA synthase inhibitors will be known to those skilled in the art. U.S. Pat. No. 5,120,729 (the disclosure of which is hereby incorporated by reference) discloses certain beta-lactam derivatives. U.S. Pat. No. 5,064,856 (the disclosure of which is hereby incorporated by reference) discloses certain spiro-lactone derivatives prepared by culturing a microorganism (MF5253). U.S. Pat. No. 4,847,271 (the disclosure of which is hereby incorporated by reference) discloses certain oxetane compounds such as 11-(3-hydroxymethyl-4-oxo-2-oxetayl)-3,5,7-trimethyl-2,4-undeca-dienoic acid derivatives.

Any compound that decreases HMG-CoA reductase gene expression may be used in the combination aspect of this invention. These agents may be HMG-CoA reductase transcription inhibitors that block the transcription of DNA or translation inhibitors that prevent or decrease translation of mRNA coding for HMG-CoA reductase into protein. Such compounds may either affect transcription or translation directly, or may be biotransformed to compounds that have the aforementioned activities by one or more enzymes in the cholesterol biosynthetic cascade or may lead to the accumulation of an isoprene metabolite that has the aforementioned activities. Such compounds may cause this effect by decreasing levels of SREBP (sterol regulatory element binding protein) by inhibiting the activity of site-1 protease (S1P) or agonizing the oxysterol receptor or antagonizing SOAP. Such regulation is readily determined by those skilled in the art according to standard assays (Meth. Enzymol. 1985; 110:9-19). Several compounds are described and referenced below, however other inhibitors of HMG-CoA reductase gene expression will be known to those skilled in the art. U.S. Pat. No. 5,041,432 (the disclosure of which is incorporated by reference) discloses certain 15-substituted lanosterol derivatives.

Other oxygenated sterols that suppress synthesis of HMG-CoA reductase are discussed by E. I. Mercer (Prog. Lip. Res. 1993; 32:357-416).

Any compound having activity as a CETP inhibitor can serve as the second compound in the combination therapy aspect of the present invention. The term CETP inhibitor refers to compounds that inhibit the cholesteryl ester transfer protein (CETP) mediated transport of various cholesteryl esters and triglycerides from HDL to LDL and VLDL. Such CETP inhibition activity is readily determined by those skilled in the art according to standard assays (e.g., U.S. Pat. No. 6,140,343). A variety of CETP inhibitors will be known to those skilled in the art, for example, those disclosed in commonly assigned U.S. Pat. No. 6,140,343 and commonly assigned U.S. Pat. No. 6,197,786. CETP inhibitors are also described in U.S. Pat. No. 6,723,752, which includes a number of CETP inhibitors including (2R)-3-{[3-(4-Chloro-3-ethyl-phenoxy)-phenyl]-[[3-(1,1,2,2-tetrafluoro-ethoxy)-phenyl]-methyl]-amino}-1,1,1-trifluoro-2-propanol. Moreover, CETP inhibitors included herein are also described in U.S. patent application Ser. No. 10/807,838 filed Mar. 23, 2004. U.S. Pat. No. 5,512,548 discloses certain polypeptide derivatives having activity as CETP inhibitors, while certain CETP-inhibitory rosenonolactone derivatives and phosphate-containing analogs of cholesteryl ester are disclosed in J. Antibiot., 49(8): 815-816 (1996), and Bioorg. Med. Chem. Lett.; 6:1951-1954 (1996), respectively.

Any PPAR modulator may be used in the combination aspect of this invention. The term PPAR modulator refers to compounds which modulate peroxisome proliferator activator receptor (PPAR) activity in mammals, particularly humans. Such modulation is readily determined by those skilled in the art according to standard assays known in the literature. It is believed that such compounds, by modulating the PPAR receptor, regulate transcription of key genes involved in lipid and glucose metabolism such as those in fatty acid oxidation and also those involved in high density lipoprotein (HDL) assembly (for example, apolipoprotein AI gene transcription), accordingly reducing whole body fat and increasing HDL cholesterol. By virtue of their activity, these compounds also reduce plasma levels of triglycerides, VLDL cholesterol, LDL cholesterol and their associated components such as apolipoprotein B in mammals, particularly humans, as well as increasing HDL cholesterol and apolipoprotein A1. Hence, these compounds are useful for the treatment and correction of the various dyslipidemias observed to be associated with the development and incidence of atherosclerosis and cardiovascular disease, including hypoalphalipoproteinemia and hypertriglyceridemia. A variety of these compounds are described and referenced below, however, others will be known to those skilled in the art. International Publication Nos. WO 02/064549 and 02/064130 and U.S. patent application Ser. No. 10/720,942, filed Nov. 24, 2003 and U.S. patent application 60/552,114 filed Mar. 10, 2004 (the disclosures of which are hereby incorporated by reference) disclose certain compounds which are PPARα activators.

Any other PPAR modulator may be used in the combination aspect of this invention. In particular, modulators of PPARβ and/or PPARγ may be useful in combination with compounds of the present invention. An example PPAR inhibitor is described in US2003/0225158 as {5-Methoxy-2-methyl-4-[4-(4-trifluoromethyl-benzyloxy)-benzylsulfanyl]-phenoxy}-acetic acid.

Any MTP/Apo B (microsomal triglyceride transfer protein and or apolipoprotein B) secretion inhibitor may be used in the combination aspect of this invention. The term MTP/Apo B secretion inhibitor refers to compounds which inhibit the secretion of triglycerides, cholesteryl ester, and phospholipids. Such inhibition is readily determined by those skilled in the art according to standard assays (e.g., Wetterau, J. R. 1992; Science 258:999). A variety of MTP/Apo B secretion inhibitors will be known to those skilled in the art, including imputapride (Bayer) and additional compounds such as those disclosed in WO 96/40640 and WO 98/23593, (two exemplary publications).

Any squalene synthetase inhibitor may be used in the combination aspect of this invention. The term squalene synthetase inhibitor refers to compounds which inhibit the condensation of 2 molecules of farnesylpyrophosphate to form squalene, catalyzed by the enzyme squalene synthetase. Such inhibition is readily determined by those skilled in the art according to standard assays (Meth. Enzymol. 1969; 15: 393-454 and Meth. Enzymol. 1985; 110:359-373 and references contained therein). A variety of these compounds are described in and referenced below however other squalene synthetase inhibitors will be known to those skilled in the art. U.S. Pat. No. 5,026,554 (the disclosure of which is incorporated by reference) discloses fermentation products of the microorganism MF5465 (ATCC 74011) including zaragozic acid. A summary of other patented squalene synthetase inhibitors has been compiled (Curr. Op. Ther. Patents (1993) 861-4).

Any squalene epoxidase inhibitor may be used in the combination aspect of this invention. The term squalene epoxidase inhibitor refers to compounds which inhibit the bioconversion of squalene and molecular oxygen into squalene-2,3-epoxide, catalyzed by the enzyme squalene epoxidase. Such inhibition is readily determined by those skilled in the art according to standard assays (Biochim. Biophys. Acta 1984; 794:466-471). A variety of these compounds are described and referenced below, however other squalene epoxidase inhibitors will be known to those skilled in the art. U.S. Pat. Nos. 5,011,859 and 5,064,864 (the disclosures of which are incorporated by reference) disclose certain fluoro analogs of squalene. EP publication 395,768 A (the disclosure of which is incorporated by reference) discloses certain substituted allylamine derivatives. PCT publication WO 9312069 A (the disclosure of which is hereby incorporated by reference) discloses certain amino alcohol derivatives. U.S. Pat. No. 5,051,534 (the disclosure of which is hereby incorporated by reference) discloses certain cyclopropyloxy-squalene derivatives.

Any squalene cyclase inhibitor may be used as the second component in the combination aspect of this invention. The term squalene cyclase inhibitor refers to compounds which inhibit the bioconversion of squalene-2,3-epoxide to lanosterol, catalyzed by the enzyme squalene cyclase. Such inhibition is readily determined by those skilled in the art according to standard assays (FEBS Lett. 1989; 244:347-350). In addition, the compounds described and referenced below are squalene cyclase inhibitors, however other squalene cyclase inhibitors will also be known to those skilled in the art. PCT publication WO9410150 (the disclosure of which is hereby incorporated by reference) discloses certain 1,2,3,5,6,7,8,8a-octahydro-5,5,8(beta)-trimethyl-6-isoquinolineamine derivatives, such as N-trifluoroacetyl-1,2,3,5,6,7,8,8a-octahydro-2-allyl-5,5,8(beta)-trimethyl-6(beta)-isoquinolineamine. French patent publication 2697250 (the disclosure of which is hereby incorporated by reference) discloses certain beta,beta-dimethyl-4-piperidine ethanol derivatives such as 1-(1,5,9-trimethyldecyl)-beta,beta-dimethyl-4-piperidineethanol Any combined squalene epoxidase/squalene cyclase inhibitor may be used as the second component in the combination aspect of this invention. The term combined squalene epoxidase/squalene cyclase inhibitor refers to compounds that inhibit the bioconversion of squalene to lanosterol via a squalene-2,3-epoxide intermediate. In some assays it is not possible to distinguish between squalene epoxidase inhibitors and squalene cyclase inhibitors; however, these assays are recognized by those skilled in the art. Thus, inhibition by combined squalene epoxidase/squalene cyclase inhibitors is readily determined by those skilled in art according to the aforementioned standard assays for squalene cyclase or squalene epoxidase inhibitors. A variety of these compounds are described and referenced below, however other squalene epoxidase/squalene cyclase inhibitors will be known to those skilled in the art. U.S. Pat. Nos. 5,084,461 and 5,278,171 (the disclosures of which are incorporated by reference) disclose certain azadecalin derivatives. EP publication 468,434 (the disclosure of which is incorporated by reference) discloses certain piperidyl ether and thio-ether derivatives such as 2-(1-piperidyl)pentyl isopentyl sulfoxide and 2-(1-piperidyl)ethyl ethyl sulfide. PCT publication WO 9401404 (the disclosure of which is hereby incorporated by reference) discloses certain acyl-piperidines such as 1-(1-oxopentyl-5-phenylthio)-4-(2-hydroxy-1-methyl)-ethyl)piperidine. U.S. Pat. No. 5,102,915 (the disclosure of which is hereby incorporated by reference) discloses certain cyclopropyloxy-squalene derivatives.

The compounds of the present invention can also be administered in combination with naturally occurring compounds that act to lower plasma cholesterol levels. These naturally occurring compounds are commonly called nutraceuticals and include, for example, garlic extract and niacin. A slow-release form of niacin is available and is known as Niaspan. Niacin may also be combined with other therapeutic agents such as lovastatin, or another HMG-CoA reductase inhibitor. This combination therapy with lovastatin is known as ADVICOR™ (Kos Pharmaceuticals Inc.).

Any cholesterol absorption inhibitor can be used as an additional compound in the combination aspect of the present invention. The term cholesterol absorption inhibition refers to the ability of a compound to prevent cholesterol contained within the lumen of the intestine from entering into the intestinal cells and/or passing from within the intestinal cells into the lymph system and/or into the blood stream. Such cholesterol absorption inhibition activity is readily determined by those skilled in the art according to standard assays (e.g., J. Lipid Res. (1993) 34: 377-395). Cholesterol absorption inhibitors are known to those skilled in the art and are described, for example, in PCT WO 94/00480. An example of a cholesterol absorption inhibitor is ZETIA™ (ezetimibe) (Schering-Plough/Merck).

Any ACAT inhibitor may be used in the combination therapy aspect of the present invention. The term ACAT inhibitor refers to compounds that inhibit the intracellular esterification of dietary cholesterol by the enzyme acyl CoA: cholesterol acyltransferase. Such inhibition may be determined readily by one of skill in the art according to standard assays, such as the method of Heider et al. described in *Journal of Lipid Research.*, 24:1127 (1983). A variety of these compounds are known to those skilled in the art, for example, U.S. Pat. No. 5,510,379 discloses certain carboxysulfonates, while WO 96/26948 and WO 96/10559 both disclose urea derivatives having ACAT inhibitory activity. Examples of ACAT inhibitors include compounds such as Avasimibe (Pfizer), CS-505 (Sankyo) and Eflucimibe (Eli Lilly and Pierre Fabre).

A lipase inhibitor may be used in the combination therapy aspect of the present invention. A lipase inhibitor is a compound that inhibits the metabolic cleavage of dietary triglycerides or plasma phospholipids into free fatty acids and the corresponding glycerides (e.g. EL, HL, etc.). Under normal physiological conditions, lipolysis occurs via a two-step process that involves acylation of an activated serine moiety of the lipase enzyme. This leads to the production of a fatty acid-lipase hemiacetal intermediate, which is then cleaved to release a diglyceride. Following further deacylation, the lipase-fatty acid intermediate is cleaved, resulting in free lipase, a glyceride and fatty acid. In the intestine, the resultant free fatty acids and monoglycerides are incorporated into bile acid-phospholipid micelles, which are subsequently absorbed at the level of the brush border of the small intestine. The micelles eventually enter the peripheral circulation as chylomicrons. Such lipase inhibition activity is readily determined by those skilled in the art according to standard assays (e.g., Methods Enzymol. 286: 190-231).

Pancreatic lipase mediates the metabolic cleavage of fatty acids from triglycerides at the 1- and 3-carbon positions. The primary site of the metabolism of ingested fats is in the duodenum and proximal jejunum by pancreatic lipase, which is usually secreted in vast excess of the amounts necessary for the breakdown of fats in the upper small intestine. Because pancreatic lipase is the primary enzyme required for the absorption of dietary triglycerides, inhibitors have utility in the treatment of obesity and the other related conditions. Such pancreatic lipase inhibition activity is readily determined by those skilled in the art according to standard assays (e.g., Methods Enzymol. 286: 190-231).

Gastric lipase is an immunologically distinct lipase that is responsible for approximately 10 to 40% of the digestion of dietary fats. Gastric lipase is secreted in response to mechanical stimulation, ingestion of food, the presence of a fatty meal or by sympathetic agents. Gastric lipolysis of ingested fats is of physiological importance in the provision of fatty acids needed to trigger pancreatic lipase activity in the intestine and is also of importance for fat absorption in a variety of physiological and pathological conditions associated with pancreatic insufficiency. See, for example, C. K. Abrams, et al., *Gastroenterology,* 92,125 (1987). Such gastric lipase inhibition activity is readily determined by those skilled in the art according to standard assays (e.g., Methods Enzymol. 286: 190-231).

A variety of gastric and/or pancreatic lipase inhibitors are known to one of ordinary skill in the art. Preferred lipase inhibitors are those inhibitors that are selected from the group consisting of lipstatin, tetrahydrolipstatin (orlistat), valilactone, esterastin, ebelactone A, and ebelactone B. The compound tetrahydrolipstatin is especially preferred. The lipase inhibitor, N-3-trifluoromethylphenyl-N'-3-chloro-4'-trifluoromethylphenylurea, and the various urea derivatives related thereto, are disclosed in U.S. Pat. No. 4,405,644. The lipase inhibitor, esteracin, is disclosed in U.S. Pat. Nos. 4,189,438 and 4,242,453. The lipase inhibitor, cyclo-O,O'-[(1,6-hexanediyl)-bis-(iminocarbonyl)]dioxime, and the various bis(iminocarbonyl)dioximes related thereto may be prepared as described in Petersen et al., *Liebig's Annalen,* 562, 205-229 (1949).

A variety of pancreatic lipase inhibitors are described herein below. The pancreatic lipase inhibitors lipstatin, (2S, 3S,5S,7Z,10Z)-5-[(S)-2-formamido-4-methyl-valeryloxy]-2-hexyl-3-hydroxy-7,10-hexadecanoic acid lactone, and tetrahydrolipstatin (orlistat), (2S,3S,5S)-5-[(S)-2-formamido-4-methyl-valeryloxy]-2-hexyl-3-hydroxy-hexadecanoic 1,3 acid lactone, and the variously substituted N-formylleucine derivatives and stereoisomers thereof, are disclosed in U.S. Pat. No. 4,598,089. For example, tetrahydrolipstatin is prepared as described in, e.g., U.S. Pat. Nos. 5,274,143; 5,420, 305; 5,540,917; and 5,643,874. The pancreatic lipase inhibitor, FL-386, 1-[4-(2-methylpropyl)cyclohexyl]-2-[(phenylsulfonyl)oxy]-ethanone, and the variously substituted sulfonate derivatives related thereto, are disclosed in U.S. Pat. No. 4,452,813. The pancreatic lipase inhibitor, WAY-121898, 4-phenoxyphenyl-4-methylpiperidin-1-yl-carboxylate, and the various carbamate esters and pharmaceutically acceptable salts related thereto, are disclosed in U.S. Pat. Nos. 5,512,565; 5,391,571 and 5,602,151. The pancreatic lipase inhibitor, valilactone, and a process for the preparation thereof by the microbial cultivation of *Actinomycetes* strain MG147-CF2, are disclosed in Kitahara, et al., *J. Antibiotics,* 40 (11), 1647-1650 (1987). The pancreatic lipase inhibitors, ebelactone A and ebelactone B, and a process for the preparation thereof by the microbial cultivation of *Actinomycetes* strain MG7-G1, are disclosed in Umezawa, et al., *J. Antibiotics,* 33, 1594-1596 (1980). The use of ebelactones A and B in the suppression of monoglyceride formation is disclosed in Japanese Kokai 08-143457, published Jun. 4, 1996.

Other compounds that are marketed for hyperlipidemia, including hypercholesterolemia and which are intended to help prevent or treat atherosclerosis include bile acid sequestrants, such as Welchol®, Colestid®, LoCholest® and Questran®; and fibric acid derivatives, such as Atromid®, Lopid® and Tricor®.

Given the association between diabetes and atherosclerosis (e.g., Metabolic Syndrome) the compounds of formula I may be administered with antidiabetic compounds. Diabetes can be treated by administering to a patient having diabetes (especially Type II), insulin resistance, impaired glucose tolerance, metabolic syndrome, or the like, or any of the diabetic complications such as neuropathy, nephropathy, retinopathy or cataracts, a therapeutically effective amount of a compound of the present invention in combination with other agents (e.g., insulin) that can be used to treat diabetes. This includes the classes of anti-diabetic agents (and specific agents) described herein.

Any glycogen phosphorylase inhibitor can be used as the second agent in combination with a compound of the present invention. The term glycogen phosphorylase inhibitor refers to compounds that inhibit the bioconversion of glycogen to glucose-1-phosphate which is catalyzed by the enzyme glycogen phosphorylase. Such glycogen phosphorylase inhibition activity is readily determined by those skilled in the art according to standard assays (e.g., J. Med. Chem. 41 (1998) 2934-2938). A variety of glycogen phosphorylase inhibitors are known to those skilled in the art including those described in WO 96/39384 and WO 96/39385.

Any aldose reductase inhibitor can be used in combination with a compound of the present invention. The term aldose reductase inhibitor refers to compounds that inhibit the bioconversion of glucose to sorbitol, which is catalyzed by the enzyme aldose reductase. Aldose reductase inhibition is readily determined by those skilled in the art according to standard assays (e.g., J. Malone, *Diabetes,* 29:861-864 (1980). "Red Cell Sorbitol, an Indicator of Diabetic Control"). A variety of aldose reductase inhibitors are known to those skilled in the art, such as those described in U.S. Pat. No. 6,579,879, which includes 6-(5-chloro-3-methyl-benzofuran-2-sulfonyl)-2H-pyridazin-3-one.

Any sorbitol dehydrogenase inhibitor can be used in combination with a compound of the present invention. The term sorbitol dehydrogenase inhibitor refers to compounds that inhibit the bioconversion of sorbitol to fructose which is catalyzed by the enzyme sorbitol dehydrogenase. Such sorbitol dehydrogenase inhibitor activity is readily determined by those skilled in the art according to standard assays (e.g., Analyt. Biochem (2000) 280: 329-331). A variety of sorbitol dehydrogenase inhibitors are known, for example, U.S. Pat. Nos. 5,728,704 and 5,866,578 disclose compounds and a method for treating or preventing diabetic complications by inhibiting the enzyme sorbitol dehydrogenase.

Any glucosidase inhibitor can be used in combination with a compound of the present invention. A glucosidase inhibitor inhibits the enzymatic hydrolysis of complex carbohydrates by glycoside hydrolases, for example amylase or maltase, into bioavailable simple sugars, for example, glucose. The rapid metabolic action of glucosidases, particularly following the intake of high levels of carbohydrates, results in a state of alimentary hyperglycemia which, in adipose or diabetic subjects, leads to enhanced secretion of insulin, increased fat synthesis and a reduction in fat degradation. Following such hyperglycemias, hypoglycemia frequently occurs, due to the augmented levels of insulin present. Additionally, it is known chyme remaining in the stomach promotes the production of gastric juice, which initiates or favors the development of gastritis or duodenal ulcers. Accordingly, glucosidase inhibitors are known to have utility in accelerating the passage of carbohydrates through the stomach and inhibiting the absorption of glucose from the intestine. Furthermore, the conversion of carbohydrates into lipids of the fatty tissue and the subsequent incorporation of alimentary fat into fatty tissue deposits is accordingly reduced or delayed, with the concomitant benefit of reducing or preventing the deleterious abnormalities resulting therefrom. Such glucosidase inhibition activity is readily determined by those skilled in the art according to standard assays (e.g., Biochemistry (1969) 8: 4214).

A generally preferred glucosidase inhibitor includes an amylase inhibitor. An amylase inhibitor is a glucosidase inhibitor that inhibits the enzymatic degradation of starch or glycogen into maltose. Such amylase inhibition activity is readily determined by those skilled in the art according to standard assays (e.g., Methods Enzymol. (1955) 1: 149). The inhibition of such enzymatic degradation is beneficial in reducing amounts of bioavailable sugars, including glucose and maltose, and the concomitant deleterious conditions resulting therefrom.

A variety of glucosidase inhibitors are known to one of ordinary skill in the art and examples are provided below. Preferred glucosidase inhibitors are those inhibitors that are selected from the group consisting of acarbose, adiposine, voglibose, miglitol, emiglitate, camiglibose, tendamistate, trestatin, pradimicin-Q and salbostatin. The glucosidase inhibitor, acarbose, and the various amino sugar derivatives related thereto are disclosed in U.S. Pat. Nos. 4,062,950 and 4,174,439 respectively. The glucosidase inhibitor, adiposine, is disclosed in U.S. Pat. No. 4,254,256. The glucosidase inhibitor, voglibose, 3,4-dideoxy-4-[[2-hydroxy-1-(hydroxymethyl)ethyl]amino]-2-C-(hydroxymethyl)-D-epi-inositol, and the various N-substituted pseudo-aminosugars related thereto, are disclosed in U.S. Pat. No. 4,701,559. The glucosidase inhibitor, miglitol, (2R,3R,4R,5S)-1-(2-hydroxyethyl)-2-(hydroxymethyl)-3,4,5-piperidinetriol, and the various 3,4,5-trihydroxypiperidines related thereto, are disclosed in U.S. Pat. No. 4,639,436. The glucosidase inhibitor, emiglitate, ethyl p-[2-[(2R,3R,4R,5S)-3,4,5-trihydroxy-2-(hydroxymethyl)piperidino]ethoxy]-benzoate, the various derivatives related thereto and pharmaceutically acceptable acid addition salts thereof, are disclosed in U.S. Pat. No. 5,192,772. The glucosidase inhibitor, MDL-25637, 2,6-dideoxy-7-O-β-D-glucopyranosyl-2,6-imino-D-glycero-L-gluco-heptitol, the various homodisaccharides related thereto and the pharmaceutically acceptable acid addition salts thereof, are disclosed in U.S. Pat. No. 4,634,765. The glucosidase inhibitor, camiglibose, methyl 6-deoxy-6-[(2R,3R,4R,5S)-3,4,5-trihydroxy-2-(hydroxymethyl)piperidino]-α-D-glucopyranoside sesquihydrate, the deoxy-nojirimycin derivatives related thereto, the various pharmaceutically acceptable salts thereof and synthetic methods for the preparation thereof, are disclosed in U.S. Pat. Nos. 5,157,116 and 5,504,078. The glycosidase inhibitor, salbostatin and the various pseudosaccharides related thereto, are disclosed in U.S. Pat. No. 5,091,524.

A variety of amylase inhibitors are known to one of ordinary skill in the art. The amylase inhibitor, tendamistat and the various cyclic peptides related thereto, are disclosed in U.S. Pat. No. 4,451,455. The amylase inhibitor AI-3688 and the various cyclic polypeptides related thereto are disclosed in U.S. Pat. No. 4,623,714. The amylase inhibitor, trestatin, consisting of a mixture of trestatin A, trestatin B and trestatin C and the various trehalose-containing aminosugars related thereto are disclosed in U.S. Pat. No. 4,273,765.

Additional anti-diabetic compounds, which can be used as the second agent in combination with a compound of the present invention, includes, for example, the following: biguanides (e.g., metformin), insulin secretagogues (e.g., sulfonylureas and glinides), glitazones, non-glitazone PPARγ agonists, PPARβ agonists, inhibitors of DPP-IV, inhibitors of PDE5, inhibitors of GSK-3, glucagon antagonists, inhibitors of f-1,6-BPase (Metabasis/Sankyo), GLP-1/analogs (AC 2993, also known as exendin-4), insulin and insulin mimetics (Merck natural products). Other examples would include PKC-β inhibitors and AGE breakers.

The compounds of the present invention can also be used in combination with cardiovascular agents such as antihypertensive agents. Any anti-hypertensive agent can be used as the second agent in such combinations and examples are provided herein. Such antihypertensive activity is readily determined by those skilled in the art according to standard assays (e.g., blood pressure measurements).

Amlodipine and related dihydropyridine compounds are disclosed in U.S. Pat. No. 4,572,909, which is incorporated herein by reference, as potent anti-ischemic and antihypertensive agents. U.S. Pat. No. 4,879,303, which is incorporated herein by reference, discloses amlodipine benzenesulfonate salt (also termed amlodipine besylate). Amlodipine and amlodipine besylate are potent and long lasting calcium channel blockers. As such, amlodipine, amlodipine besylate, amlodipine maleate and other pharmaceutically acceptable acid addition salts of amlodipine have utility as antihypertensive agents and as antiischemic agents. Amlodipine besylate is currently sold as Norvasc®.

Calcium channel blockers which are within the scope of this invention include, but are not limited to: bepridil, which may be prepared as disclosed in U.S. Pat. No. 3,962, 238 or U.S. Reissue No. 30,577; clentiazem, which may be prepared as disclosed in U.S. Pat. No. 4,567,175; diltiazem, which may be prepared as disclosed in U.S. Pat. No. 3,562, fendiline, which may be prepared as disclosed in U.S. Pat. No. 3,262, 977; gallopamil, which may be prepared as disclosed in U.S. Pat. No. 3,261,859; mibefradil, which may be prepared as disclosed in U.S. Pat. No. 4,808,605; prenylamine, which may be prepared as disclosed in U.S. Pat. No. 3,152,173; semotiadil, which may be prepared as disclosed in U.S. Pat. No. 4,786,635; terodiline, which may be prepared as disclosed in U.S. Pat. No. 3,371,014; verapamil, which may be prepared as disclosed in U.S. Pat. No. 3,261,859; aranipine, which may be prepared as disclosed in U.S. Pat. No. 4,572, 909; barnidipine, which may be prepared as disclosed in U.S. Pat. No. 4,220,649; benidipine, which may be prepared as disclosed in European Patent Application Publication No. 106,275; cilnidipine, which may be prepared as disclosed in U.S. Pat. No. 4,672,068; efonidipine, which may be prepared as disclosed in U.S. Pat. No. 4,885,284; elgodipine, which may be prepared as disclosed in U.S. Pat. No. 4,952,592; felodipine, which may be prepared as disclosed in U.S. Pat. No. 4,264,611; isradipine, which may be prepared as disclosed in U.S. Pat. No. 4,466,972; lacidipine, which may be prepared as disclosed in U.S. Pat. No. 4,801,599; lercanidipine, which may be prepared as disclosed in U.S. Pat. No. 4,705,797; manidipine, which may be prepared as disclosed in U.S. Pat. No. 4,892,875; nicardipine, which may be prepared as disclosed in U.S. Pat. No. 3,985,758; nifedipine, which may be prepared as disclosed in U.S. Pat. No. 3,485, 847; nilvadipine, which may be prepared as disclosed in U.S. Pat. No. 4,338,322; nimodipine, which may be prepared as disclosed in U.S. Pat. No. 3,799,934; nisoldipine, which may be prepared as disclosed in U.S. Pat. No. 4,154,839; nitrendipine, which may be prepared as disclosed in U.S. Pat. No.

3,799,934; cinnarizine, which may be prepared as disclosed in U.S. Pat. No. 2,882,271; flunarizine, which may be prepared as disclosed in U.S. Pat. No. 3,773,939; lidoflazine, which may be prepared as disclosed in U.S. Pat. No. 3,267,104; lomerizine, which may be prepared as disclosed in U.S. Pat. No. 4,663,325; bencyclane, which may be prepared as disclosed in Hungarian Patent No. 151,865; etafenone, which may be prepared as disclosed in German Patent No. 1,265,758; and perhexiline, which may be prepared as disclosed in British Patent No. 1,025,578. The disclosures of all such U.S. patents are incorporated herein by reference. Examples of presently marketed products containing antihypertensive agents include calcium channel blockers, such as Cardizem®, Adalat®, Calan®, Cardene®, Covera®, Dilacor®, DynaCirc®, Procardia XL®, Sular®, Tiazac®, Vascor®, Verelan®, Isoptin®, Nimotop®, Norvasc®, and Plendil®; angiotensin converting enzyme (ACE) inhibitors, such as Accupril®, Altace®, Captopril®, Lotensin®, Mavik®, Monopril®, Prinivil®, Univasc®, Vasotec® and Zestril®.

Angiotensin Converting Enzyme Inhibitors (ACE-Inhibitors) which are within the scope of this invention include, but are not limited to: alacepril, which may be prepared as disclosed in U.S. Pat. No. 4,248,883; benazepril, which may be prepared as disclosed in U.S. Pat. No. 4,410,520; captopril, which may be prepared as disclosed in U.S. Pat. Nos. 4,046,889 and 4,105,776; ceronapril, which may be prepared as disclosed in U.S. Pat. No. 4,452,790; delapril, which may be prepared as disclosed in U.S. Pat. No. 4,385,051; enalapril, which may be prepared as disclosed in U.S. Pat. No. 4,374,829; fosinopril, which may be prepared as disclosed in U.S. Pat. No. 4,337,201; imadapril, which may be prepared as disclosed in U.S. Pat. No. 4,508,727; lisinopril, which may be prepared as disclosed in U.S. Pat. No. 4,555,502; moveltopril, which may be prepared as disclosed in Belgian Patent No. 893,553; perindopril, which may be prepared as disclosed in U.S. Pat. No. 4,508,729; quinapril, which may be prepared as disclosed in U.S. Pat. No. 4,344,949; ramipril, which may be prepared as disclosed in U.S. Pat. No. 4,587,258; spirapril, which may be prepared as disclosed in U.S. Pat. No. 4,470,972; temocapril, which may be prepared as disclosed in U.S. Pat. No. 4,699,905; and trandolapril, which may be prepared as disclosed in U.S. Pat. No. 4,933,361. The disclosures of all such U.S. patents are incorporated herein by reference.

Angiotensin-II receptor antagonists (A-II antagonists) which are within the scope of this invention include, but are not limited to: candesartan, which may be prepared as disclosed in U.S. Pat. No. 5,196,444; eprosartan, which may be prepared as disclosed in U.S. Pat. No. 5,185,351; irbesartan, which may be prepared as disclosed in U.S. Pat. No. 5,270,317; losartan, which may be prepared as disclosed in U.S. Pat. No. 5,138,069; and valsartan, which may be prepared as disclosed in U.S. Pat. No. 5,399,578. The disclosures of all such U.S. patents are incorporated herein by reference.

Beta-adrenergic receptor blockers (beta- or β-blockers) which are within the scope of this invention include, but are not limited to: acebutolol, which may be prepared as disclosed in U.S. Pat. No. 3,857,952; alprenolol, which may be prepared as disclosed in Netherlands Patent Application No. 6,605,692; amosulalol, which may be prepared as disclosed in U.S. Pat. No. 4,217,305; arotinolol, which may be prepared as disclosed in U.S. Pat. No. 3,932,400; atenolol, which may be prepared as disclosed in U.S. Pat. No. 3,663,607 or 3,836,671; befunolol, which may be prepared as disclosed in U.S. Pat. No. 3,853,923; betaxolol, which may be prepared as disclosed in U.S. Pat. No. 4,252,984; bevantolol, which may be prepared as disclosed in U.S. Pat. No. 3,857,981; bisoprolol, which may be prepared as disclosed in U.S. Pat. No. 4,171,370; bopindolol, which may be prepared as disclosed in U.S. Pat. No. 4,340,541; bucumolol, which may be prepared as disclosed in U.S. Pat. No. 3,663,570; bufetolol, which may be prepared as disclosed in U.S. Pat. No. 3,723,476; bufuralol, which may be prepared as disclosed in U.S. Pat. No. 3,929,836; bunitrolol, which may be prepared as disclosed in U.S. Pat. Nos. 3,940,489 and 3,961,071; buprandolol, which may be prepared as disclosed in U.S. Pat. No. 3,309,406; butiridine hydrochloride, which may be prepared as disclosed in French Patent No. 1,390,056; butofilolol, which may be prepared as disclosed in U.S. Pat. No. 4,252,825; carazolol, which may be prepared as disclosed in German Patent No. 2,240,599; carteolol, which may be prepared as disclosed in U.S. Pat. No. 3,910,924; carvedilol, which may be prepared as disclosed in U.S. Pat. No. 4,503,067; celiprolol, which may be prepared as disclosed in U.S. Pat. No. 4,034,009; cetamolol, which may be prepared as disclosed in U.S. Pat. No. 4,059,622; cloranolol, which may be prepared as disclosed in German Patent No. 2,213,044; dilevalol, which may be prepared as disclosed in Clifton et al., Journal of Medicinal Chemistry, 1982, 25, 670; epanolol, which may be prepared as disclosed in European Patent Publication Application No. 41,491; indenolol, which may be prepared as disclosed in U.S. Pat. No. 4,045,482; labetalol, which may be prepared as disclosed in U.S. Pat. No. 4,012,444; levobunolol, which may be prepared as disclosed in U.S. Pat. No. 4,463,176; mepindolol, which may be prepared as disclosed in Seeman et al., Helv. Chim. Acta, 1971, 54, 241; metipranolol, which may be prepared as disclosed in Czechoslovakian Patent Application No. 128,471; metoprolol, which may be prepared as disclosed in U.S. Pat. No. 3,873,600; moprolol, which may be prepared as disclosed in U.S. Pat. No. 3,501,7691; nadolol, which may be prepared as disclosed in U.S. Pat. No. 3,935,267; nadoxolol, which may be prepared as disclosed in U.S. Pat. No. 3,819,702; nebivalol, which may be prepared as disclosed in U.S. Pat. No. 4,654,362; nipradilol, which may be prepared as disclosed in U.S. Pat. No. 4,394,382; oxprenolol, which may be prepared as disclosed in British Patent No. 1,077,603; perbutolol, which may be prepared as disclosed in U.S. Pat. No. 3,551,493; pindolol, which may be prepared as disclosed in Swiss Patent Nos. 469,002 and 472,404; practolol, which may be prepared as disclosed in U.S. Pat. No. 3,408,387; pronethalol, which may be prepared as disclosed in British Patent No. 909,357; propranolol, which may be prepared as disclosed in U.S. Pat. Nos. 3,337,628 and 3,520,919; sotalol, which may be prepared as disclosed in Uloth et al., Journal of Medicinal Chemistry, 1966, 9, 88; sufinalol, which may be prepared as disclosed in German Patent No. 2,728,641; talindol, which may be prepared as disclosed in U.S. Pat. Nos. 3,935,259 and 4,038,313; tertatolol, which may be prepared as disclosed in U.S. Pat. No. 3,960,891; tilisolol, which may be prepared as disclosed in U.S. Pat. No. 4,129,565; timolol, which may be prepared as disclosed in U.S. Pat. No. 3,655,663; toliprolol, which may be prepared as disclosed in U.S. Pat. No. 3,432,545; and xibenolol, which may be prepared as disclosed in U.S. Pat. No. 4,018,824. The disclosures of all such U.S. patents are incorporated herein by reference.

Alpha-adrenergic receptor blockers (alpha- or a-blockers) which are within the scope of this invention include, but are not limited to: amosulalol, which may be prepared as disclosed in U.S. Pat. No. 4,217,307; arotinolol, which may be prepared as disclosed in U.S. Pat. No. 3,932,400; dapiprazole, which may be prepared as disclosed in U.S. Pat. No. 4,252,721; doxazosin, which may be prepared as disclosed in U.S. Pat. No. 4,188,390; fenspiride, which may be prepared as disclosed in U.S. Pat. No. 3,399,192; indoramin, which may be prepared as disclosed in U.S. Pat. No. 3,527,761; labetolol, which may be prepared as disclosed above; naftopidil, which may be prepared as disclosed in U.S. Pat. No. 3,997,666; nicergoline, which may be prepared as disclosed in U.S. Pat. No. 3,228,943; prazosin, which may be prepared as disclosed in U.S. Pat. No. 3,511,836; tamsulosin, which may be prepared as disclosed in U.S. Pat. No. 4,703,063; tolazoline, which may be prepared as disclosed in U.S. Pat. No. 2,161,938; trimazosin, which may be prepared as disclosed in U.S. Pat. No. 3,669,968; and yohimbine, which may be isolated from natural sources according to methods well known to those skilled in the art. The disclosures of all such U.S. patents are incorporated herein by reference.

The term "vasodilator," where used herein, is meant to include cerebral vasodilators, coronary vasodilators and peripheral vasodilators. Cerebral vasodilators within the scope of this invention include, but are not limited to: bencyclane, which may be prepared as disclosed above; cinnarizine, which may be prepared as disclosed above; citicoline, which may be isolated from natural sources as disclosed in Kennedy et al., Journal of the American Chemical Society, 1955, 77, 250 or synthesized as disclosed in Kennedy, Journal of Biological Chemistry, 1956, 222, 185; cyclandelate, which may be prepared as disclosed in U.S. Pat. No. 3,663,597; ciclonicate, which may be prepared as disclosed in German Patent No. 1,910,481; diisopropylamine dichloroacetate, which may be prepared as disclosed in British Patent No. 862,248; eburnamonine, which may be prepared as disclosed in Hermann et al., Journal of the American Chemical Society, 1979, 101, 1540; fasudil, which may be prepared as disclosed in U.S. Pat. No. 4,678,783; fenoxedil, which may be prepared as disclosed in U.S. Pat. No. 3,818,021; flunarizine, which may be prepared as disclosed in U.S. Pat. No. 3,773,939; ibudilast, which may be prepared as disclosed in U.S. Pat. No. 3,850,941; ifenprodil, which may be prepared as disclosed in U.S. Pat. No. 3,509,164; lomerizine, which may be prepared as disclosed in U.S. Pat. No. 4,663,325; nafronyl, which may be prepared as disclosed in U.S. Pat. No. 3,334,096; nicametate, which may be prepared as disclosed in Blicke et al., Journal of the American Chemical Society, 1942, 64, 1722; nicergoline, which may be prepared as disclosed above; nimodipine, which may be prepared as disclosed in U.S. Pat. No. 3,799,934; papaverine, which may be prepared as reviewed in Goldberg, Chem. Prod. Chem. News, 1954, 17, 371; pentifylline, which may be prepared as disclosed in German Patent No. 860,217; tinofedrine, which may be prepared as disclosed in U.S. Pat. No. 3,563,997; vincamine, which may be prepared as disclosed in U.S. Pat. No. 3,770,724; vinpocetine, which may be prepared as disclosed in U.S. Pat. No. 4,035,750; and viquidil, which may be prepared as disclosed in U.S. Pat. No. 2,500,444. The disclosures of all such U.S. patents are incorporated herein by reference.

Coronary vasodilators within the scope of this invention include, but are not limited to: amotriphene, which may be prepared as disclosed in U.S. Pat. No. 3,010,965; bendazol, which may be prepared as disclosed in J. Chem. Soc. 1958, 2426; benfurodil hemisuccinate, which may be prepared as disclosed in U.S. Pat. No. 3,355,463; benziodarone, which may be prepared as disclosed in U.S. Pat. No. 3,012,042; chloracizine, which may be prepared as disclosed in British Patent No. 740,932; chromonar, which may be prepared as disclosed in U.S. Pat. No. 3,282,938; clobenfural, which may be prepared as disclosed in British Patent No. 1,160,925; clonitrate, which may be prepared from propanediol according to methods well known to those skilled in the art, e.g., see Annalen, 1870, 155, 165; cloricromen, which may be prepared as disclosed in U.S. Pat. No. 4,452,811; dilazep, which may be prepared as disclosed in U.S. Pat. No. 3,532,685; dipyridamole, which may be prepared as disclosed in British Patent No. 807,826; droprenilamine, which may be prepared as disclosed in German Patent No. 2,521,113; efloxate, which may be prepared as disclosed in British Patent Nos. 803,372 and 824,547; erythrityl tetranitrate, which may be prepared by nitration of erythritol according to methods well-known to those skilled in the art; etafenone, which may be prepared as disclosed in German Patent No. 1,265,758; fendiline, which may be prepared as disclosed in U.S. Pat. No. 3,262,977; floredil, which may be prepared as disclosed in German Patent No. 2,020,464; ganglefene, which may be prepared as disclosed in U.S.S.R. Patent No. 115,905; hexestrol, which may be prepared as disclosed in U.S. Pat. No. 2,357,985; hexobendine, which may be prepared as disclosed in U.S. Pat. No. 3,267,103; itramin tosylate, which may be prepared as disclosed in Swedish Patent No. 168,308; khellin, which may be prepared as disclosed in Baxter et al., Journal of the Chemical Society, 1949, S 30; lidoflazine, which may be prepared as disclosed in U.S. Pat. No. 3,267,104; mannitol hexanitrate, which may be prepared by the nitration of mannitol according to methods well-known to those skilled in the art; medibazine, which may be prepared as disclosed in U.S. Pat. No. 3,119,826; nitroglycerin; pentaerythritol tetranitrate, which may be prepared by the nitration of pentaerythritol according to methods well-known to those skilled in the art; pentrinitrol, which may be prepared as disclosed in German Patent No. 638,422-3; perhexilline, which may be prepared as disclosed above; pimefylline, which may be prepared as disclosed in U.S. Pat. No. 3,350,400; prenylamine, which may be prepared as disclosed in U.S. Pat. No. 3,152,173; propatyl nitrate, which may be prepared as disclosed in French Patent No. 1,103,113; trapidil, which may be prepared as disclosed in East German Patent No. 55,956; tricromyl, which may be prepared as disclosed in U.S. Pat. No. 2,769,015; trimetazidine, which may be prepared as disclosed in U.S. Pat. No. 3,262,852; trolnitrate phosphate, which may be prepared by nitration of triethanolamine followed by precipitation with phosphoric acid according to methods well-known to those skilled in the art; visnadine, which may be prepared as disclosed in U.S. Pat. Nos. 2,816,118 and 2,980,699. The disclosures of all such U.S. patents are incorporated herein by reference.

Peripheral vasodilators within the scope of this invention include, but are not limited to: aluminum nicotinate, which may be prepared as disclosed in U.S. Pat. No. 2,970,082; bamethan, which may be prepared as disclosed in Corrigan et al., Journal of the American Chemical Society, 1945, 67, 1894; bencyclane, which may be prepared as disclosed above; betahistine, which may be prepared as disclosed in Walter et al.; Journal of the American Chemical Society, 1941, 63, 2771; bradykinin, which may be prepared as disclosed in Hamburg et al., Arch. Biochem. Biophys., 1958, 76, 252; brovincamine, which may be prepared as disclosed in U.S. Pat. No. 4,146,643; bufeniode, which may be prepared as disclosed in U.S. Pat. No. 3,542,870; buflomedil, which may be prepared as disclosed in U.S. Pat. No. 3,895,030; butalamine, which may be prepared as disclosed in U.S. Pat. No. 3,338,899; cetiedil, which may be prepared as disclosed in French Patent Nos. 1,460,571; ciclonicate, which may be prepared as disclosed in German Patent No. 1,910,481; cinepazide, which may be prepared as disclosed in Belgian Patent No. 730,345; cinnarizine, which may be prepared as disclosed above; cyclandelate, which may be prepared as disclosed above; diisopropylamine dichloroacetate, which may be prepared as disclosed above; eledoisin, which may be prepared as disclosed in British Patent No. 984,810;

fenoxedil, which may be prepared as disclosed above; flunarizine, which may be prepared as disclosed above; heproni-cate, which may be prepared as disclosed in U.S. Pat. No. 3,384,642; ifenprodil, which may be prepared as disclosed above; iloprost, which may be prepared as disclosed in U.S. Pat. No. 4,692,464; inositol niacinate, which may be prepared as disclosed in Badgett et al., Journal of the American Chemical Society, 1947, 69, 2907; isoxsuprine, which may be prepared as disclosed in U.S. Pat. No. 3,056,836; kallidin, which may be prepared as disclosed in Biochem. Biophys. Res. Commun., 1961, 6, 210; kallikrein, which may be prepared as disclosed in German Patent No. 1,102,973; moxisylyte, which may be prepared as disclosed in German Patent No. 905,738; nafronyl, which may be prepared as disclosed above; nicametate, which may be prepared as disclosed above; nicergoline, which may be prepared as disclosed above; nicofuranose, which may be prepared as disclosed in Swiss Patent No. 366,523; nylidrin, which may be prepared as disclosed in U.S. Pat. Nos. 2,661,372 and 2,661,373; pentifylline, which may be prepared as disclosed above; pentoxifylline, which may be prepared as disclosed in U.S. Pat. No. 3,422,107; piribedil, which may be prepared as disclosed in U.S. Pat. No. 3,299,067; prostaglandin $E_1$, which may be prepared by any of the methods referenced in the Merck Index, Twelfth Edition, Budaveri, Ed., New Jersey, 1996, p. 1353; suloctidil, which may be prepared as disclosed in German Patent No. 2,334,404; tolazoline, which may be prepared as disclosed in U.S. Pat. No. 2,161,938; and xanthinol niacinate, which may be prepared as disclosed in German Patent No. 1,102,750 or Korbonits et al., Acta. Pharm. Hung., 1968, 38, 98. The disclosures of all such U.S. patents are incorporated herein by reference.

The term "diuretic," within the scope of this invention, is meant to include diuretic benzothiadiazine derivatives, diuretic organomercurials, diuretic purines, diuretic steroids, diuretic sulfonamide derivatives, diuretic uracils and other diuretics such as amanozine, which may be prepared as disclosed in Austrian Patent No. 168,063; amiloride, which may be prepared as disclosed in Belgian Patent No. 639,386; arbutin, which may be prepared as disclosed in Tschitschibabin, Annalen, 1930, 479, 303; chlorazanil, which may be prepared as disclosed in Austrian Patent No. 168,063; ethacrynic acid, which may be prepared as disclosed in U.S. Pat. No. 3,255,241; etozolin, which may be prepared as disclosed in U.S. Pat. No. 3,072,653; hydracarbazine, which may be prepared as disclosed in British Patent No. 856,409; isosorbide, which may be prepared as disclosed in U.S. Pat. No. 3,160,641; mannitol; metochalcone, which may be prepared as disclosed in Freudenberg et al., Ber., 1957, 90, 957; muzolimine, which may be prepared as disclosed in U.S. Pat. No. 4,018,890; perhexiline, which may be prepared as disclosed above; ticrynafen, which may be prepared as disclosed in U.S. Pat. No. 3,758,506; triamterene which may be prepared as disclosed in U.S. Pat. No. 3,081,230; and urea. The disclosures of all such U.S. patents are incorporated herein by reference.

Diuretic benzothiadiazine derivatives within the scope of this invention include, but are not limited to: althiazide, which may be prepared as disclosed in British Patent No. 902,658; bendroflumethiazide, which may be prepared as disclosed in U.S. Pat. No. 3,265,573; benzthiazide, McManus et al., 136th Am. Soc. Meeting (Atlantic City, September 1959), Abstract of papers, pp 13-O; benzylhydrochlorothiazide, which may be prepared as disclosed in U.S. Pat. No. 3,108,097; buthiazide, which may be prepared as disclosed in British Patent Nos. 861,367 and 885,078; chlorothiazide, which may be prepared as disclosed in U.S. Pat. Nos. 2,809,194 and 2,937,169; chlorthalidone, which may be prepared as disclosed in U.S. Pat. No. 3,055,904; cyclopenthiazide, which may be prepared as disclosed in Belgian Patent No. 587,225; cyclothiazide, which may be prepared as disclosed in Whitehead et al., Journal of Organic Chemistry, 1961, 26, 2814; epithiazide, which may be prepared as disclosed in U.S. Pat. No. 3,009,911; ethiazide, which may be prepared as disclosed in British Patent No. 861,367; fenquizone, which may be prepared as disclosed in U.S. Pat. No. 3,870,720; indapamide, which may be prepared as disclosed in U.S. Pat. No. 3,565,911; hydrochlorothiazide, which may be prepared as disclosed in U.S. Pat. No. 3,164,588; hydroflumethiazide, which may be prepared as disclosed in U.S. Pat. No. 3,254,076; methyclothiazide, which may be prepared as disclosed in Close et al., Journal of the American Chemical Society, 1960, 82, 1132; meticrane, which may be prepared as disclosed in French Patent Nos. M2790 and 1,365,504; metolazone, which may be prepared as disclosed in U.S. Pat. No. 3,360,518; paraflutizide, which may be prepared as disclosed in Belgian Patent No. 620,829; polythiazide, which may be prepared as disclosed in U.S. Pat. No. 3,009,911; quinethazone, which may be prepared as disclosed in U.S. Pat. No. 2,976,289; teclothiazide, which may be prepared as disclosed in Close et al., Journal of the American Chemical Society, 1960, 82, 1132; and trichlormethiazide, which may be prepared as dislcosed in deStevens et al., Experientia, 1960, 16, 113. The disclosures of all such U.S. patents are incorporated herein by reference.

Diuretic sulfonamide derivatives within the scope of this invention include, but are not limited to: acetazolamide, which may be prepared as disclosed in U.S. Pat. No. 2,980,679; ambuside, which may be prepared as disclosed in U.S. Pat. No. 3,188,329; azosemide, which may be prepared as disclosed in U.S. Pat. No. 3,665,002; bumetanide, which may be prepared as disclosed in U.S. Pat. No. 3,634,583; butazolamide, which may be prepared as disclosed in British Patent No. 769,757; chloraminophenamide, which may be prepared as disclosed in U.S. Pat. Nos. 2,809,194, 2,965,655 and 2,965,656; clofenamide, which may be prepared as disclosed in Olivier, Rec. Tray. Chim., 1918, 37, 307; clopamide, which may be prepared as disclosed in U.S. Pat. No. 3,459,756; clorexolone, which may be prepared as disclosed in U.S. Pat. No. 3,183,243; disulfamide, which may be prepared as disclosed in British Patent No. 851,287; ethoxolamide, which may be prepared as disclosed in British Patent No. 795,174; furosemide, which may be prepared as disclosed in U.S. Pat. No. 3,058,882; mefruside, which may be prepared as disclosed in U.S. Pat. No. 3,356,692; methazolamide, which may be prepared as disclosed in U.S. Pat. No. 2,783,241; piretanide, which may be prepared as disclosed in U.S. Pat. No. 4,010,273; torasemide, which may be prepared as disclosed in U.S. Pat. No. 4,018,929; tripamide, which may be prepared as disclosed in Japanese Patent No. 73 05,585; and xipamide, which may be prepared as disclosed in U.S. Pat. No. 3,567,777. The disclosures of all such U.S. patents are incorporated herein by reference.

The starting materials and reagents for the above-described compounds of the present invention and combination agents are also readily available or can be easily synthesized by those skilled in the art using conventional methods of organic synthesis. For example, many of the compounds used herein, are related to, or are derived from compounds in which there is a large scientific interest and commercial need, and accordingly many such compounds are commercially available or are reported in the literature or are easily prepared from other commonly available substances by methods which are reported in the literature.

Some of the compounds or combination agents of the present invention or intermediates in their synthesis have asymmetric carbon atoms and therefore are enantiomers or diastereomers. Diasteromeric mixtures can be separated into their individual diastereomers on the basis of their physical chemical differences by methods known per se, for example, by chromatography and/or fractional crystallization. Enantiomers can be separated by, for example, chiral HPLC methods or converting the enantiomeric mixture into a diastereomeric mixture by reaction with an appropriate optically active compound (e.g., alcohol), separating the diastereomers and converting (e.g., hydrolyzing) the individual diastereomers to the corresponding pure enantiomers. Also, an enantiomeric mixture of the compounds or an intermediate in their synthesis which contain an acidic or basic moiety may be separated into their compounding pure enantiomers by forming a diastereomeric salt with an optically pure chiral base or acid (e.g., 1-phenyl-ethyl amine or tartaric acid) and separating the diasteromers by fractional crystallization followed by neutralization to break the salt, thus providing the corresponding pure enantiomers. All such isomers, including diastereomers, enantiomers and mixtures thereof are considered as part of the present invention. Also, some of the compounds of the present invention are atropisomers (e.g., substituted biaryls) and are considered as part of the present invention.

More specifically, the compounds or combination agents of the present invention can be obtained by fractional crystallization of the basic intermediate with an optically pure chiral acid to form a diastereomeric salt. Neutralization techniques are used to remove the salt and provide the enantiomerically pure compounds. Alternatively, the compounds of the present invention may be obtained in enantiomerically enriched form by resolving the racemate of the final compound or an intermediate in its synthesis (preferably the final compound) employing chromatography (preferably high pressure liquid chromatography [HPLC]) on an asymmetric resin (preferably Chiralcel™ AD or OD (obtained from Chiral Technologies, Exton, Pa.)) with a mobile phase consisting of a hydrocarbon (preferably heptane or hexane) containing between 0 and 50% isopropanol (preferably between 2 and 20%) and between 0 and 5% of an alkyl amine (preferably 0.1% of diethylamine). Concentration of the product containing fractions affords the desired materials.

Some of the compounds of this invention or combination agents are basic or zwitterionic and form salts with pharmaceutically acceptable anions. All such salts are within the scope of this invention and they can be prepared by conventional methods such as combining the acidic and basic entities, usually in a stoichiometric ratio, in either an aqueous, non-aqueous or partially aqueous medium, as appropriate. The salts are recovered either by filtration, by precipitation with a non-solvent followed by filtration, by evaporation of the solvent, or, in the case of aqueous solutions, by lyophilization, as appropriate. The compounds are obtained in crystalline form according to procedures known in the art, such as by dissolution in an appropriate solvent(s) such as ethanol, hexanes or water/ethanol mixtures.

Some of the combination agents of the present invention are acidic and they form a salt with a pharmaceutically acceptable cation. All such salts are within the scope of the present invention and they can be prepared by conventional methods such as combining the acidic and basic entities, usually in a stoichiometric ratio, in either an aqueous, non-aqueous or partially aqueous medium, as appropriate. The salts are recovered either by filtration, by precipitation with a non-solvent followed by filtration, by evaporation of the solvent, or, in the case of aqueous solutions, by lyophilization, as appropriate. The compounds can be obtained in crystalline form by dissolution in an appropriate solvent(s) such as ethanol, hexanes or water/ethanol mixtures.

Certain compounds of the present invention or combination agents may exist in more than one crystal form (generally referred to as "polymorphs"). Polymorphs may be prepared by crystallization under various conditions, for example, using different solvents or different solvent mixtures for recrystallization; crystallization at different temperatures; and/or various modes of cooling, ranging from very fast to very slow cooling during crystallization. Polymorphs may also be obtained by heating or melting the compound of the present invention followed by gradual or fast cooling. The presence of polymorphs may be determined by solid probe NMR spectroscopy, IR spectroscopy, differential scanning calorimetry, powder X-ray diffraction or such other techniques.

Isotopically-labelled compounds of Formula I or combination agents can generally be prepared by conventional techniques known to those skilled in the art or by processes analogous to those described in the accompanying Examples and Preparations using an appropriate isotopically-labelled reagents in place of the non-labelled reagent previously employed.

Proprotein convertase subtilisin/kexin type 9, also known as PCSK9, is an enzyme that in humans is encoded by the PCSK9 gene. As defined herein, and typically known to those skilled in the art, the definition of PCSK9 also includes greater than 50 gain and loss of function mutations, GOF and LOF, respectively, thereof. (http://www.ucl.ac.uk/ldlr/LOVDv.1.1.0/search.php?select_db=PCSK9&srch=all).

The compounds of this invention inhibit the translation of PCSK9 mRNA to PCSK9 protein.

It is believed that some portion(s) of the first 100 codons of the mRNA that encode for the PCSK9 protein are determinative of whether a compound is an inhibitor of the translation of PCSK9 mRNA to PCSK9. Thus, it is believed there is an interaction between a portion(s) of the first 100 codons (encoding for PCSK9), the inhibitor compound and other components of the PCSK9 translation process that results in inhibition of the translation process. It is believed that these first codons are also a determinative of the inhibitory activity of a compound since when certain codon changes are made to the first 100 codons that encode for the same PCSK9 amino acid sequence (non-synonymous changes) the changes result in a loss of inhibitory activity by an "inhibitor compound". As is known in the art, the mature secreted PCSK9 protein does not contain the signal sequence (e.g., encompassing the first 30 amino acids).

However, it is also believed that when certain codon changes are made to the first 100 codons that encode for the PCSK9 amino acid sequence (synonymous changes) the translation is still inhibited (i.e., inhibitory activity by the compounds is retained). This suggests that the nature of the nascent peptide (newly formed amino acid sequence from translation) is at least one determinant of "inhibitor" compound activity.

Inhibition of the translation of PCSK9 provides advantages over other methods of blocking the action of PCSK9 (e.g., inhibiting the direct interaction of PCSK9 with the LDL receptor). One advantage of inhibiting the translation of PCSK9 is that mature PCSK9 is not made and its action within the cell will also be interrupted. Intracellular PCSK9 reportedly (Arterioscler Thromb Vasc Biol 2012; 32: 1585-1595) binds to apolipoprotein B100 (ApoB100) and protects it from degradation. Reducing intracellular PCSK9 levels thus have the potential benefit of reducing the secretion of very low-density lipoprotein (VLDL). This pharmacology is not likely with anti-PCSK9 antibodies as they act outside of the cell.

As defined herein inhibition of translation of PCSK9 mRNA to PCSK9 protein is determined by the "Cell Free PCSK9 Assay" provided herein in the specification. This "Cell Free PCSK9 Assay" is specific to the production of PCSK9 protein from PCSK9 mRNA and therefore detects inhibitors of this translational process rather than other mechanisms by which PCSK9 protein may be reduced. Any compound that presents an $IC_{50}$ (μM) below about 50 μM in the "Cell Free PCSK9 Assay" is considered as inhibiting PCSK9 translation. It is preferred that the $IC_{50}$ of the compound is less than about 30 μM and especially preferred that the $IC_{50}$ of the compound is less than about 20 μM.

It is preferred that the compound "selectively" inhibits translation of PCSK9 mRNA to PCSK9 protein. The term "selective" is defined as "inhibiting" translation of less than 1 percentage of proteins in a typical global proteomic assay. It is preferred that the level is below about 0.5% of proteins and especially preferred that the level is below about 0.1 of proteins. Typically in a standard assay the 1% level equates to about 40 non-PCSK9 proteins out of about 4000 proteins.

"Inhibition" of a particular protein in the Global Proteomic Assay (assay provided herein below) is defined as a decrease in protein expression in the Global Proteomic Assay to below about 50% of its starting level relative to vehicle. This definition of "inhibition" related to the Global Proteomic Assay is not to be confused with the previous definition of "inhibition" related to the Cell Free PCSK9 Assay.

Exemplary compounds that are useful as selective inhibitors of PCSK9 translation are provided herein and others can be determined by routine screening (known to those skilled in the art) of, for example, conventional compound libraries with the above described Cell Free PCSK9 Assay and Global Proteomic Assay provided below. Thus, high throughput screening (HTS) of existing and new compound libraries using the above assays (or appropriate modifications of them readily determined by routine skill in the art) provide compounds useful in this invention. Identification of those compounds can also provide leads suitable for routine medicinal chemistry efforts to identify further compounds useful in this invention. Such compounds are useful in the methods and uses described herein below including the treatment of dyslipidemia. Preferably such compounds have a molecular weight of about 300 to about 650

The compounds of the present invention, their prodrugs and the salts of such compounds and prodrugs are all adapted to therapeutic use as agents that antagonize extracellular proprotein convertase subtilisin kexin type 9 (PCSK9) activity, including its interaction with the low density lipoprotein (LDL) receptor (LDLR), in mammals, particularly humans. Thus, it is believed as has been demonstrated in human individuals with loss of function (LOF) PCSK9 mutations (e.g. Hobbs et. al. NEJM, 2006 and Hobbs et. al. Am. J. Hum. Gen., 2006) the compounds of the present invention, by decreasing PCSK9 levels, increase the cell surface expression of the LDL receptor and accordingly reduce LDL cholesterol. Hence, these compounds are useful for the treatment and correction of the various dyslipidemias observed to be associated with the development and incidence of atherosclerosis and cardiovascular disease, including hypoalphalipoproteinemia and hypertriglyceridemia.

Given the positive correlation between LDL cholesterol, and their associated apolipoproteins in blood with the development of cardiovascular, cerebral vascular and peripheral vascular diseases, the compounds of the present invention and the salts of such compounds, by virtue of their pharmacologic action, are useful for the prevention, arrestment and/or regression of atherosclerosis and its associated disease states. These include cardiovascular disorders (e.g., coronary artery disease, cerebrovascular disease, coronary artery disease, ventricular dysfunction, cardiac arrhythmia, pulmonary vascular disease, vascular hemostatic disease, cardiac ischemia and myocardial infarction), complications due to cardiovascular disease, transient cerebral ischemic attacks).

The utility of the compounds of the present invention and the salts of such compounds as medical agents in the treatment of the above described disease/conditions in mammals (e.g. humans, male or female) is demonstrated by the activity of the compounds of the present invention in one or more of the conventional assays and in vivo assays described below. The in vivo assays (with appropriate modifications within the skill in the art) can be used to determine the activity of other lipid or triglyceride controlling agents as well as the compounds of the present invention. Thus, the protocols described below can also be used to demonstrate the utility of the combinations of the agents (i.e., the compounds of the present invention) described herein. In addition, such assays provide a means whereby the activities of the compounds of the present invention and the salts of such compounds (or the other agents described herein) can be compared to each other and with the activities of other known compounds. The results of these comparisons are useful for determining dosage levels in mammals, including humans, for the treatment of such diseases. The following protocols can of course be varied by those skilled in the art.

PCSK9 AlphaLISA Assay

PCSK9 Lowering in WT7 Cells

An in-vitro AlphaLISA assay (Perkin Elmer) was developed in order to quantitate the level of PCSK9 secreted into the cell culture media following compound treatment. To detect and measure PCSK9 protein an in-house generated anti-PCSK9 antibody was coupled to AlphaLISA acceptor beads by an external vendor (PerkinElmer) and a second internally developed anti-PCSK9 antibody with an epitope distinct from that of the acceptor beads was biotinylated in house. Streptavidin coated-donor beads (Perkin Elmer) are also included in the assay mixture which then binds the biotinylated anti-PCSK9 antibody and in the presence of PCSK9 this donor complex and acceptor beads are brought into close proximity. Upon excitation of the donor beads at 680 nm singlet oxygen molecules are released that trigger an energy transfer cascade within the acceptor beads resolving as a single peak of light emitted at 615 nm. The ability of compound to modulate PCSK9 protein levels in conditioned media by AlphaLISA was assessed in the human hepatocellular carcinoma cell line Huh7, stably over-expressing human PCSK9. This cell line, termed WT7, was established by transfecting Huh7 cells with an in-house modified pcDNA 3.1 (+) Zeo expression vector (Life Technologies) containing the full-length human PCSK9 sequence (NCBI reference identifier, NM_174936.3, where coding sequence start annotated at position 363) and a c-terminal V5 and 6x-His tag. Following plasmid transfection the stable WT7 clone was identified and maintained under Zeocin selection. Compound screening was performed in 384-well plates where WT7 cells were plated at a density of 7500 cells per well in 20 μL of tissue culture media containing compound in an eleven point, 0.5 log dilution format at a high treatment concentration of 20 μM in a final volume of 0.5% DMSO. In additional to these test compound conditions each screening plate also included wells that contained 20 μM puromycin as a positive assay control defined as high percent effect, HPE, as well as wells containing media in 0.5% DMSO as a negative treatment control defined as zero percent effect, ZPE. After overnight compound incubation (16-24 h) the tissue culture media was collected and an aliquot from each sample was transferred to individual wells of a 384-well white Optiplate (Perkin Elmer). The coupled antibodies and donor beads were added to the assay plates in a buffer composed of 30 mM Tris pH 7.4, 0.02% Tween-20 and 0.02% Casein. Anti-PCSK9 acceptor beads (final concentration of 10 μg/mL) and anti-PCSK9 biotinylated antibody (final concentration of 3 nM) were added and incubated for 30 minutes at room temperature followed by the addition of the streptavidin donor beads (final concentration 40 μg/mL) for an additional 60 minutes. Additionally a standard curve was generated where AlphaLISA reagents were incubated in wells spiked with recombinant human PCSK9 diluted in tissue culture media from 5000 ng/mL to 0.6 ng/mL. Following incubation with AlphaLISA reagents plates were read on an EnVision (Perkin Elmer) plate reader at an excitation wavelength of 615 nM and emission/detection wavelength of 610 nM. To determine compound $IC_{50}$ the data for HPE and ZPE control wells were first analyzed and the mean, standard deviation and Z prime calculated for each plate. The test compound data were converted into percent effect, using the ZPE and HPE controls as 0% and 100% activity, respectively. The equation used for converting each well reading into percent effect was:

$$\frac{(\text{Test well activity value} - ZPE \text{ activity value})}{(HPE \text{ activity value} - ZPE \text{ activity value})} \times 100 \quad \text{Equation 1}$$

$IC_{50}$ was then calculated and reported as the midpoint in the percent effect curve in molar units and the values are reported under the Cell Based PCSK9 $IC_{50}$ (μM) column header within Table 1 Biological Data. Additionally, to monitor the selectivity of compound response for PCSK9 the level of a second secreted protein, Transferrin, was measured from the same conditioned media treated with test compound by AlphaLISA. The anti-Transferrin AlphaLISA bead conjugated by PerkinElmer is a mouse monoclonal IgG1 to human transferrin (clone M10021521; cat#10-T34C; Fitzgerald). The biotinylated labeled antibody is an affinity purified goat anti-human polyclonal antibody (Cat # A80-128A; Bethyl Laboratories). To detect and quantify effects on Transferrin 0.01 mL of the culture media was transferred to a 384-well white Optiplate and 0.01 mL of media was added to bring the volume to 0.02 ml. Anti-Transferrin acceptor beads were added to a final concentration of 10 μg/mL, biotinylated anti-Transferrin at 3 nM and streptavidin donor beads at 40 μg/mL. Percent effect and $IC_{50}$ for Transferrin was computed in a similar manner as that described for PCSK9.

PCSK9 Lowering and Compound Concentration Determination in Sandwich Culture Human Hepatocytes (SCHH)

Test compound in-vitro pharmacokinetic and pharmacodynamic relationships were measured in sandwich culture primary cryopreserved human hepatocytes. Within these studies SCHH cells (BD Biosciences IVT) were thawed at 37° C. then placed on ice, after which the cells were added to pre-warmed (37° C.) InVitroGRO-HT media and centrifuged at 50×g for 3 min. The cell pellet was re-suspended to $0.8 \times 10^6$ cells/mL in InVitroGRO-CP plating medium and cell viability determined by trypan blue exclusion. On day 1, hepatocyte suspensions were plated in BioCoat 96-well plates at a density of 80000 cells/well in a volume of 0.1 mL/well. After 18 to 24 hours of incubation at 37° C. in 5% $CO_2$, cells were overlaid with ice-cold 0.25 mg/mL BD Matrigel Matrix Phenol Red-Free in incubation medium at 0.1 mL/well. Cultures were maintained at 37° C. in 5% $CO_2$ in InVitroGRO-HI (FBS-free media), which was replaced every 24 hours and time course treatments were initiated on day 5. Prior to compound treatment cell plates were washed 3 times with 0.1 mL/well InVitroGRO-HI and 0.09 mL of media was added back in preparation for the compound additions. 1 uL of either DMSO or compound DMSO stocks at 30 mM, 10 mM, 3 mM and 1 mM were stamped into 96 well V bottom polypropylene plates. 0.099 mL of media was added to the compound plate and mixed thoroughly before the addition of 0.010 mL from the interim compound plate to the cell plate. This resulted in a final concentration of 0.1% DMSO where compounds were evaluated at 30 μM, 10 μM, 3 μM and 1 μM (in some instances compound concentrations were increased to 300 μM). Cells were incubated with compound for 5, 15, 30, 60, 180, 360, 480 and 1440 minutes at 37° C. in 5% $CO_2$. At the indicated time, 0.08 mL of media was removed from the cell plates and frozen for subsequent analysis of secreted PCSK9 by AlphaLISA and for determination of drug levels in the media by liquid chromatography-tandem mass spectrometry (LC-MS/MS). The remaining media was then aspirated and the cell layers were washed 3× with ice cold Hanks Balanced Salt Solution (HBSS) under shaking conditions to remove the matrigel overlay and plates were then stored at −20° C. for subsequent determination of drug levels in the cells by LC-MS/MS. AlphaLISA determination of PCSK9 protein levels within the conditioned media was performed ultilizing the identical reagents and detection protocols described above for the WT7 cells. Percent PCSK9 lowering versus vehicle treated cells was then determined for each time point and the maximum response (and the corresponding concentration and time when observed) is reported under the Sandwich Culture Hepatocyte (SCHH) PCSK9 lowering column header within Table 1 Biological Data.

Media samples used for test compound level determination were processed by adding 20 μL of the conditioned media to 180 μL of MeOH-IS solution or 20 μL of media matrix containing known concentrations of analyte (0-5 μM) to 180 μL of MeOH-IS. Samples were then dried under a stream of nitrogen and re-suspended in 200 μL of 50/50 MeOH/$H_2O$. LC-MS/MS analyses were conducted on an API-4000 triple quadrupole mass spectrometer with an atmospheric pressure electrospray ionization source (MDS SCIEX, Concord, Ontario, Canada) coupled to two Shimadzu LC-20AD pumps with a CBM-20A controller. A 10 μL sample was injected onto a Kinetex C18 column (2.6 μm, 100 Å, 30×2.1 mm, Phenomenex, Torrance, Calif.) and eluted by a mobile phase at a flow rate of 0.5 mL/min with initial conditions of 10% solvent B for 0.2 min, followed by a gradient of 10% solvent B to 90% solvent B over 1 min (solvent A: 100% $H_2O$ with 0.1% formic acid; solvent B: 100% acetonitrile with 0.1% formic acid), with 90% solvent B held for 0.5 min, followed by a return to initial conditions that was maintained for 0.75 min.

To determine the levels of test compound within the SCHH cells, cell plates were removed from the freezer and cell layers lysed in 0.1 mL of methanol containing the internal standard (MeOH-IS), carbamazepine, by shaking for 20 min at room temperature. The lysate (90 μL) was then transferred to a new 96-well plate, dried under a stream of nitrogen, and re-suspended in 90 uL of 50/50 MeOH/H₂O. Standard curves were constructed by adding 0.1 mL of MeOH-IS with known concentrations of analyte (0-500 nM) to vehicle-treated cell layers (matrix blanks). All standards were then processed in the same manner as the unknown samples. For LC-MS/MS analysis the multiple reaction monitoring (MRM) acquisition methods were constructed with tuned transitions for each analyte and the optimal declustering potentials, collision energies, and collision cell exit potentials determined for each analyte with a 4.5 kV spray voltage, 10 eV entrance potential, and 550° C. source temperature. The peak areas of the analyte and internal standard were quantified using Analyst 1.5.2 (MDS SCIEX, Ontario, Canada). The resulting drug levels were then normalized to the hepatocyte protein content in a well as determined by the BCA Protein Assay Kit (Pierce Biotechnology).

In order to eliminate the permeability barrier inherent to the WT7 and SCHH cell-based assays a cell-free system was also established to access compound activity. A sequence containing the full length human PCSK9 (NCBI reference identifier, NM_174936.3, where coding sequence start annotated at position 363) along with 84 additional 3' nucleotides, comprising a V5 tag and polylinkinker followed by an in frame modified firefly luciferase reporter (corresponding to nucleotide positions 283-1929 of pGL3, Gen Bank reference identifier JN542721.1) was cloned into the pT7CFE1 expression vector (ThermoScientific). The construct was then in-vitro transcribed using the MEGAscript T7 Kit (Life Technologies) and RNA subsequently purified incorporating the MEGAclear Kit (Life Technologies) according to manufacturer's protocols. HeLa cell lysates were prepared following the protocols described by Mikami (reference is Cell-Free Protein Synthesis Systems with Extracts from Cultured Human Cells, S. Mikami, T. Kobayashi and H. Imataka; from Methods in Molecular Biology, vol. 607, pages 43-52, Y. Endo et al. (eds.), Humana Press, 2010) with the following modifications. Cells were grown in a 20 L volume of CD293 medium (Gibco 11765-054) with Glutamax increased to 4 mM, penicillin at 100 U/mL and other additions as previously described by Mikami. Growth was in a 50 L wavebag at a rocker speed of 25 rpm and angle 6.1 with 5% CO₂ and 0.2 LPM flow rate with cells harvested at a density of 2-2.5e6/ml. Lysates additionally contained 1 tablet of Roche cOmplete-EDTA protease inhibitors per 50 ml with tris(2-carboxyethyl) phosphine (Biovectra) substituted for dithiothreitol, and were clarified by an additional final centrifugation at 10,000 rpm in a Sorvall SS34 rotor at 4° C. for 10 minutes. Compound screening was performed in 384-well plates in an eleven point, 0.5 log dilution format at a top test compound concentration of 100 µM in a final volume of 0.5% DMSO. In additional to these test compound conditions each screening plate also included wells that contained 100 µM of compound example 16 (N-(3-chloropyridin-2-yl)-N-[(3R)-piperidin-3-yl]-4-(3H-[1,2,3]triazolo[4,5-b]pyridin-3-yl)benzamide) as a positive assay control defined as high percent effect, HPE, as well as wells containing media in 0.5% DMSO as a negative treatment control defined as zero percent effect, ZPE. Compounds were incubated at 30° C. for 45 minutes in a solution containing 0.1 µg of purified, in-vitro transcribed RNA together with the cell-free reaction mixture (consisting of 1.6 mM Mg and 112 mM K salts, 4.6 mM tris(2-carboxyethyl)phosphine (Biovectra), 5.0 µL HeLa lysate, 0.2 µL RNAsin (Promega) and 1.0 µL energy mix (containing 1.25 mM ATP (Sigma), 0.12 mM GTP (Sigma), 20 mM creatine phosphate (Santa Cruz), 60 µg/mL creatine phosphokinase (Sigma), 90 µg/mL tRNA (Sigma) and the 20 amino acids (Life Technologies) at final concentrations described by Mikami) and brought up in water to a final volume of 10 µL in water. Upon assay completion 1 µL from each reaction solution was removed and transferred to a second 384-well Optiplate (Perkin Elmer) containing 24 µL of SteadyGlo (Promega) and signal intensity was measured on the Envision (Perkin Elmer) using the enhanced luminescence protocol. To determine compound $IC_{50}$ the data for HPE and ZPE control wells were first analyzed and the mean, standard deviation and Z prime calculated for each plate. The test compound data were converted into percent effect, using the ZPE and HPE controls as 0% and 100% activity, respectively, applying Equation 1 above. $IC_{50}$ was then calculated and reported as the midpoint in the percent effect curve in molar units and the values are reported under the Cell Free PCSK9 $IC_{50}$ (µM) column header within Table 1 Biological Data.

TABLE 1

BIOLOGICAL DATA*

| Example | Cell Based PCSK9 $IC_{50}$ (µM) | Cell Free PCSK9 $IC_{50}$ (µM) | Sandwich Culture Hepatocyte (SCHH) PCSK9 Lowering |
|---|---|---|---|
| 1 | 3.2 | 0.44 | 74% at 8 h at 30 µM |
| 2 | 1.7 | 0.69 | Not tested |
| 3 | 0.8 | Not tested | Not tested |
| 4 | >20* | 3.8 | Not tested |
| 5 | 1.5 | Not tested | Not tested |
| 6 | 1.5 | 1.7 | 80% at 8 h at 30 µM |
| 7 | >20* | 18 | 26% at 8 h at 100 µM |
| 8 | 9.5 | 3.7 | 70% at 8 h at 30 µM |
| 9 | 1.8 | Not tested | Not tested |
| 10 | 1.5 | 0.64 | 87% at 8 h at 30 µM |
| 11 | 11.7 | 2.1 | Not tested |
| 12 | >20* | 1.7 | 36% at 8 h at 30 µM |
| 13 | 2.3 | 0.80 | 83% at 8 h at 30 µM |
| 14 | 4.5 | Not tested | 54% at 8 h at 30 µM |
| 15a | 7.3 | 3.1 | 72% at 8 h at 30 µM |
| 15b | 10.7 | 5.0 | 58% at 8 h at 30 µM |
| 16 | 0.8 | 0.52 | 87% at 8 h at 30 µM |
| 17 | >20* | 3.05 | 63% at 8 h at 100 uM |
| 18 | >20* | 5.61 | 15% at 8 h at 100 uM |
| 21 | >20 | Not tested | 57% at 6 h at 30 uM |
| 22 | >20* | 5.80 | Not tested |
| 24 | >20* | 25.3 | Not tested |
| 25 | >20* | 2.97 | Not tested |
| 26 | >20* | 5.75 | Not tested |
| 27 | >20* | 14.3 | Not tested |
| 28 | >20* | 16.8 | Not tested |
| 29 | >20* | Not tested | 72% at 6 h at 30 uM |
| 30 | >16.7* | Not tested | 11% at 8 h at 30 uM |
| 31 | >20* | Not tested | 19% at 8 h at 30 uM |
| 32 | >20* | 7.26 | 0% at 6 h at 30 uM |
| 33 | >20* | 23.7 | 32% at 6 h at 30 uM |
| 34 | >20* | 5.22 | 20% at 6 h at 30 uM |
| 35 | >20* | 6.20 | 28% at 6 h at 30 uM |
| 36 | >20* | 5.43 | 27% at 6 h at 30 uM |
| 37 | >20* | 22.9 | 25% at 6 h at 30 uM |
| 38 | >19.4* | 2.19 | 3% at 6 h at 30 uM |
| 39 | 11.82 | 0.592 | 0% at 6 h at 30 uM |
| 40 | >20* | 18.2 | 26% at 6 h at 30 uM |
| 41 | >19.4* | 15.4 | 35% at 6 h at 30 uM |
| 42 | >20* | 7.38 | 19% at 6 h at 30 uM |
| 43 | >20* | 31.9 | 21% at 6 h at 30 uM |
| 44 | >20* | 4.39 | 12% at 6 h at 30 uM |
| 45 | >20* | 25.1 | 8% at 6 h at 30 uM |
| 46 | >20* | 4.67 | 45% at 6 h at 30 uM |
| 47 | >20* | 33.4 | 12% at 6 h at 30 uM |
| 48 | >20* | 7.68 | 16% at 6 h at 30 uM |
| 49 | >20* | 15.4 | 0% at 6 h at 30 uM |
| 50 | >20* | 8.03 | 37% at 6 h at 30 uM |
| 51 | >20* | 3.56 | 48% at 6 h at 30 uM |
| 52 | >20* | 10.7 | 25% at 6 h at 30 uM |
| 53 | >20* | 31.8 | 0% at 6 h at 30 uM |

TABLE 1-continued

BIOLOGICAL DATA*

| Example | Cell Based PCSK9 $IC_{50}$ (μM) | Cell Free PCSK9 $IC_{50}$ (μM) | Sandwich Culture Hepatocyte (SCHH) PCSK9 Lowering |
|---|---|---|---|
| 54 | >20* | 12.8 | 29% at 6 h at 30 uM |
| 55 | >19.2* | 19.8 | 40% at 6 h at 30 uM |

*Certain compounds with poor passive cell permeability have $IC_{50}$s in excess of the top concentration of the WT7 cell based assay (20 μM). Using the cell free assay, the action of these compounds is not blocked by a cell membrane and they are active. Also, when compounds are dosed at higher concentrations in the SCHH assay, these compounds can show activity in spite of their poor cellular penetration. The activity of compounds was determined by a composite of the three assays. Compounds with activity in the cell based assay were not always tested in other activity assays.

Global Proteomic Assay-Stable Isotope Labeling of Amino Acids in Cell Culture (SILAC) Assay:

Human hepatocarcinoma Huh7 cells for stable isotope labeling by amino acids (SILAC) were grown in RPMI media (minus lysine and arginine) in 10% dialyzed fetal bovine serum supplemented with either unlabeled lysine and arginine (light label), L-arginine:HCl U-13C6 99% and L-lysine:2HCl 4,4,5,5-D4, 96-98% (medium label) or L-arginine:HCl U13C6, 99%; U-15N4, 99% and L-lysine:2HCl U13C6, 99%; U-15N2, 99% (heavy label). Cells were passaged for 5-6 doublings with an incorporation efficiency for labeling of >95% achieved. Prior to the start of the experiment, cells were cultured to full confluence to facilitate a synchronized cell population in G0/G1 phase (cell cycle analysis with propidium iodide showed that 75% of cells were in G0/G1 phase). Cells were then re-plated in fresh media supplemented with 0.5% dialyzed fetal bovine serum containing either light, medium or heavy lysine (Lys) and arginine (Arg) and vehicle (light) or Example 16 at 0.25 uM (medium) or 1.30 μM (heavy) was added for either 1, 4 or 16 hours. At the end of the indicated time points, media was removed and protease/phosphatase inhibitors added prior to freezing at −80° C. Cell layers were rinsed with PBS before adding cell dissociation buffer to detach the cells, cells were collected by rinsing with PBS and spun at 1000 rpm for 5 minutes. The cell pellet was resuspended in PBS for washing, spun at 1000 rpm for 5 minutes and the supernatant aspirated. The cell layer was then frozen at −80° C. and both the media and cell pellet were subjected to proteomic analysis.

For proteomic analysis of secreted proteins, equal volume of the conditioned media from light, medium, and heavy cells was mixed, followed by depletion of bovine serum albumin by anti-BSA agarose beads. The resulting proteins were subsequently concentrated using 3 KDa MWCO spin columns, reduced with dithiothreitol and alkylated with iodoacetamide.

For the analysis of cellular proteins, cell pellets were lysed in SDS-PAGE loading buffer in the presence of protease/phosphatase inhibitor cocktails. Cell lysates were centrifuged at 12000×g at 4° C. for 10 min. The resulting supernatants were collected, and protein concentrations were measured by BCA assay. Equal amount proteins in the light, medium, and heavy cell lysates were combined, reduced with dithiothreitol and alkylated with iodoacetamide.

The proteins derived from conditioned media and cell pellets were subsequently fractionated by SDS-PAGE. The gels were stained with Coomassie blue. After destaining, the gels were cut into 12-15 bands. Proteins were in-gel digested by trypsin overnight, after which peptides were extracted from the gels with $CH_3CN$:1% formic acid (1:1, v/v). The resulting peptide mixtures were desalted with $C_{18}$ Stage-Tips, dried in speedvac and stored at −20° C. until further analysis.

The peptide mixtures were reconstituted in 0.1% formic acid. An aliquot of each sample was loaded onto a $C_{18}$ PicoFrit column (75 μm×10 cm) coupled to an LTQ Orbitrap Velos mass spectrometer. Peptides were separated using a 2-hour linear gradient. The instrumental method consisted of a full MS scan followed by data-dependent CID scans of the 20 most intense precursor ions, and dynamic exclusion was activated to maximize the number of ions subjected to fragmentation. Peptide identification and relative protein quantification were carried out by searching the mass spectra against the human IPI database using Mascot search engine on Proteome Discoverer 1.3. The mass spectra for peptides derived from the conditioned media were also searched against bovine IPI database to discern proteins carried over from fetal bovine serum. The search parameters took into account static modification of S-carboxamidomethylation at Cys, and variable modifications of oxidation on Met and stable isotopic labeling on Lys and Arg. Peptide spectrum matches (PSMs) at 1% false discovery rate were used for protein identifications. Changes in protein expression upon compound treatment were calculated from the relative intensity of isotope-labeled and unlabeled peptides derived from that protein. The protein candidates thus identified by the software with altered expression (<=2-fold or 50% decrease) were further validated for accuracy by manual inspection of the MS and MS/MS spectra of the respective peptides and those meeting this criteria were determined to be significantly decreased upon compound treatment.

Following 16 hours of treatment with 0.3 μM and 1.5 μM (Example 16 compound), the level of PCSK9 protein expression in the conditioned media was decreased by 2- and 5-fold respectively. Among the approximate 900 additional proteins identified within the cell culture media, only two proteins (0.22%), Lamin B1 and Tropomyosin Alpha-4, demonstrated a significant <=50% decrease in protein expression relative to vehicle. Likewise, the compound exhibited very minimal effects on the protein expression of cellular proteins where of a total population of greater than 3000 proteins only 2 additional proteins (0.067%), Apolipoprotein C3 and Cadherin 1, were determined to be significantly decreased in the presence of the PCSK9 inhibitor 16 compound. Taken together this SILAC study suggests that the compound is selective for inhibiting protein expression of PCSK9 where only an additional 0.098% (4 of 4083) proteins demonstrated significant reduction in expression.

A second SILAC study utilizing Example 15b was performed following a similar protocol to that described above except for the following adjustments: a single 10 μM treatment concentration along with vehicle was used, analysis time points were reduced to 4 and 16 h post-treatment and analysis focused only on proteins secreted into the conditioned media. Applying these experimental conditions and analysis approach a total of approx. 1500 proteins were detected. Along with PCSK9 only two additional proteins, Apolipoprotein A2 and Cadherin 1 were found to be significantly reduced relative to vehicle. These findings confirm the selectivity of the compound class for PCSK9 where only an additional approx. 0.13% of the proteins measured exhibited a significant decrease in expression.

For administration to human patients, an oral daily dose of the compounds herein may be in the range 1 mg to 5000 mg depending, of course, on the mode of and frequency of administration, the disease state, and the age and condition of the patient, etc. By patient is meant a human, either male or female. The patient may be of any age group including infants (under the age of 2), children (under the age of 12), teenagers (between the ages of 13-19), adults (between the ages of 20-65), pre-menopausal females, post menopausal females and the elderly (over the age of 65). A therapeutically effective amount is about 1 mg to about 4000 mg per day. Preferably the therapeutically effective amount is about 1 mg to about 2000 mg per day. It is especially preferred that a therapeutically effective amount is about 50 mg to about 500 mg per day. An oral daily dose is in the range of 3 mg to 2000 mg may be used. A further oral daily dose is in the range of 5 mg to 1000 mg. For convenience, the compounds of the present invention can be administered in a unit dosage form. If desired, multiple doses per day of the unit dosage form can be used to increase the total daily dose. The unit dosage form, for example, may be a tablet or capsule containing about 0.1, 0.5, 1, 5, 10, 15, 20, 25, 30, 35, 40, 45, 50, 55, 60, 65, 70, 75, 80, 85, 90, 95, 100, 125, 150, 175, 200, 250, 500, 1000 or 2000 mg of the compound of the present invention. The total daily dose may be administered in single or divided doses and may, at the physician's discretion, fall outside of the typical ranges given herein.

For administration to human patients, an infusion daily dose of the compounds herein may be in the range 1 mg to 2000 mg depending, of course, on the mode of and frequency of administration, the disease state, and the age and condition of the patient, etc. A further infusion daily dose is in the range of 5 mg to 1000 mg. The total daily dose may be administered in single or divided doses and may, at the physician's discretion, fall outside of the typical ranges given herein.

These compounds may also be administered to animals other than humans, for example, for the indications detailed above. The precise dosage administered of each active ingredient will vary depending upon any number of factors, including but not limited to, the type of animal and type of disease state being treated, the age of the animal, and the route(s) of administration.

A dosage of the combination pharmaceutical agents to be used in conjunction with the Formula I compounds is used that is effective for the indication being treated. Such dosages can be determined by standard assays such as those referenced above and provided herein. The combination agents may be administered simultaneously or sequentially in any order.

These dosages are based on an average human subject having a weight of about 60 kg to 70 kg. The physician will readily be able to determine doses for subjects whose weight falls outside this range, such as infants and the elderly.

Dosage regimens may be adjusted to provide the optimum desired response. For example, a single bolus may be administered, several divided doses may be administered over time or the dose may be proportionally reduced or increased as indicated by the exigencies of the therapeutic situation. It is especially advantageous to formulate parenteral compositions in dosage unit form for ease of administration and uniformity of dosage. Dosage unit form, as used herein, refers to physically discrete units suited as unitary dosages for the mammalian subjects to be treated; each unit containing a predetermined quantity of active compound calculated to produce the desired therapeutic effect in association with the required pharmaceutical carrier. The specification for the dosage unit forms of the invention are dictated by and directly dependent on (a) the unique characteristics of the chemotherapeutic agent and the particular therapeutic or prophylactic effect to be achieved, and (b) the limitations inherent in the art of compounding such an active compound for the treatment of sensitivity in individuals.

Thus, one of skill in the art would appreciate, based upon the disclosure provided herein, that the dose and dosing regimen is adjusted in accordance with methods well-known in the therapeutic arts. That is, the maximum tolerable dose can be readily established, and the effective amount providing a detectable therapeutic benefit to a patient may also be determined, as can the temporal requirements for administering each agent to provide a detectable therapeutic benefit to the patient. Accordingly, while certain dose and administration regimens are exemplified herein, these examples in no way limit the dose and administration regimen that may be provided to a patient in practicing the present invention.

It is to be noted that dosage values may vary with the type and severity of the condition to be alleviated, and may include single or multiple doses. It is to be further understood that for any particular subject, specific dosage regimens should be adjusted over time according to the individual need and the professional judgment of the person administering or supervising the administration of the compositions, and that dosage ranges set forth herein are exemplary only and are not intended to limit the scope or practice of the claimed composition. For example, doses may be adjusted based on pharmacokinetic or pharmacodynamic parameters, which may include clinical effects such as toxic effects and/or laboratory values. Thus, the present invention encompasses intra-patient dose-escalation as determined by the skilled artisan. Determining appropriate dosages and regiments for administration of the chemotherapeutic agent are well-known in the relevant art and would be understood to be encompassed by the skilled artisan once provided the teachings disclosed herein.

The present invention further comprises use of a compound of Formula I for use as a medicament (such as a unit dosage tablet or unit dosage capsule). In another embodiment, the present invention comprises the use of a compound of Formula I for the manufacture of a medicament (such as a unit dosage tablet or unit dosage capsule) to treat one or more of the conditions previously identified in the above sections discussing methods of treatment.

A pharmaceutical composition of the invention may be prepared, packaged, or sold in bulk, as a single unit dose, or as a plurality of single unit doses. As used herein, a "unit dose" is discrete amount of the pharmaceutical composition comprising a predetermined amount of the active ingredient. The amount of the active ingredient is generally equal to the dosage of the active ingredient which would be administered to a subject or a convenient fraction of such a dosage such as, for example, one-half or one-third of such a dosage.

The compounds described herein may be administered as a formulation comprising a pharmaceutically effective amount of a compound of Formula I, in association with one or more pharmaceutically acceptable excipients including carriers, vehicles and diluents. The term "excipient" herein means any substance, not itself a therapeutic agent, used as a diluent, adjuvant, or vehicle for delivery of a therapeutic agent to a subject or added to a pharmaceutical composition to improve its handling or storage properties or to permit or facilitate formation of a solid dosage form such as a tablet, capsule, or a solution or suspension suitable for oral, parenteral, intradermal, subcutaneous, or topical application. Excipients can include, by way of illustration and not limitation, diluents, disintegrants, binding agents, adhesives, wetting agents, polymers, lubricants, glidants, stabilizers, and substances added to mask or counteract a disagreeable taste or odor, flavors, dyes, fragrances, and substances added to improve appearance of the composition. Acceptable excipients include (but are not limited to) stearic acid, magnesium stearate, magnesium oxide, sodium and calcium salts of phosphoric and sulfuric acids, magnesium carbonate, talc, gelatin, acacia gum, sodium alginate, pectin, dextrin, mannitol, sorbitol, lactose, sucrose, starches, gelatin, cellulosic materials, such as cellulose esters of alkanoic acids and cellulose alkyl esters, low melting wax, cocoa butter or powder, polymers such as polyvinyl-pyrrolidone, polyvinyl alcohol, and polyethylene glycols, and other pharmaceutically acceptable materials. Examples of excipients and their use may be found in *Remington's Pharmaceutical Sciences,* 20th Edition (Lippincott Williams & Wilkins, 2000). The choice of excipient will to a large extent depend on factors such as the particular mode of administration, the effect of the excipient on solubility and stability, and the nature of the dosage form.

The compounds herein may be formulated for oral, buccal, intranasal, parenteral (e.g., intravenous, intramuscular or subcutaneous) or rectal administration or in a form suitable for administration by inhalation. The compounds of the invention may also be formulated for sustained delivery.

Methods of preparing various pharmaceutical compositions with a certain amount of active ingredient are known, or will be apparent in light of this disclosure, to those skilled in this art. For examples of methods of preparing pharmaceutical compositions see *Remington's Pharmaceutical Sciences,* 20th Edition (Lippincott Williams & Wilkins, 2000).

Pharmaceutical compositions according to the invention may contain 0.1%-95% of the compound(s) of this invention, preferably 1%-70%. In any event, the composition to be administered will contain a quantity of a compound(s) according to the invention in an amount effective to treat the disease/condition of the subject being treated.

Since the present invention has an aspect that relates to the treatment of the disease/conditions described herein with a combination of active ingredients which may be administered separately, the invention also relates to combining separate pharmaceutical compositions in kit form. The kit comprises two separate pharmaceutical compositions: a compound of Formula I a prodrug thereof or a salt of such compound or prodrug and a second compound as described above. The kit comprises a means for containing the separate compositions such as a container, a divided bottle or a divided foil packet. Typically the kit comprises directions for the administration of the separate components. The kit form is particularly advantageous when the separate components are preferably administered in different dosage forms (e.g., oral and parenteral), are administered at different dosage intervals, or when titration of the individual components of the combination is desired by the prescribing physician.

An example of such a kit is a so-called blister pack. Blister packs are well known in the packaging industry and are being widely used for the packaging of pharmaceutical unit dosage forms (tablets, capsules, and the like). Blister packs generally consist of a sheet of relatively stiff material covered with a foil of a preferably transparent plastic material. During the packaging process recesses are formed in the plastic foil. The recesses have the size and shape of the tablets or capsules to be packed. Next, the tablets or capsules are placed in the recesses and the sheet of relatively stiff material is sealed against the plastic foil at the face of the foil which is opposite from the direction in which the recesses were formed. As a result, the tablets or capsules are sealed in the recesses between the plastic foil and the sheet. Preferably the strength of the sheet is such that the tablets or capsules can be removed from the blister pack by manually applying pressure on the recesses whereby an opening is formed in the sheet at the place of the recess. The tablet or capsule can then be removed via said opening.

It may be desirable to provide a memory aid on the kit, e.g., in the form of numbers next to the tablets or capsules whereby the numbers correspond with the days of the regimen which the tablets or capsules so specified should be ingested. Another example of such a memory aid is a calendar printed on the card, e.g., as follows "First Week, Monday, Tuesday, etc. . . . Second Week, Monday, Tuesday, . . . " etc. Other variations of memory aids will be readily apparent. A "daily dose" can be a single tablet or capsule or several pills or capsules to be taken on a given day. Also, a daily dose of Formula I compound can consist of one tablet or capsule while a daily dose of the second compound can consist of several tablets or capsules and vice versa. The memory aid should reflect this.

In another specific embodiment of the invention, a dispenser designed to dispense the daily doses one at a time in the order of their intended use is provided. Preferably, the dispenser is equipped with a memory-aid, so as to further facilitate compliance with the regimen. An example of such a memory-aid is a mechanical counter which indicates the number of daily doses that has been dispensed. Another example of such a memory-aid is a battery-powered microchip memory coupled with a liquid crystal readout, or audible reminder signal which, for example, reads out the date that the last daily dose has been taken and/or reminds one when the next dose is to be taken.

Also, as the present invention has an aspect that relates to the treatment of the disease/conditions described herein with a combination of active ingredients which may be administered jointly, the invention also relates to combining separate pharmaceutical compositions in a single dosage form, such as (but not limited to) a single tablet or capsule, a bilayer or multilayer tablet or capsule, or through the use of segregated components or compartments within a tablet or capsule.

The active ingredient may be delivered as a solution in an aqueous or non-aqueous vehicle, with or without additional solvents, co-solvents, excipients, or complexation agents selected from pharmaceutically acceptable diluents, excipients, vehicles, or carriers.

The active ingredient may be formulated as an immediate release or modified release tablet or capsule. Alternatively, the active ingredient may be delivered as the active ingredient alone within a capsule shell, without additional excipients.

General Experimental Procedures

The following examples are put forth so as to provide those of ordinary skill in the art with a disclosure and description of how the compounds, compositions, and methods claimed herein are made and evaluated, and are intended to be purely exemplary of the invention and are not intended to limit the scope of what the inventors regard as their invention. Unless indicated otherwise, percent is percent by weight given the component and the total weight of the composition, temperature is in ° C. or is at ambient temperature, and pressure is at or near atmospheric. Commercial reagents were utilized without further purification. Room or ambient temperature refers to 18-25° C. All non-aqueous reactions were run under a nitrogen atmosphere for convenience and to maximize yields. Concentration in vacuo means that a rotary evaporator was used. The names for the compounds of the invention were created by the Autonom 2.0 PC-batch version from Beilstein Informationssysteme GmbH (ISBN 3-89536-976-4). "DMSO" means dimethyl sulfoxide.

Proton nuclear magnetic spectroscopy ($^1$H NMR) was recorded with 400 and 500 MHz spectrometers. Chemical shifts are expressed in parts per million downfield from tetramethylsilane. The peak shapes are denoted as follows: s, singlet; d, doublet; t, triplet; q, quartet; m, multiplet; br s, broad singlet; br m, broad multiplet. Mass spectrometry (MS) was performed via atmospheric pressure chemical ionization (APCI) or electron scatter (ES) ionization sources. Silica gel chromatography was performed primarily using a medium pressure system using columns pre-packaged by various commercial vendors. Microanalyses were performed by Quantitative Technologies Inc. and were within 0.4% of the calculated values. The terms "concentrated" and "evaporated" refer to the removal of solvent at reduced pressure on a rotary evaporator with a bath temperature less than 60° C. The abbreviation "min" and "h" stand for "minutes" and "hours" respectively. The abbreviation "g" stand for grams. The abbreviation "µl" or "µL" or "uL" stand for microliters.

The powder X-ray diffraction was carried out on a Bruker AXS-D4 diffractometer using copper radiation (wavelength: 1.54056A). The tube voltage and amperage were set to 40 kV and 40 mA, respectively. The divergence and scattering slits were set at 1 mm, and the receiving slit was set at 0.6 mm. Diffracted radiation was detected by a PSD-Lynx Eye detector. A step size of 0.02° and a step time of 0.3 sec from 3.0 to 40 ° 2θ were used. Data were collected and analyzed using Bruker Diffrac Plus software (Version 2.6). Samples were prepared by placing them in a customized holder and rotated during collection.

To perform an X-ray diffraction measurement on a Bragg-Brentano instrument like the Bruker system used for measurements reported herein, the sample is typically placed into a holder which has a cavity. The sample powder is pressed by a glass slide or equivalent to ensure a random surface and proper sample height. The sample holder is then placed into the instrument. The incident X-ray beam is directed at the sample, initially at a small angle relative to the plane of the holder, and then moved through an arc that continuously increases the angle between the incident beam and the plane of the holder. Measurement differences associated with such X-ray powder analyses result from a variety of factors including: (a) errors in sample preparation (e.g., sample height), (b) instrument errors (e.g. flat sample errors), (c) calibration errors, (d) operator errors (including those errors present when determining the peak locations), and (e) the nature of the material (e.g. preferred orientation and transparency errors). Calibration errors and sample height errors often result in a shift of all the peaks in the same direction. Small differences in sample height when using a flat holder will lead to large displacements in XRPD peak positions. A systematic study showed that, using a Shimadzu XRD-6000 in the typical Bragg-Brentano configuration, sample height difference of 1 mm lead to peak shifts as high as 1 °2θ (Chen et al.; *J Pharmaceutical and Biomedical Analysis*, 2001; 26,63). These shifts can be identified from the X-ray Diffractogram and can be eliminated by compensating for the shift (applying a systematic correction factor to all peak position values) or recalibrating the instrument. As mentioned above, it is possible to rectify measurements from the various machines by applying a systematic correction factor to bring the peak positions into agreement. In general, this correction factor will bring the measured peak positions from the Bruker into agreement with the expected peak positions and may be in the range of 0 to 0.2 °2θ.

Analytical UPLC-MS Method 1:
Column: Waters Acquity HSS T3, $C_{18}$ 2.1×5 0 mm, 1.7 µm; Column T=60° C.
Gradient: Initial conditions: A-95%:B-5%; hold at initial from 0.0-0.1 min; Linear Ramp to A-5%:B-95% over 0.1-1.0 min; hold at A-5%:B-95% from 1.0-1.1 min; return to initial conditions 1.1-1.5 min
Mobile Phase A: 0.1% formic acid in water (v/v)
Mobile Phase B: 0.1% formic acid in acetonitrile (v/v)
Flow rate: 1.25 mL/min Analytical UPLC-MS Method 2:
Column: Waters Acquity HSS T3, $C_{18}$ 2.1×5 0 mm, 1.7 µm; Column T=60° C.
Gradient: Initial conditions: A-95%:B-5%; hold at initial from 0.0-0.1 min; Linear Ramp to A-5%:B-95% over 0.1-2.6 min; hold at A-5%:B-95% from 2.6-2.95 min; return to initial conditions 2.95-3.0 min
Mobile Phase A: 0.1% formic acid in water (v/v)
Mobile Phase B: 0.1% formic acid in acetonitrile (v/v)
Flow rate: 1.25 mL/min Analytical LC-MS Method 3:
Column: Welch Materials Xtimate 2.1 mm×30 mm, 3 µm
Gradient: 0%-30% (solvent B) over 0.9 min and holding at 30% for 0.6 min.
Mobile Phase A: 0.0375% TFA in water
Mobile Phase B: 0.01875% TFA in acetonitrile
Flow rate: 1.2 mL/min Analytical LC-MS Method 4:
Column: Welch Materials Xtimate 2.1 mm×30 mm, 3 µm
Gradient: 0-60% (solvent B) over 2.0 min
Mobile Phase A: 0.0375% TFA in water
Mobile Phase B: 0.01875% TFA in acetonitrile
Flow rate: 1.2 mL/min Analytical LC-MS Method 5:
Column: Welch Materials Xtimate 2.1 mm×30 mm, 3 µm
Gradient: 10-80% (solvent B) over 2.0 min
Mobile Phase A: 0.0375% TFA in water
Mobile Phase B: 0.01875% TFA in acetonitrile
Flow rate: 1.2 mL/min Analytical HPLC Method 1:
Column: Waters BEH C8 2.1×100 mm, 1.7 µm
Gradient: Initial conditions: A-95%:B-5%; Linear Ramp to A-0%:B-100% over 0.0-8.20 min; hold at A-0%:B-100% from 8.2-8.7 min; return to initial conditions 8.7-8.8 min; hold at A-95%:B-5% from 8.8-10.3 min.
Mobile Phase A: 0.2% of 70% perchloric acid in water (v/v)
Mobile Phase B: acetonitrile
Flow rate: 0.5 mL/min
Detection: UV-210 nm Analytical HPLC Method 2:
Column: Waters BEH RP C18 2.1×100 mm, 1.7 µm
Gradient: Initial conditions: A-95%:B-5%; Linear Ramp to A-0%:B-100% over 0.0-8.20 min; hold at A-0%:B-100% from 8.2-8.7 min; return to initial conditions 8.7-8.8 min; hold at A-95%:B-5% from 8.8-10.3 min.
Mobile Phase A: 0.1% methanesulfonic acid in water (v/v)
Mobile Phase B: acetonitrile (v/v)
Flow rate: 0.5 mL/min
Detection: UV-210 nm Analytical HPLC Method 3:
Column: Waters HSS T3 2.1×100 mm, 1.8 µm
Gradient: Initial conditions: A-95%:B-5%; Linear Ramp to A-0%:B-100% over 0.0-8.20 min; hold at A-0%:B-100% from 8.2-8.7 min; return to initial conditions 8.7-8.8 min; hold at A-95%:B-5% from 8.8-10.3 min.
Mobile Phase A: 0.1% methanesulfonic acid in water (v/v)
Mobile Phase B: acetonitrile (v/v)
Flow rate: 0.5 mL/min
Detection: UV-210 nm Analytical UPLC Method 4:
Column: Waters HSS T3 2.1×100 mm, 1.8 µm; Column T=45° C.
Gradient: Initial conditions: A-95%:B-5%; Linear Ramp to A-0%:B-100% over 0-8.2 min; hold at A-0%:B-100% from 8.2-8.7 min; return to initial conditions 8.7-8.8 min Mobile Phase A: 10 mM ammonium bicarbonate in water
Mobile Phase B: acetonitrile
Flow rate: 0.5 mL/min
Analytical HPLC Method 5:
Column: Waters Atlantis dC18 4.6×50, 5 μm
Gradient: Initial conditions A-95%:B-5%; Linear Ramp to A-5%:B-95% over 0-4.0 min; hold at A-5%:B-95% from 4.0-5.0 min
Mobile phase A: 0.05% TFA in water (v/v)
Flow rate: 2 mL/min
Chiral Preparative Chromatography Method 1:
Column: Chiralcel-OD-H 20×250 mm, 5 μm; Column T=40° C.
Mobile phase of 75% supercritical fluid CO2/25% acetonitrile; isocratic conditions, operating back pressure=120 bar
Flow rate: 65 mL/min
Chiral Preparative Chromatography Method 2:
Column: Chiralpak AD 5 cm×25 cm, 20 μm; Column T=ambient
Mobile phase of 100% MeOH; isocratic conditions
Operating back pressure=120 bar
Flow rate: 118 mL/min
Injection Volume: 17.5 mL
Feed Concentration 245 g/L
Chiral Preparative Chromatography Method 3:
Column: Chiralpak IC 2.1 cm×25 cm, 5 μm
Mobile Phase: 85/15 $CO_2$/methanol
Flow Rate: 65 mL/min
Column Temp: Ambient
Wavelength: 280 nm
Injection Volume: 2.0 mL
Feed Concentration: 125 g/L
Chiral Preparative Chromatography Method 4
Column: Chiral Tech IC 500 mm×21.2 mm, 5 μm; Column T=ambient
Mobile Phase: 90% $CO_2$/10% isopropanol; isocratic conditions
Flow Rate: 80.0 mL/min
Chiral Preparative Chromatography Method 5
Column: Chiral Tech AD-H 500 mm×21.2 mm, 5 μm; Column T=ambient
Mobile Phase: 80% $CO_2$/20% isopropanol; isocratic conditions
Flow Rate: 80.0 mL/min
Chiral Preparative Chromatography Method 6
Column: Chiral OD-H 500 mm×21.2 mm, 5 μm; Column T=ambient
Mobile Phase: 90% $CO_2$/10% isopropanol; isocratic conditions
Flow Rate: 80.0 mL/min
Chiral Preparative Chromatography Method 7
Column: Chiral Tech AD-H 500 mm×21.2 mm, 5 μm; Column T=ambient
Mobile Phase: 95% $CO_2$/5% isopropanol; isocratic conditions
Flow Rate: 80.0 mL/min
Chiral Preparative Chromatography Method 8
Column: Chiral Tech IC 250 mm×21.2 mm, 5 μm; Column T=ambient
Mobile Phase: 60% $CO_2$/40% MeOH; isocratic conditions
Flow Rate: 80.0 mL/min
Chiral Preparative Chromatography Method 9
Column: Lux Cellulose-3 500 mm×21.2 mm, 5 μm; Column T=ambient
Mobile Phase: 95% $CO_2$15% isopropanol; isocratic conditions
Flow Rate: 80.0 mL/min
Chiral Preparative Chromatography Method 10
Column: Lux Amylose-2 500 mm×21.2 mm, 5 μm; Column T=ambient
Mobile Phase: 95% $CO_2$15% 1:1 MeOH/MeCN; isocratic conditions
Flow Rate: 80.0 mL/min
Chiral Preparative Chromatography Method 11
Column: Lux Amylose-2 250 mm×50.0 mm, 5 μm; Column T=ambient
Mobile Phase: 65% $CO_2$/35% MeOH; isocratic conditions
Flow Rate: 250 mL/min
Chiral Preparative Chromatography Method 12
Column: Chiral Tech IC 500 mm×10.0 mm, 5 μm; Column T=ambient
Mobile Phase: 90% $CO_2$/10% isopropanol; isocratic conditions
Flow Rate: 15 mL/min
Chiral Preparative Chromatography Method 13
Column: Lux Amylose IC 500 mm×21.2 mm, 5 μm; Column T=ambient
Mobile Phase: 95% $CO_2$15% isopropanol; isocratic conditions
Flow Rate: 80.0 mL/min
Chiral Preparative Chromatography Method 14
Column: Chiral Tech OJ-H 500 mm×21.2 mm, 5 μm; Column T=ambient
Mobile Phase: 95% $CO_2$15% isopropanol; isocratic conditions
Flow Rate: 80.0 mL/min
Chiral Analytical Chromatography Method 1
Column: Chiral Tech IC 250 mm×4.6 mm, 5 μm
Gradient: Initial conditions: A-95%:B-5%; linear ramp to A-40%:B-60% over 1.0-9.0 min; hold at A-40%:B-60% from 9.0-9.5 min; linear ramp to A-95%:B-5% over 9.5-10.0 min.
Mobile Phase A: $CO_2$
Mobile Phase B: isopropanol
Flow rate: 3.0 mL/min
Detection: UV-210 nm
Chiral Analytical Chromatography Method 2
Column: Chiral Tech AD-H 250 mm×4.6 mm, 5 μm
Gradient: Initial conditions: A-95%:B-5%; linear ramp to A-40%:B-60% over 1.0-9.0 min; hold at A-40%:B-60% from 9.0-9.5 min; linear ramp to A-95%:B-5% over 9.5-10.0 min.
Mobile Phase A: $CO_2$
Mobile Phase B: isopropanol
Flow rate: 3.0 mL/min
Detection: UV-210 nm
Chiral Analytical Chromatography Method 3
Column: Chiral Tech OD-H 250 mm×4.6 mm, 5 μm
Gradient: Initial conditions: A-95%:B-5%; linear ramp to A-40%:B-60% over 1.0-9.0 min; hold at A-40%:B-60% from 9.0-9.5 min; linear ramp to A-95%:B-5% over 9.5-10.0 min.
Mobile Phase A: $CO_2$
Mobile Phase B: isopropanol
Flow rate: 3.0 mL/min
Detection: UV-210 nm
Chiral Analytical Chromatography Method 4
Column: Chiral Tech IC 250 mm×4.6 mm, 5 μm
Gradient: Initial conditions: A-95%:B-5%; linear ramp to A-40%:B-60% over 1.0-9.0 min; hold at A-40%:B-60% from 9.0-9.5 min; linear ramp to A-95%:B-5% over 9.5-10.0 min.
Mobile Phase A: $CO_2$
Mobile Phase B: MeOH Flow rate: 3.0 mL/min
Detection: UV-210 nm
Chiral Analytical Chromatography Method 5
Column: Lux Cellulose-3 250 mm×4.6 mm, 5 μm
Gradient: Initial conditions: A-95%:B-5%; linear ramp to A-40%:B-60% over 1.0-9.0 min; hold at A-40%:B-60% from 9.0-9.5 min; linear ramp to A-95%:B-5% over 9.5-10.0 min.
Mobile Phase A: $CO_2$
Mobile Phase B: isopropanol
Flow rate: 3.0 mL/min
Detection: UV-210 nm
Chiral Analytical Chromatography Method 6
Column: Chiral Tech OJ-H 250 mm×4.6 mm, 5 μm
Gradient: Initial conditions: A-95%:B-5%; linear ramp to A-40%:B-60% over 1.0-9.0 min; hold at A-40%:B-60% from 9.0-9.5 min; linear ramp to A-95%:B-5% over 9.5-10.0 min.
Mobile Phase A: $CO_2$
Mobile Phase B: isopropanol
Flow rate: 3.0 mL/min
Detection: UV-210 nm
Chiral Analytical Chromatography Method 7
Column: Lux Amylose-2 250 mm×4.6 mm, 5 μm
Gradient: Initial conditions: A-95%:B-5%; linear ramp to A-40%:B-60% over 1.0-9.0 min; hold at A-40%:B-60% from 9.0-9.5 min; linear ramp to A-95%:B-5% over 9.5-10.0 min.
Mobile Phase A: $CO_2$
Mobile Phase B: 1:1 MeOH/MeCN
Flow rate: 3.0 mL/min Detection: UV-210 nm
Chiral Analytical Chromatography Method 8
Column: Lux Amylose-2 250 mm×4.6 mm, 5 μm
Gradient: Initial conditions: A-95%:B-5%; linear ramp to A-40%:B-60% over 1.0-9.0 min; hold at A-40%:B-60% from 9.0-9.5 min; linear ramp to A-95%:B-5% over 9.5-10.0 min.
Mobile Phase A: $CO_2$
Mobile Phase B: isopropanol
Flow rate: 3.0 mL/min
Detection: UV-210 nm

PREPARATIONS

Preparation 1 tert-butyl (3R)-3-[(3-chloropyridin-2-yl)amino]piperidine-1-carboxylate

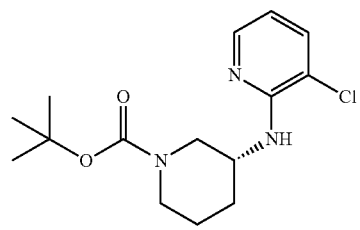 [SMILES: CC(C)(C)OC(=O)N1CCC[C@@H](Nc2ncccc2Cl)C1]

A mixture of 2-bromo-3-chloropyridine (203.8 g, 1.06 moles), sodium tert-amylate (147 g, 1.27 moles), tert-butyl (3R)-3-aminopiperidine-1-carboxylate (249.5 g, 1.25 moles) in toluene (2 L) was heated to 80° C. To this solution was added chloro(di-2-norbornylphosphino)(2-dimethylaminoferrocen-1-yl) palladium (II) (6.1 g, 10.06 mmol) followed by heating to 105° C. and holding for 3 h. The reaction mixture was cooled to room temperature, 1 L of water was added, then the biphasic mixture was filtered through Celite®. After layer separation, the organic phase was washed with 1 L of water followed by treatment with 60 g of Darco® G-60 at 50° C. The mixture was filtered through Celite®, and concentrated to a final total volume 450 mL, resulting in the precipitation of solids. To the slurry of solids was added 1 L of heptane. The solids were collected via filtration and then dried to afford the title compound as a dull orange solid (240.9 g, 73% yield).
$^1$H NMR (CDCl$_3$) δ 8.03 (m, 1H), 7.45 (m, 1H), 6.54 (m, 1H), 5.08 (br s, 1H), 4.14 (br s, 1H), 3.85-3.30 (m, 4H), 2.00-1.90 (m, 1H), 1.80-1.55 (m, 4H), 1.43 (br s, 9H).
UPLC (UPLC-MS Method 1): $t_R$=0.72 min.
MS (ES+) 312.0 (M+H)$^+$ Preparation 2 tert-butyl (3R)-3-[(3-methylpyridin-2-yl)amino]piperidine-1-carboxylate

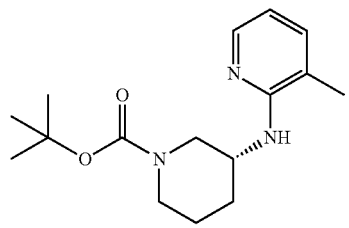 [SMILES: Cc1cccnc1N[C@@H]1CCCN(C(=O)OC(C)(C)C)C1]

To a solution of 2-bromo-3-methylpyridine (75.0 g, 436 mmol) and tert-butyl (3R)-3-aminopiperidine-1-carboxylate (87.3 g, 436 mmol) in toluene (1.2 L) were added Cs$_2$CO$_3$ (426 g, 1.31 mol), 2-(dimethylaminomethyl)ferrocen-1-yl-palladium(II) chloride dinorbornylphosphine (MFCD05861622) (1.56 g, 4.36 mmol) and Pd(OAc)$_2$ (0.490 g, 2.18 mmol) under N$_2$ atmosphere. The mixture was stirred at 110° C. for 48 h. The mixture was cooled to room temperature then poured into water (500 mL) and extracted with EtOAc (3×300 mL). The organic layers were dried over Na$_2$SO$_4$, filtered, and the filtrate was concentrated in vacuo. The residue was purified by silica gel column chromatography to give the title compound as a yellow solid (65 g, 60%).
$^1$H NMR (CDCl$_3$) δ 8.00 (d, 1H), 7.20 (d, 1H), 6.51 (dd, 1H), 4.36 (br s, 1H), 4.16 (br s, 1H), 3.63 (d, 1H), 3.52 (br s, 2H), 3.36-3.30 (m, 1H), 2.06 (s, 3H), 1.90 (br s, 1H), 1.73 (br s 2H), 1.59 (br s, 1H), 1.38 (br s, 9H).

Preparation 3 tert-butyl (3R)-3-(isoquinolin-1-ylamino)piperidine-1-carboxylate

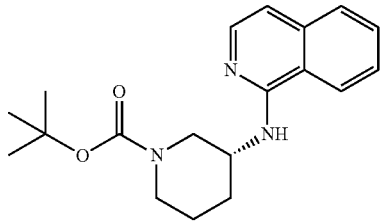 [SMILES: CC(C)(C)OC(=O)N1CCC[C@@H](Nc2nccc3ccccc23)C1]

To a solution of 1-chloroisoquinoline (5.00 g, 30.6 mmol) and tert-butyl (3R)-3-aminopiperidine-1-carboxylate (7.34 g, 36.6 mmol) in anhydrous toluene (150 mL) was added t-BuOK (10.27 g, 91.7 mmol), BINAP (951 mg, 1.53 mmol), and Pd(OAc)$_2$ (343 mg, 1.53 mmol). The reaction mixture was purged with nitrogen three times, and heated at 110° C. overnight. The reaction mixture was cooled to room temperature and poured into water. The mixture was then extracted with EtOAc (4×150 mL). The combined organic layers were dried over anhydrous sodium sulfate, filtered, and the filtrate was concentrated under reduced pressure. The resulting dark solid was purified by silica gel column chromatography eluting with a gradient of (10-15%) EtOAc/petroleum ether to deliver the title compound (4.89 g, 49%) as a yellow solid.

$^1$H NMR (400 MHz, CDCl$_3$) δ 7.97 (d, 1H), 7.72 (d, 1H), 7.68 (d, 1H), 7.56 (dd, 1H), 7.43 (dd, 1H), 6.92 (d, 1H), 5.34 (br s, 1H), 4.33-4.29 (m, 1H), 3.70-3.55 (m, 3H), 3.36-3.30 (m, 1H), 2.04-1.77 (m, 4H), 1.35 (br s, 9H).

Preparation 4 tert-butyl (3R)-3-[(1-methyl-1H-pyrrolo[2,3-c]pyridin-7-yl)amino]piperidine-1-carboxylate

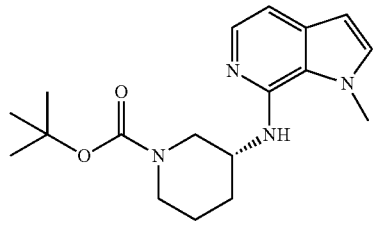 [SMILES: Cn1ccc2ccnc(N[C@@H]3CCCN(C(=O)OC(C)(C)C)C3)c21]

Step 1: 7-chloro-1-methyl-1H-pyrrolo[2,3-c]pyridine

To a solution of 7-chloro-1H-pyrrolo[2,3-c]pyridine (3.00 g, 19.7 mmol) in THF (30 mL) cooled to 0° C. was added 60% NaH in mineral oil (0.940 g, 23.6 mmol NaH). The reaction mixture was stirred at 0° C. for 20 minutes. Iodomethane (6.20 g, 43.7 mmol) was added and the reaction mixture was stirred at 0° C. for 1 h and at 20° C. for 2 h. The mixture was poured into water (20 mL) and extracted with EtOAc (3×20 mL). The organic layers were dried over Na$_2$SO$_4$, filtered, and the filtrate was concentrated in vacuo. The residue was purified by silica gel column chromatography, eluting with a gradient of 17-33% EtOAc/petroleum ether to give the title compound as a yellow solid (2.8 g, 85%).

$^1$H NMR (CDCl$_3$) δ 7.96 (d, 1H), 7.43 (d, 1H), 7.17 (d, 1H), 6.50 (d, 1H), 4.18 (s, 3H).

Step 2: (R)-tert-butyl 3-((1-methyl-1H-pyrrolo[2,3-c]pyridin-7-yl)amino)piperidine-1-carboxylate A solution of Pd$_2$(dba)$_3$ (1.53 g, 1.68 mmol), BrettPhos (1.86 g, 3.36 mmol) in toluene (40 mL) under N$_2$ atmosphere was stirred for 20 min. NaOtBu (3.23 g, 33.6 mmol), the compound from Step 1 7-chloro-1-methyl-1H-pyrrolo[2,3-c]pyridine (2.80 g, 16.8 mmmol) and tert-butyl (3R)-3-aminopiperidine-1-carboxylate (4.04 g, 20.2 mmol) were added. The reaction was stirred at 105° C. for 3 h. The reaction mixture was poured into water (20 mL) and extracted with EtOAc (3×20 mL). The organic layers were dried over Na$_2$SO$_4$, filtered and the filtrate was concentrated in vacuo. The residue was purified by silica gel column chromatography, eluting with a gradient of 17-50% EtOAc/petroleum ether to give the title compound as a brown solid (5.2 g, 94%).

$^1$H NMR (CDCl$_3$) δ 7.69 (d, 1H), 6.91 (d, 1H), 6.99 (d, 1H), 6.31 (d, 1H), 4.75 (br s, 1H), 4.33 (br s, 1H), 4.08 (s, 3H), 3.89-3.77 (m, 2H), 3.44 (d, 1H), 3.14 (dd, 1H), 1.90 (br s, 1H), 1.75-1.72 (m, 1H), 1.42 (br s, 2H), 1.22 (br s, 9H).

Preparation 5

4-(3H-[1,2,3]triazolo[4,5-b]pyridin-3-yl)benzoic acid

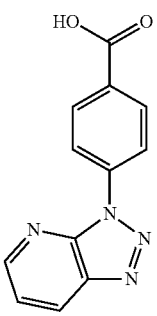 [SMILES: O=C(O)c1ccc(-n2nnc3cccnc32)cc1]

Step 1: ethyl 4-((3-nitropyridin-2-yl)amino)benzoate

General Procedure E. To a solution of 2-chloro-3-nitropyridine (95.0 g, 0.600 mol) and ethyl 4-aminobenzoate (99.0 g, 0.600 mol) in toluene (3 L) was added K$_2$OC$_3$ (166 g, 1.20 mol), BINAP (7.40 g, 11.8 mmol), Pd(OAc)$_2$ (2.80 g, 12.5 mmol) and NaI (2.70 g, 18.0 mmol). The mixture was stirred at 110° C., for 6 h. The reaction mixture was cooled to 30° C., filtered through Celite®, and the filtrate was concentrated in vacuo. The residue was transferred to a separatory funnel with water (300 mL) and extracted with EtOAc (3×300 mL). The organic layers were dried over Na$_2$SO$_4$, filtered and the filtrate was concentrated in vacuo to give a dark solid residue, which was washed with acetone/water (5/1, 100 mL) and filtered to give the title compound as a yellow solid (142 g, 82%).

$^1$H NMR (DMSO-d$_6$) δ 8.60-8.57 (m, 2H), 7.96-7.94 (m, 2H), 7.89-7.87 (m, 2H), 7.12 (dd, 1H), 4.31 (q, 2H), 1.33 (t, 3H).

Step 2: ethyl 4-((3-aminopyridin-2-yl)amino)benzoate

General Procedure F. To a solution of the compound from Step 1 ethyl 4-((3-nitropyridin-2-yl)amino)benzoate (120 g, 0.417 mol), in ethanol (2.00 L), was added Raney-Ni (30 g). The reaction mixture was hydrogenated under a H$_2$ atmosphere (50 psi) at 30° C. for 20 h. The mixture was filtered through Celite®. The filtrate was dried over Na$_2$SO$_4$, filtered, and the filtrate was concentrated in vacuo to afford a yellow solid. The yellow solid was washed with DCM to give the title compound as a yellow solid (75 g, 70%).

$^1$H NMR (DMSO-d$_6$) δ 10.05 (br, 1H), 7.94 (d, 2H) 7.54 (d, 1H), 7.46 (d, 2H), 7.40 (d, 1H), 7.09 (dd, 1H), 4.30 (q, 2H), 1.31 (t, 3H).

Step 3: ethyl 4-(3H-[1,2,3]triazolo[4,5-b]pyridin-3-yl)benzoate

General Procedure G. To a solution of the compound from Step 2 ethyl 4-((3-aminopyridin-2-yl)amino)benzoate (70.0 g, 0.272 mol) in a mixture of AcOH (70 mL) and water (70 mL), was added NaNO$_2$ (23.8 g, 0.345 mol) at 0° C. The mixture was stirred at 30° C. for 20 min. The mixture was diluted with DCM (100 mL), washed with water (3×50 mL). The organic phase was dried over Na$_2$SO$_4$, filtered, and the filtrate was concentrated in vacuo to afford a dark solid. The solid was washed with acetone (30 mL) to afford the title compound as a white solid (63 g, 86%).

$^1$H NMR (DMSO-d$_6$) δ 8.91 (d, 1H), 8.91 (dd, 1H), 8.50 (d, 2H), 8.24 (d, 2H), 7.66 (dd, 1H), 4.37 (q, 2H), 1.36 (t, 3H).

Step 4:
4-(3H-[1,2,3]triazolo[4,5-b]pyridin-3-yl)benzoic acid

General Procedure H. To a solution of the compound from Step 3 ethyl 4-(3H-[1,2,3]triazolo[4,5-b]pyridin-3-yl)benzoate (60.0 g, 0.224 mol) in MeOH (700 mL), was added 2N NaOH (260 mL, 0.520 mmol). The mixture was stirred at 60° C. for 2 h. The mixture was acidified with 1N HCl so that the pH of the solution was approximately pH 1. The reaction mixture was extracted with EtOAc (3×100 mL). The combined organic layers were dried over Na$_2$SO$_4$, filtered, and the filtrate was concentrated in vacuo to afford the title compound as a white solid (52 g, 97%).

$^1$H NMR (DMSO-d$_6$) δ 13.23 (br, 1H), 8.91 (d, 1H), 8.76 (d, 1H), 8.48 (d, 2H), 8.24 (d, 2H), 7.67 (dd, 1H).

Preparation 6

4-(6-methyl-3H-[1,2,3]triazolo[4,5-b]pyridin-3-yl)benzoic acid

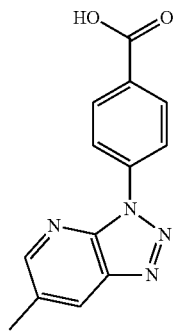 [SMILES: Cc1cnc2c(c1)nnn2-c1ccc(C(=O)O)cc1]

Step 1: ethyl 4-((5-methyl-3-nitropyridin-2-yl)amino)benzoate

Prepared according to General Procedure E starting from 2-chloro-5-methyl-3-nitropyridine (10.0 g, 57.9 mmol) to afford the title compound as a brown solid (16.5 g, 95%).

$^1$H NMR (DMSO-d$_6$) δ 10.01 (s, 1H), 8.48 (d, 1H), 8.44 (d, 1H), 7.93 (d, 2H), 7.85 (d, 2H), 4.30 (q, 2H), 2.33 (s, 3H), 1.33 (t, 3H).

Step 2: ethyl 4-((3-amino-5-methylpyridin-2-yl)amino)benzoate

Prepared according to General Procedure F starting from the compound from Step 1 ethyl 4-((5-methyl-3-nitropyridin-2-yl)amino)benzoate (16.5 g, 54.8 mmol) to afford the title compound as a black solid (13.8 g, 93%).

Step 3: ethyl 4-(6-methyl-3H-[1,2,3]triazolo[4,5-b]pyridin-3-yl)benzoate

Prepared according to General Procedure G starting from the compound from Step 2 ethyl 4-((3-amino-5-methylpyridin-2-yl)amino)benzoate (13.8 g, 50.8 mmol) to afford the title compound as a black solid (13 g, 91%).

Step 4: 4-(6-methyl-3H-[1,2,3]triazolo[4,5-b]pyridin-3-yl)benzoic acid

Prepared according to General Procedure H starting from the compound from Step 3 ethyl 4-(6-methyl-3H-[1,2,3]triazolo[4,5-b]pyridin-3-yl)benzoate (13.0 g, 46.1 mmol) to afford the title compound as a brown solid (10.5 g, 90%).

$^1$H NMR (DMSO-d$_6$) δ 8.78 (s, 1H), 8.54 (s, 1H), 8.48 (d, 2H), 8.24 (d, 2H), 2.56 (s, 3H).

Preparation 7

5-(3H-[1,2,3]triazolo[4,5-b]pyridin-3-yl)pyridine-2-carboxylic acid

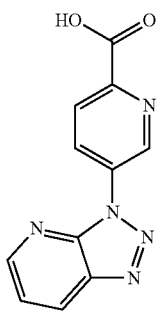 [SMILES: O=C(O)c1ccc(-n2nnc3cccnc32)cn1]

Step 1: ethyl 5-aminopicolinate

To a solution of 5-aminopicolinic acid (13.5 g, 97.7 mmol) in anhydrous ethanol (200 mL) was added SOCl$_2$ (60.0 mL, 504 mmol) dropwise at 0° C. under N$_2$ atmosphere. The resulting mixture was heated at reflux and stirred overnight. The reaction mixture was concentrated in vacuo. The residue was dissolved in a saturated aqueous NaHCO$_3$ solution so that that pH of the solution was approximately pH 9-10. The reaction mixture was extracted with EtOAc (8×250 mL). The combined organic phases were dried over Na$_2$SO$_4$, filtered, and the filtrate was concentrated in vacuo to afford the title compound as a brown solid (14.3 g, 88%)

$^1$H NMR (CDCl$_3$) δ 8.14 (d, 1H), 7.94 (d, 1H), 6.97 (dd, 1H), 4.41 (q, 2H), 4.16 (br s, 2H), 1.39 (t, 3H).

Step 2

Prepared according to General Procedure E starting from the compound from Step 1 ethyl 5-aminopicolinate (13.3 g, 80.0 mmol) and 2-chloro-3-nitropyridine (15.2 g, 95.9 mmol) to give the title compound as a yellow solid (9.3 g, 40%).

$^1$H NMR (CDCl$_3$) δ 10.34 (s, 1H), 8.95 (d, 1H), 8.61-8.55 (m, 2H), 8.47 (dd, 1H), 8.16 (d, 1H), 7.02 (dd, 1H), 4.48 (q, 2H), 1.45 (t, 3H).

Step 3: ethyl 5-((3-aminopyridin-2-yl)amino)picolinate

Prepared according to General Procedure F starting from the compound from Step 2 ethyl 5-((3-nitropyridin-2-yl)

amino)picolinate (9.30 g, 32.3 mmol) to afford the title compound as a yellow solid (quantitative yield).

¹H NMR (CDCl₃) δ 8.53 (d, 1H), 8.14 (dd, 1H), 8.06 (d, 1H), 7.87 (dd, 1H), 7.08 (dd, 1H), 6.87-6.84 (m, 2H), 4.43 (q, 2H), 3.54 (br s, 2H), 1.41 (t, 3H).

Step 4: ethyl 5-(3H-[1,2,3]triazolo[4,5-b]pyridin-3-yl)picolinate

Prepared according to General Procedure G starting from the compound from Step 3 ethyl 5-((3-aminopyridin-2-yl)amino)picolinate (8.70 g, 33.7 mmol) to afford the title compound as a yellow solid (9.0 g, 99%).

¹H NMR (CDCl₃) δ 9.88 (d, 1H), 8.97 (dd, 1H), 8.82 (dd, 1H), 8.51 (dd, 1H), 8.39 (d, 1H), 7.50 (dd, 1H), 4.53 (q, 2H), 1.49 (t, 3H).

Step 5: 5-(3H-[1,2,3]triazolo[4,5-b]pyridin-3-yl)pyridine-2-carboxylic acid

Prepared according to General Procedure H starting from the compound from Step 4 ethyl 5-(3H-[1,2,3]triazolo[4,5-b]pyridin-3-yl)picolinate (9.00 g, 33.4 mmol) to afford the title compound as a red solid (8.1 g, 99%).

¹H NMR (CDCl₃) δ 13.50 (br s, 1H), 9.62 (d, 1H), 8.93-8.87 (m, 2H), 8.77 (d, 1H), 8.36 (d, 1H), 7.68 (dd, 1H).

Preparation 8

5-(6-methyl-3H-[1,2,3]triazolo[4,5-b]pyridin-3-yl)pyridine-2-carboxylic acid

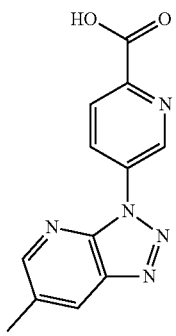 [SMILES: Cc1cnc2c(c1)nnn2-c1ccc(C(=O)O)nc1]

Step 1: ethyl 5-((5-methyl-3-nitropyridin-2-yl)amino)picolinate

Prepared according to General Procedure E starting from ethyl 5-aminopicolinate (14.0 g, 84.2 mmol) and 2-chloro-5-methyl-3-nitropyridine (17.4 g, 101 mmol) to give the title compound as a yellow solid (13.6 g, 53%).

¹H NMR (CDCl₃) δ 10.22 (s, 1H), 8.94 (d, 1H), 8.46-8.40 (m, 3H), 8.15 (d, 1H), 4.47 (q, 2H), 2.39 (s, 3H), 1.45 (t, 3H).

Step 2: ethyl 5-((3-amino-5-methylpyridin-2-yl)amino)picolinate

Prepared according to General Procedure F starting from the compound from Step 1 ethyl 5-((5-methyl-3-nitropyridin-2-yl)amino)picolinate (13.6 g, 45.0 mmol) to afford the title compound as a red solid (12.2 g, 99%).

¹H NMR (CDCl₃) δ 8.43 (d, 1H), 8.01 (d, 1H), 7.88 (dd, 1H), 7.68 (d, 1H), 6.90 (d, 1H), 6.83 (s, 1H), 4.41 (q, 2H), 3.47 (br s, 2H), 2.24 (s, 3H), 1.40 (t, 3H).

Step 3: ethyl 5-(6-methyl-3H-[1,2,3]triazolo[4,5-b]pyridin-3-yl)picolinate

Prepared according to General Procedure G starting from the compound from Step 2 ethyl 5-((3-amino-5-methylpyridin-2-yl)amino)picolinate (12.2 g, 44.8 mmol) to afford the title compound as a red solid (12.6 g, 99%).

¹H NMR (CDCl₃) δ 9.87 (d, 1H), 8.95 (dd, 1H), 8.65 (d, 1H), 8.37 (d, 1H), 8.25 (s, 1H), 4.53 (q, 2H), 2.59 (s, 3H), 1.47 (t, 3H).

Step 4: 5-(6-methyl-3H-[1,2,3]triazolo[4,5-b]pyridin-3-yl)pyridine-2-carboxylic acid Prepared according to General Procedure H starting from the compound from Step 3 ethyl 5-(6-methyl-3H-[1,2,3]triazolo[4,5-b]pyridin-3-yl)picolinate (12.6 g, 44.5 mmol) to afford the title compound as a red solid (10.8 g, 95%).

¹H NMR (DMSO-d₆) δ 13.50 (br s, 1H), 9.60 (d, 1H), 8.87 (dd, 1H), 8.78 (s, 1H), 8.55 (s, 1H), 8.35 (d, 1H), 2.55 (s, 3H).

Preparation 9 tert-butyl (3R)-3-[(4-bromobenzoyl)(isoquinolin-1-yl)amino]piperidine-1-carboxylate

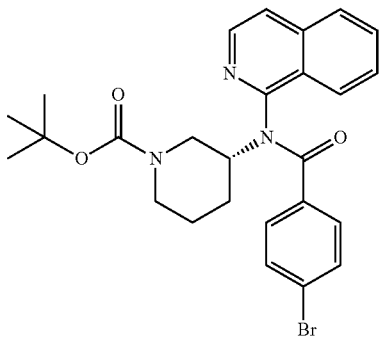 [SMILES: CC(C)(C)OC(=O)N1CCC[C@@H](N(C(=O)c2ccc(Br)cc2)c2nccc3ccccc23)C1]

To a suspension of 4-bromobenzoic acid (3.30 g, 16.4 mmol) in anhydrous DCM (120 mL) was added oxalyl chloride (6.26 g, 49.3 mmol) dropwise at 0° C. followed by 3 drops of DMF. The resulting mixture was stirred at room temperature for 2 h. The mixture was then concentrated in vacuo to give 4-bromobenzoyl chloride as a yellow solid. The solid was dissolved in anhydrous THF (40 mL) and a solution of Preparation 3 tert-butyl (3R)-3-(isoquinolin-1-ylamino)piperidine-1-carboxylate (4.89 g, 14.9 mmol) in anhydrous THF (50 mL) was added. The resulting solution was treated with lithium bis(trimethylsilyl)amide (44.8 mL, 44.8 mmol, 1 M) dropwise at 0° C. The reaction mixture was stirred at room temperature overnight. The mixture was poured into water and extracted with EtOAc (4×100 mL). The combined organic layers were dried over Na₂SO₄, filtered, and the filtrate was concentrated under reduced pressure. The crude product was purified by silica gel chromatography eluting with a gradient of (0-25%) EtOAc/petroleum ether to afford the title compound (4.80 g, 63%) as a yellow solid.

¹H NMR (400 MHz, CDCl₃, mixture of rotomers) δ 8.42 (s, 1H), 7.98-7.83 (m, 1H), 7.73 (d, 1H), 7.65-7.47 (m, 3H), 7.10-7.06 (m, 4H), 4.94-4.45 (m, 2H), 4.26-3.91 (m, 1.5H), 3.50-3.45 (m, 0.5H), 2.65-2.15 (m, 2H), 1.86-1.56 (m, 3H), 1.52 & 1.43 (s, 9H).

Preparation 10 tert-butyl (3R)-3-[(4-bromobenzoyl)(3-chloropyridin-2-yl)amino]piperidine-1-carboxylate

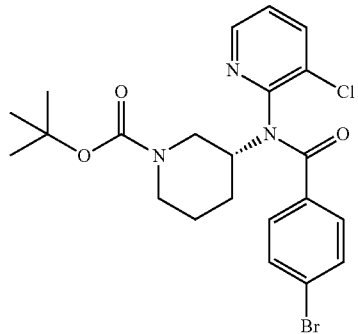 [SMILES: CC(C)(C)OC(=O)N1CCC[C@@H](N(C(=O)c2ccc(Br)cc2)c2ncccc2Cl)C1]

Preparation 1 tert-Butyl (3R)-3-[(3-chloropyridin-2-yl)amino]piperidine-1-carboxylate (214.4 g, 687.7 mmol) was dissolved in 260 mL of THF and the resulting suspension was cooled to −10° C. Lithium bis(trimethylsilyl)amide (1 mol/L in THF, 687.7 mL, 687.1 mmol) was added over 25 min followed by warming to 20° C. and stirring for 1 h before cooling back to −10° C. 4-Bromobenzoyl chloride (140.0 g, 625.2 mmol) was added as a solution in 230 mL of THF over 1.5 h, maintaining the internal temperature at less than −7° C. After complete addition, the reaction mixture was warmed to 0° C. at which point HPLC indicated the reaction was complete. MeOH was added (101 mL), then the reaction was warmed to room temperature and concentrated in vacuo to a low volume. The solvent was then exchanged to 2-MeTHF. The crude product solution (700 mL in 2-MeTHF) was washed with 700 mL of half-saturated aqueous NaHCO$_3$, followed by 200 mL of half-saturated brine. The 2-MeTHF solution was concentrated to a low volume followed by addition of 400 mL of heptane resulting in precipitation of solids which were collected via filtration. The collected solids were dried to afford the title compound as a tan powder (244 g, 79% yield).

$^1$H NMR (acetonitrile-d$_3$) δ 8.57-8.41 (m, 1H), 7.85-7.62 (m, 1H), 7.37 (d, 2H), 7.31 (dd, 1H), 7.23 (d, 2H), 4.63-4.17 (m, 2H), 4.06-3.89 (m, 1H), 3.35-3.08 (br s, 0.5H), 2.67-2.46 (m, 1H), 2.26-2.10 (br s, 0.5H), 1.92-1.51 (m, 3H), 1.46 (s, 9H), 1.37-1.21 (m, 1H).

UPLC (UPLC Method 4): t$_R$=7.03 min.

Alternative Method for Preparation 10:

To a solution of Preparation 1 (R)-tert-butyl 3-((3-chloropyridin-2-yl)amino)piperidine-1-carboxylate (100 g, 321 mmol) and 4-bromobenzoyl chloride (73.7 g, 336 mmol) in dry THF (500 mL) was added 1 M lithium bis(trimethylsilyl)amide (362 mL, 362 mmol) dropwise at 0° C. The reaction mixture was warmed and stirred at room temperature overnight. The reaction was quenched with water and extracted with EtOAc (3×1000 mL). The combined organic layers were washed with brine, dried over Na$_2$SO$_4$, filtered and the filtrate was concentrated in vacuo. The residue was purified by chromatography on silica gel to give afford the title compound as a yellow solid (100 g, 63%).

$^1$H NMR (CDCl$_3$) δ 8.43 (br s, 1H), 7.56 (br s, 1H), 7.28-7.14 (m, 5H), 4.48 (br s, 2H), 4.24 (br s, 1H), 4.09 (br s, 1H), 3.28 (br s, 1H), 2.54 (br s, 1H), 2.27 (br s, 1H), 1.63-1.54 (br m, 1H), 1.46 (br s, 10H).

Preparation 11 tert-butyl (3R)-3-[(4-bromobenzoyl)(1-methyl-1H-pyrrolo[2,3-c]pyridin-7-yl)amino]piperidine-1-carboxylate

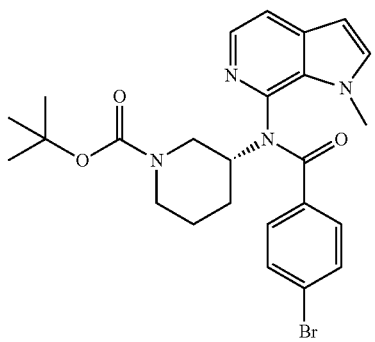 [SMILES: Cn1ccc2ccnc(N(C(=O)c3ccc(Br)cc3)[C@@H]3CCCN(C(=O)OC(C)(C)C)C3)c21]

To a solution of Preparation 4 (R)-tert-butyl 3-((1-methyl-1H-pyrrolo[2,3-c]pyridin-7-yl)amino)piperidine-1-carboxylate (45.0 g, 136 mmol) and 4-bromobenzoyl chloride (31.3 g, 143 mmol) in dry THF (250 mL) was added 1 M lithium bis(trimethylsilyl)amide (163 mL, 163 mmol) dropwise at 0° C. The reaction mixture was warmed to room temperature and stirred for 15 h. The reaction was quenched with aqueous NH$_4$Cl and extracted with EtOAc (3×500 mL). The combined organic layers were washed with brine, dried over Na$_2$SO$_4$, filtered, and the filtrate was concentrated in vacuo. The residue was purified by recrystallization (petroleum ether: EtOAc=2:1) to afford the title compound as an off-white solid (50 g, 72%).

$^1$H NMR (CDCl$_3$) δ 8.13 (d, 1H), 7.43 (br s, 1H), 7.14 (br s, 4H), 6.99 (br s, 1H), 6.38 (br s, 1H), 4.75-4.65 (br m, 2H), 4.11 (br s, 1H), 3.96-3.82 (br m, 4H), 3.45 (br 2, 1 H), 2.61 (br s, 1H), 2.25 (br s, 1H) 1.78 (br s, 1H), 1.41 (br s, 10H).

Preparation 12 tert-butyl (3R)-3-[(4-bromobenzoyl)(3-methylpyridin-2-yl)amino]piperidine-1-carboxylate

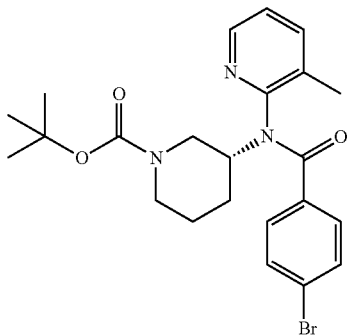 [SMILES: Cc1cccnc1N(C(=O)c1ccc(Br)cc1)[C@@H]1CCCN(C(=O)OC(C)(C)C)C1]

To a solution of Preparation 2 (R)-tert-butyl 3-((3-methylpyridine-2-yl)amino)piperidine-1-carboxylate (33.3 g, 114 mmol) and 4-bromobenzoyl chloride (26.3 g, 120 mmol) in dry THF (300 mL) was added 1 M lithium bis(trimethylsilyl) amide (137 mL, 137 mmol) dropwise at 0° C. The reaction mixture was warmed and stirred at room temperature for 16 h. The reaction was quenched with water and extracted with EtOAc (3×1000 mL). The combined organic layers were washed with brine, dried over $Na_2SO_4$, filtered, and the filtrate was concentrated in vacuo. The residue was purified by silica gel chromatography to afford the title compound as a yellow solid (27 g, 50%).

$^1$H NMR (CDCl$_3$) δ 8.41 (br s, 1H), 7.34 (br s, 1H), 7.25 (d, 2H), 7.16-7.14 (m, 3H), 4.65 (br s, 1H), 4.48 (br d, 1H), 4.15-4.04 (br m, 2H), 3.39 (br s, 1H), 2.55 (br s, 1H), 2.37 (br s, 1H), 2.01-1.98 (br d, 3H), 1.74 (br s, 1H), 1.47-1.43 (br d, 10H).

Preparation 13 ethyl 4-iodo-1-methyl-1H-pyrazole-5-carboxylate

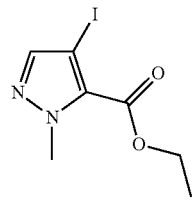

4-Iodo-1-methyl-1H-pyrazole-5-carboxylic acid (301.68 g, 1.2 moles) was slurried in 1.2 L of DCM and DMF (2.3 g, 31 mmol) followed by addition of oxalyl chloride (115 mL, 1.3 moles) over 37 minutes and then stirred at room temperature for 3 h. To the resulting solution was added EtOH (750 mL, 12.9 mol) over 5 min followed by stirring at room temperature for 2 h. The crude product solution was concentrated to dryness in vacuo and then reconstituted in 1.2 L of warm heptane followed by filtration. The filtrate was concentrated by removing 500 mL of heptane, resulting in precipitation of solids. The solids were collected via filtration and dried to afford ethyl 4-iodo-1-methyl-1H-pyrazole-5-carboxylate as a white solid (297.6 g, 89% yield).

$^1$H NMR (CDCl$_3$) δ 7.57 (s, 1H), 4.43 (q, 2H), 4.21 (s, 3H), 1.47 (t, 3H).

UPLC (UPLC Method 4): $t_R$=5.10 min.
MS (ES+) 280.9 (M+H)$^+$

Preparation 14 tert-butyl (3R)-3-[(3-methyl-1-oxidopyridin-2-yl)amino]piperidine-1-carboxylate

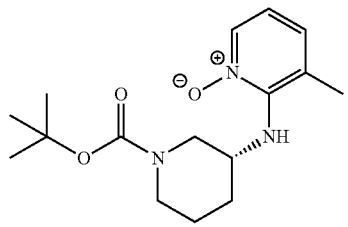 [SMILES: Cc1ccc[n+]([O-])c1N[C@@H]1CCCN(C(=O)OC(C)(C)C)C1]

Step 1: 2-chloro-3-methylpyridine 1-oxide

To a mixture of 2-chloro-3-methylpyridine (15 g, 118 mmol) and urea hydrogen peroxide (44.07 g, 468.5 mmol) in DCM (300 mL) was added trifluoroacetic anhydride (98.55 g, 469.2 mmol) dropwise at 0° C. The mixture was stirred at room temperature for 20 h. The mixture was then poured into water (150 mL), and the layers were separated. The organic layer was washed with saturated aqueous $Na_2S_2O_3$ (20 mL), dried over $Na_2SO_4$, filtered, and the filtrate was concentrated under reduced pressure. The crude product was purified by silica gel flash chromatography (DCM:MeOH, 100:0 to 10:1) to afford the title compound (14.5 g, 86%) as a colorless solid.

$^1$H NMR (400 MHz, CDCl$_3$) δ 8.41 (d, 1H), 7.39 (d, 1H), 7.27 (m, 1H), 2.50 (s, 3H).

Step 2: (R)-2-(1-(tert-butoxycarbonyl)piperidin-3-ylamino)-3-methylpyridine 1-oxide To a solution of the compound from Step 1 2-chloro-3-methylpyridine 1-oxide (14.5 g, 101 mmol) and tert-butyl (3R)-3-aminopiperidine-1-carboxylate (24.27 g, 121.2 mmol) in n-BuOH (120 mL) were added diisopropylethyl amine (14.35 g, 111 mmol) and DMAP (1.22 g, 9.99 mmol) slowly at 0° C. The resulting mixture was heated at 100° C. for 36 h. The reaction was cooled, and water was added. The mixture was then extracted with EtOAc (3×50 mL). The combined organic layers were dried over $Na_2SO_4$, filtered, and the filtrate was concentrated under reduced pressure. The crude compound was purified by silica gel chromatography eluting with a gradient of petroleum ether:EtOAc (80:20 to 50:50) to afford the title compound (7.9 g, 25%) as a yellow oil.

$^1$H NMR (400 MHz, CDCl$_3$) δ 8.05 (d, 1H), 7.13 (br s, 1H), 6.97 (d, 1H), 6.59 (dd, 1H), 4.09-3.93 (m, 1H), 3.90-3.77 (m, 1H), 3.74-3.63 (m, 1H), 2.98-2.86 (m, 1H), 2.85-2.75 (m, 1H), 2.42 (s, 3H), 2.14-2.06 (m, 1H), 1.83-1.74 (m, 1H), 1.57-1.48 (m, 2H), 1.45 (s, 9H).

Preparation 15 tert-butyl (3R)-3-[(2-oxidoisoquinolin-1-yl)amino]piperidine-1-carboxylate

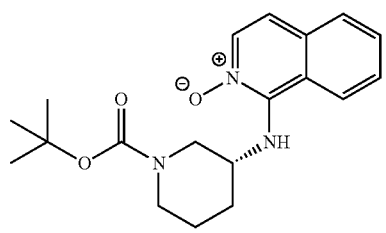 [SMILES: CC(C)(C)OC(=O)N1CCC[C@@H](Nc2c3ccccc3cc[n+]2[O-])C1]

Step 1: 1-chloroisoquinoline 2-oxide

To a solution of 1-chloroisoquinoline (3.0 g, 18 mmol) in DCM (50 mL) was added m-CPBA (9.5 g, 55 mmol). The mixture was stirred at room temperature for 48 h. The mixture was diluted with DCM, and then washed with brine, dried over $Na_2SO_4$, filtered, and the filtrate was concentrated under reduced pressure. The resulting residue was purified by silica gel flash column chromatography eluting with a gradient of petroleum ether: EtOAc (5:1 to 0:1) to afford the title compound (1.2 g, 36%) as a yellow solid.

$^1$H NMR (400 MHz, DMSO-d$_6$) δ 8.38 (d, 1H), 8.05 (d, 2H), 7.98 (d, 1H), 7.82 (dd, 1H), 7.72 (dd, 1H).

Step 2: tert-butyl (3R)-3-[(2-oxidoisoquinolin-1-yl)amino]piperidine-1-carboxylate To a solution of the compound from Step 2 1-chloroisoquinoline 2-oxide (1.2 g, 6.68 mmol) and tert-butyl (3R)-3-aminopiperidine-1-carboxylate (2.0 g, 10.02 mmol) in n-BuOH (20 mL) was added DIPEA (0.95 g, 7.35 mmol) and DMAP (81 mg, 0.668 mmol). The mixture was stirred at 120° C. for 16 h. The mixture was then poured into water (20 mL) and extracted with EtOAc (3×10 mL). The combined layers organic were dried over $Na_2SO_4$, filtered, and the filtrate was concentrated in vacuo. The crude product was purified by silica gel flash column chromatography eluting with a gradient of petroleum ether: EtOAc (1:1 to 0:1) to afford the title compound (0.8 g, 35%).

$^1$HNMR (400 MHz, DMSO-$d_6$) δ 8.31 (d, 1H), 8.02 (d, 1H), 7.92-7.90 (m, 1H), 7.76-7.70 (m, 2H), 7.33 (d, 1H), 4.39 (s, 1H), 3.91-3.83 (m, 1H), 3.50-3.37 (m, 3H), 2.15-2.11 (m, 1H), 1.84 (s, 2H), 1.60 (s, 1H), 1.47-1.32 (m, 9H).

LC (LC-MS Method 3), $t_R$=1.15 min
MS (ES+) 344.3 (M+H)$^+$

Preparation 16 tert-butyl (3R)-3-{isoquinolin-1-yl[4-(4,4,5,5-tetramethyl-1,3,2-dioxaborolan-2-yl)benzoyl]amino}piperidine-1-carboxylate

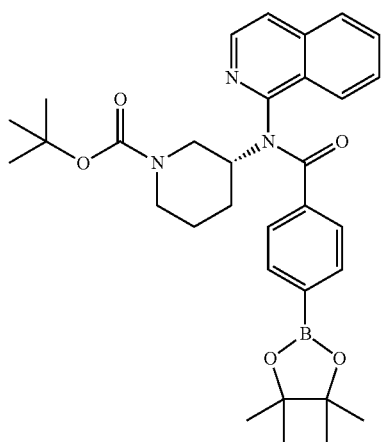 [SMILES: CC(C)(C)OC(=O)N1CCC[C@@H](N(C(=O)c2ccc(B3OC(C)(C)C(C)(C)O3)cc2)c2nccc3ccccc23)C1]

To a suspension of Preparation 9 tert-butyl (3R)-3-[(4-bromobenzoyl)(isoquinolin-1-yl)amino]-piperidine-1-carboxylate (3.7 g, 7.2 mmol), bis(pinacolato)diboron (3.68 g, 14.5 mmol) and KOAc (2.14 g, 21.8 mmol) in 1,4-dioxane (25 mL) was added PdCl$_2$(dppf) (0.53 g, 0.73 mmol). The resulting mixture was purged with N$_2$ and heated at 80-90° C. for 4 h. The reaction was cooled and concentrated under reduced pressure. The crude compound was purified by silica gel flash chromatography eluting with a gradient of petroleum ether: EtOAc (50:1 to 1.5:1) to give a yellow gum. The yellow gum was triturated with petroleum ether and filtered to afford the title compound (3.8 g, 94%) as a white solid.

$^1$H NMR (400 MHz, MeOH-$d_4$, mixture of rotomers) δ 8.46 (br s, 0.75H), 8.38 (br s, 0.25H), 8.08 (br s, 0.25H), 7.99 (br s, 0.75H), 7.83 (br s, 1H), 7.79-7.61 (m, 4H), 7.33 (br s, 2H), 7.21 (br s, 2H), 4.65-4.58 (m, 1H), 4.28-4.25 (m, 1H), 4.04-3.96 (m, 1H), 3.45-3.40 (m, 1H), 2.67-2.55 (m, 1H), 2.30-2.09 (m, 1H), 1.87-1.84 (m, 1H), 1.51 (s, 5.4H), 1.42 (s, 3.6H), 1.26 (s, 7.2H), 1.22 (s, 4.8H).

Preparation 17 tert-butyl (3R)-3-{(3-chloropyridin-2-yl)[4-(4,4,5,5-tetramethyl-1,3,2-dioxaborolan-2-yl)benzoyl]amino}piperidine-1-carboxylate

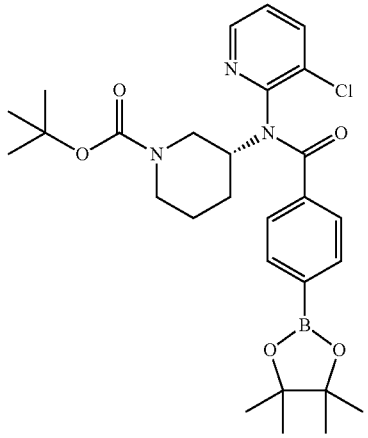 [SMILES: CC(C)(C)OC(=O)N1CCC[C@@H](N(C(=O)c2ccc(B3OC(C)(C)C(C)(C)O3)cc2)c2ncccc2Cl)C1]

To a solution of Preparation 10 (R)-tert-butyl 3-(4-bromo-N-(3-chloropyridin-2-yl)benzamido)piperidine-1-carboxylate (40.0 g, 80.8 mmol) in 1,4-dioxane (250 mL) were added bis(pinacolato)diboron (41.1 g, 162 mmol), KOAc (23.8 g, 244 mmol) and PdCl$_2$(dppf) (5.9 g, 8.1 mmol). The resulting mixture was purged with N$_2$ and stirred at 80-90° C. for 10 h. The reaction was cooled and filtered. The organic solution was concentrated in vacuo. The residue was purified by silica gel column chromatography, eluting with a gradient of 2-25% EtOAc/petroleum ether to give the title compound as a yellow gum. The yellow gum was triturated with petroleum ether to afford the title compound as a white solid (30 g, 69%).

$^1$H NMR (MeOH-$d_4$) δ 8.52 (br s, 1H), 7.74 (br s, 1H), 7.55 (br s, 2H), 7.31 (br s, 3H), 4.53 (br s, 1H), 4.30 (br s, 1H), 4.05-4.02 (br m, 1H), 2.80-2.29 (br m, 2H), 1.95-1.68 (m, 3H), 1.50 (br s, 10H), 1.32 (br s, 12H).

Preparation 18 tert-butyl 3-[(3-chloropyridin-2-yl){4-[5-(ethoxycarbonyl)-1-methyl-1H-pyrazol-4-yl]benzoyl}amino]piperidine-1-carboxylate

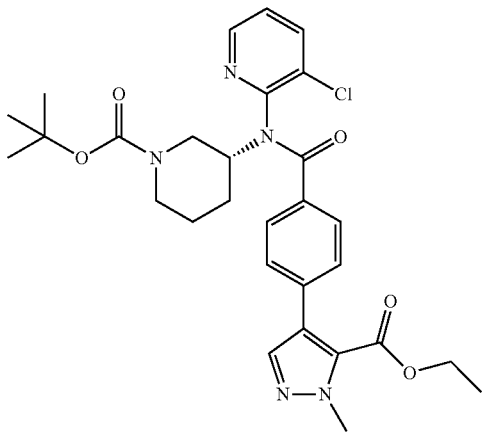 [SMILES: CCOC(=O)c1c(-c2ccc(C(=O)N(c3ncccc3Cl)[C@@H]3CCCN(C(=O)OC(C)(C)C)C3)cc2)cnn1C]

Preparation 13 ethyl 4-iodo-1-methyl-1H-pyrazole-5-carboxylate (108.5 g, 387.4 mmol) was dissolved in 1 L of THF and the resulting solution was cooled to −52° C. Isopropylmagnesium chloride (2 mol/L solution in THF, 200 mL, 400 mmol) was added over 27 minutes keeping the internal temperature <−39° C., followed by addition of zinc chloride (1.9 mol/L in 2-MeTHF, 120 mL, 230 mmol) over 15 minutes keeping the internal temperature <−39° C. The reaction was then warmed to 40° C. followed by addition of Preparation 10 tert-butyl (3R)-3-[(4-bromobenzoyl)(3-chloropyridin-2-yl)amino]piperidine-1-carboxylate (158.27 g, 319.9 mmol) and 1,1'-bis(di-tert-butylphosphino)ferrocene palladium dichloride (4.60 g, 6.92 mmol). The reaction was warmed further to 55° C. and held for 2 h. After cooling to room temperature, the crude reaction mixture was filtered through Celite® and the filtrate was concentrated to give a foam. This material was re-dissolved in 1 L of 2-MeTHF and washed with 400 mL of water followed by filtration of the biphasic mixture and phase separation. 2-MeTHF was removed in vacuo and replaced with EtOH, then the solution was concentrated to a final volume of 1.5 L, resulting in precipitation of solids which were collected via filtration. After drying, the title compound was isolated as a tan solid (141.5 g, 78% yield).

$^1$H NMR (acetonitrile-$d_3$) δ 8.56-8.44 (m, 1H), 7.81-7.64 (m, 1H), 7.48 (s, 1H), 7.41-7.31 (m, 2H), 7.30 (dd, 1H), 7.29-7.18 (m, 2H), 4.68-4.23 (m, 2H), 4.18 (q, 2H), 4.10 (s, 3H), 4.06-3.90 (m, 1H), 3.40-3.08 (br s, 0.5H), 2.69-2.45 (m, 1H), 2.3-2.08 (br s, 0.5H), 1.93-1.51 (m, 3H), 1.47 (s, 9H), 1.38-1.21 (br s, 1H), 1.08 (t, 3H).

UPLC (UPLC Method 4): $t_R$=6.73 min.
MS (ES+) 468.1 (M+H)$^+$

Preparation 19

4-(pyrazolo[1,5-a]pyrimidin-3-yl)benzoic acid

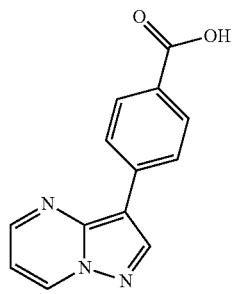 [SMILES: O=C(O)c1ccc(-c2cnn3cccnc23)cc1]

Step 1: ethyl 4-(pyrazolo[1,5-a]pyrimidin-3-yl)benzoate

Water (160 mL) was added dropwise at room temperature to a mixture of 4-ethoxycarbonylphenylboronic acid (50 g, 0.26 mol), 3-bromopyrazolo[1,5-a]pyrimidine (56.25 g, 0.28 mol), Pd(ddpf)Cl$_2$.CH$_2$Cl$_2$ (4.25 g, 5.21 mmol), and Cs$_2$CO$_3$ (169.42 g, 0.52 mol) in 1,4-dioxane (1 L). The reaction mixture was then heated 85° C. for 4 h. The reaction mixture was cooled, poured into water and extracted with EtOAc (2×300 mL). The combined organic layers were dried over Na$_2$SO$_4$, filtered, and the filtrate was concentrated under reduced pressure. The crude product was purified by silica gel chromatography eluting with a gradient of petroleum ether: EtOAc (100:10 to 3:1) to deliver the title compound (64 g, 93%) as a yellow solid.

$^1$H NMR (400 MHz, CDCl$_3$) δ 8.73 (d, 1H), 8.63 (d, 1H), 8.52 (s, 1H), 8.20-8.09 (m, 4H), 6.92 (dd, 1H), 4.41 (q, 2H), 1.43 (t, 3H).

Step 2: 4-(pyrazolo[1,5-a]pyrimidin-3-yl)benzoic acid

To a mixture of the compound form Step 1 ethyl 4-(pyrazolo[1,5-a]pyrimidin-3-yl)benzoate (64 g, 0.24 mol) in MeOH (1 L) was added an aqueous solution of sodium hydroxide (600 mL, 1.2 mol, 2 M). The mixture was heated at 50° C. for 3 h. The mixture was then concentrated to remove the volatiles. The resulting suspension was diluted with water, and aqueous HCl (1 N) was added dropwise until pH 4. The acidified suspension was filtered, and the solids were collected and dried to give the title compound (57 g, 99%) as a yellow solid.

$^1$H NMR (400 MHz, DMSO-$d_6$) δ 12.83 (br, 1H), 9.21 (d, 1H), 8.88 (s, 1H), 8.73 (d, 1H), 8.30 (d, 2H), 8.00 (d, 2H), 7.18-7.16 (m, 1H).

LC (LC-MS Method 3) $t_R$=0.78 min
MS (ES+) 238 (M+H)$^+$

Preparation 20

4-iodo-1-methyl-1H-pyrazole-5-carboxamide

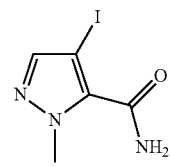

A round-bottom flash was charged with 4-iodo-1-methyl-1H-pyrazole-5-carboxylic acid (297 g, 1.18 mol), DCM (2.97 L), and 1,1'-carbonyldiimidazole (CDI) (207 g, 97% by mass, 1.24 mol). The reaction mixture was stirred at room temperature for 45 min. Ammonium chloride (189 g, 3.53 mol) and triethylamine (498 mL, 3.53 mol) were added and the reaction mixture was stirred at room temperature overnight. The reaction mixture was concentrated in vacuo and the residue was suspended in H$_2$O (~3 L) and granulated at room temperature for 1 h. The solid was collected via filtration, washed with H$_2$O, and dried in a vacuum oven to afford 4-iodo-1-methyl-1H-pyrazole-5-carboxamide as a colorless solid (222 g, 75% yield).

$^1$H NMR (CDCl$_3$) δ: 7.53 (s, 1H), 6.56 (br s, 1H), 6.01 (br s, 1H), 4.21 (s, 3H).

UPLC (UPLC-MS Method 1): $t_R$=0.15 min.
MS (ES+): 251.1 (M+H)$^+$.

Preparation 21

4-iodo-1-methyl-1H-pyrazole-5-carbonitrile

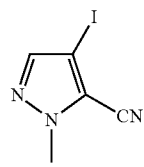

A round-bottom flash was charged with Preparation 20, 4-iodo-1-methyl-1H-pyrazole-5-carboxamide (222 g, 886 mmol) and DCM (2.22 L) and the reaction mixture was cooled to 0° C. 2,6-Lutidine (310 mL, 2.66 mol) and trifluoroacetic anhydride (253 mL, 1.77 mol) were added. After reaction was complete, saturated aqueous sodium bicarbonate (800 mL) was added and the layers separated. The aqueous layer was washed with DCM (800 mL). The organic layers were combined and washed with saturated aqueous ammonium chloride (800 mL), 1N HCl (800 mL), and brine (800 mL). The organic layer was dried over magnesium sulfate, filtered, and concentrated in vacuo. The residue was suspended in heptanes (~2 L) and granulated at 0-5° C. for 30 min. The solid was collected via filtration and dried in a vacuum oven to afford 4-iodo-1-methyl-1H-pyrazole-5-carbonitrile as a colorless solid (196 g, 95% yield).

$^1$H NMR (CDCl$_3$) δ: 7.60 (s, 1H), 4.09 (s, 3H).
UPLC (UPLC-MS Method 1): t$_R$=0.70 min.
MS (ES+): 233.8 (M+H)$^+$.

Preparation 22

5-(4-iodo-1-methyl-1H-pyrazol-5-yl)-2H-tetrazole

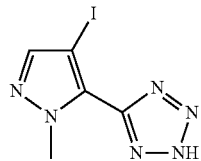

Caution: This reaction generates hydrazoic acid and requires appropriate safety measures.

A reaction vessel was charged with DMF (1.225 L), Preparation 21, 4-iodo-1-methyl-1H-pyrazole-5-carbonitrile (175 g, 751 mmol), sodium azide (147 g, 2.25 mol), and ammonium chloride (121 g, 2.25 mol). H$_2$O (525 mL) was added slowly to minimize exotherm. The reaction mixture was heated at 100° C. overnight. The reaction mixture was cooled to room temperature and poured into a mixture of H$_2$O (2 L) and ice (1 kg). An aqueous solution of NaNO$_2$ (600 mL, 120 g NaNO$_2$, 20% by weight) was added followed by the slow addition of aqueous H$_2$SO$_4$ until the pH of the reaction mixture was 1. The precipitate was collected via filtration, washed with H$_2$O and dried in vacuo to afford 5-(4-iodo-1-methyl-1H-pyrazol-5-yl)-2H-tetrazole as a colorless solid (187 g, 90%).

Alternative Method for Preparation 22:

To a solution of Preparation 21, 4-iodo-1-methyl-1H-pyrazole-5-carbonitrile (500 mg, 2.15 mmol) in 2-methyl tetrahydrofuran (4 mL) was added P$_2$S$_5$ (24 mg, 0.11 mmol) followed by hydrazine monohydrate (523 μL, 10.7 mmol). The reaction mixture was heated in a sealed vial at 70° C. for 17 h. The reaction mixture was added slowly to heptane with vigorous stirring until an oily precipitate formed. The mother liquor was decanted away and the residue triturated with heptane and dried under vacuum to afford a light yellow solid (520 mg). The residue was dissolved in EtOH (5 mL). HCl (2.0 mL, 3.0 M aqueous solution) was added followed by NaNO$_2$ (405 mg, 5.88 mmol) dissolved in H$_2$O (1.5 mL) dropwise to control exotherm and gas evolution. The reaction mixture was concentrated in vacuo to a volume of ~3 mL. H$_2$O (20 mL) and DCM (15 mL) were added, followed by saturated aqueous NaHCO$_3$ (5 mL) to make the pH of the solution >7. The reaction mixture was partitioned and the organic layer discarded. The aqueous layer was acidified to pH 1 with 6M HCl. The reaction mixture was extracted with EtOAc (2×40 mL). The combined organic layers were dried with MgSO$_4$ and concentrated in vacuo to afford 5-(4-iodo-1-methyl-1H-pyrazol-5-yl)-2H-tetrazole as an off-white solid (390 mg, 66%).

$^1$H NMR (MeOH-d$_4$) δ: 7.69 (s, 1H), 4.08 (s, 3H).
UPLC (UPLC-MS Method 1): t$_R$=0.52 min.
MS (ES+): 276.9 (M+H)$^+$.

Preparation 23 ethyl 1-[5-(4-iodo-1-methyl-1H-pyrazol-5-yl)-2H-tetrazol-2-yl]ethyl carbonate

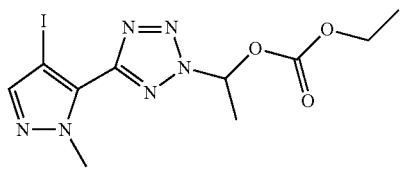 [SMILES: CCOC(=O)OC(C)n1nnc(-c2c(I)cnn2C)n1]

A round-bottom flask was charged with Preparation 22, 5-(4-iodo-1-methyl-1H-pyrazol-5-yl)-2H-tetrazole (191 g, 692 mmol), 4-dimethylaminopyridine (4.27 g, 34.6 mmol), THF (1.72 L), acetaldehyde (43 mL, 760 mmol), and triethylamine (107 mL, 762 mmol). The reaction solution was stirred and then ethyl chloroformate (86.2 mL, 97% by mass, 692 mmol) was added. The reaction mixture was stirred overnight at room temperature. The reaction mixture was diluted with EtOAc (965 mL) and H$_2$O (965 mL). The layers were separated. The aqueous layer was extracted with EtOAc (965 mL). The combined organic layers were dried over magnesium sulfate and concentrated in vacuo to afford ethyl 1-[5-(4-iodo-1-methyl-1H-pyrazol-5-yl)-2H-tetrazol-2-yl]ethyl carbonate as a colorless oil (261 g, 96% yield).

Preparation 23a and 23b

23a: (S)-ethyl 1-[5-(4-iodo-1-methyl-1H-pyrazol-5-yl)-2H-tetrazol-2-yl]ethyl carbonate

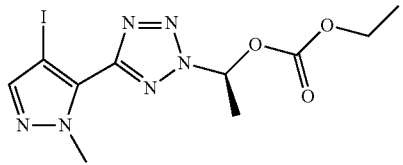 [SMILES: CCOC(=O)O[C@@H](C)n1nnc(-c2c(I)cnn2C)n1]

23b: (R)-ethyl 1-[5-(4-iodo-1-methyl-1H-pyrazol-5-yl)-2H-tetrazol-2-yl]ethyl carbonate

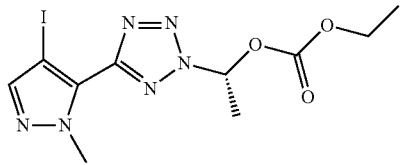 [SMILES: CCOC(=O)O[C@H](C)n1nnc(-c2c(I)cnn2C)n1]

407.5 g of Preparation 23, ethyl 1-[5-(4-iodo-1-methyl-1H-pyrazol-5-yl)-2H-tetrazol-2-yl]ethyl carbonate was processed according to Chiral Preparative Chromatography Method 3, followed by concentration of each enantiomer to dryness in vacuo to give isomer 23a (177.4 g, 99.22%, 99.79% e.e.; $t_R$=2.12 min) and isomer 23b (177.74 g, 98.83%, 98.46% e.e; $t_R$=2.59 min).

$^1$H NMR (MeOH-d$_4$) δ: 7.63 (s, 1H), 7.28 (q, 1H), 4.32-4.24 (m, 2H), 4.23 (s, 3H), 2.10 (d, 3), 1.33 (t, 3H).

UPLC (UPLC-MS Method 1): $t_R$=0.87 min.

MS (ES+): 393.0 (M+H)$^+$.

Figure 8:
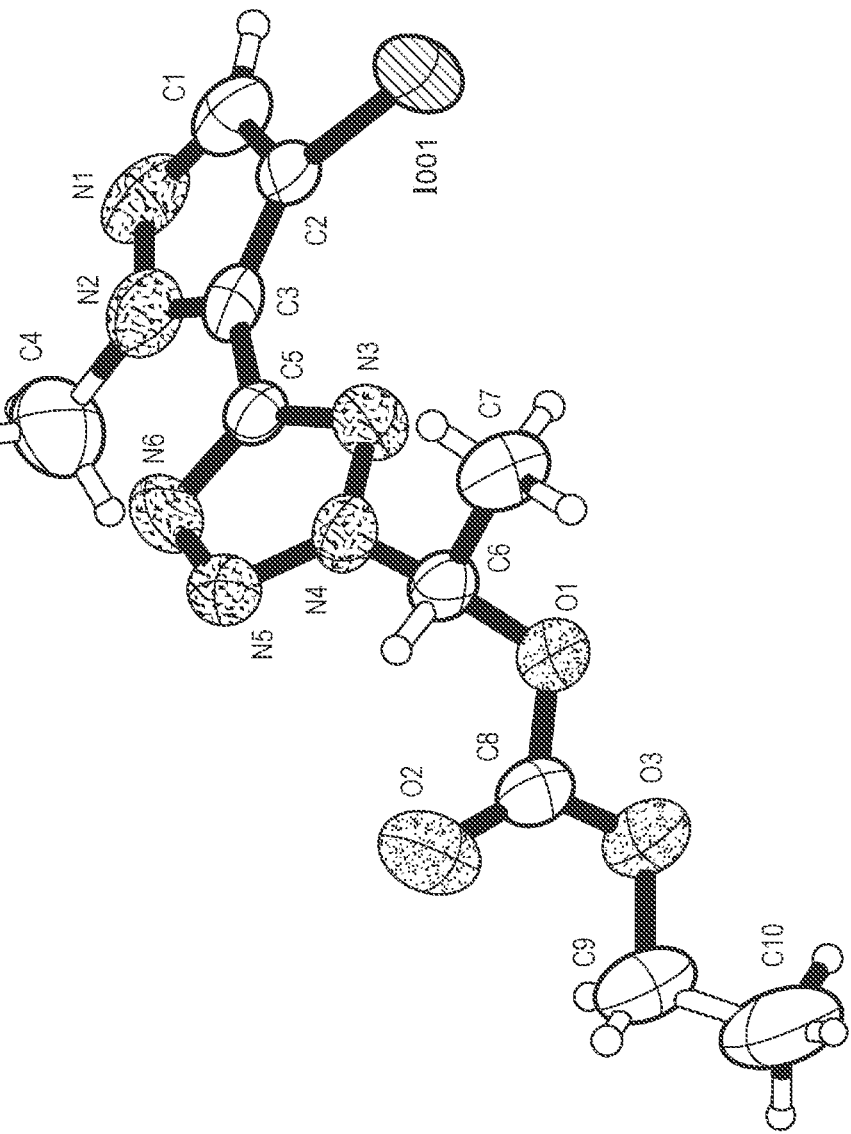

FIG. 8 is an ORTEP drawing of (S)-ethyl 1-[5-(4-iodo-1-methyl-1H-pyrazol-5-yl)-2H-tetrazol-2-yl]ethyl carbonate (23a).

Single Crystal X-Ray Analysis for (S)-ethyl 1-[5-(4-iodo-1-methyl-1H-pyrazol-5-yl)-2H-tetrazol-2-yl]ethyl carbonate (23a): Data collection was performed on a Bruker APEX diffractometer at room temperature. Data collection consisted of omega and phi scans. The structure was solved by direct methods using SHELX software suite in the space group P2$_1$. The structure was subsequently refined by the full-matrix least squares method. All non-hydrogen atoms were found and refined using anisotropic displacement parameters.

All hydrogen atoms were placed in calculated positions and were allowed to ride on their carrier atoms. The final refinement included isotropic displacement parameters for all hydrogen atoms. Absolute configuration was determined be examination of the Flack parameter. In this case, the parameter=0.0396 with an esd of 0.003. These values are within range for absolute configuration determination.

The final R-index was 3.5%. A final difference Fourier revealed no missing or misplaced electron density.

Pertinent crystal, data collection and refinement are summarized in Table 2.

TABLE 2

Crystal data and structure refinement for (S)-ethyl 1-[5-(4-iodo-1-methyl-1H-pyrazol-5-yl)-2H-tetrazol-2-yl]ethyl carbonate.

| | |
|---|---|
| Empirical formula | C10 H13 I N6 O3 |
| Formula weight | 392.16 |
| Temperature | 293(2) K |
| Wavelength | 1.54178 Å |
| Crystal system | Monoclinic |
| Space group | P2(1) |
| Unit cell dimensions | a = 4.5885(4) Å   α = 90°. |
| | b = 10.0115(9) Å   β = 90.413(5)°. |
| | c = 16.2053(13) Å   γ = 90°. |
| Volume | 744.42(11) Å$^3$ |
| Z | 2 |
| Density (calculated) | 1.750 Mg/m$^3$ |
| Absorption coefficient | 17.076 mm$^{-1}$ |
| F(000) | 384 |
| Crystal size | 0.31 × 0.1 × 0.08 mm$^3$ |
| Theta range for data collection | 5.19 to 70.22°. |
| Index ranges | −5 <= h <= 5, −12 <= k <= 11, −18 <= l <= 18 |
| Reflections collected | 12126 |
| Independent reflections | 2625 [R(int) = 0.0527] |
| Completeness to theta = 70.22° | 95.5% |
| Absorption correction | None |
| Refinement method | Full-matrix least-squares on F$^2$ |
| Data/restraints/parameters | 2625/1/184 |
| Goodness-of-fit on F$^2$ | 1.039 |
| Final R indices [I > 2sigma(I)] | R1 = 0.0355, wR2 = 0.0787 |

TABLE 2-continued

Crystal data and structure refinement for (S)-ethyl 1-[5-(4-iodo-1-methyl-1H-pyrazol-5-yl)-2H-tetrazol-2-yl]ethyl carbonate.

| | |
|---|---|
| R indices (all data) | R1 = 0.0511, wR2 = 0.0864 |
| Absolute structure parameter | 0.040(10) |
| Largest diff. peak and hole | 0.727 and −0.373 e.Å$^{-3}$ |

Preparation 24 tert-butyl (3R)-3-{(3-methylpyridin-2-yl)[4-(4,4,5,5-tetramethyl-1,3,2-dioxaborolan-2-yl)benzoyl]amino}piperidine-1-carboxylate

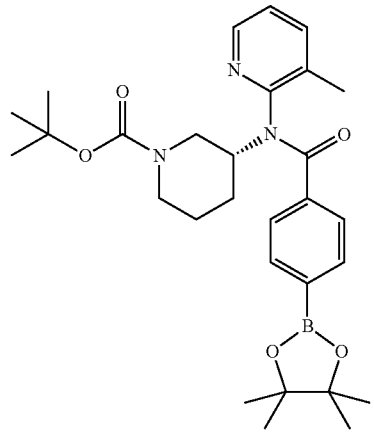 [SMILES: Cc1cccnc1N(C(=O)c1ccc(B2OC(C)(C)C(C)(C)O2)cc1)[C@@H]1CCCN(C(=O)OC(C)(C)C)C1]

A round-bottom flask was charged with Preparation 12, tert-butyl (3R)-3-[(4-bromobenzoyl)(3-methylpyridin-2-yl)amino]piperidine-1-carboxylate (150 g, 317 mmol), bis(pinacolato)diboron (97.8 g, 381 mmol), potassium acetate (100 g, 1.01 mol, and 2-methyltetrahydrofuran (750 mL). The reaction mixture was warmed to 75° C. 1,1'-bis(diphenylphosphino)ferrocene-palladium(II)dichloride dichloromethane complex (Pd(dppf)Cl$_2$CH$_2$Cl$_2$) (5.12 g, 6.21 mmol) was added and the reaction mixture was heated under reflux for 19 h. The reaction mixture was cooled to room temperature and H$_2$O was added. The reaction mixture was passed through a pad of Celite and the layers separated. The organic layer was concentrated in vacuo. The brown residue was purified by column chromatography on silica gel, eluting with a gradient of 30-50% EtOAc in heptane. The product-containing fractions were concentrated in vacuo. The residue was filtered through a pad of Celite using warm heptane and DCM to solubilize product. The reaction mixture was concentrated in vacuo until product started to crystallize. The solids were granulated for 16 h at room temperature, collected via filtration and dried in a vacuum oven to afford tert-butyl (3R)-3-{(3-methylpyridin-2-yl)[4-(4,4,5,5-tetramethyl-1,3,2-dioxaborolan-2-yl)benzoyl]amino}piperidine-1-carboxylate as a light pink solid (142 g, 86%).

$^1$H NMR (CDCl$_3$) δ: 8.40 (m, 1H), 7.53-7.27 (m, 5H), 7.14-6.92 (m, 1H), 4.75-4.45 (m, 2H), 4.20-3.90 (m, 1H), 3.63-3.21 (m, 1H), 2.84-2.10 (m, 3H), 2.06-1.88 (m, 3H), 1.81-1.56 (m, 2H), 1.53-1.37 (m, 9H), 1.31 (s, 12H).

UPLC (UPLC-MS Method 1): $t_R$=1.08 min.

MS (ES+): 522.4 (M+H)$^+$.

Preparation 25 tert-butyl (3R)-3-(4-(1-methyl-5-(2H-tetrazol-5-yl)-1H-pyrazol-4-yl)-N-(3-methylpyridin-2-yl)benzamido)piperidine-1-carboxylate

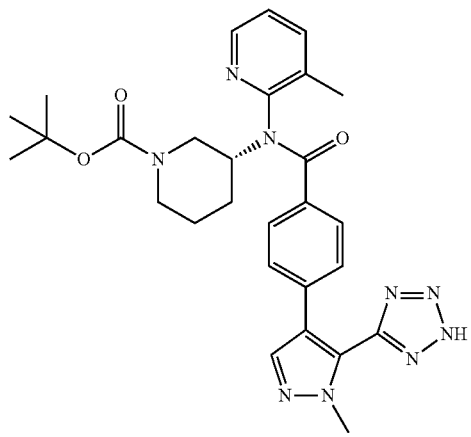 [SMILES: Cc1cccnc1N(C(=O)c1ccc(-c2cnn(C)c2-c2nn[nH]n2)cc1)[C@@H]1CCCN(C(=O)OC(C)(C)C)C1]

To a round-bottom flask charged with a stir bar was added Preparation 24, tert-butyl (3R)-3-{(3-methylpyridin-2-yl)[4-(4,4,5,5-tetramethyl-1,3,2-dioxaborolan-2-yl)benzoyl]amino}piperidine-1-carboxylate (1.53 g, 2.93 mmol) and Preparation 22, 5-(4-iodo-1-methyl-1H-pyrazol-5-yl)-2H-tetrazole (674 mg, 2.44 mmol). To this was added dioxane (12.2 mL) and aqueous NaOH (4.07 mL, 3M solution, 12.2 mmol). The reaction mixture was heated to 70° C. under nitrogen atmosphere for 30 min. To a microwave vial was added the Pd(OAc)$_2$ (34.3 mg, 0.153 mmol) and Catacxium A (123 mg, 0.342 mmol). The atmosphere was exchanged for nitrogen, and toluene was added. The catalyst was stirred at room temperature for 15 min, until a bright yellow slurry formed. At this point, the catalyst was added to the reaction mixture, and the temperature was adjusted to 100° C. The reaction mixture was stirred for 3 h at 100° C. After complete consumption of the starting material, the reaction was concentrated under reduced pressure. H$_2$O (10 mL) was added. The reaction mixture was extracted with MTBE (3×25 mL). The aq. phase was cooled to 0° C., and 1M HCl was added dropwise to form a precipitate which was collected via suction filtration and dried in vacuo to obtain tert-butyl (3R)-3-(4-(1-methyl-5-(2H-tetrazol-5-yl)-1H-pyrazol-4-yl)-N-(3-methylpyridin-2-yl)benzamido)piperidine-1-carboxylate (1.2 g, 90%).

$^1$H NMR (MeOH-d$_4$) δ: 8.42 (d, 1H), 7.80 (s, 1H), 7.72-7.51 (m, 1H), 7.30-7.05 (m, 5H), 4.62-4.44 (m, 2H), 4.18-3.98 (m, 2H), 3.95 (s, 3H), 2.75-2.62 (m, 1H), 2.18-2.04 (m, 2H), 1.79-1.70 (m, 2H), 1.53-1.42 (m, 4H), 1.31 (s, 9H).

UPLC (UPLC-MS Method 1): t$_R$=0.82 min.
MS (ES+): 544.4 (M+H)$^+$.

Preparation 26 tert-butyl (3R)-3-{[4-(5-cyano-1-methyl-1H-pyrazol-4-yl)benzoyl](3-methylpyridin-2-yl)amino}piperidine-1-carboxylate

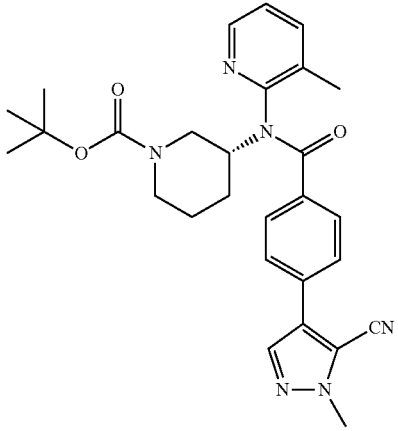 [SMILES: Cc1cccnc1N(C(=O)c1ccc(-c2cnn(C)c2C#N)cc1)[C@@H]1CCCN(C(=O)OC(C)(C)C)C1]

Preparation 24, tert-butyl (3R)-3-{(3-methylpyridin-2-yl)[4-(4,4,5,5-tetramethyl-1,3,2-dioxaborolan-2-yl)benzoyl]amino}piperidine-1-carboxylate (2.67 g, 5.12 mmol), Preparation 21, 4-iodo-1-methyl-1H-pyrazole-5-carbonitrile (1.19 g, 5.12 mmol), Pd$_2$(dba)$_3$ (234 mg, 0.256 mmol), and XPhos (257 mg, 0.512 mmol) were dissolved in dioxane (27 mL) under nitrogen atmosphere. A solution of Na$_2$CO$_3$ (1.63 g, 15.4 mmol) in H$_2$O (3 mL) was added. The reaction was heated at 80° C. for 6 h, then stirred at room temperature overnight. The reaction mixture was diluted with EtOAc (150 mL), washed by 50% brine solution (100 mL). The separated organic phase was dried over MgSO$_4$, concentrated. The residue was purified by silica gel column chromatography eluting with a gradient of 15-100% EtOAc/heptane to afford tert-butyl (3R)-3-{[4-(5-cyano-1-methyl-1H-pyrazol-4-yl)benzoyl](3-methylpyridin-2-yl)amino}piperidine-1-carboxylate as a colorless solid (1.87 g, 73% yield).

$^1$H NMR (CDCl$_3$) δ: 8.43 (m, 1H), 7.72 (s, 1H), 7.40-7.35 (m, 5H), 7.21-7.02 (m, 1H), 4.87-4.32 (m, 2H), 4.07 (s, 3H), 3.49 (d, 1H), 2.82-2.21 (m, 2H), 2.05 (s, 3H), 1.80-1.48 (m, 4H), 1.47 (d, 9H).

UPLC (UPLC-MS Method 1): t$_R$=1.01 min.
MS (ES+): 501.4 (M+H)$^+$.

Preparation 27 tert-butyl (3R)-3[{4-[5-(2-{(1S)-1-[(ethoxycarbonyl)oxy]ethyl}-2H-tetrazol-5-yl)-1-methyl-1H-pyrazol-4-yl]benzoyl}(3-methylpyridin-2-yl)amino]piperidine-1-carboxylate

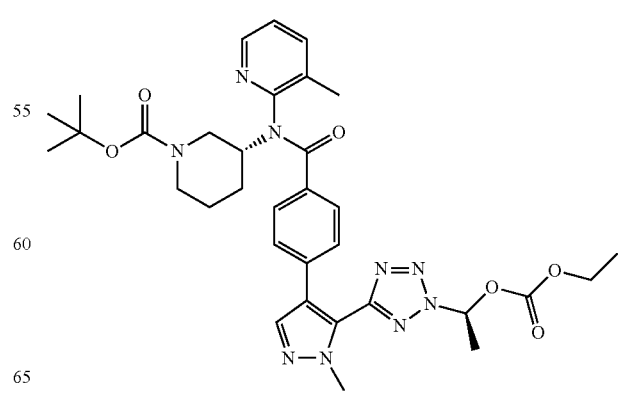

A 3-neck round-bottom flask fitted with a reflux condenser was charged with dioxane (8.5 mL) and aqueous CsF (7.65 mL, 1M solution, 7.65 mmol). This was heated to 80° C. for 0.5 h under nitrogen atmosphere. After 30 min, Preparation 24, tert-butyl (3R)-3-{(3-methylpyridin-2-yl)[4-(4,4,5,5-tetramethyl-1,3,2-dioxaborolan-2-yl)benzoyl]amino}piperidine-1-carboxylate (1.66 g, 3.19 mmol) was added followed by Preparation 23a, (S)-ethyl 1-[5-(4-iodo-1-methyl-1H-pyrazol-5-yl)-2H-tetrazol-2-yl]ethyl carbonate (1.00 g, 2.55 mmol), and Pd(amphos)Cl$_2$ catalyst (90.6 mg, 0.128 mmol). The reaction was stirred at 80° C. for 5.5 h. Aqueous ammonium chloride solution (10 mL) was added followed by EtOAc (10 mL). The layers were separated, and the aqueous phase was further extracted with EtOAc (3×15 mL), dried with MgSO$_4$, passed through a plug of silica, and concentrated. The crude material was purified via MPLC using a gradient of 20-70% EtOAc/heptane to afford tert-butyl (3R)-3-[{4-[5-(2-{(1S)-1-[(ethoxycarbonyl)oxy]ethyl}-2H-tetrazol-5-yl)-1-methyl-1H-pyrazol-4-yl]benzoyl}(3-methylpyridin-2-yl)amino]piperidine-1-carboxylate as a colorless solid (1.05 g, 77%). $^1$H NMR (CDCl$_3$) δ: 8.41 (d, 1H), 7.61 (s, 1H), 7.36-7.32 (m, 1H), 7.24-7.10 (m, 6H), 4.76-4.46 (m, 2H), 4.32 (q, 2H), 4.07 (s, 3H), 3.47-3.36 (m, 1H), 2.67-2.14 (m, 3H), 2.06-1.99 (m, 6H), 1.81-1.59 (m, 3H), 1.47 (s, 9H), 1.36 (t, 3H).

UPLC (UPLC-MS Method 2): $t_R$=1.95 min.
MS (ES+): 660.4 (M+H)$^+$.

Preparation 28 tert-butyl (3R)-3-[{4-[5-(2-{(1R)-1-[(ethoxycarbonyl)oxy]ethyl}-2H-tetrazol-5-yl)-1-methyl-1H-pyrazol-4-yl]benzoyl}(3-methylpyridin-2-yl)amino]piperidine-1-carboxylate

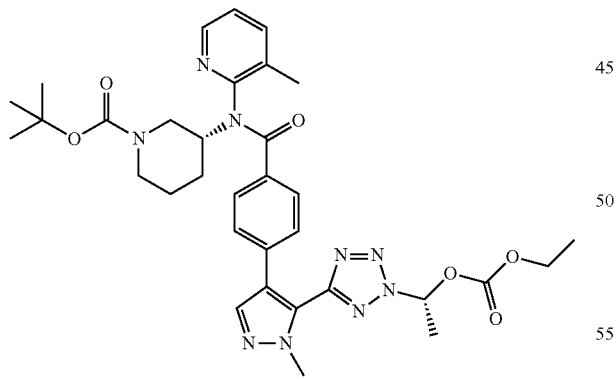

The title compound was made in an analogous manner to Preparation 27 using Preparation 23b.

$^1$H NMR (CDCl$_3$) δ: 8.42 (d, 1H), 7.63 (s, 1H), 7.42-7.35 (m, 1H), 7.28-7.03 (m, 6H), 4.79-4.20 (m, 2H), 4.30 (q, 2H), 4.09 (s, 3H), 3.55-3.33 (m, 1H), 2.73-2.17 (m, 3H), 2.06-2.01 (m, 6H), 1.84-1.71 (m, 3H), 1.47 (br s, 9H), 1.36 (t, 3H).

UPLC (UPLC-MS Method 2): $t_R$=1.98 min.
MS (ES+): 660.4 (M+H)$^+$.

Preparation 29

4-(4-{[(3R)-1-(tert-butoxycarbonyl)piperidin-3-yl](3-methylpyridin-2-yl)carbamoyl}phenyl)-1-methyl-1H-pyrazole-5-carboxylic acid

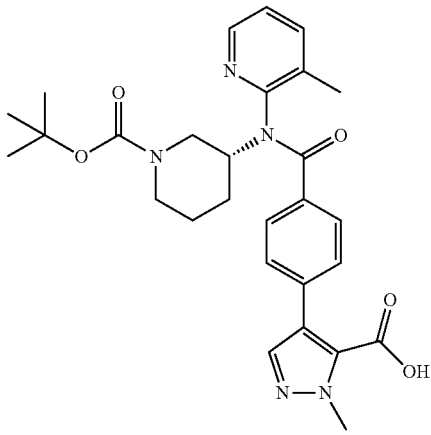 [SMILES: Cc1cccnc1N(C(=O)c1ccc(-c2cnn(C)c2C(=O)O)cc1)[C@@H]1CCCN(C(=O)OC(C)(C)C)C1]

A suspension of the product of Step 1 of EXAMPLE 13, tert-butyl (3R)-3-[{4-[5-(methoxycarbonyl)-1-methyl-1H-pyrazol-4-yl]benzoyl}(3-methylpyridin-2-yl)amino]piperidine-1-carboxylate (0.85 g, 0.59 mmol) in MeOH (2 mL) and potassium hydroxide solution in MeOH (1.67 mL, 1M solution, 1.67 mmol) was heated to 70° C. in a sealed pressure tube for 2 h. The reaction mixture was then concentrated and toluene (10 mL) was added to the mixture. The solvents were evaporated in vacuo and dried under vacuum for 2 h. The solid was then slurried in methyl tert-butyl ether (15 mL) and heptanes (15 mL) for 1 h, collected via filtration and dried under vacuum for 16 h to afford 4-(4-{[(3R)-1-(tert-butoxycarbonyl)piperidin-3-yl](3-methylpyridin-2-yl)carbamoyl}phenyl)-1-methyl-1H-pyrazole-5-carboxylic acid (800 mg, 90%).

$^1$H NMR (DMSO-d$_6$) δ: 8.43 (m, 1H), 7.76-7.40 (m, 3H), 7.34-7.21 (m, 2H), 7.20-6.96 (m, 2H), 4.76-4.37 (m, 1H), 4.27 (br s, 1H), 3.86 (br s, 1H), 3.73 (s, 3H), 2.23-1.85 (m, 4H), 1.80-1.52 (m, 2H), 1.54-1.30 (m, 12H).

UPLC (UPLC-MS Method 1): $t_R$=0.92 min.
MS (ES+): 520.3 (M+H)$^+$.

Preparation 30 ethyl 1-[5-(4-iodo-1-methyl-1H-pyrazol-5-yl)-2H-tetrazol-2-yl]propyl carbonate

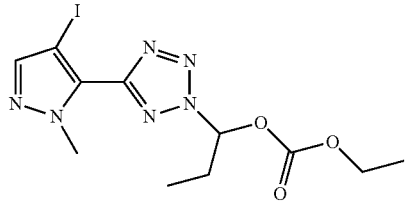 [SMILES: CCOC(=O)OC(CC)n1nnc(-c2c(I)cnn2C)n1]

The title compound was made in an analogous manner to Preparation 23 using Preparation 22, propionaldehyde and ethyl chloroformate.

¹H NMR (CDCl₃) δ: 7.63 (s, 1H), 7.07 (t, 1H), 4.33-4.20 (m, 2H), 4.23 (s, 3H), 2.55-2.40 (m, 2H), 1.33 (t, 3H), 1.04 (t, 3H).
UPLC (UPLC-MS Method 2): $t_R$=1.71 min.
MS (ES+): 407.1 (M+H)⁺.

Preparation 30a and 30b

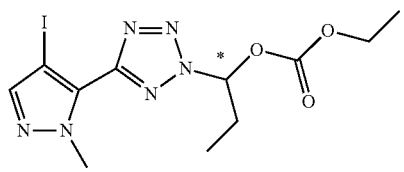 [SMILES: CCOC(=O)OC(CC)n1nnc(-c2c(I)cnn2C)n1]

630 mg of Preparation 30 was processed according to Chiral Preparative Chromatography Method 4, followed by concentration of each enantiomer to dryness in vacuo to give Preparation 30a (190 mg, 99% e.e., $t_R$=4.22 min (Chiral Analytical Chromatography Method 1)) and Preparation 30b (200 mg, 99% e.e., $t_R$=5.01 min (Chiral Analytical Chromatography Method 1)). The absolute configuration of the enantiomers 30a and 30b was not determined. The first enantiomer to elute off the column is Preparation 30a and the second enantiomer is Preparation 30b.

Preparation 31

Diastereomer A

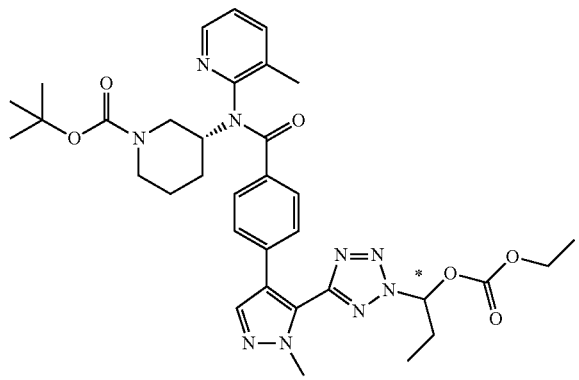

The title compound was made in an analogous manner to Preparation 27 using Preparation 24 and Preparation 30a. The asterisk denotes the chiral carbon and while the absolute configuration (e.g., R/S) of Diastereomer A was not determined, this Preparation 31 is a single diasteromer with unique characteristics as shown by the uniqueness of the chiral chromatography retention time of Preparation 30a from which Preparation 31 was prepared.
¹H NMR (CDCl₃) δ: 8.56-8.34 (m, 1H), 7.61 (s, 1H), 7.41-7.31 (m, 1H), 7.24-7.20 (m, 2H), 7.18-7.09 (m, 3H), 6.98 (t, 1H), 4.80-4.42 (m, 2H), 4.35-4.19 (m, 2H), 4.07 (s, 3H), 3.54-3.26 (m, 1H), 2.73-2.13 (m, 4H), 2.44-2.28 (m, 3H), 1.83-1.55 (m, 4H), 1.51-1.40 (m, 9H), 1.34 (t, 3H), 0.97 (t, 3H).
UPLC (UPLC-MS Method 2): $t_R$=2.09 min.
MS (ES+): 674.4 (M+H)⁺.

Preparation 32

Diastereomer B

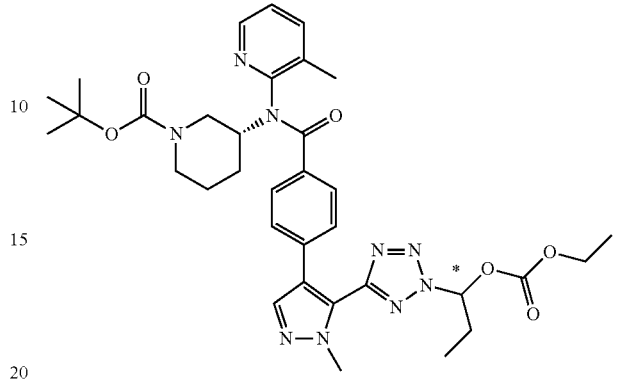

The title compound was made in an analogous manner to Preparation 27 using Preparation 24 and Preparation 30b. The asterisk denotes the chiral carbon and while the absolute configuration (e.g., R/S) of Diastereomer B, was not determined this Preparation 32 is a single diasteromer with unique characteristics as shown by the uniqueness of the chiral chromatography retention time of Preparation 30b from which Preparation 32 was prepared.
¹H NMR (CDCl₃) δ: 8.40 (d, 1H), 7.61 (s, 1H), 7.38-7.33 (m, 1H), 7.26-7.07 (m, 5H), 6.98 (t, 1H), 4.75-4.62 (m, 1H), 4.54-4.45 (m, 1H), 4.31-4.22 (m, 2H), 4.06 (s, 3H), 3.46-3.37 (m, 1H), 2.68-2.13 (m, 4H), 2.06-1.95 (m, 3H), 1.79-1.56 (m, 4H), 1.41-1.52 (m, 6H), 1.33 (t, 3H), 0.97 (t, 3H).
UPLC (UPLC-MS Method 1): $t_R$=1.05 min.
MS (ES+): 674.4 (M+H)⁺.

Preparations 33a and 33b

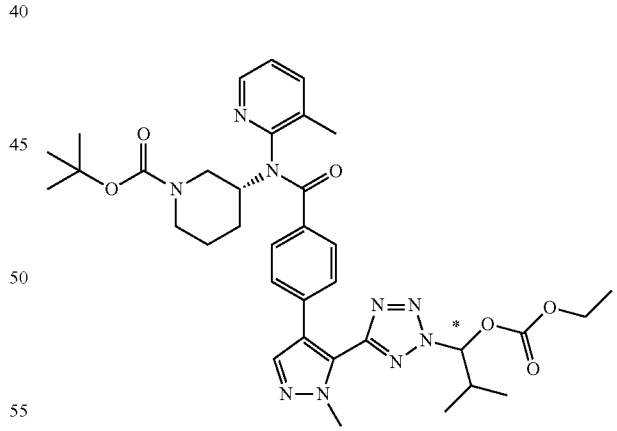

Preparation 33A (Diastereomer A) and
Preparation 33B (Diastereomer B)

To a solution of Preparation 25 (500 mg, 0.920 mmol) and DABCO (5.6 mg, 0.050 mmol) in THF (5 mL) was added piperidine (10 uL, 0.10 mmol), triethylamine (0.303 mL, 2.17 mmol), isobutyraldehyde (0.204 mL, 2.17 mmol), and ethyl chloroformate (0.209 mL, 2.12 mmol). The reaction mixture was stirred at room temperature for 16 h. The reaction mixture was diluted with H₂O (30 mL) and extracted with EtOAc (2×50 mL). The combined organic phases were dried over MgSO$_4$ and concentrated in vacuo. The residue was purified by column chromatography on silica gel, eluting with a gradient of 10-60% EtOAc in heptane to afford the title compound as a colorless solid (364 mg, 58%).

364 mg of the solid was processed according to Chiral Preparative Chromatography Method 5, followed by concentration of each diastereomer to dryness in vacuo to give Preparation 33a (139 mg, 99% e.e., $t_R$=6.19 min (Chiral Analytical Chromatography Method 2)) and Preparation 33b (143 mg, 94% e.e., $t_R$=6.48 min (Chiral Analytical Chromatography Method 2)). The asterisk denotes the chiral carbon and while the absolute configuration (e.g., R/S) of Preparations 33a and 33b were not determined each is a single diasteromer with unique characteristics as shown by the uniqueness of the chiral chromatography retention times of Preparation 33a and Preparation 33b. The first diastereomer to elute off the column is Preparation 33a and the second diastereomer is Preparation 33b.

Diastereomer 33a:

$^1$H NMR (CDCl$_3$) δ: 8.41 (br s, 1H), 7.62 (s, 1H), 7.38-7.31 (m, 1H), 7.24-7.19 (m, 2H), 7.04-7.18 (m, 3H), 6.74 (d, 1H), 4.83-4.43 (m, 2H), 4.35-4.18 (m, 2H), 4.06 (s, 3H), 3.56-3.26 (m, 1H), 2.74-2.11 (m, 3H), 2.04-1.92 (m, 3H), 1.79-1.55 (m, 4H), 1.52-1.40 (m, 9H), 1.33 (t, 3H), 1.15 (d, 3H), 0.83 (d, 3H).

UPLC (UPLC-MS Method 2): $t_R$=2.17 min.

MS (ES+): 688.4 (M+H)$^+$.

Diastereomer 33b:

$^1$H NMR (CDCl$_3$) δ: 8.41 (br s, 1H), 7.62 (s, 1H), 7.38-7.31 (m, 1H), 7.24-7.19 (m, 2H), 7.04-7.18 (m, 3H), 6.74 (d, 1H), 4.83-4.43 (m, 2H), 4.35-4.18 (m, 2H), 4.06 (s, 3H), 3.56-3.26 (m, 1H), 2.74-2.11 (m, 3H), 2.04-1.92 (m, 3H), 1.79-1.55 (m, 4H), 1.52-1.40 (m, 9H), 1.33 (t, 3H), 1.15 (d, 3H), 0.83 (d, 3H).

UPLC (UPLC-MS Method 2): $t_R$=2.16 min.

MS (ES+): 688.4 (M+H)$^+$.

Preparation 34 ethyl 1-[5-(4-iodo-1-methyl-1H-pyrazol-5-yl)-2H-tetrazol-2-yl]-2,2-dimethylpropyl carbonate

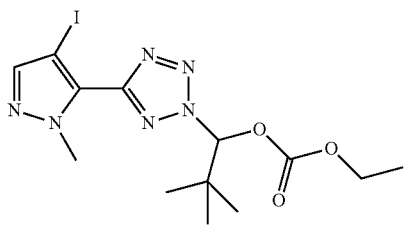 [SMILES: CCOC(=O)OC(n1nnc(-c2c(I)cnn2C)n1)C(C)(C)C]

The title compound was made in an analogous manner to Preparation 23 using Preparation 22, trimethylacetaldehyde and ethyl chloroformate $^1$H NMR (CDCl$_3$) δ: 7.66 (s, 1H), 6.87 (s, 1H), 4.16-4.36 (m, 5H), 1.34 (t, 3H), 1.18 (9H). UPLC (UPLC-MS Method 2): $t_R$=1.93 min.

MS (ES+): 435.1 (M+H)$^+$.

Preparation 34a and 34b

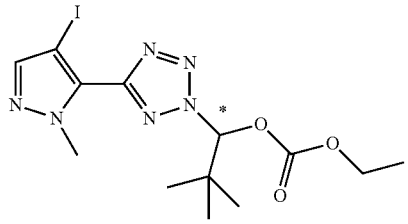 [SMILES: CCOC(=O)OC(n1nnc(-c2c(I)cnn2C)n1)C(C)(C)C]

821 mg of Preparation 34 was processed according to Chiral Preparative Chromatography Method 6, followed by concentration of each enantiomer to dryness in vacuo to give Preparation 34a (240 mg, 97% e.e., $t_R$=3.37 min (Chiral Analytical Chromatography Method 3)) and Preparation 34b (268 mg, 96% e.e., $t_R$=3.77 min (Chiral Analytical Chromatography Method 3)). The absolute configuration of the enantiomers 34a and 34b was not determined. The first enantiomer to elute off the column is Preparation 34a and the second enantiomer is Preparation 34b.

Preparation 35

Diastereomer A

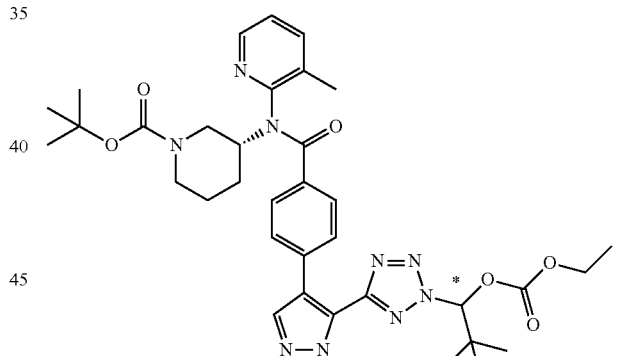

The title compound was made in an analogous manner to Preparation 27 using Preparation 24 and Preparation 34a. The asterisk denotes the chiral carbon and while the absolute configuration (e.g., R/S) of Diastereomer A was not determined, this Preparation 35 is a single diasteromer with unique characteristics as shown by the uniqueness of the chiral chromatography retention time of Preparation 34a from which Preparation 35 was prepared.

$^1$H NMR (CDCl$_3$) δ: 8.45 (d, 1H), 7.63 (s, 1H), 7.42-7.33 (m, 1H), 7.27-7.21 (m, 2H), 7.20-7.08 (m, 3H), 6.76 (s, 1H), 4.58-4.43 (m, 1H), 4.30-4.18 (m, 2H), 4.05 (s, 3H), 3.50-3.35 (m, 1H), 2.71-2.14 (m, 4H), 2.02 (s, 3H), 1.86-1.65 (m, 3H), 1.49 (br s, 9H), 1.33 (m, 3H), 1.08 (s, 9H).

UPLC (UPLC-MS Method 2): $t_R$=2.23 min.

MS (ES+): 702.5 (M+H)$^+$.

Preparation 36

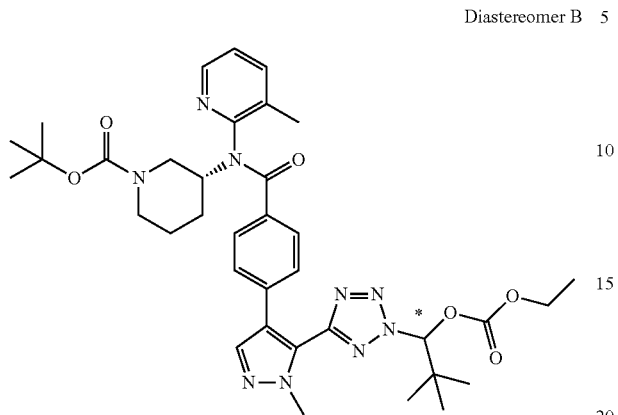

Diastereomer B

The title compound was made in an analogous manner to Preparation 27 using Preparation 24 and Preparation 34b. The asterisk denotes the chiral carbon and while the absolute configuration (e.g., R/S) of diastereomer B was not determined, this Preparation 36 is a single diasteromer with unique characteristics as shown by the uniqueness of the chiral chromatography retention time of Preparation 34b from which Preparation 36 was prepared.

$^1$H NMR (CDCl$_3$) δ: 8.40 (br s, 1H), 7.60 (br s, 1H), 7.38-7.29 (m, 1H), 7.24-7.17 (m, 2H), 7.15-7.08 (m, 3H), 6.73 (s, 1H), 4.51-4.42 (m, 1H), 4.22 (q, 2H), 4.04 (s, 3H), 3.41 (br s, 1H), 2.67-2.32 (m, 2H), 2.27-2.11 (m, 1H), 2.02-1.86 (m, 3H), 1.56 (s, 9H), 1.53-1.39 (m, 4H), 1.31 (t, 3H), 1.05 (s, 9H).

UPLC (UPLC-MS Method 2): t$_R$=2.23 min.

MS (ES+): 702.5 (M+H)$^+$.

Preparation 37 isopropyl 1-[5-(4-iodo-1-methyl-1H-pyrazol-5-yl)-2H-tetrazol-2-yl]ethyl carbonate

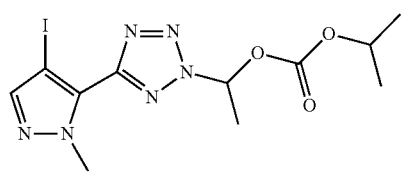 [SMILES: CC(C)OC(=O)OC(C)n1nnc(-c2c(I)cnn2C)n1]

The title compound was made in an analogous manner to Preparation 23 using Preparation 22, acetaldehyde and isopropyl chloroformate.

$^1$H NMR (CDCl$_3$) δ: 7.64 (s, 1H), 7.27 (q, 1H), 4.94 (septet, 1H), 4.23 (s, 3H), 2.10 (d, 3H), 1.34 (d, 3H), 1.30 (d, 3H).

UPLC (UPLC-MS Method 2): t$_R$=1.70 min.

MS (ES+): 407.1 (M+H)$^+$.

Preparation 37a and 37b

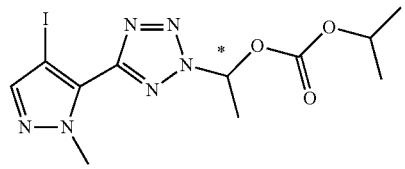 [SMILES: CC(C)OC(=O)OC(C)n1nnc(-c2c(I)cnn2C)n1]

731 mg of Preparation 37 was processed according to Chiral Preparative Chromatography Method 7, followed by concentration of each enantiomer to dryness in vacuo to give Preparation 37a (68 mg, 94% e.e., t$_R$=3.83 min (Chiral Analytical Chromatography Method 2)) and Preparation 37b (91 mg, 91% e.e., t$_R$=4.21 min (Chiral Analytical Chromatography Method 2)). The absolute configuration of the enantiomers 37a and 37b was not determined. The first enantiomer to elute off the column is Preparation 37a and the second enantiomer is Preparation 37b.

Preparation 38

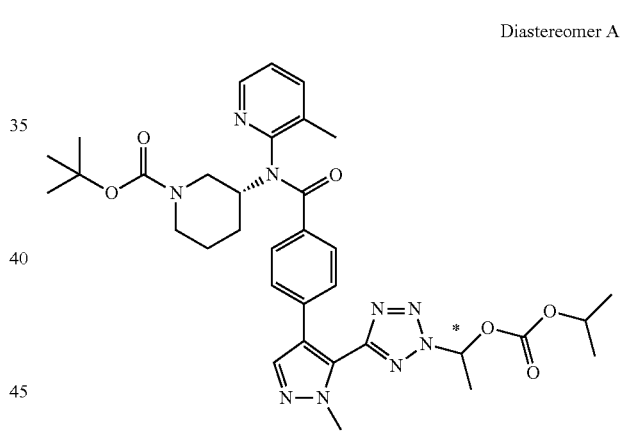

Diastereomer A

The title compound was made in an analogous manner to Preparation 27 using Preparation 24 and Preparation 37a. The asterisk denotes the chiral carbon and while the absolute configuration (e.g., R/S) of diastereomer A was not determined this Preparation 38 is a single diasteromer with unique characteristics as shown by the uniqueness of the chiral chromatography retention time of Preparation 37a from which Preparation 38 was prepared.

$^1$H NMR (CDCl$_3$) δ: 8.48-8.25 (m, 1H), 7.69-7.57 (m, 1H), 7.41-7.32 (m, 1H), 7.22-7.30 (m, 3H), 7.21-7.05 (m, 3H), 5.07-4.85 (m, 1H), 4.60-4.39 (m, 1H), 4.08 (s, 3H), 3.56-3.31 (m, 1H), 2.73-2.08 (m, 3H), 2.00-1.98 (m, 6H), 1.75-1.55 (m, 4H), 1.47 (br s, 9H), 1.35 (d, 3H), 1.30 (d, 3H).

UPLC (UPLC-MS Method 2): t$_R$=2.08 min.

MS (ES+): 674.4 (M+H)$^+$.

Preparation 39

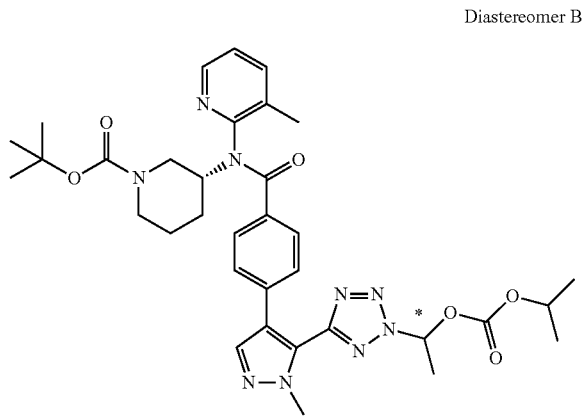 [SMILES: Cc1cccnc1N(C(=O)c1ccc(-c2cnn(C)c2-c2nnn(C(C)OC(=O)OC(C)C)n2)cc1)[C@@H]1CCCN(C(=O)OC(C)(C)C)C1]

Diastereomer B

The title compound was made in an analogous manner to Preparation 27 using Preparation 24 and Preparation 37b. The asterisk denotes the chiral carbon and while the absolute configuration (e.g., R/S) of diastereomer B was not determined this Preparation 39 is a single diasteromer with unique characteristics as shown by the uniqueness of the chiral chromatography retention time of Preparation 37b from which Preparation 39 was prepared.

$^1$H NMR (MeOH-$d_4$) δ: 8.44-8.34 (m, 1H), 7.71 (s, 1H), 7.58-7.47 (m, 1H), 7.30-7.12 (m, 6H), 4.89 (septet, 1H), 4.64-4.45 (m, 2H), 4.16-4.08 (m, 1H), 4.07-3.96 (m, 4H), 2.72-2.47 (m, 1H), 2.35-2.00 (m, 4H), 1.94 (br d, 3H), 1.85-1.40 (m, 13H), 1.31 (d, 3H), 1.26 (d, 3H).

UPLC (UPLC-MS Method 2): $t_R$=2.08 min.

MS (ES+): 674.4 (M+H)$^+$.

Preparation 40 isopropyl 1-[5-(4-iodo-1-methyl-1H-pyrazol-5-yl)-2H-tetrazol-2-yl]propyl carbonate

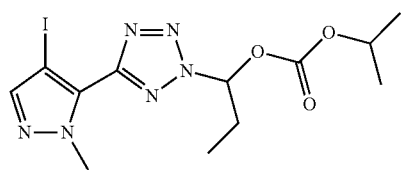 [SMILES: CCC(OC(=O)OC(C)C)n1nnc(-c2c(I)cnn2C)n1]

The title compound was made in an analogous manner to Preparation 23 using Preparation 22, propionaldehyde and isopropyl chloroformate.

$^1$H NMR (CDCl$_3$) δ: 7.64 (s, 1H), 7.07 (t, 1H), 4.94 (septet, 1H), 4.24 (s, 3H), 2.54-2.41 (m, 2H), 1.35 (d, 3H), 1.31 (d, 3H), 1.04 (t, 3H).

UPLC (UPLC-MS Method 1): $t_R$=0.97 min.

MS (ES+): 421.0 (M+H)$^+$.

Preparation 40a and 40b

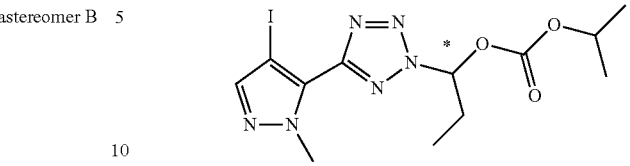

631 mg of Preparation 40 was processed according to Chiral Preparative Chromatography Method 7, followed by concentration of each enantiomer to dryness in vacuo to give Preparation 40a (174 mg, 92% e.e., $t_R$=4.10 min (Chiral Analytical Chromatography Method 2)) and Preparation 40b (192 mg, 88% e.e., $t_R$=4.33 min (Chiral Analytical Chromatography Method 2)). The absolute configuration of the enantiomers 40a and 40b was not determined. The first enantiomer to elute off the column is Preparation 40a and the second enantiomer is Preparation 40b.

Preparation 41

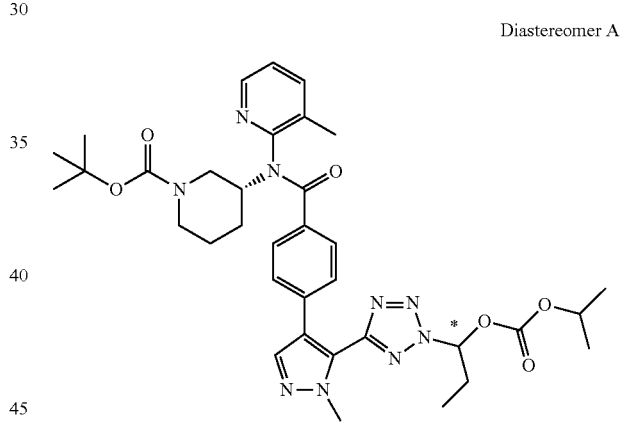

Diastereomer A

The title compound was made in an analogous manner to Preparation 27 using Preparation 24 and Preparation 40a. The asterisk denotes the chiral carbon and while the absolute configuration (e.g., R/S) of diastereomer A was not determined this Preparation 41 is a single diasteromer with unique characteristics as shown by the uniqueness of the chiral chromatography retention time of Preparation 40a from which Preparation 41 was prepared.

$^1$H NMR (CDCl$_3$) δ: 8.42-8.40 (m, 1H), 7.61 (s, 1H), 7.40-7.32 (m, 1H), 7.26-7.22 (m, 3H), 7.18-7.09 (m, 2H), 7.01 (dd, 1H), 4.96-4.98 (m, 1H), 4.75-4.45 (m, 2H), 4.22-4.10 (m, 1H), 4.07 (s, 3H), 3.54-3.35 (m, 2H), 2.58-2.47 (m, 3H), 2.39-2.32 (m, 3H), 2.06-1.96 (s, 3H), 1.46 (s, 9H), 1.36 (d, 3H), 1.30 (d, 3H), 1.27-1.25 (m, 2H), 0.98 (m, 3H).

UPLC (UPLC-MS Method 2): $t_R$=1.11 min.

MS (ES+): 688.5 (M+H)$^+$.

Preparation 42

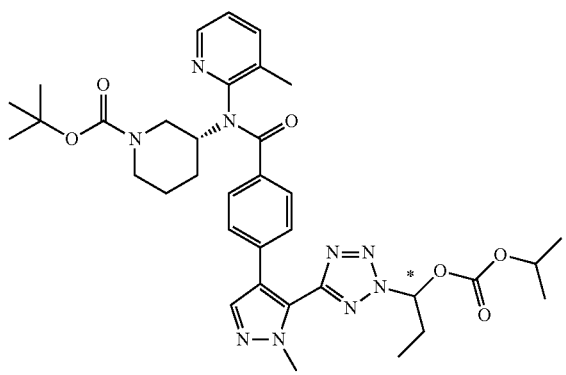

Diastereomer B

The title compound was made in an analogous manner to Preparation 27 using Preparation 24 and Preparation 40b. The asterisk denotes the chiral carbon and while the absolute configuration (e.g., R/S) of diastereomer B was not determined this Preparation 42 is a single diasteromer with unique characteristics as shown by the uniqueness of the chiral chromatography retention time of Preparation 40b from which Preparation 42 was prepared.

UPLC (UPLC-MS Method 1): $t_R$=1.08 min.
MS (ES+): 688.4 (M+H)$^+$.

Preparation 43a and 43b

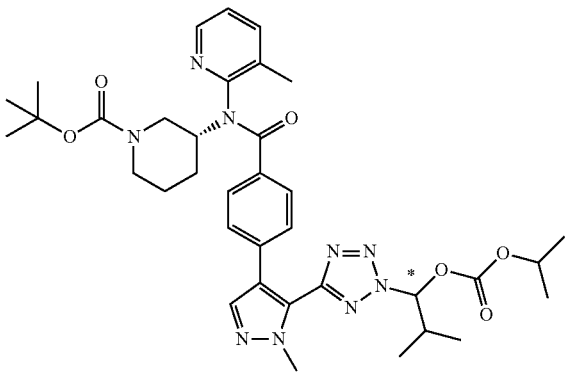

Preparation 43a (Diastereomer A) and
Preparation 43b (Diastereomer B)

To a solution of Preparation 25 (393 mg, 0.723 mmol) and DMAP (4.9 mg, 0.039 mmol) in THF (4 mL) was added triethylamine (0.171 mL, 1.23 mmol), isobutyraldehyde (0.113 mL, 1.23 mmol), and isopropyl chloroformate (1.21 mL, 1.21 mmol, 1.0 M solution in PhMe). The reaction mixture was stirred at room temperature for 16 h. The reaction mixture was diluted with H$_2$O (30 mL) and extracted with EtOAc (2×50 mL). The combined organic phases were dried over MgSO$_4$ and concentrated in vacuo. The residue was purified by column chromatography on silica gel, eluting with a gradient of 10-60% EtOAc in heptane to afford a mixture of diastereomers as a colorless solid (192 mg, 38%). 192 mg of the solid was processed according to Chiral Preparative Chromatography Method 8, followed by concentration of each diastereomer to dryness in vacuo to give Preparation 43a (55 mg, 97% e.e., $t_R$=8.70 min (Chiral Analytical Chromatography Method 4)) and Preparation 43b (45 mg, 97% e.e., $t_R$=9.48 min (Chiral Analytical Chromatography Method 4)). The asterisk denotes the chiral carbon and while the absolute configuration (e.g., R/S) of Preparations 43a and 43b were not determined each is a single diasteromer with unique characteristics as shown by the uniqueness of the chiral chromatography retention times of Preparation 43a and Preparation 43b. The first diastereomer to elute off the column is Preparation 43a and the second diastereomer is Preparation 43b.

Diastereomer 43a:
$^1$H NMR (CDCl$_3$) δ: 8.41 (br s, 1H), 7.61 (s, 1H), 7.42-7.29 (m, 1H), 7.26-7.20 (m, 2H), 7.17-7.09 (m, 3H), 6.74 (d, 1H), 4.90 (t, 1H), 4.75-4.08 (m, 2H), 4.05 (s, 3H), 3.55-3.28 (m, 1H), 2.77-2.27 (m, 3H), 2.02 (br s, 3H), 1.83-1.54 (m, 4H), 1.52-1.40 (m, 9H), 1.34 (d, 3H), 1.28 (d, 3H), 1.15 (d, 3H), 0.83 (d, 3H).
UPLC (UPLC-MS Method 2): $t_R$=2.24 min.
MS (ES+): 702.4 (M+H)$^+$.

Diastereomer 43b:
$^1$H NMR (CDCl$_3$) δ: 8.41 (br. s., 1H), 7.61 (s, 1H), 7.42-7.29 (m, 1H), 7.26-7.20 (m, 2H), 7.17-7.09 (m, 3H), 6.74 (d, 1H), 4.90 (t, 1H), 4.75-4.08 (m, 2H), 4.05 (s, 3H), 3.55-3.28 (m, 1H), 2.77-2.27 (m, 3H), 2.02 (br. s., 3H), 1.83-1.54 (m, 4H), 1.52-1.40 (m, 9H), 1.34 (d, 3H), 1.28 (d, 3H), 1.15 (d, 3H), 0.83 (d, 3H).
UPLC (UPLC-MS Method 2): $t_R$=2.24 min.
MS (ES+): 702.4 (M+H)$^+$.

Preparation 44

1-[5-(4-iodo-1-methyl-1H-pyrazol-5-yl)-2H-tetrazol-2-yl]ethyl propanoate

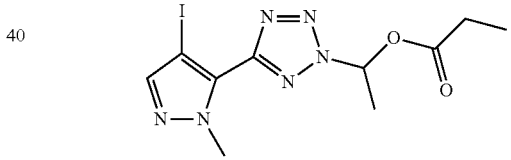

The title compound was made in an analogous manner to Preparation 23 using Preparation 22, acetaldehyde and propionyl chloride.

$^1$H NMR (CDCl$_3$) δ: 7.64 (s, 1H), 7.43 (q, 1H), 4.24 (s, 3H), 2.50-2.39 (m, 2H), 2.07 (d, 3H), 1.18 (t, 3H).
UPLC (UPLC-MS Method 1): $t_R$=0.88 min.
MS (AP+): 377.0 (M+H)$^+$.

Preparation 44a and 44b

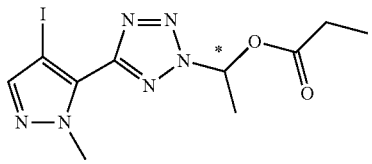 [SMILES: CCC(=O)OC(C)n1nnc(-c2c(I)cnn2C)n1]

916 mg of Preparation 44 was processed according to Chiral Preparative Chromatography Method 9, followed by concentration of each enantiomer to dryness in vacuo to give Preparation 44a (228 mg, 96% e.e., $t_R$=2.97 min (Chiral Analytical Chromatography Method 5)) and Preparation 44b (244 mg, 94% e.e., $t_R$=3.23 min (Chiral Analytical Chromatography Method 5)). The absolute configuration of the enantiomers 44a and 44b was not determined. The first enantiomer to elute off the column is Preparation 44a and the second enantiomer is Preparation 44b.

Preparation 45

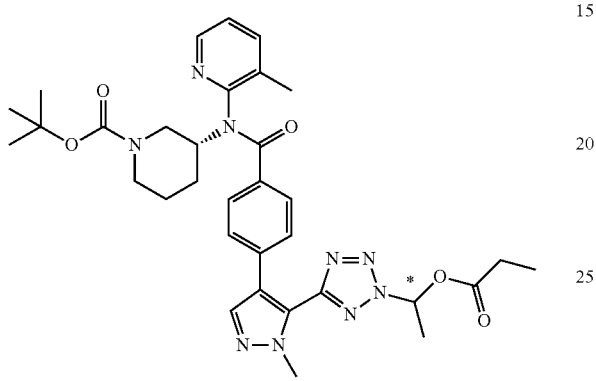

Diasteromer A

The title compound was made in an analogous manner to Preparation 27 using Preparation 24 and Preparation 44a. The asterisk denotes the chiral carbon and while the absolute configuration (e.g., R/S) of diastereomer A was not determined, this Preparation 45 is a single diastereomer with unique characteristics as shown by the uniqueness of the chiral chromatography retention time of Preparation 44a from which Preparation 45 was prepared.

$^1$H NMR (CDCl$_3$) δ: 8.42 (d, 1H), 7.62 (s, 1H), 7.43-7.32 (m, 2H), 7.30-7.23 (m, 2H), 7.21-7.07 (m, 3H), 4.56-4.44 (m, 1H), 4.08 (s, 3H), 2.52-2.34 (m, 2H), 2.11-1.99 (m, 4H), 2.03 (s, 3H), 1.96 (d, 3H), 1.74-1.64 (m, 4H), 1.48 (d, 9H), 1.18 (t, 3H).

UPLC (UPLC-MS Method 1): $t_R$=1.02 min.
MS (ES+): 644.4 (M+H)$^+$.

Preparation 46

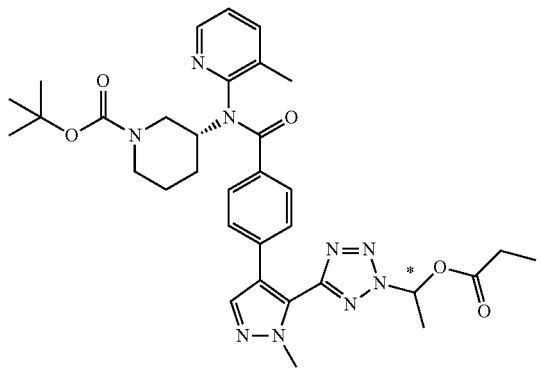

Diastereomer B

The title compound was made in an analogous manner to Preparation 27 using Preparation 24 and Preparation 44b. The asterisk denotes the chiral carbon and while the absolute configuration (e.g., R/S) of diastereomer B was not determined, this Preparation 46 is a single diasteromer with unique characteristics as shown by the uniqueness of the chiral chromatography retention time of Preparation 44b from which Preparation 46 was prepared.

UPLC (UPLC-MS Method 1): $t_R$=1.03 min.
MS (ES+): 644.4 (M+H)$^+$.

Preparation 47

1-[5-(4-iodo-1-methyl-1H-pyrazol-5-yl)-2H-tetrazol-2-yl]propyl propanoate

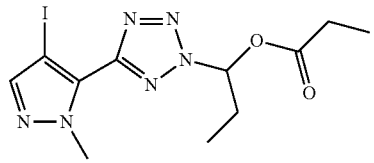 [SMILES: CCC(=O)OC(CC)n1nnc(-c2c(I)cnn2C)n1]

The title compound was made in an analogous manner to Preparation 23 using Preparation 22, propionaldehyde and propionic anhydride.

$^1$H NMR (CDCl$_3$) δ: 7.64 (s, 1H), 7.23 (t, 1H), 4.24 (s, 3H), 2.51-2.36 (m, 4H), 1.18 (t, 3H), 1.02 (t, 3H).

UPLC (UPLC-MS Method 1): $t_R$=0.93 min.
MS (AP+): 391.0 (M+H)$^+$.

Preparation 47a and 47b

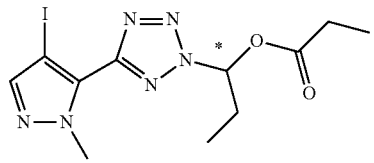 [SMILES: CCC(=O)OC(CC)n1nnc(-c2c(I)cnn2C)n1]

535 mg of Preparation 47 was processed according to Chiral Preparative Chromatography Method 14, followed by concentration of each enantiomer to dryness in vacuo to give Preparation 47a (101 mg, 96% e.e., $t_R$=3.28 min (Chiral Analytical Chromatography Method 6)) and Preparation 47b (170 mg, 93% e.e., $t_R$=3.57 min (Chiral Analytical Chromatography Method 6)). The absolute configuration of the enantiomers 47a and 47b was not determined. The first enantiomer to elute off the column is Preparation 47a and the second enantiomer is Preparation 47b.

Preparation 48

Diastereomer A

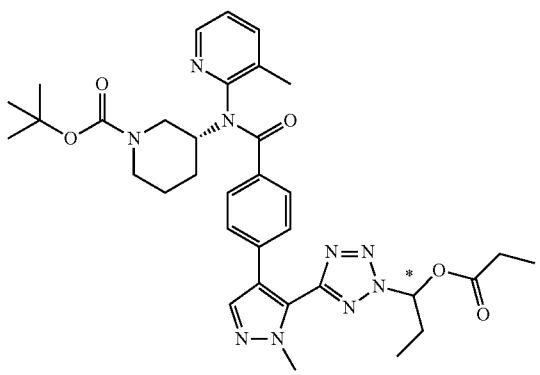

The title compound was made in an analogous manner to Preparation 27 using Preparation 24 and Preparation 47a. The asterisk denotes the chiral carbon and while the absolute configuration (e.g., R/S) of diastereomer A was not determined this Preparation 48 is a single diasteromer with unique characteristics as shown by the uniqueness of the chiral chromatography retention time of Preparation 47a from which Preparation 48 was prepared.

$^1$H NMR (CDCl$_3$) δ: 8.48-8.31 (m, 1H), 7.61 (s, 1H), 7.43-7.31 (m, 2H), 7.27-7.20 (m, 2H), 7.16-7.07 (m, 3H), 4.57-4.30 (m, 1H), 4.06 (s, 3H), 3.64-3.29 (m, 2H), 2.72-2.52 (m, 1H), 2.47-2.25 (m, 5H), 2.08-1.92 (m, 3H), 1.47 (br s, 9H), 1.75-1.44 (m, 4H), 1.16 (t, 3H), 0.94 (t, 3H).

UPLC (UPLC-MS Method 2): $t_R$=2.10 min.

MS (ES+): 658.4 (M+H)$^+$.

Preparation 49

Diastereomer B

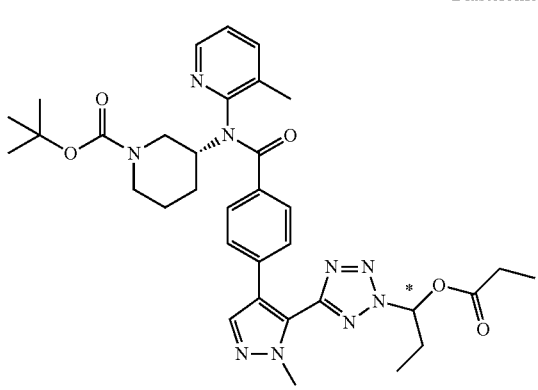

The title compound was made in an analogous manner to Preparation 27 using Preparation 24 and Preparation 47b. The asterisk denotes the chiral carbon and while the absolute configuration (e.g., R/S) of diastereomer B was not determined, this Preparation 49 is a single diasteromer with unique characteristics as shown by the uniqueness of the chiral chromatography retention time of Preparation 47b from which Preparation 49 was prepared.

UPLC (UPLC-MS Method 1): $t_R$=1.06 min.

MS (ES+): 658.4 (M+H)$^+$.

Preparation 50

1-[5-(4-iodo-1-methyl-1H-pyrazol-5-yl)-2H-tetrazol-2-yl]-2-methylpropyl propanoate

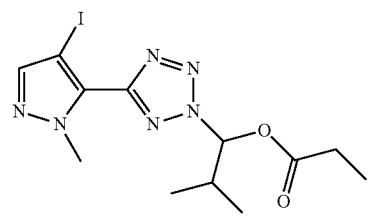 [SMILES: CCC(=O)OC(C(C)C)n1nnc(-c2c(I)cnn2C)n1]

The title compound was made in an analogous manner to Preparation 23 using Preparation 22, isobutyraldehyde and propionic anhydride. $^1$H NMR (CDCl$_3$) δ: 7.63 (s, 1H), 7.00 (d, 1H), 4.22 (s, 3H), 2.79-2.73 (m, 1H), 2.52-2.41 (m, 2H), 1.18 (t, 3H), 1.14 (d, 3H), 0.92 (d, 3H).

UPLC (UPLC-MS Method 2): $t_R$=1.85 min.

MS (ES+): 405.1 (M+H)$^+$.

Preparation 50a and 50b

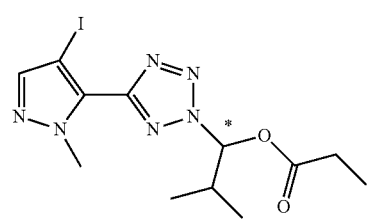 [SMILES: CCC(=O)OC(C(C)C)n1nnc(-c2c(I)cnn2C)n1]

475 mg of Preparation 50 was processed according to Chiral Preparative Chromatography Method 9, followed by concentration of each enantiomer to dryness in vacuo to give Preparation 50a (148 mg, 97% e.e., $t_R$=2.77 min (Chiral Analytical Chromatography Method 5)) and Preparation 50b (133 mg, 94% e.e., $t_R$=3.21 min (Chiral Analytical Chromatography Method 5)). The absolute configuration of the enantiomers 50a and 50b was not determined. The first enantiomer to elute off the column is Preparation 50a and the second enantiomer is Preparation 50b.

Preparation 51

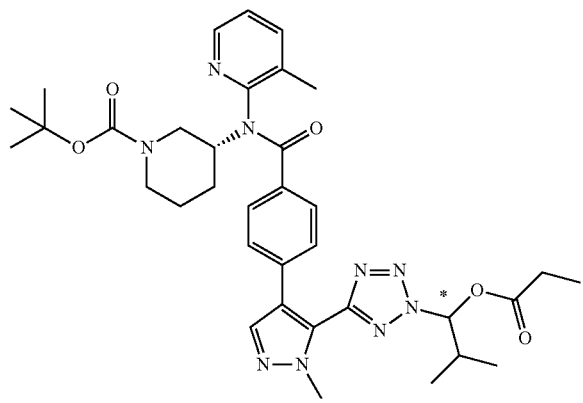

Diastereomer A

The title compound was made in an analogous manner to Preparation 27 using Preparation 24 and Preparation 50a. The asterisk denotes the chiral carbon and while the absolute configuration (e.g., R/S) of diastereomer A was not determined, this Preparation 51 is a single diasteromer with unique characteristics as shown by the uniqueness of the chiral chromatography retention time of Preparation 50a from which Preparation 51 was prepared.

UPLC (UPLC-MS Method 1): $t_R$=1.10 min.
MS (ES+): 672.5 (M+H)$^+$.

Preparation 52

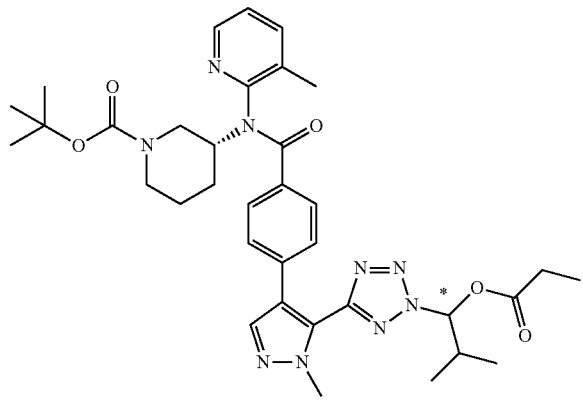

Diastereomer B

The title compound was made in an analogous manner to Preparation 27 using Preparation 24 and Preparation 50b. The asterisk denotes the chiral carbon and while the absolute configuration (e.g., R/S) of diastereomer B was not determined, this Preparation 52 is a single diasteromer with unique characteristics as shown by the uniqueness of the chiral chromatography retention time of Preparation 50b from which Preparation 52 was prepared.

$^1$H NMR (CDCl$_3$) δ: 8.40 (br s, 1H), 7.60 (s, 1H), 7.34 (br s, 1H), 7.21 (br s, 2H), 7.16-7.04 (m, 3H), 6.89 (d, 1H), 4.57-4.40 (m, 1H), 4.18-4.09 (m, 2H), 4.04 (s, 3H), 3.41 (br s, 1H), 2.64-2.57 (m, 2H), 2.51-2.32 (m, 2H), 2.06-1.91 (m, 3H), 1.57 (s, 9H), 1.50-1.38 (m, 4H), 1.33-1.21 (m, 3H), 1.15 (t, 3H), 1.08 (d, 3H).
UPLC (UPLC-MS Method 2): $t_R$=2.18 min.
MS (ES+): 672.4 (M+H)$^+$.

Preparation 53

1-[5-(4-iodo-1-methyl-1H-pyrazol-5-yl)-2H-tetrazol-2-yl]ethyl 2-methylpropanoate

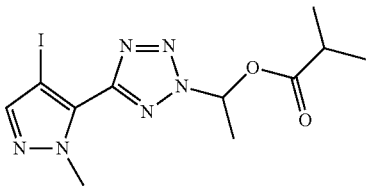 [SMILES: CC(C)C(=O)OC(C)n1nnc(-c2c(I)cnn2C)n1]

The title compound was made in an analogous manner to Preparation 23 using Preparation 22, acetaldehyde and isobutyryl chloride.
$^1$H NMR (CDCl$_3$) δ: 7.64 (s, 1H), 7.40 (q, 1H), 4.24 (s, 3H), 2.70-2.59 (m, 4H), 2.05 (d, 3H), 1.22 (2, 3H), 1.19 (d, 3H).
UPLC (UPLC-MS Method 1): $t_R$=0.94 min.
MS (AP+): 391.0 (M+H)$^+$.

Preparation 53a and 53b

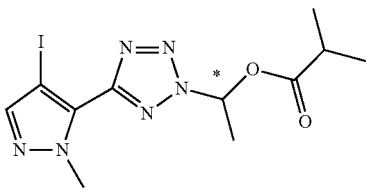 [SMILES: CC(C)C(=O)OC(C)n1nnc(-c2c(I)cnn2C)n1]

593 mg of Preparation 53 was processed according to Chiral Preparative Chromatography Method 10, followed by concentration of each enantiomer to dryness in vacuo to give Preparation 53a (165 mg, 98% e.e., $t_R$=3.66 min (Chiral Analytical Chromatography Method 7)) and Preparation 53b (172 mg, 92% e.e., $t_R$=3.86 min (Chiral Analytical Chromatography Method 7)). The absolute configuration of the enantiomers 53a and 53b was not determined. The first enantiomer to elute off the column is Preparation 53a and the second enantiomer is Preparation 53b.

Alternative Method for Preparation 53b:
To a solution of Preparation 22 (1.00 g, 3.62 mmol) and {(2S)-2-{bis[3,5-bis(trifluoromethyl)phenyl]hydroxymethyl}-1-pyrrolidinyl}[4-(1-pyrrolidinyl)-3-pyridinyl]methanone (25.2 mg, 0.036 mmol) in methyl tert-butyl ether (36 mL) was added triethylamine (0.608 mL, 4.35 mmol), acetaldehyde (0.244 mL, 4.35 mmol), and isobutyric anhydride (0.782 mL, 4.71 mmol). The reaction mixture was stirred at room temperature for 64 h. The reaction mixture was poured into water (40 mL) and extracted with EtOAc (2×50 mL). The combined organic phases were dried and concentrated in vacuo. The residue was purified by column chromatography on silica gel, eluting with a gradient of 0-30% EtOAc in heptane to afford the title compound as a colorless oil (904 mg, 64%, 90% e.e.).

Preparation 54

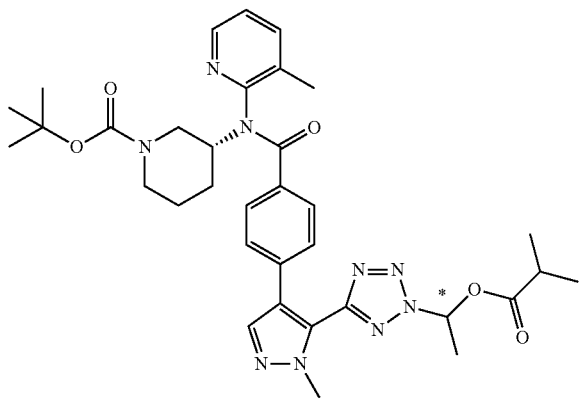

Diastereomer A

The title compound was made in an analogous manner to Preparation 27 using Preparation 24 and Preparation 53a. The asterisk denotes the chiral carbon and while the absolute configuration (e.g., R/S) of diastereomer A was not determined, this Preparation 54 is a single diasteromer with unique characteristics as shown by the uniqueness of the chiral chromatography retention time of Preparation 53a from which Preparation 54 was prepared.

$^1$H NMR (CDCl$_3$) δ: 8.40 (br s, 1H), 7.60 (s, 1H), 7.35 (br s, 1H), 7.30 (q, 1H), 7.23 (br s, 2H), 7.17-7.08 (br m, 3H), 4.48 (br d, 1H), 4.16-3.95 (br m, 4H), 3.42 (br s, 1H), 2.63-2.50 (m, 2H), 2.39 (br s, 1H), 2.05-1.98 (br m, 3H), 1.94 (d, 3H), 1.67-1.57 (br m, 4H), 1.49-1.43 (br d, 9H), 1.19 (d, 3H), 1.14 (d, 3H).

UPLC (UPLC-MS Method 1): t$_R$=1.07 min.
MS (ES+): 658.4 (M+H)$^+$.

Preparation 55

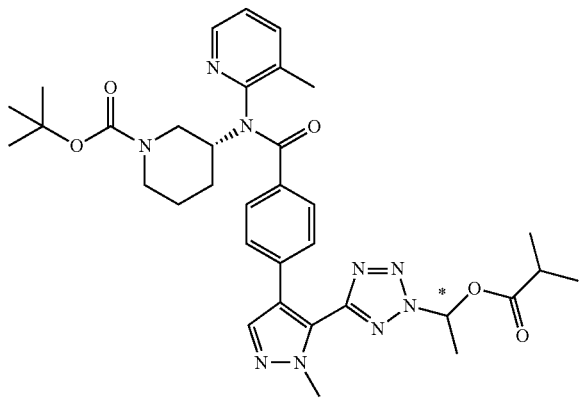

Diastereomer B

The title compound was made in an analogous manner to Preparation 27 using Preparation 24 and Preparation 53b. The asterisk denotes the chiral carbon and while the absolute configuration (e.g., R/S) of diastereomer B was not determined, this Preparation 55 is a single diasteromer with unique characteristics as shown by the uniqueness of the chiral chromatography retention time of Preparation 53b from which Preparation 55 was prepared.

$^1$H NMR (CDCl$_3$) δ: 8.40 (br s, 1H), 7.60 (s, 1H), 7.34 (br s, 1H), 7.30 (q, 1H), 7.23 (br s, 2H), 7.17-7.07 (br m, 3H), 4.48 (br d, 1H), 4.15-3.95 (br m, 4H), 3.42 (br s, 1H), 2.63-2.50 (m, 2H), 2.39 (br s, 1H), 2.05-1.93 (br m, 6H), 1.76-1.62 (br m, 4H), 1.50-1.42 (br m, 9H), 1.19 (d, 3H), 1.14 (d, 3H).

UPLC (UPLC-MS Method 1): t$_R$=1.06 min.
MS (ES+): 658.3 (M+H)$^+$.

Alternative Method for Preparation 55:

To a solution of Preparation 25 (7.50 g, 13.8 mmol) and {(2S)-2-{bis[3,5-bis(trifluoromethyl)phenyl]hydroxymethyl}-1-pyrrolidinyl}[4-(1-pyrrolidinyl)-3-pyridinyl]methanone (965 mg, 1.38 mmol) in PhMe (69 mL) was added triethylamine (3.85 mL, 27.6 mmol), acetaldehyde (1.54 mL, 27.6 mmol), and isobutyric anhydride (4.58 mL, 27.6 mmol). The reaction mixture was stirred at room temperature for 16 h. The reaction mixture concentrated in vacuo and the residue was purified by column chromatography on silica gel, eluting with a gradient of 20-100% EtOAc in heptane to afford the title compound as a colorless solid (6.3 g, 69%, 70% e.e.). The solid was processed according to Chiral Preparative Chromatography Method 11, followed by concentration to dryness in vacuo to give Preparation 55 (4.65 g, 99% e.e.).

Preparation 56

1-[5-(4-iodo-1-methyl-1H-pyrazol-5-yl)-2H-tetrazol-2-yl]propyl 2-methylpropanoate

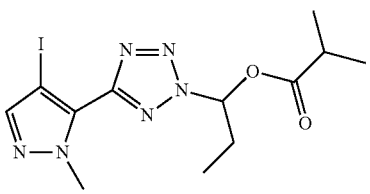 [SMILES: CCC(OC(=O)C(C)C)n1nnc(-c2c(I)cnn2C)n1]

The title compound was made in an analogous manner to Preparation 23 using Preparation 22, propionaldehyde and isobutyryl chloride.

$^1$H NMR (CDCl$_3$) δ: 7.64 (s, 1H), 7.21 (t, 1H), 4.23 (s, 3H), 2.72-2.61 (m, 1H), 2.51-2.35 (m, 2H), 1.23 (d, 3H), 1.19 (d, 3H), 1.03 (t, 3H).

UPLC (UPLC-MS Method 1): t$_R$=0.99 min.
MS (AP+): 405.0 (M+H)$^+$.

Preparation 56a and 56b

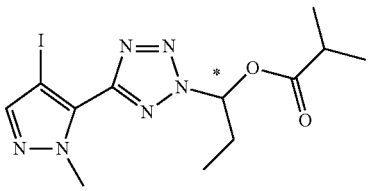 [SMILES: CCC(OC(=O)C(C)C)n1nnc(-c2c(I)cnn2C)n1]

617 mg of Preparation 56 was processed according to Chiral Preparative Chromatography Method 12, followed by concentration of each enantiomer to dryness in vacuo to give Preparation 56a (126 mg, 92% e.e., t$_R$=4.57 min (Chiral Analytical Chromatography Method 1)) and Preparation 56b (116 mg, 95% e.e., $t_R$=5.01 min (Chiral Analytical Chromatography Method 1)). The absolute configuration of the enantiomers 56a and 56b was not determined. The first enantiomer to elute off the column is Preparation 56a and the second enantiomer is Preparation 56b.

Preparation 57

Diastereomer A

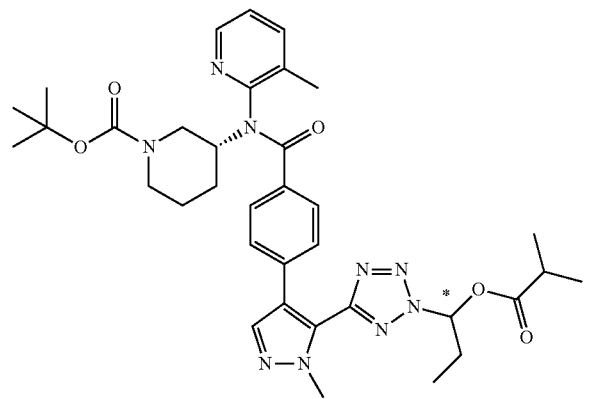

The title compound was made in an analogous manner to Preparation 27 using Preparation 24 and Preparation 56a. The asterisk denotes the chiral carbon and while the absolute configuration (e.g., R/S) of diastereomer A was not determined, this Preparation 57 is a single diasteromer with unique characteristics as shown by the uniqueness of the chiral chromatography retention time of Preparation 56a from which Preparation 57 was prepared.

$^1$H NMR (CDCl$_3$) δ: 8.41 (s, 1H), 7.62 (s, 1H), 7.40-7.32 (m, 1H), 7.24-7.21 (m, 3H), 7.13-7.11 (m, 3H), 4.62-4.45 (m, 2H), 4.08-4.00 (s, 3H), 3.51-3.36 (m, 1H), 2.65-2.60 (m, 1H), 2.58-2.48 (m, 2H), 2.33-2.29 (m, 1H), 2.22-2.12 (m, 1H), 2.03 (s, 3H), 1.80-1.59 (m, 1H), 1.48 (s, 9H), 1.32-1.26 (m, 3H), 1.22 (d, 3H), 1.16 (d, 3H), 0.97 (t, 3H).

UPLC (UPLC-MS Method 2): $t_R$=2.19 min.
MS (ES+): 672.4 (M+H)$^+$.

Preparation 58

Diastereomer B

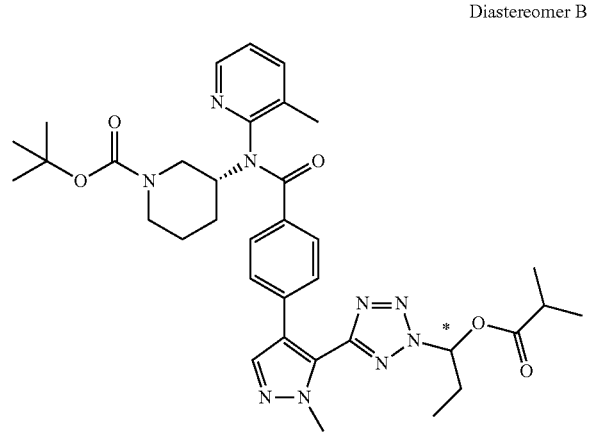 [SMILES: CCC(OC(=O)C(C)C)n1nnc(-c2c(-c3ccc(C(=O)N(c4ncccc4C)[C@@H]4CCCN(C(=O)OC(C)(C)C)C4)cc3)cnn2C)n1]

The title compound was made in an analogous manner to Preparation 27 using Preparation 24 and Preparation 56b. The asterisk denotes the chiral carbon and while the absolute configuration (e.g., R/S) of diastereomer B was not determined this Preparation 58 is a single diasteromer with unique characteristics as shown by the uniqueness of the chiral chromatography retention time of Preparation 56b from which Preparation 58 was prepared.

UPLC (UPLC-MS Method 1): $t_R$=1.09 min.
MS (ES+): 672.4 (M+H)$^+$.

Preparation 59

1-[5-(4-iodo-1-methyl-1H-pyrazol-5-yl)-2H-tetrazol-2-yl]-2-methylpropyl 2-methylpropanoate

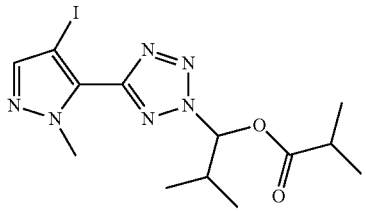 [SMILES: CC(C)C(=O)OC(C(C)C)n1nnc(-c2c(I)cnn2C)n1]

The title compound was made in an analogous manner to Preparation 23 using Preparation 22, isobutyraldehyde and isobutyric anhydride.

$^1$H NMR (MeOH-d$_4$) δ: 7.63 (s, 1H), 6.98 (d, 1H), 4.22 (s, 3H), 2.79-2.73 (m, 1H), 2.71-2.64 (m, 1H), 1.24 (d, 3H), 1.19 (d, 3H), 1.14 (d, 3H), 0.92 (d, 3H).

UPLC (UPLC-MS Method 2): $t_R$=1.98 min.
MS (ES+): 419.1 (M+H)$^+$.

Preparation 59a and 59b

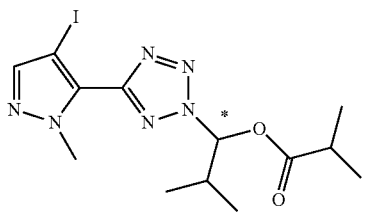 [SMILES: CC(C)C(=O)OC(C(C)C)n1nnc(-c2c(I)cnn2C)n1]

482 mg of Preparation 59 was processed according to Chiral Preparative Chromatography Method 13, followed by concentration of each enantiomer to dryness in vacuo to give Preparation 59a (172 mg, >99% e.e., $t_R$=3.95 min (Chiral Analytical Chromatography Method 8)) and Preparation 59b (168 mg, 98% e.e., $t_R$=4.07 min (Chiral Analytical Chromatography Method 8)). The absolute configuration of the enantiomers 59a and 59b was not determined. The first enantiomer to elute off the column is Preparation 59a and the second enantiomer is Preparation 59b.

Alternative Method for Preparation 59b:

To a solution of Preparation 22 (5.00 g, 18.1 mmol) and {(2S)-2-{bis[3,5-bis(trifluoromethyl)phenyl]hydroxymethyl}-1-pyrrolidinyl}[4-(1-pyrrolidinyl)-3-pyridinyl]methanone (507 mg, 0.725 mmol) in PhMe (181 mL) was added triethylamine (3.04 mL, 21.7 mmol), isobutryaldehyde (1.98 mL, 21.7 mmol), and isobutyric anhydride (3.91 mL, 23.5 mmol). The reaction mixture was stirred at room temperature for 65 h. The reaction mixture was poured into water and extracted twice with EtOAc. The combined organic phases were dried and concentrated in vacuo. The residue was purified by column chromatography on silica gel, eluting with a gradient of 0-30% EtOAc in heptane to afford the title compound as a colorless oil (7.11 g, 90%, 86% e.e.). 7.11 g of was processed according to Chiral Preparative Chromatography Method 13, followed by concentration to dryness in vacuo to give Preparation 59b (5.8 g, 98% e.e.).

Preparation 60

Diastereomer A

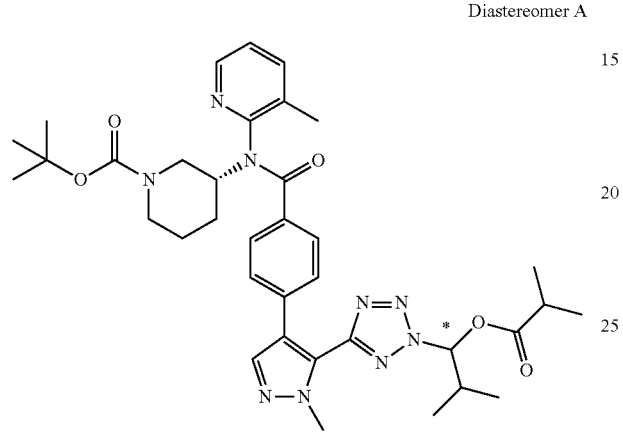

The title compound was made in an analogous manner to Preparation 27 using Preparation 24 and Preparation 59a. The asterisk denotes the chiral carbon and while the absolute configuration (e.g., R/S) of diastereomer A was not determined, this Preparation 60 is a single diastereomer with unique characteristics as shown by the uniqueness of the chiral chromatography retention time of Preparation 59a from which Preparation 60 was prepared.

UPLC (UPLC-MS Method 1): $t_R$=1.13 min.
MS (ES+): 686.5 (M+H)$^+$.

Preparation 61

Diastereomer B

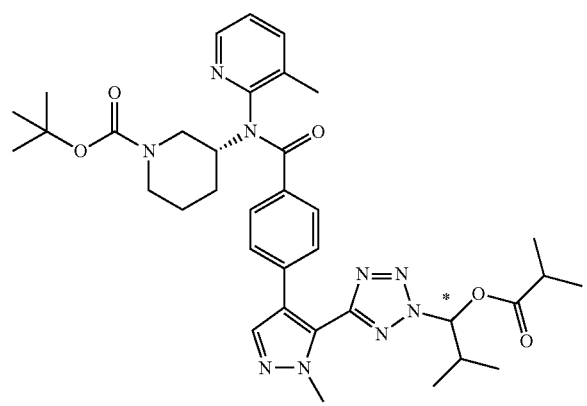

The title compound was made in an analogous manner to Preparation 27 using Preparation 24 and Preparation 59b. The asterisk denotes the chiral carbon and while the absolute configuration (e.g., R/S) of diastereomer B was not determined, this Preparation 61 is a single diasteromer with unique characteristics as shown by the uniqueness of the chiral chromatography retention time of Preparation 59b from which Preparation 61 was prepared.

$^1$H NMR (CDCl$_3$) δ: 8.39 (br s, 1H), 7.60 (s, 1H), 7.33 (br s, 1H), 7.21 (br s, 2H), 7.16-7.03 (m, 3H), 6.88 (d, 1H), 4.66 (br s, 1H), 4.55-4.39 (m, 1H), 4.03 (s, 3H), 3.41 (br s, 1H), 2.67-2.58 (m, 1H), 2.05-1.91 (m, 3H), 1.58 (s, 9H), 1.49-1.39 (m, 4H), 1.35-1.22 (m, 4H), 1.21 (d, 3H), 1.14 (d, 3H), 1.09 (d, 3H), 0.83 (d, 3H).

UPLC (UPLC-MS Method 2): $t_R$=2.26 min.
MS (ES+): 686.5 (M+H)$^+$.

General procedure A: acyl chloride formation;
General procedure B: MeMgCl mediated amide formation;
General procedure C: LiHMDS mediated amide formation;
General procedure D: HCl deprotection of Boc;
General procedure E: Buchwald on 2-chloro-3-nitropyridine;
General procedure F: reduction of nitro;
General procedure G: diazotization/ring closure;
General Procedure H: ester hydrolysis to give acid;
General procedure I: ester hydrolysis to give potassium salt;
General procedure J: alkylation to form carbonate.

EXAMPLE 1

N-(3-methylpyridin-2-yl)-N-[(3R)-piperidin-3-yl]-4-(pyrazolo[1,5-a]pyrimidin-3-yl)benzamide

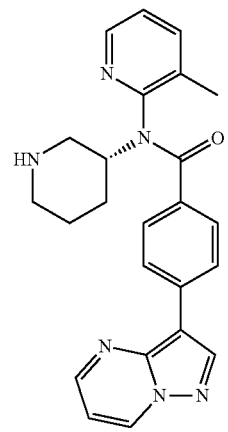 [SMILES: Cc1cccnc1N(C(=O)c1ccc(-c2cnn3cccnc23)cc1)[C@@H]1CCCNC1]

Step 1: (R)-2-(N-(1-(tert-butoxycarbonyl)piperidin-3-yl)-4-(pyrazolo[1,5-a]pyrimidin-3-yl)benzamido)-3-methylpyridine 1-oxide To a solution of Preparation 14 (R)-2-(1-(tert-butoxycarbonyl)piperidin-3-ylamino)-3-methylpyridine 1-oxide (540 mg, 1.76 mmol) and Preparation 19 4-(pyrazolo[1,5-a]pyrimidin-3-yl)benzoic acid (420 mg, 1.76 mmol) in DMF (10 mL) was added HATU (803 mg, 2.11 mmol) at 30° C. The reaction was stirred at room temperature for 30 min. Diisopropylethyl amine (682 mg, 5.28 mmol) was then added at 0° C. dropwise. The reaction was stirred at 30° C. for 2 h. The resulting mixture poured into water then extracted with EtOAc (3×30 mL). The combined organic layers were washed with brine, dried over Na$_2$SO$_4$, filtered and the filtrate was concentrated under reduced pressure. The crude product was purified by silica gel chromatography to deliver the title compound (760 mg, 82%) as a brown oil.

¹H NMR (400 MHz, CDCl₃) δ 8.69 (d, 1H), 8.57 (s, 1H), 8.40 (s, 1H), 8.20-8.14 (m, 1H), 7.93 (d, 2H), 7.66-7.56 (m, 2H), 7.07-6.99 (m, 1H), 6.94-6.85 (m, 2H), 2.80-2.63 (m, 1H), 2.23 (s, 1H), 2.14 (s, 2H), 2.02-1.57 (m, 5H), 1.47 (s, 9H).

Step 2: (R)-tert-butyl 3-(N-(3-methylpyridin-2-yl)-4-(pyrazolo[1,5-a]pyrimidin-3-yl)benzamido)piperidine-1-carboxylate To a solution of the compound from Step 1 (R)-2-(1-(tert-butoxycarbonyl)-piperidin-3-ylamino)-3-methylpyridine 1-oxide (760 mg, 1.44 mmol) in acetonitrile (15 mL) was added tetrahydroxydiboron (387 mg, 4.32 mmol) at room temperature. The reaction was stirred at 60° C. overnight. The resulting mixture was treated with water then extracted with EtOAc (3×30 mL). The combined organic layers were dried over Na₂SO₄, filtered, and the filtrate was concentrated under reduced pressure to afford the title compound (760 mg) as a white gum. This material was used in the next step without further purification.

Step 3: N-(3-methylpyridin-2-yl)-N-[(3R)-piperidin-3-yl]-4-(pyrazolo[1,5-a]pyrimidin-3-yl)benzamide hydrochloride To a solution of the compound from Step 2 (R)-tert-butyl 3-(N-(3-methylpyridin-2-yl)-4-(pyrazolo[1,5-a]pyrimidin-3-yl)benzamido)piperidine-1-carboxylate (737 mg, 1.44 mmol) in 1,4-dioxane (10 mL) was added HCl/1,4-dioxane (7.2 mL of 4 M, 28.8 mmol) dropwise at 0° C. The reaction was stirred at room temperature for 3 h. The resulting mixture was concentrated under reduced pressure. The crude product was purified by preparatory HPLC to deliver the hydrochloride salt of the title compound (325 mg, 52%) as a yellow solid ¹H NMR (400 MHz, DMSO-d₆) δ 9.60 (br s, 1H), 9.19 (br s, 1H), 9.09 (d, 1H), 8.73-8.60 (m, 2H), 8.45 (br s, 1H), 7.98 (d, 2H), 7.60 (d, 1H), 7.35-7.22 (m, 3H), 7.10 (dd, 1H), 3.60-3.48 (m, 1H), 3.26-3.16 (m, 1H), 2.80-2.66 (m, 1H), 2.08 (s, 3H), 2.02-1.79 (m, 4H).

LC (LC-MS Method 3): t$_R$=0.838 min
MS (ES+): 413.1 (M+H)⁺

EXAMPLE 2

N-(3-chloropyridin-2-yl)-N-[(3R)-piperidin-3-yl]-4-(pyrazolo[1,5-a]pyrimidin-3-yl)benzamide

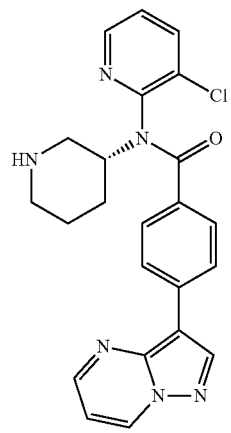 [SMILES: O=C(c1ccc(-c2cnn3cccnc23)cc1)N(c1ncccc1Cl)[C@@H]1CCCNC1]

Step 1: tert-butyl (3R)-3-{(3-chloropyridin-2-yl)[4-(pyrazolo[1,5-a]pyrimidin-3-yl)benzoyl]amino}piperidine-1-carboxylate General procedure A. Oxalyl chloride (3.86 mL, 44 mmol) was added to a solution of Preparation 19 4-(pyrazolo[1,5-a]pyrimidin-3-yl)benzoic acid (10 g, 39.4 mmol) in DCM (200 mL) and DMF (0.5 mL). The reaction mixture was stirred at room temperature for 2 h and then evaporated. The residue was diluted with toluene and evaporated to dryness. This step was repeated 5 times and the residue was used in the next step.

Step 2:

General procedure B. A solution of Preparation 1 tert-butyl (3R)-3-[(3-chloropyridin-2-yl)amino]piperidine-1-carboxylate (12.2 g, 39 mmol) in degassed toluene (90 mL) was treated with methyl magnesium chloride (3 M solution in THF) (13.1 mL, 39 mmol) at 0° C. The mixture was stirred for 1 h at 0° C., before the addition of the suspension of the solid acyl chloride from Step 1 in THF (150 mL). The resulting mixture was stirred at 65° C. overnight. The reaction mixture was cooled to room temperature, diluted with water (80 mL) and EtOAc (200 mL). The aqueous layer was extracted with EtOAc (2×300 mL) and the combined organic layers were dried over MgSO₄, filtered, and the filtrate was concentrated. The residue was purified by silica gel column chromatography eluting with a gradient of 25-100% EtOAc/heptane to afford the title compound as a yellow solid (17 g, 81%).

¹H NMR (CDCl₃) δ 8.70 (dd, 1H), 8.58 (dd, 1H), 8.49 (d, 1H), 8.42 (s, 1H), 7.91 (d, 2H), 7.63-7.53 (m, 1H), 7.45 (d, 2H), 7.15 (dd, 1H), 6.88 (dd, 1H), 4.89-4.24 (m, 3H), 4.12 (m, 1H), 3.52-3.22 (m, 1H), 2.77-2.48 (m, 1H), 2.44-2.26 (m, 1H), 2.02-1.90 (m, 1H), 1.82-1.65 (m, 1H), 1.49 (s, 9H).

UPLC (UPLC-MS Method 1): t$_R$=0.72 min.
MS (ES+): 533.3 (M+H)⁺.

Step 3: N-(3-chloropyridin-2-yl)-N-[(3R)-piperidin-3-yl]-4-(pyrazolo[1,5-a]pyrimidin-3-yl)benzamide General procedure D. A solution of the compound from Step 2 tert-butyl (3R)-3-{(3-chloropyridin-2-yl)[4-(pyrazolo[1,5-a]pyrimidin-3-yl)benzoyl]amino}piperidine-1-carboxylate (0.929 g, 1.74 mmol) in DCM (20 mL) and MeOH (15 mL) was treated with HCl (4 M solution in 1,4-dioxane) (4.59 mL, 18.3 mmol). The mixture was then stirred at room temperature overnight. The reaction mixture was concentrated. The resulting residue was triturated in diethyl ether to yield the hydrochloride salt of the title compound as the light yellow solid (0.702 g, 86%).

¹H NMR (MeOH-d₄, 400 MHz): δ 8.93 (dd, 1H), 8.63 (dd, 1H), 8.60 (s, 1H), 8.56 (s, 1H), 8.01 (d, 2H), 7.87-7.74 (m, 1H), 7.39 (dd, 3H), 7.07 (dd, 1H), 5.26-5.01 (m, 1H), 3.92-3.72 (m, 1H), 3.68-3.53 (m, 1H), 3.39 (m, 1H), 2.92 (m, 1H), 2.04 (m, 2H), 1.99-1.78 (m, 1H), 1.63-1.37 (m, 1H).

HPLC purity (HPLC Method 2): 99.6%, t$_R$=2.533 min.
UPLC (UPLC-MS Method 1): t$_R$=0.37 min.
MS (ES+): 433.3 (M+H)⁺.

A powder X-ray diffraction of N-(3-chloropyridin-2-yl)-N-[(3R)-piperidin-3-yl]-4-(pyrazolo[1,5-a]pyrimidin-3-yl)benzamide is provided in FIG. 1.

EXAMPLE 3

N-(3-chloropyridin-2-yl)-4-(6-methyl-3H-[1,2,3]triazolo[4,5-b]pyridin-3-yl)-N-[(3R)-piperidin-3-yl]benzamide

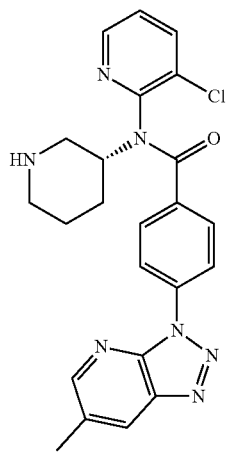 [SMILES: Cc1cnc2c(c1)nnn2-c1ccc(C(=O)N(c2ncccc2Cl)[C@@H]2CCCNC2)cc1]

Step 1: tert-butyl (3R)-3-{(3-chloropyridin-2-yl)[4-(6-methyl-3H-[1,2,3]triazolo[4,5-b]pyridin-3-yl)benzoyl]amino}piperidine-1-carboxylate Oxalyl chloride (0.97 mL, 10.8 mmol) was added to a solution of Preparation 6 4-(6-methyl-3H-[1,2,3]triazolo[4,5-b]pyridin-3-yl)benzoic acid (2.5 g, 9.83 mmol) in DCM (63 mL) and DMF (1.5 mL). The reaction mixture was stirred at room temperature for 2 h and then evaporated. The residue was diluted with toluene and evaporated to dryness. This step was repeated 5 times.

Step 2

General procedure C. The solution of the compound from Step 1 and Preparation 1 tert-butyl (3R)-3-[(3-chloropyridin-2-yl)amino]piperidine-1-carboxylate (3.22 g, 10.3 mmol) in THF (100 mL) was cooled to 0° C., then lithium bis(trimethylsilyl)amide (10.3 mL, 10.3 mmol, 1 M solution in THF) was added dropwise. The resulting mixture was warmed to room temperature and stirred overnight. The reaction mixture was diluted with water and extracted with EtOAc (2×80 mL). The combined organic layers were dried over $MgSO_4$, filtered, and the filtrate was concentrated. The residue was purified by silica gel column chromatography eluting with a gradient of 0-60% EtOAc/heptane to afford the title compound as a yellow solid (3.56 g, 66% yield).

$^1$H NMR ($CDCl_3$) δ 8.61 (d, 2H), 8.26 (d, 2H), 8.21 (dd, 1H), 7.60 (m, 3H), 7.23-7.12 (m, 1H), 4.78-4.42 (m, 2H), 4.39-4.16 (m, 1H), 3.49-3.26 (m, 1H), 2.59 (s, 4H), 2.06-1.95 (m, 1H), 1.88-1.63 (m, 2H), 1.50 (s, 9H), 1.30 (m, 1H).

UPLC (UPLC-MS Method 1): $t_R$=1.04 min.
MS (ES+): 548.2 (M+H)$^+$.

Step 3

Prepared according to General Procedure D starting from the compound from Step 2 tert-butyl (3R)-3-{(3-chloropyridin-2-yl)[4-(6-methyl-3H-[1,2,3]triazolo[4,5-b]pyridin-3-yl)benzoyl]amino}piperidine-1-carboxylate (3.56 g, 6.5 mmol) to provide 2.82 g (90%) of the hydrochloride salt of the title compound as a solid.

$^1$H NMR ($CDCl_3$) δ 10.19-9.98 (m, 1H), 9.93-9.70 (m, 1H), 8.57 (s, 1H), 8.53-8.39 (m, 1H), 8.23 (d, 2H), 8.17 (s, 1H), 7.65-7.50 (m, 3H), 7.20 (dd, 1H), 5.18-4.70 (m, 1H), 4.03-3.73 (m, 2H), 3.66-3.38 (m, 1H), 3.07-2.70 (m, 1H), 2.57 (s, 3H), 2.49-2.32 (m, 1H), 2.30-1.70 (m, 3H).

HPLC purity (HPLC Method 1): 99.5%, $t_R$=3.378 min.
UPLC (UPLC-MS Method 1): $t_R$=0.6 min.
MS (ES+): 449.6 (M+H)$^+$.

EXAMPLE 4

4-(4-{isoquinolin-1-yl[(3R)-piperidin-3-yl]carbamoyl}phenyl)-1-methyl-1H-pyrazole-5-carboxylic acid

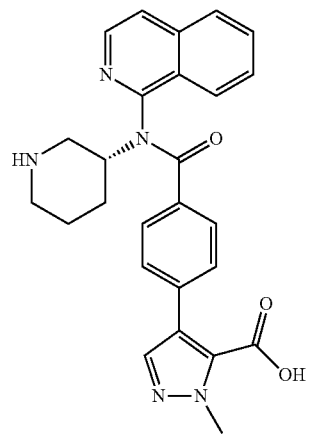 [SMILES: Cn1ncc(-c2ccc(C(=O)N(c3nccc4ccccc34)[C@@H]3CCCNC3)cc2)c1C(=O)O]

Step 1

A suspension of Preparation 16 (50 mg, 0.0897 mmol), 4-iodo-2-methyl-2H-pyrazole-3-carboxylic acid (MFCD00461121) (23 mg, 0.0897 mmol), $Cs_2CO_3$ (58 mg, 0.179 mmol) and $PdCl_2(dppf)_2 \cdot CH_2Cl_2$ (4 mg, 0.00448 mmoL) in 1,4-dioxane (0.8 mL) and $H_2O$ (0.2 mL) was stirred at 80° C. for 16 h. LCMS showed the reaction was complete. The reaction was dried over $Na_2SO_4$ and filtered. The filtrate was concentrated to dryness and purified by prep-HPLC (petroleum ether:EtOAc, 1:1) to give the N-BOC intermediate (10 mg, 20%) as a white solid. The reaction was repeated to obtain additional material.

Step 2

To a solution of the combined lots of material from Step 1 (20 mg, 0.036 mmol) in DCM (2 mL) at 0° C. was added TFA (0.5 mL) dropwise. The resulting mixture was stirred at room temperature for 30 min. LCMS showed the reaction was complete. The solvent was removed by vacuum to give crude (20 mg), which was purified by prep-HPLC to give the title compound (5.8 mg, 35.4%) as a white solid.

$^1$H NMR (400 MHz, DMSO-$d_6$, T=80° C.) δ 8.45 (d, 1H), 8.02 (d, 1H), 7.92 (d, 1H), 7.82 (d, 1H), 7.73-7.65 (m, 2H), 7.41 (s, 1H), 7.18 (d, 2H), 7.12 (d, 2H), 4.99-4.90 (m, 1H), 3.98 (s, 3H), 3.68 (m, 1H), 2.78-2.71 (m, 2H), 2.53 (m, 1H), 2.16-2.02 (m, 1H), 1.81-1.72 (m, 2H), 1.38-1.26 (m, 1H).

MS (ES+): 456.2040 (M+H)$^+$

EXAMPLE 5

N-(3-chloropyridin-2-yl)-N-[(3R)-piperidin-3-yl]-5-(3H-[1,2,3]triazolo[4,5-b]pyridin-3-yl)pyridine-2-carboxamide

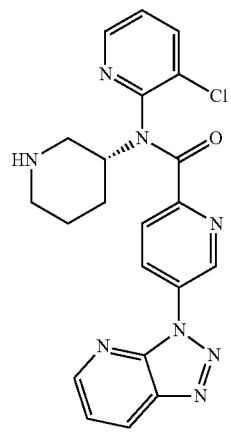 [SMILES: O=C(c1ccc(-n2nnc3cccnc32)cn1)N(c1ncccc1Cl)[C@@H]1CCCNC1]

Step 1: tert-butyl (3R)-3-[(3-chloropyridin-2-yl){[5-(3H-[1,2,3]triazolo[4,5-b]pyridin-3-yl)pyridin-2-yl]carbonyl}amino]piperidine-1-carboxylate Prepared using General Procedures A and C starting from Preparation 1 tert-butyl (3R)-3-[(3-chloropyridin-2-yl)amino]piperidine-1-carboxylate (3.22 g, 10.3 mmol) and Preparation 7 5-(3H-[1,2,3]triazolo[4,5-b]pyridin-3-yl)pyridine-2-carboxylic acid (2.37 g, 9.83 mmol) to provide 2.72 g (52%) of the product isolated as a solid.

$^1$H NMR (CDCl$_3$) δ: 9.24-9.12 (m, 1H), 8.92-8.84 (m, 1H), 8.80 (dd, 1H), 8.49 (dd, 2H), 8.32-8.13 (m, 1H), 7.77-7.58 (m, 1H), 7.49 (dd, 1H), 7.25-7.16 (m, 1H), 4.77-4.49 (m, 2H), 4.45-4.26 (m, 1H), 3.63-3.32 (m, 1H), 2.74-2.53 (m, 1H), 2.48-2.14 (m, 1H), 2.05-1.96 (m, 1H), 1.89-1.60 (m, 2H), 1.54-1.38 (m, 9H).

UPLC (UPLC-MS Method 1): $t_R$=0.98 min.
MS (ES+): 535.5 (M+H)$^+$.

Step 2: N-(3-chloropyridin-2-yl)-N-[(3R)-piperidin-3-yl]-5-(3H-[1,2,3]triazolo[4,5-b]pyridin-3-yl)pyridine-2-carboxamide Prepared according to General Procedure D starting from the compound in Step 1 tert-butyl (3R)-3-[(3-chloropyridin-2-yl){[5-(3H-[1,2,3]triazolo[4,5-b]pyridin-3-yl)pyridin-2-yl]carbonyl}amino]piperidine-1-carboxylate (2.72 g, 5.08 mmol) to provide 2.35 g (98%) of the hydrochloride salt of the product isolated as a solid.

$^1$H NMR (DMSO-d$_6$) δ 9.23 (br s, 1H), 9.02 (br s, 1H), 8.89 (d, 1H), 8.84-8.63 (m, 2H), 8.57 (d, 1H), 8.51-8.41 (m, 1H), 8.19 (d, 1H), 7.96 (d, 1H), 7.66 (dd, 1H), 7.47 (dd, 1H), 5.14-4.51 (m, 1H), 3.61 (m, 1H), 3.53-3.34 (m, 1H), 3.23 (m, 1H), 2.91-2.64 (m, 1H), 2.23-2.07 (m, 1H), 1.98-1.70 (m, 2H), 1.49-1.34 (m, 1H).

HPLC purity (HPLC Method 1): 100%, $t_R$=2.880 min.
UPLC (UPLC-MS Method 1): $t_R$=0.53 min.
MS (ES+): 436.9 (M+H)$^+$.

EXAMPLE 6 ethyl 4-(4-{(3-chloropyridin-2-yl)[(3R)-piperidin-3-yl]carbamoyl}phenyl)-1-methyl-1H-pyrazole-5-carboxylate

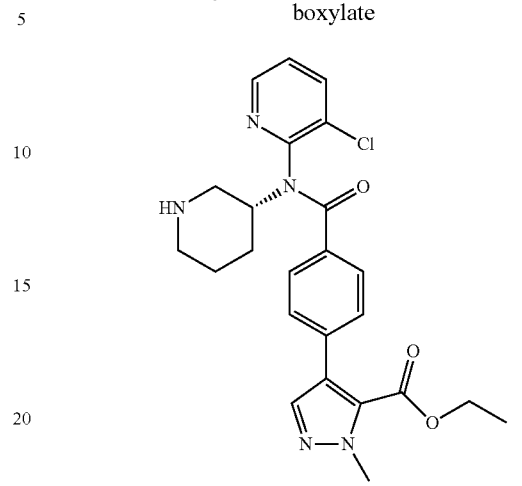

The compound from Preparation 18 (R)-tert-Butyl 3-(N-(3-chloropyridin-2-yl)-4-(5-(ethoxycarbonyl)-1-methyl-1H-pyrazol-4-yl)benzamido)piperidine-1-carboxylate (145.87 g, 256.8 mmol) was dissolved in 1.4 L of DCM and then treated with hydrochloric acid (3 mol/L in cyclopentyl methyl ether, 428 mL, 1284 mmol). The reaction was stirred at room temperature for 19 h then 500 mL of DCM was added followed by warming to 40° C. and then filtering through Celite®. The filtrate was concentrated to 500 mL total volume in vacuo and then added to 1.4 L of EtOAc, resulting in precipitation of solids which were isolated via filtration. After drying, the hydrochloride salt of the title compound was isolated as an off-white solid (125.2 g, 97%).

$^1$H NMR (MeOH-d$_4$, 400 MHz) δ 8.57 (br s, 1H), 7.80 (d, 1H), 7.48 (s, 1H), 7.39 (dd, 1H), 7.32 (d, 2H), 7.29-7.21 (m, 2H), 5.49 (s, 1H), 5.07 (br s, 1H), 4.18 (q, 2H), 4.12 (s, 3H), 3.77 (d, 1H), 3.58 (t, 1H), 3.37 (br s, 1H), 2.96-2.82 (m, 1H), 2.45-1.17 (m, 4H), 1.08 (t, 3H).

UPLC (UPLC Method 4): $t_R$=3.46 min.
MS (ES+) 468.0 (M+H)$^+$

Figure 2:
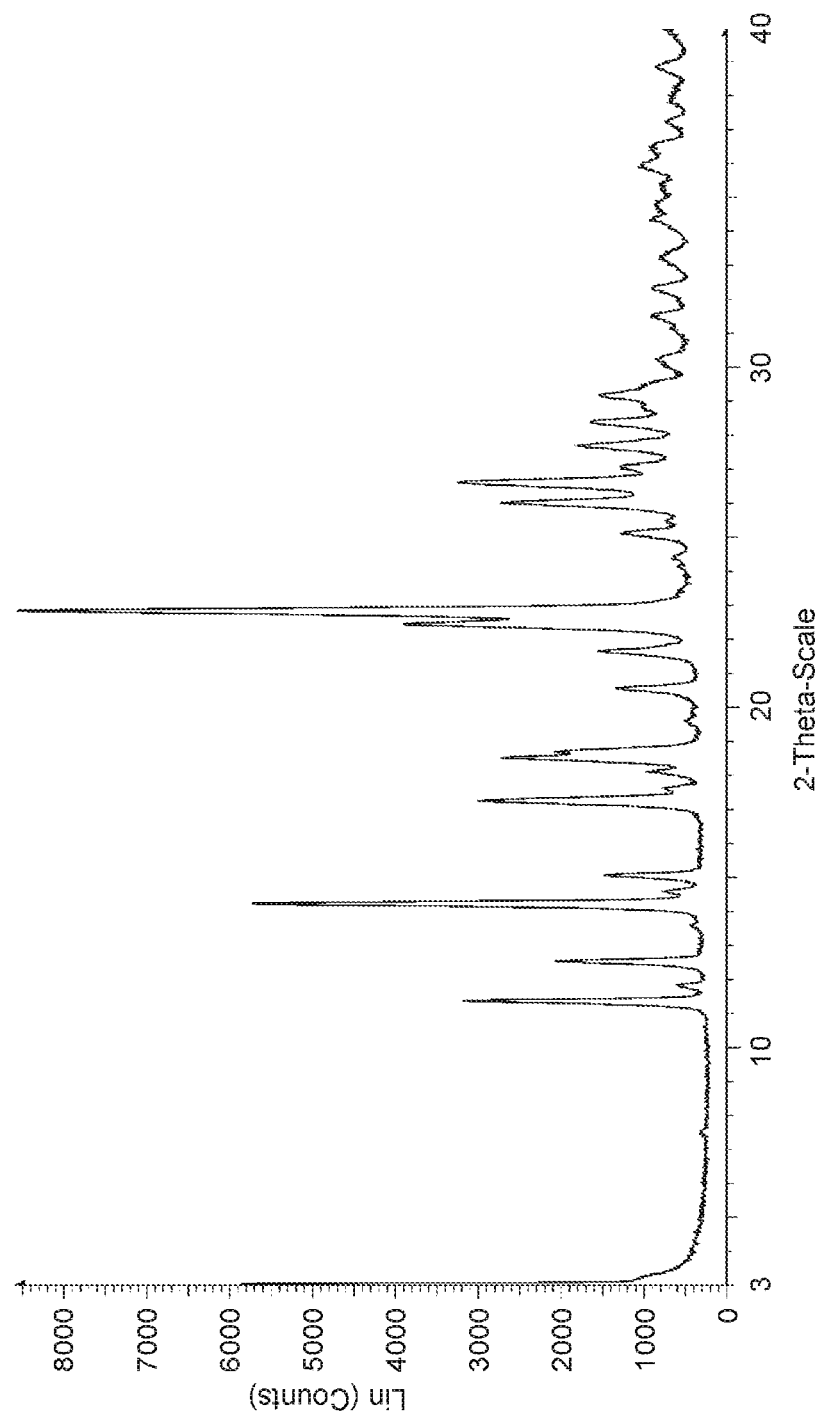
FIG. 2 is a characteristic X-ray powder diffraction pattern showing a crystalline form of Example 6 (Vertical Axis: Intensity (CPS); Horizontal Axis: Two theta (degrees)).

A powder X-ray diffraction of ethyl 4-(4-{(3-chloropyridin-2-yl)[(3R)-piperidin-3-yl]carbamoyl}phenyl)-1-methyl-1H-pyrazole-5-carboxylate is provided in FIG. 2.

EXAMPLE 7

4-(4-{(3-chloropyridin-2-yl)[(3R)-piperidin-3-yl]carbamoyl}phenyl)-1-methyl-1H-pyrazole-5-carboxylic acid

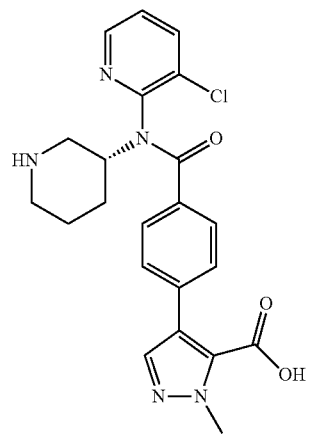 [SMILES: Cn1ncc(-c2ccc(C(=O)N(c3ncccc3Cl)[C@@H]3CCCNC3)cc2)c1C(=O)O]

EXAMPLE 6 Ethyl 4-(4-{(3-chloropyridin-2-yl)[(3R)-piperidin-3-yl]carbamoyl}phenyl)-1-methyl-1H-pyrazole-5-carboxylate hydrochloride salt (7.65 g, 15.2 mmol) was slurried in 50 mL THF followed by the addition of aqueous NaOH (1 mol/L, 50 mL, 50 mmol). Another 23 mL of water was added and the reaction stirred at room temperature for 1.5 h. THF solvent was removed in vacuo, then pH of residual aqueous phase was adjusted to pH 7 with 1 M aqueous HCl, resulting in precipitation of solids. The solids were collected via filtration and after drying afforded the hydrochloride salt of the title compound as an off-white solid (6.49 g, 97%).

$^1$H NMR (400 MHz, DMSO-d$_6$) δ 9.56 (br s, 1H), 9.12 (d, 1H), 8.73-8.45 (m, 1H), 8.06-7.79 (m, 1H), 7.59 (s, 1H), 7.43 (dd, 1H), 7.38-7.11 (m, 4H), 5.11-4.58 (m, 1H), 4.03 (s, 3H), 3.56 (d, 1H), 3.29 (d, 1H), 3.18 (d, 1H), 2.69 (br s, 1H), 2.25-1.18 (m, 4H).

UPLC (UPLC Method 4): t$_R$=2.11 min.
MS (ES+) 439.9 (M+H)$^+$

EXAMPLE 8

1-[(ethoxycarbonyl)oxy]ethyl 4-(4-{(3-chloropyridin-2-yl)[(3R)-piperidin-3-yl]carbamoyl}phenyl)-1-methyl-1H-pyrazole-5-carboxylate

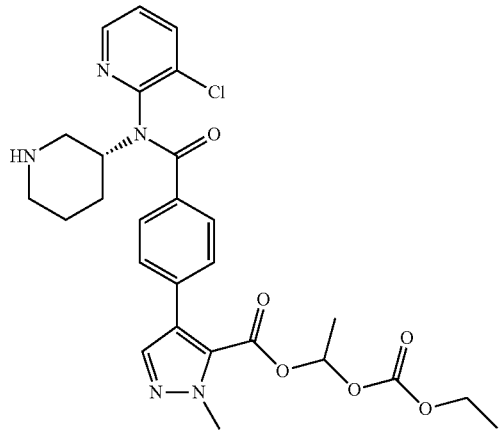 [SMILES: CCOC(=O)OC(C)OC(=O)c1c(-c2ccc(C(=O)N(c3ncccc3Cl)[C@@H]3CCCNC3)cc2)cnn1C]

Step 1: 4-(4-{[(3R)-1-(tert-butoxycarbonyl)piperidin-3-yl](3-chloropyridin-2-yl)carbamoyl}phenyl)-1-methyl-1H-pyrazole-5-carboxylic acid potassium salt General Procedure I. A suspension of the compound from Preparation 18 tert-butyl (3R)-3-[(3-chloropyridin-2-yl){4-[5-(ethoxycarbonyl)-1-methyl-1H-pyrazol-4-yl]benzoyl}amino]piperidine-1-carboxylate (34.03 g, 59.9 mmol) in potassium hydroxide solution in MeOH (1 N, 60 mL, 60 mmol) was heated to 85° C. in a 450 mL sealed pressure tube for 1.5 h. The reaction mixture was then concentrated and toluene (100 mL) was added to the mixture. The solvents were evaporated in vacuo and dried under high vacuum for 2 h. The solid was then slurried in methyl-tert-butyl ether (150 mL) and heptanes (60 mL) for 1 h. The title compound (34.8 g, 100%) was obtained through filtration and dried under high vacuum for 16 h.

Alternative Preparation:

The compound from Preparation 18 (R)-tert-butyl 3-(N-(3-chloropyridin-2-yl)-4-(5-(ethoxycarbonyl)-1-methyl-1H-pyrazol-4-yl)benzamido)piperidine-1-carboxylate (62.9 g, 111 mmol) was combined with potassium hydroxide (1 mol/L in MeOH, 116 mL, 116 mmol) and the mixture was heated at reflux and held for 1 h. The solvent was removed in vacuo and replaced with toluene followed by concentration to a low volume. Toluene (315 mL) was added followed by slow addition of heptane (315 mL) which resulted in precipitation of solids. The solids were isolated via filtration and dried to afford the title compound as a tan solid (66.0 g). This material could be used as is for subsequent reactions.

$^1$H NMR (400 MHz, DMSO-d$_6$) δ 8.57 (br s, 1H), 7.90 (br s, 1H), 7.55 (d, 2H), 7.51 (s, 1H), 7.39 (dd, 1H), 7.11 (d, 2H), 4.37 (m, 1H), 3.15-3.87 (m, 4H), 3.34 (br s, 3H), 2.55-2.10 (br, m, 2H) 1.67 (br s, 2H), 1.41 (br s, 9H).

UPLC-MS (UPLC-MS Method 1): t$_R$=0.87 min
MS (ES+): 540.3 (M+H)$^+$

Step 2: tert-butyl (3R)-3-[(3-chloropyridin-2-yl){4-[5-({1-[(ethoxycarbonyl)oxy]ethoxy}carbonyl)-1-methyl-1H-pyrazol-4-yl]benzoyl}amino]piperidine-1-carboxylate General Procedure J. To a suspension of the compound from Step 1 4-(4-{[(3R)-1-(tert-butoxycarbonyl)piperidin-3-yl](3-chloropyridin-2-yl)carbamoyl}phenyl)-1-methyl-1H-pyrazole-5-carboxylic acid potassium salt (51.72 g, 89.46 mmol) in acetonitrile (100 mL) was added chloroethyl ethylcarbonate (13.3 mL, 98.5 mmol) dropwise at room temperature in a 450 mL pressure tube. The reaction was heated to 70° C. for 2 h or until LC-MS indicated consumption of the starting materials. Potassium chloride was filtered off and rinsed with acetonitrile (30 mL). The filtrate was concentrated and the crude product was purified by Combiflash Chromatography (0-60% gradient) EtOAc/heptane to obtain the title compound (56.1 g, 96%).

Alternative Preparation:

The compound from Step 1 Potassium (R)-4-(4-((1-(tert-butoxycarbonyl)piperidin-3-yl)(3-chloropyridin-2-yl)carbamoyl)phenyl)-1-methyl-1H-pyrazole-5-carboxylate (62.0 g, 115 mmol) was dissolved in 248 mL of acetonitrile followed by addition of 1-chloroethyl ethyl carbonate (21.0 g, 138 mmol) and the mixture was heated at reflux. The reaction was maintained at reflux for 6 h and then cooled to room temperature. After treatment with Darco® G60, the mixture was filtered through Celite® and then concentrated to dryness to give the title compound as a tan foam (66.7 g, 88%). This material could be crystallized as follows: The crude product (6 g) was dissolved in 24 mL of iPrOAc, then 120 mL of heptanes was slowly added resulting in solid precipitation. The solids were isolated via filtration and dried to give crystallized title compound as a tan solid (4.5 g, 75% yield).

$^1$H NMR (400 MHz, DMSO-d$_6$) δ 8.57 (br s, 1H), 7.90 (br s, 1H), 7.66 (s, 1H), 7.41 (m, 1H), 7.24 (br s, 4H), 6.77 (q, 1H), 4.48-4.31 (m, 3H), 4.18 (q, 2H), 4.06 (s, 3H), 3.88 (br s, 2H), 2.14-2.55 (m, 2H), 1.70 (m, 2H), 1.42 (br s, 9H), 1.26 (m, 6H).

UPLC (UPLC Method 4): t$_R$=7.00 min
UPLC-MS (UPLC-MS Method 2): t$_R$=2.07 min
MS (ES+): 656.3 (M+H)

Step 3: 1-[(ethoxycarbonyl)oxy]ethyl 4-(4-{(3-chloropyridin-2-yl)[(3R)-piperidin-3-yl]carbamoyl}phenyl)-1-methyl-1H-pyrazole-5-carboxylate tert-Butyl (3R)-3-[(3-chloropyridin-2-yl){4-[5-({1-[(ethoxycarbonyl)oxy]ethoxy}carbonyl)-1-methyl-1H-pyrazol-4-yl]benzoyl}amino]piperidine-1-carboxylate. The compound from Step 2 (45.05 g, 68.66 mmol) was dissolved in DCM (300 mL) and to the solution was added HCl in 1,4- dioxane (4.0M, 172 mL, 687 mmol) and stirred at room temperature for 1 h or until LC-MS showed consumption of the starting materials. The solvent was removed in vacuo and to the residue was added toluene (300 mL x 2). The solvent was evaporated and the residue was resuspended in heptane (400 mL x 2) and evaporated. The residue was then triturated with heptane (500 mL) and stirred in heptane for 24 h. The hydrochloride salt of title compound (40.8 g, 100%) was obtained by filtration as white powder.

Alternative Preparation:

(3R)-tert-Butyl 3-(N-(3-chloropyridin-2-yl)-4-(5-((1-(ethoxycarbonyloxy)ethoxy)carbonyl)-1-methyl-1H-pyrazol-4-yl)benzamido)piperidine-1-carboxylate. The compound from Step 2 (6.0 g, 9.1 mmol) was dissolved in 40 mL of DCM and then treated with hydrochloric acid (12.1 mol/L in water, 11 mL, 140 mmol). The reaction was stirred for 1 h at room temperature, followed by the addition of 30 mL of water and phase separation. The organic phase was dried over $MgSO_4$, filtered, and the filtrate was concentrated to a low volume. Residual DCM was displaced with heptane to give solids which were collected via filtration and dried to afford the hydrochloride salt of the title compound as a tan solid (4.95 g, 91% yield).

$^1$H NMR (DMSO-$d_6$) δ 8.58 (s, 1H), 7.91 (d, 1H), 7.66 (s, 1H), 7.44 (m, 1H), 7.25 (br s, 4H), 6.77 (q, 1H), 5.02-4.70 (br m, 1H), 4.18 (q, 2H), 4.07 (s, 3H), 3.57-3.26 (m, 4H), 2.72 (br s, 1H), 1.67-2.23 (m, 3H), 1.20-1.34 (m, 6H).

UPLC-MS (UPLC-MS Method 2): $t_R$=0.88 min

MS (ES+): 556.3 (M+H)$^+$

HPLC (HPLC Method 3): $t_R$=3.66 min, 99.65%

Elemental Analysis: $C_{27}H_{30}ClN_5O_6$. HCl 0.75; $H_2O$. Calc'd C, 53.52; H, 5.41; N, 11.56. Found C, 53.67; H, 5.40; N, 11.34.

EXAMPLE 9

N-(3-chloropyridin-2-yl)-5-(6-methyl-3H-[1,2,3]triazolo[4,5-b]pyridin-3-yl)-N-[(3R)-piperidin-3-yl]pyridine-2-carboxamide

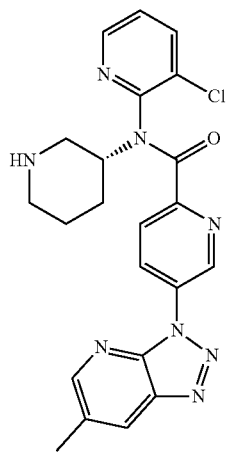 [SMILES: Cc1cnc2c(c1)nnn2-c1ccc(C(=O)N(c2ncccc2Cl)[C@@H]2CCCNC2)nc1]

Step 1: tert-butyl (3R)-3-[(3-chloropyridin-2-yl){[5-(6-methyl-3H-[1,2,3]triazolo[4,5-b]pyridin-3-yl)pyridin-2-yl]carbonyl}amino]piperidine-1-carboxylate Prepared according to General Procedure A and C starting from Preparation 1 tert-butyl (3R)-3-[(3-chloropyridin-2-yl)amino]piperidine-1-carboxylate (3.22 g, 10.3 mmol) and Preparation 8 5-(6-methyl-3H-[1,2,3]triazolo[4,5-b]pyridin-3-yl)pyridine-2-carboxylic acid (2.51 g, 9.83 mmol) to provide 2.33 g (43%) of the product as a solid.

$^1$H NMR (CDCl$_3$) δ 9.27-9.07 (m, 1H), 8.96-8.78 (m, 1H), 8.63 (d, 1H), 8.56-8.37 (m, 1H), 8.30-8.16 (m, 2H), 7.79-7.55 (m, 1H), 7.26-7.12 (m, 1H), 4.86-4.47 (m, 2H), 4.45-4.01 (m, 2H), 3.70-3.29 (m, 1H), 2.60 (s, 3H), 2.47-1.95 (m, 2H), 1.90-1.55 (m, 2H), 1.54-1.33 (s, 9H).

UPLC (UPLC-MS Method 1): $t_R$=1.02 min.

MS (ES+): 549.4 (M+H)$^+$.

Step 2: N-(3-chloropyridin-2-yl)-5-(6-methyl-3H-[1,2,3]triazolo[4,5-b]pyridin-3-yl)-N-[(3R)-piperidin-3-yl]pyridine-2-carboxamide Prepared according to General Procedure D starting from the compound in Step 1 (2.33 g, 4.25 mmol) to provide 2.03 g (98%) of the hydrochloride salt of the product as a solid.

$^1$H NMR (MeOH-$d_4$) δ 9.27-9.09 (m, 1H), 8.95-8.84 (m, 1H), 8.72 (s, 1H), 8.61-8.50 (m, 1H), 8.49-8.41 (m, 1H), 8.37 (s, 1H), 8.22-8.11 (m, 1H), 8.02-7.80 (m, 1H), 7.54-7.30 (m, 1H), 5.17-4.41 (m, 1H), 3.97-3.60 (m, 2H), 3.56-3.36 (m, 1H), 3.10-2.84 (m, 1H), 2.60 (s, 3H), 2.43-1.80 (m, 3H), 1.74-1.47 (m, 1H).

HPLC purity (HPLC Method 1): 99.85%, $t_R$=3.215 min.

UPLC (UPLC-MS Method 1): $t_R$=0.61 min.

MS (ES+): 449.4 (M+H)$^+$.

EXAMPLE 10

Methyl 4-(4-{(3-chloropyridin-2-yl)[(3R)-piperidin-3-yl]carbamoyl}phenyl)-1-methyl-1H-pyrazole-5-carboxylate

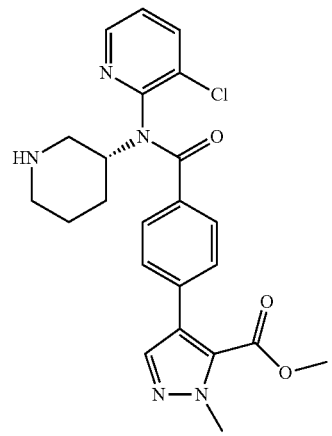 [SMILES: COC(=O)c1c(-c2ccc(C(=O)N(c3ncccc3Cl)[C@@H]3CCCNC3)cc2)cnn1C]

Step 1: tert-butyl 3-[(3-chloropyridin-2-yl){4-[5-(methoxycarbonyl)-1-methyl-1H-pyrazol-4-yl]benzoyl}amino]piperidine-1-carboxylate NaOMe (10.19 mL, 5.09 mmol, 0.5 M solution in MeOH) was added to a suspension of Preparation 18 (2.63 g, 4.6 mmol) in MeOH (20 mL). The resulting mixture was heated at reflux for 2 hr, before concentrating in vacuo to yield a mixture of the methyl ester as the major component, along with the corresponding acid as the minor component. This crude mixture was treated with $K_2OC_3$ (320 mg, 2.32 mmol)

and MeI (144 uL, 2.32 mmol) in acetonitrile (20 mL) at reflux for 4 hr. The reaction mixture was cooled to room temperature, diluted with water (30 mL) and extracted with EtOAc (3×70 mL). The combined organic phases were dried over MgSO$_4$, filtered, and the filtrate was concentrated. The residue was purified by silica gel column chromatography eluting with a gradient of 0-70% EtOAc/heptane to afford the title compound as a white solid (2.23 g, 87% yield).

$^1$H NMR (CDCl$_3$) δ 8.48 (m, 1H), 7.59 (m, 1H), 7.44 (s, 1H), 7.37-7.25 (m, 2H), 7.17 (m, 3H), 4.77-4.27 (m, 2H), 4.26-3.92 (m, 4H), 3.70 (s, 3H), 3.35 (m, 1H), 2.58 (m, 1H), 2.04-1.64 (m, 2H), 1.56-1.07 (m, 11H).

UPLC (UPLC-MS Method 2), $t_R$=1.86 min.
MS (ES+): 554.3 (M+H)$^+$.

Step 2: methyl 4-(4-{(3-chloropyridin-2-yl)[(3R)-piperidin-3-yl]carbamoyl}phenyl)-1-methyl-1H-pyrazole-5-carboxylate Prepared according to General Procedure D starting from the compound in Step 2 tert-butyl 3-[(3-chloropyridin-2-yl){4-[5-(methoxycarbonyl)-1-methyl-1H-pyrazol-4-yl]benzoyl}amino]piperidine-1-carboxylate (2.22 g, 4.0 mmol) to provide 1.82 g (93%) of the hydrochloride salt of the product as a solid.

$^1$H NMR (DMSO-d$_6$) δ 9.43-9.12 (m, 1H), 9.10-8.86 (m, 1H), 8.68-8.38 (m, 1H), 7.95 (d, 1H), 7.65 (s, 1H), 7.46 (dd, 1H), 7.24 (m, 4H), 5.10-4.60 (m, 1H), 4.05 (s, 3H), 3.78-3.60 (m, 4H), 3.20-2.90 (m, 2H), 2.73 (m, 1H), 2.11-1.84 (m, 3H), 1.26 (m, 1H).

HPLC purity (HPLC Method 3): 99.44%, $t_R$=2.993 min.
UPLC (UPLC-MS Method 1): $t_R$=0.54 min.
MS (ES+): 454.3 (M+H)$^+$.

EXAMPLE 11

1-[(ethoxycarbonyl)oxy]ethyl 4-(4-{isoquinolin-1-yl[(3R)-piperidin-3-yl]carbamoyl}phenyl)-1-methyl-1H-pyrazole-5-carboxylate

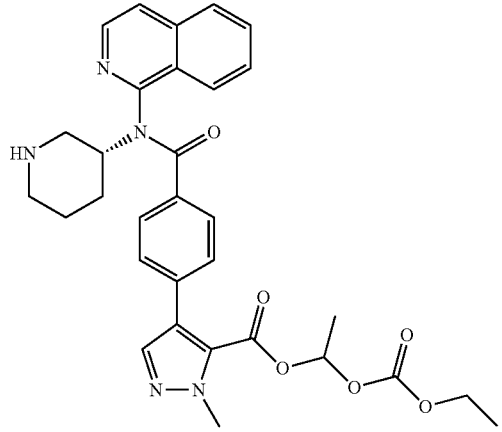 [SMILES: CCOC(=O)OC(C)OC(=O)c1c(-c2ccc(C(=O)N(c3nccc4ccccc34)[C@@H]3CCCNC3)cc2)cnn1C]

To a suspension of the compound from EXAMPLE 4, Step 1 4-(4-{isoquinolin-1-yl[tert-butyl (3R)-piperidin-3-yl]carbamoyl}phenyl)-1-methyl-1H-pyrazole-5-carboxylic acid (96 mg, 0.17 mmol) in acetonitrile (2 mL) was added K$_2$OC$_3$ (36 mg, 0.26 mmol) and chloroethyl ethylcarbonate (46 uL, 0.35 mmol). The mixture was stirred at 65° C. in a sealed tube for 16 h. The reaction mixture was then filtered through Celite® and concentrated. The residue was dissolved in DCM (1 mL) and HCl in 1,4-dioxane (4 M, 1 mL, 4 mmol) was added. The mixture was stirred at room temperature for 30 min then concentrated. The residue was dried under high vacuum for 2 h then slurried in MTBE (1 mL) for 16 h. The title compound hydrochloride salt (107 mg, 99%) was obtained by filtration.

$^1$H NMR (400 MHz, DMSO-d$_6$) δ 8.51 (t, 1H), 8.05-7.53 (m, 6H), 7.19 (d, 2H), 7.08 (d, 2H), 6.68 (m, 1H), 5.15 (m, 1H), 4.17 (q, 2H), 4.01 (s, 3H), 3.74-3.18 (m, 4H), 2.68 (br s, 1H), 2.34-1.78 (m, 3H), 1.26-1.12 (m, 6H).

UPLC-MS (UPLC-MS Method 1): $t_R$=0.66 min
MS (ES+): 572.5 (M+H)$^+$

EXAMPLE 12

1-methyl-4-(4-{(1-methyl-1H-pyrrolo[2,3-c]pyridin-7-yl)[(3R)-piperidin-3-yl]carbamoyl}phenyl)-1H-pyrazole-5-carboxylic acid

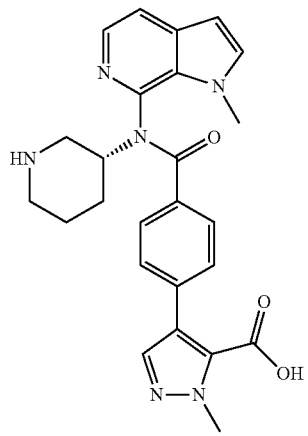 [SMILES: Cn1ncc(-c2ccc(C(=O)N(c3nccc4ccn(C)c34)[C@@H]3CCCNC3)cc2)c1C(=O)O]

Step 1: (R)-tert-butyl 3-(N-(1-methyl-1H-pyrrolo[2,3-c]pyridin-7-yl)-4-(4,4,5,5-tetramethyl-1,3,2-dioxaborolan-2-yl)benzamido)piperidine-1-carboxylate To a solution of Preparation 11 (R)-tert-butyl 3-(4-bromo-N-(1-methyl-1H-pyrrolo[2,3-c]pyridin-7-yl)benzamido)-piperidine-1-carboxylate (0.35 g, 0.68 mmol) in 1,4-dioxane (10 mL) was added bis(pinacolato)-diboron (0.35 g, 1.38 mmol), Pd(dppf)Cl$_2$ (0.05 g, 0.068 mmol) and KOAc (0.200 g, 2.04 mmol). The reaction was heated at 85° C. for 2 h. The reaction mixture was concentrated under reduced pressure to give the title compound (0.5 g), which was used in the next step without purification.

Step 2: (R)-tert-butyl 3-(4-(5-(ethoxycarbonyl)-1-methyl-1H-pyrazol-4-yl)-N-(1-methyl-1H-pyrrolo[2,3-c]pyridin-7-yl)benzamido)piperidine-1-carboxylate To a solution of the compound from Step 1 (R)-tert-butyl 3-(N-(1-methyl-1H-pyrrolo[2,3-c]pyridin-7-yl)-4-(4,4,5,5-tetramethyl-1,3,2-dioxaborolan-2-yl)benzamido)piperidine- 1-carboxylate (0.5 g, 0.89 mmol) in 1,4-dioxane (10 mL) was added ethyl 4-bromo-1-methyl-1H-pyrazole-5-carboxylate (0.21 g, 0.90 mmol), Pd(dppf)Cl$_2$ (0.065 g, 0.089 mmol) and Cs$_2$CO$_3$ (0.58 g, 1.78 mmol). The reaction was heated 85° C. for 16 h. The reaction mixture was concentrated under reduced pressure. The resulting crude product was purified by silica gel chromatography eluting with a gradient of petroleum ether: EtOAc (5:1 to 0:1) to afford the title compound (0.45 g, 86%) as yellow solid.

$^1$H NMR (400 MHz, DMSO-d$_6$, T=80° C.) δ 8.09 (d, 0.6H), 8.07 (d, 0.4H), 7.54-7.38 (m, 3H), 7.30 (m, 2H), 7.19 (m, 2H), 6.46 (d, 0.4H), 6.44 (d, 0.6H), 4.13-4.07 (m, 2H), 4.03 (s, 3H), 3.94-3.90 (m, 1H), 3.89 (s, 3H), 2.60-2.50 (m, 2H), 1.82-1.48 (m, 3H), 1.45 (s, 6H), 1.38 (s, 3H), 1.03-0.93 (m, 3H).

LC (LC-MS Method 3): t$_R$=1.12 min

MS (ES+): 359.1 (M+H)$^+$

Step 3: (R)-4-(4-((1-(tert-butoxycarbonyl)piperidin-3-yl)(1-methyl-1H-pyrrolo[2,3-c]pyridin-7-yl)carbamoyl)phenyl)-1-methyl-1H-pyrazole-5-carboxylic acid To a solution of the compound from Step 2 (R)-tert-butyl 3-(4-(5-(ethoxycarbonyl)-1-methyl-1H-pyrazol-4-yl)-N-(1-methyl-1H-pyrrolo[2,3-c]pyridin-7-yl)benzamido)piperidine-1-carboxylate (0.2 g, 0.34 mmol) in MeOH (10 mL) was added aqueous NaOH (2 N, 1.5 mL). The reaction mixture was stirred at room temperature for 2 h. The solvent was removed under reduced pressure, and the pH was adjusted with 1N HCl until pH 4. The acidified mixture was extracted with EtOAc (3×10 mL). The combined organic layers were dried over Na$_2$SO$_4$, filtered, and the filtrate was concentrated under reduced pressure to deliver the title compound (0.18 g) as yellow oil which was used in the next step without purification.

Step 4: (R)-1-methyl-4-(4-((1-methyl-1H-pyrrolo[2,3-c]pyridin-7-yl)(piperidin-3-yl)carbamoyl)phenyl)-1H-pyrazole-5-carboxylic acid hydrochloride To a solution of the compound from Step 3 (R)-4-(4-((1-(tert-butoxycarbonyl)piperidin-3-yl)(1-methyl-1H-pyrrolo[2,3-c]pyridin-7-yl)carbamoyl)phenyl)-1-methyl-1H-pyrazole-5-carboxylic acid (0.18 g, 0.17 mmol) in 1,4-dioxane (10 mL) was added HCl in 1,4-dioxane (10 mL, 4 N). The mixture was stirred at room temperature for 1 h. The mixture was concentrated in vacuo. The resulting residue was triturated with EtOAc to deliver the hydrochloride salt of the title compound (0.12 g, 70% over 2 steps) as a brown solid. $^1$H NMR (400 MHz, DMSO-d$_6$, T=80° C.) δ 9.38 (br s, 1H), 9.11 (br s, 1H), 8.11 (d, 0.75H), 8.08 (d, 0.25H), 7.57 (d, 1H), 7.52-7.46 (m, 2H), 7.28-7.17 (m, 4H), 6.61 (d, 0.25H), 6.49 (d, 0.75H), 4.02 (s, 3H), 3.98-3.94 (m, 1H), 3.90 (s, 3H), 3.76-3.67 (m, 1H), 3.61-3.50 (m, 1H), 3.28-3.15 (m, 1H), 2.86-2.64 (m, 2H), 1.90-1.69 (m, 3H).

LC (LC-MS Method 3): t$_R$=0.937 min

MS (ES+): 459.0 (M+H)$^+$

EXAMPLE 13

Methyl 1-methyl-4-(4-{(3-methylpyridin-2-yl)[(3R)-piperidin-3-yl]carbamoyl}phenyl)-1H-pyrazole-5-carboxylate

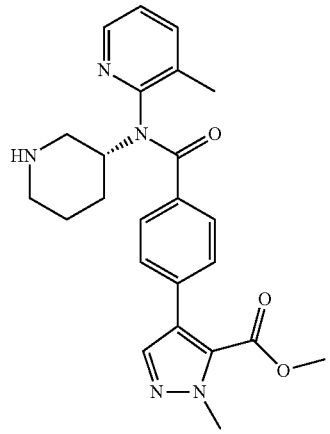 [SMILES: COC(=O)c1c(-c2ccc(C(=O)N(c3ncccc3C)[C@@H]3CCCNC3)cc2)cnn1C]

Step 1: tert-butyl (3R)-3-[{4-[5-(methoxycarbonyl)-1-methyl-1H-pyrazol-4-yl]benzoyl}(3-methylpyridin-2-yl)amino]piperidine-1-carboxylate To a solution of 4-iodo-2-methyl-2H-pyrazole-3-carboxylic acid methyl ester (8.1 g, 30.45 mmol) in THF (anhydrous, 60 mL) was added isopropyl magnesium chloride (16.5 mL, 16.5 mmol) at −45° C. The solution turned from clear to light green-yellowish. Stirred at this temperature for 30 min, GC-MS (sample in CD$_3$OD) indicated all halogen-metal exchange completed. To the mixture was added 1.9 N ZnCl$_2$ in 2-MeTHF (9.62 mL, 18.3 mmol) dropwise and the reaction was warmed to room temperature. The mixture was stirred for 2 h, over which time it turned from clear yellowish to an opaque yellowish mixture. To this reaction was added Preparation 2 tert-butyl 3-[(4-bromobenzoyl)(3-methylpyridin-2-yl)amino]piperidine-1-carboxylate (12.04 g, 25.37 mmol) as a solid in one batch. The reaction temperature was then raised to 50° C., 1'-bis(di-tert-butylphosphino)ferrocene palladium dichloride (166 mg, 0.254 mmol) was added. The reaction was then stirred at 60° C. for 2 h then cooled to room temperature. The reaction was quenched with water and extracted 3× EtOAc. The organic layer was dried and concentrated. Purification was performed by Combiflash ISCO column (220 g) 0-75% EtOAc/heptane to isolate the desired title compound (12.8 g, 78%).

$^1$H NMR (DMSO-d$_6$) δ 8.45 (br s, 1H), 7.54-7.67 (m, 3H), 7.11-7.33 (m, 5H), 4.27-4.54 (m, 1H), 4.05 (s, 4H), 3.80-3.96 (m, 1H), 3.65 (s, 4H), 1.92-2.14 (m, 4H), 1.34-1.56 (m, 13H)

UPLC-MS (UPLC-MS method 1): t$_R$=0.96 min

MS (ES+): 534.5 (M+H)$^+$

Step 2: methyl 1-methyl-4-(4-{(3-methylpyridin-2-yl)[(3R)-piperidin-3-yl]carbamoyl}phenyl)-1H-pyrazole-5-carboxylate To the compound prepared in Step 1 (31.45 mg, 58.94 mmol) in MeOH (100 mL) was added HCl in 1,4-dioxane (147 mL, 589 mmol) and stirred at room temperature for 30 min. The solvent was removed in vacuo to give a solid that was dried under high vacuum for 2 h. EtOAc (700 mL) and MeOH (20 mL) were added and the mixture was stirred at room temperature for 16 h. The title compound was obtained by filtration as the dihydrochloride salt (29.8 g, 99.8%).

$^1$H NMR (DMSO-$d_6$) δ 9.07-9.40 (br m, 1H), 8.35-8.53 (m, 1H), 7.55-7.72 (m, 2H), 7.28-7.37 (m, 1H), 7.20 (d, 4H), 4.96 (br m, 1H), 4.05 (s, 3H), 3.65 (s, 3H), 3.59 (d, 1H), 3.39 (d, 1H), 3.20 (d, 1H), 2.68 (br s, 1H), 2.00 (s, 3H), 1.80 (br s, 4H).

UPLC-MS (UPLC-MS Method 1): $t_R$=0.52 min

MS (ES+): 434.4 (M+H)$^+$

HPLC (HPLC Method 2): $t_R$=2.17 min, 99.88%

Figure 3:
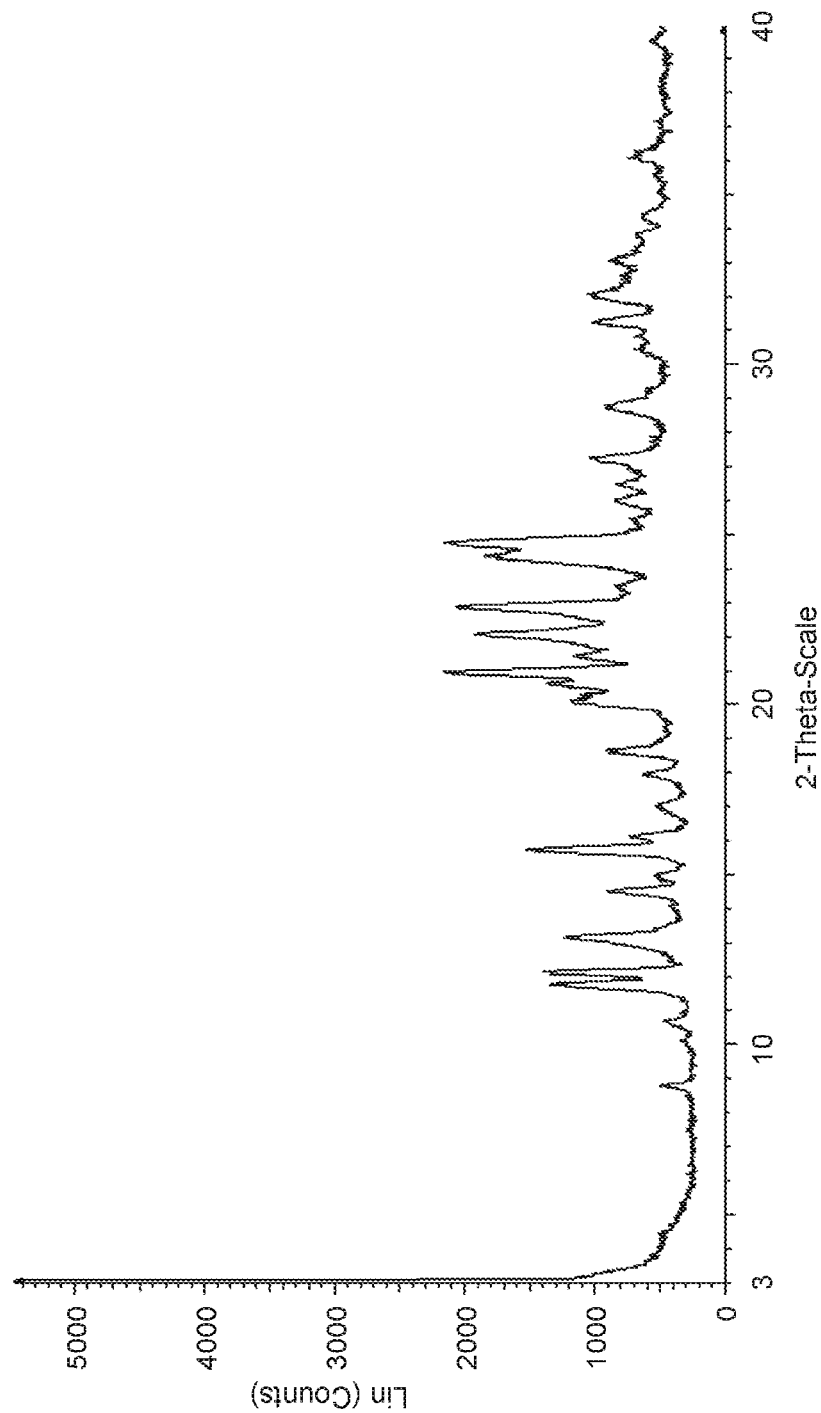
FIG. 3 is a characteristic X-ray powder diffraction pattern showing a crystalline form of Example 13 (Vertical Axis: Intensity (CPS); Horizontal Axis: Two theta (degrees)).

A powder X-ray diffraction of methyl 1-methyl-4-(4-{(3-methylpyridin-2-yl)[(3R)-piperidin-3-yl]carbamoyl}phenyl)-1H-pyrazole-5-carboxylate is provided in FIG. 3.

EXAMPLE 14

1-[(ethoxycarbonyl)oxy]ethyl 1-methyl-4-(4-{(1-methyl-1H-pyrrolo[2,3-c]pyridin-7-yl)[(3R)-piperidin-3-yl]carbamoyl}phenyl)-1H-pyrazole-5-carboxylate

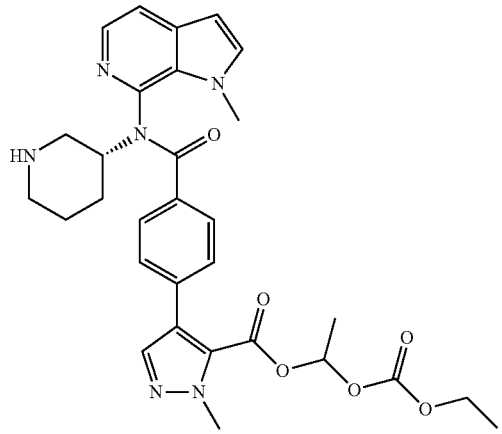 [SMILES: CCOC(=O)OC(C)OC(=O)c1c(-c2ccc(C(=O)N(c3nccc4ccn(C)c34)[C@@H]3CCCNC3)cc2)cnn1C]

The title compound was prepared using General Procedures I, J, and D.

$^1$H NMR (DMSO-$d_6$) δ 8.07-8.17 (m, 1H), 7.58 (br s, 2H), 7.52 (br s, 1H), 7.21 (br s, 2H), 7.09-7.17 (m, 2H), 6.71 (d, 1H), 6.47 (br s, 1H), 4.18 (q, 2H), 4.03 (s, 3H), 3.81-3.96 (m, 3H), 3.63-3.76 (m, 1H), 3.57 (s, 3H), 3.49 (m, 1H), 3.21 (d, 1H), 2.68-2.75 (m, 1H), 1.67-1.84 (m, 2H), 1.22-1.31 (m, 3H), 1.06-1.17 (m, 3H).

UPLC-MS (UPLC-MS Method 1): $t_R$=0.63 min

MS (ES+): 575.3 (M+H)$^+$

EXAMPLE 15a and 15b 15a-(1S)-1-[(ethoxycarbonyl)oxy]ethyl 4-(4-{(3-chloropyridin-2-yl)[(3R)-piperidin-3-yl]carbamoyl}phenyl)-1-methyl-1H-pyrazole-5-carboxylate

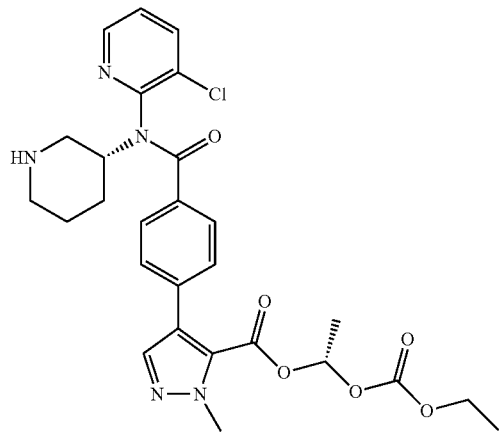 [SMILES: CCOC(=O)O[C@@H](C)OC(=O)c1c(-c2ccc(C(=O)N(c3ncccc3Cl)[C@@H]3CCCNC3)cc2)cnn1C]

15b-(1R)-1-[(ethoxycarbonyl)oxy]ethyl 4-(4-{(3-chloropyridin-2-yl)[(3R)-piperidin-3-yl]carbamoyl}phenyl)-1-methyl-1H-pyrazole-5-carboxylate

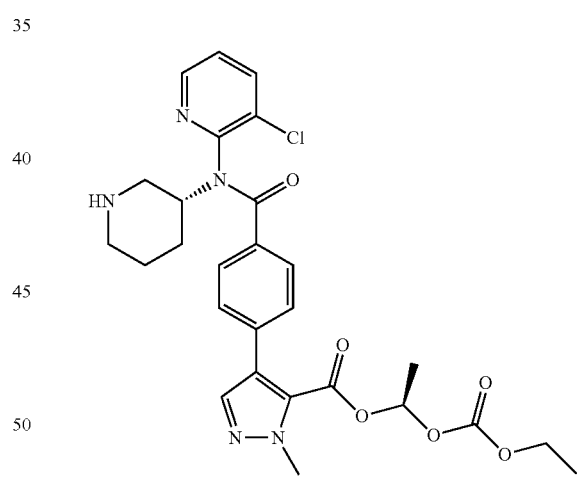

Step 1

50 g of the compound from EXAMPLE 8, Step 2 (3R)-tert-butyl 3-(N-(3-chloropyridin-2-yl)-4-(5-((1 (ethoxycarbonyl-oxy)ethoxy)carbonyl)-1-methyl-1H-pyrazol-4-yl)benzamido)piperidine-1-carboxylate was processed according to Chiral Preparative Chromatography Method 1, followed by concentration of each diastereomer to dryness in vacuo to give isomer 1 (20.3 g, 81% yield, 100% e.e.; $t_R$=6.6 min) and isomer 2 (22.0 g, 88% yield, 98.5% e.e; $t_R$=6.9 min).

Each isomer was independently subjected to deprotection as described below.

Step 2a

To a solution of isomer 1 (566 mg, 0.863 mmol) in DCM (3 mL) was added 4M HCl in 1,4-dioxane (3 mL, 12 mmol) and stirred at room temperature for 30 min. The solvent was evaporated and the residue was slurried in MTBE (10 mL) and heptane (10 mL) for 16 h. Example 15a hydrochloride salt (511 mg, 99%) was obtained by filtration to give a white amorphous powder.

EXAMPLE 15a $^1$H NMR (DMSO-$d_6$) δ 8.45-8.71 (m, 1H), 7.92 (d, 1H), 7.67 (br s, 1H), 7.45 (m, 1H), 7.25 (br s, 4H), 6.77 (d, 1H), 5.02 (br s, 1H), 4.18 (q, 2H), 4.07 (s, 3H), 3.59 (br s, 2H), 3.21 (d, 2H), 2.73 (br s, 1H), 1.75-2.38 (m, 3H), 1.25 (m, 6H)
UPLC-MS (UPLC-MS Method 1): $t_R$=0.63 min
MS (ES+): 556.4 (M+H)$^+$
Optical rotation: $[\alpha]^{20}$=−107.3° (c=0.87 g/dL, acetonitrile)

Step 2b

To a solution of isomer 2 (2.8 g, 4.3 mmol) in DCM (30 mL) was added 4M HCl in 1,4-dioxane (10 mL, 40 mmol) and stirred at room temperature for 30 min. The solvent was then evaporated and the residue was slurried in MTBE (10 mL) and heptane (10 mL) for 16 h. Example 15b hydrochloride salt (2.5 g, 99%) was obtained by filtration as white amorphous powder. The amorphous powder was suspended in a mixture of acetonitrile (20 mL), DCM (10 mL) and MTBE (300 mL) and the mixture was heated at reflux for 48 h. The crystalline compound as the hydrochloride salt (2.2 g, 87%) was obtained by filtration.

EXAMPLE 15b $^1$H NMR (DMSO-$d_6$) δ 8.50-8.66 (m, 1H), 7.92 (d, 1H), 7.66 (s, 1H), 7.40-7.51 (m, 1H), 7.25 (br s, 4H), 6.77 (d, 1H), 5.00 (br s, 1H), 4.18 (q, 2H), 4.07 (s, 3H), 3.60 (br s, 2H), 3.21 (d, 2H), 2.74 (br s, 1H), 1.67-2.23 (m, 3H), 1.20-1.34 (m, 6H)
UPLC-MS (UPLC-MS Method 1): $t_R$=0.64 min
MS (ES+): 556.4 (M+H)$^+$
Optical rotation: $[\alpha]^{20}$=−25.0° (c=0.81 g/dL, acetonitrile)
Elemental Analysis: Calc'd for $C_{27}H_{31}Cl_2N_5O_6$ C, 54.74; H, 5.27; N, 11.82; Cl 11.97. Found C, 54.53; H, 5.11; N, 11.72; Cl 11.72.

Figure 4:
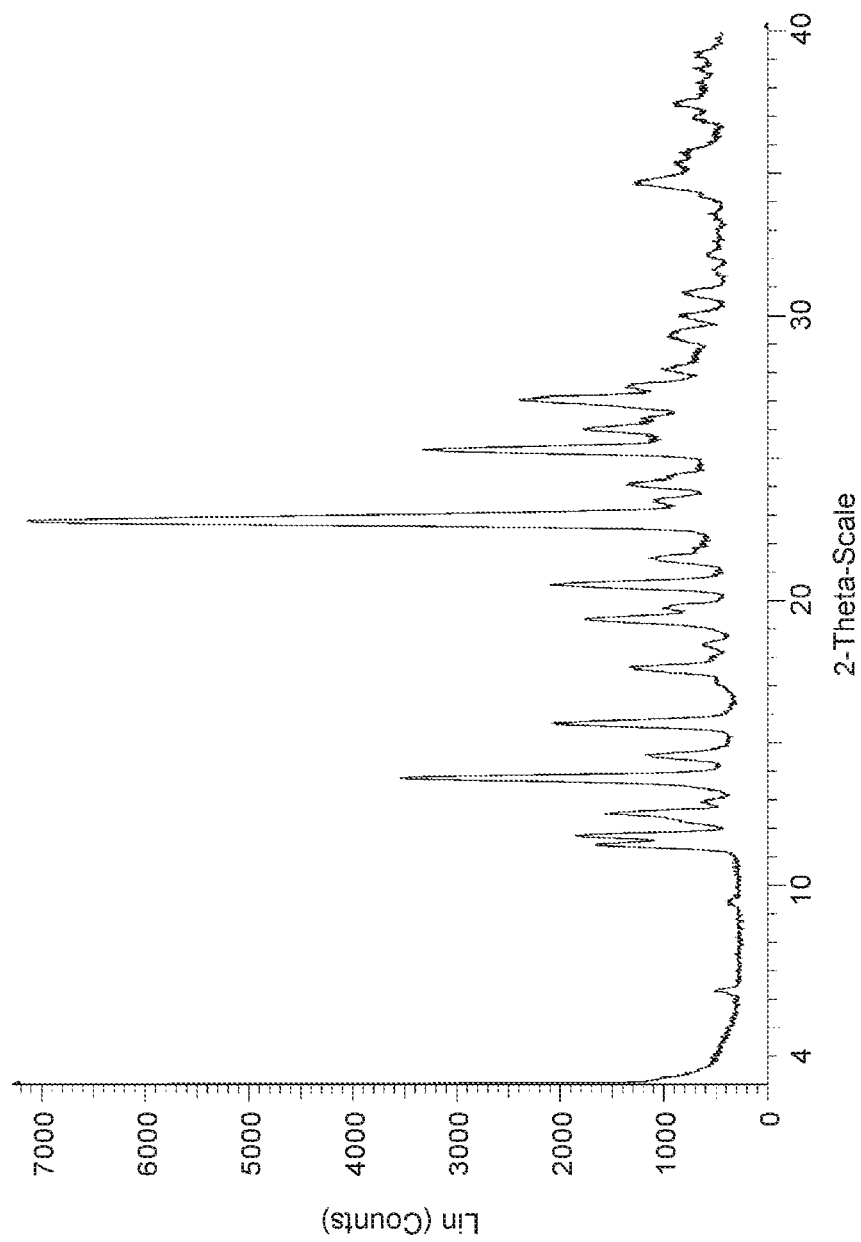
FIG. 4 is a characteristic X-ray powder diffraction pattern showing a crystalline form of Example 15b (Vertical Axis: Intensity (CPS); Horizontal Axis: Two theta (degrees)).

A powder X-ray diffraction of (1R)-1-[(ethoxycarbonyl)oxy]ethyl 4-(4-{(3-chloropyridin-2-yl)[(3R)-piperidin-3-yl]carbamoyl}phenyl)-1-methyl-1H-pyrazole-5-carboxylate is provided in FIG. 4.

Figure 5:
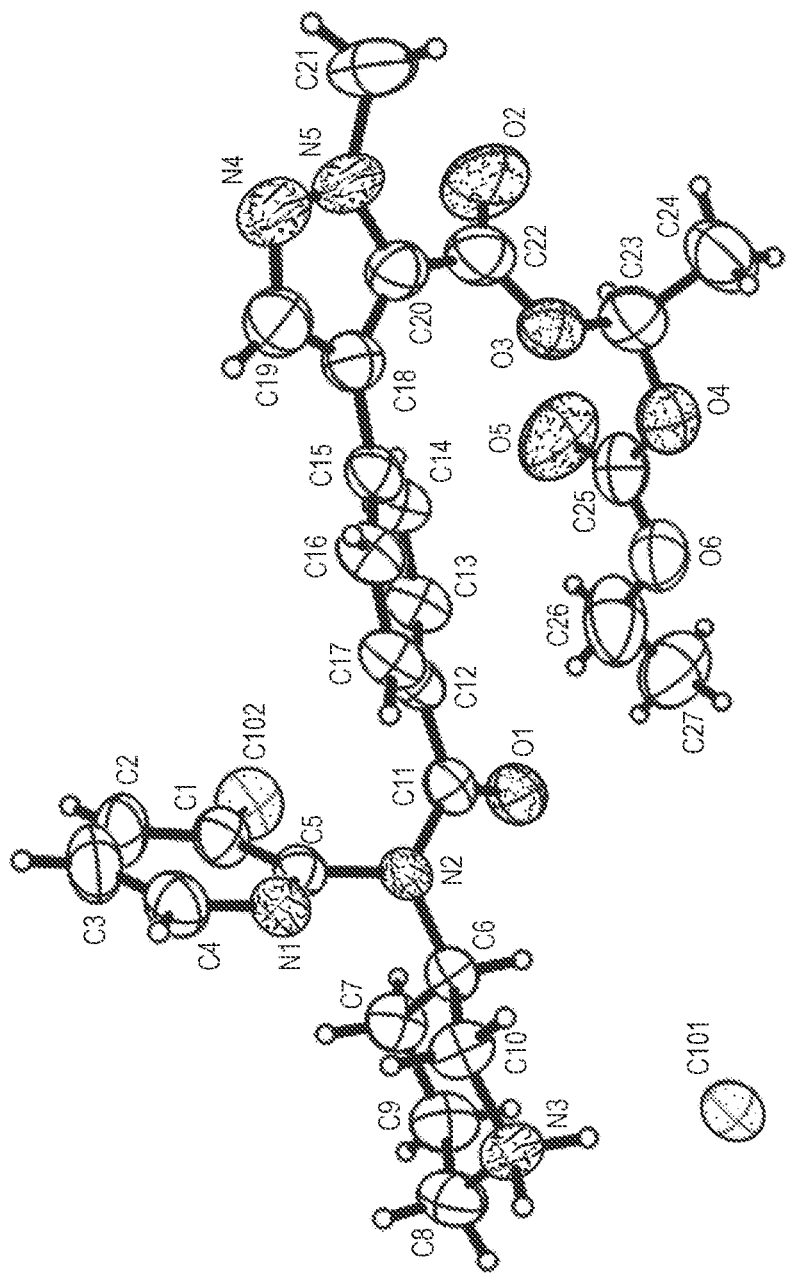
FIG. 5 is an X-ray crystal structure (ORTEP drawing) of Example 15b.

FIG. 5 is an ORTEP drawing of (1R)-1-[(ethoxycarbonyl)oxy]ethyl 4-(4-{(3-chloropyridin-2-yl)[(3R)-piperidin-3-yl]carbamoyl}phenyl)-1-methyl-1H-pyrazole-5-carboxylate.

Single Crystal X-Ray Analysis for (1R)-1-[(ethoxycarbonyl)oxy]ethyl 4-(4-{(3-chloropyridin-2-yl)[(3R)-piperidin-3-yl]carbamoyl}phenyl)-1-methyl-1H-pyrazole-5-carboxylate: Data collection was performed on a Bruker APEX diffractometer at room temperature. Data collection consisted of omega and phi scans. The structure was solved by direct methods using SHELX software suite in the space group $P2_12_12_1$. The structure was subsequently refined by the full-matrix least squares method. All non-hydrogen atoms were found and refined using anisotropic displacement parameters. The hydrogen atoms located on nitrogen were found from the Fourier difference map and refined with distances restrained. The remaining hydrogen atoms were placed in calculated positions and were allowed to ride on their carrier atoms. The final refinement included isotropic displacement parameters for all hydrogen atoms. Absolute configuration was determined, in this case, by examination of the Flack parameter. Here, the parameter=0.0308 with esd 0.0138; within range for absolute configuration determination. The final R-index was 3.8%. A final difference Fourier revealed no missing or misplaced electron density. Pertinent crystal, data collection and refinement are summarized in Table 3.

TABLE 3

Crystal data and structure refinement for (1R)-1-[(ethoxycarbonyl)oxy]ethyl 4-(4-{(3-chloropyridin-2-yl)[(3R)-piperidin-3-yl]carbamoyl}phenyl)-1-methyl-1H-pyrazole-5-carboxylate

| | |
|---|---|
| Empirical formula | C27 H31 Cl2 N5 O6 |
| Formula weight | 592.47 |
| Temperature | 298(2) K |
| Wavelength | 1.54178 Å |
| Crystal system | Orthorhombic |
| Space group | P2(1)2(1)2(1) |
| Unit cell dimensions | a = 6.7302(2) Å    α = 90° |
| | b = 7.7861(2) Å    β = 90° |
| | c = 56.2192(13) Å    γ = 90° |
| Volume | 2946.00(13) Å$^3$ |
| Z | 4 |
| Density (calculated) | 1.336 Mg/m$^3$ |
| Absorption coefficient | 2.392 mm$^{-1}$ |
| F(000) | 1240 |
| Crystal size | 0.42 × 0.17 × 0.06 mm$^3$ |
| Theta range for data collection | 3.14 to 70.21°. |
| Index ranges | −7 <= h <= 6, −9 <= k <= 9, −66 <= l <= 68 |
| Reflections collected | 18638 |
| Independent reflections | 5336 [R(int) = 0.0360] |
| Completeness to theta = 70.22° | 96.8% |
| Absorption correction | Empirical |
| Max. and min. transmission | 0.8698 and 0.4332 |
| Refinement method | Full-matrix least-squares on F$^2$ |
| Data/restraints/parameters | 5336/2/372 |
| Goodness-of-fit on F$^2$ | 1.037 |
| Final R indices [I > 2sigma(I)] | R1 = 0.0386, wR2 = 0.0937 |
| R indices (all data) | R1 = 0.0493, wR2 = 0.0995 |
| Absolute structure parameter | 0.031(14) |
| Largest diff. peak and hole | 0.193 and −0.208 e.Å |

EXAMPLE 16

N-(3-chloropyridin-2-yl)-N-[(3R)-piperidin-3-yl]-4-(3H-[1,2,3]triazolo[4,5-b]pyridin-3-yl)benzamide

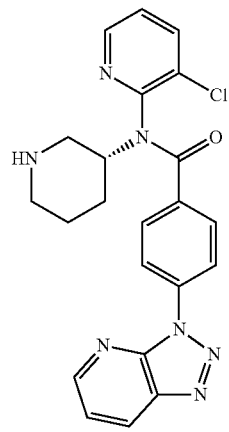 [SMILES: O=C(c1ccc(-n2nnc3cccnc32)cc1)N(c1ncccc1Cl)[C@@H]1CCCNC1]

Step 1: tert-butyl (3R)-3-(4-(3H-[1,2,3]triazolo[4,5-b]pyridin-3-yl)-N-(3-chloropyridin-2-yl)benzamido)piperidine-1-carboxylate Prepared according to General Procedure A and C starting from Preparation 1 tert-butyl (3R)-3-[(3-chloropyridin-2-yl)amino]piperidine-1-carboxylate (26.7 g, 85.5 mmol) and Preparation 5 4-(3H-[1,2,3]triazolo[4,5-b]pyridin-3-yl)benzoic acid (20.1 g, 83.5 mmol) to provide 35.2 g (79%) of the product as a solid.

UPLC (UPLC-MS Method 2): $t_R$=0.75 min.
MS (ES+): 534.3 (M+H)+.

Step 2: N-(3-chloropyridin-2-yl)-N-[(3R)-piperidin-3-yl]-4-(3H-[1,2,3]triazolo[4,5-b]pyridin-3-yl)benzamide Prepared according to General Procedure D starting from the compound in Step 1 (33.0 g, 61.8 mmol) to provide 28.5 g (98%) of the hydrochloride salt of the product as a solid.

$^1$H NMR (CDCl$_3$) δ 10.06 (br s, 1H), 9.78 (br d, 1H), 8.73 (d, 1H), 8.35-8.57 (m, 2H), 8.23 (d, 2H), 7.49-7.68 (m, 3H), 7.42 (m, 1H), 7.20 (m, 1H), 5.14 (br s, 1H), 3.71-4.07 (m, 2H), 3.58 (d, 1H), 2.86 (d, 1H), 1.67-2.48 (m, 4H).

HPLC purity (analytical HPLC Method 1): 99.52%, $t_R$=3.048 min.
UPLC (UPLC-MS Method 2): $t_R$=0.84 min.
MS (ES+): 434.2 (M+H)+.

Figure 6:
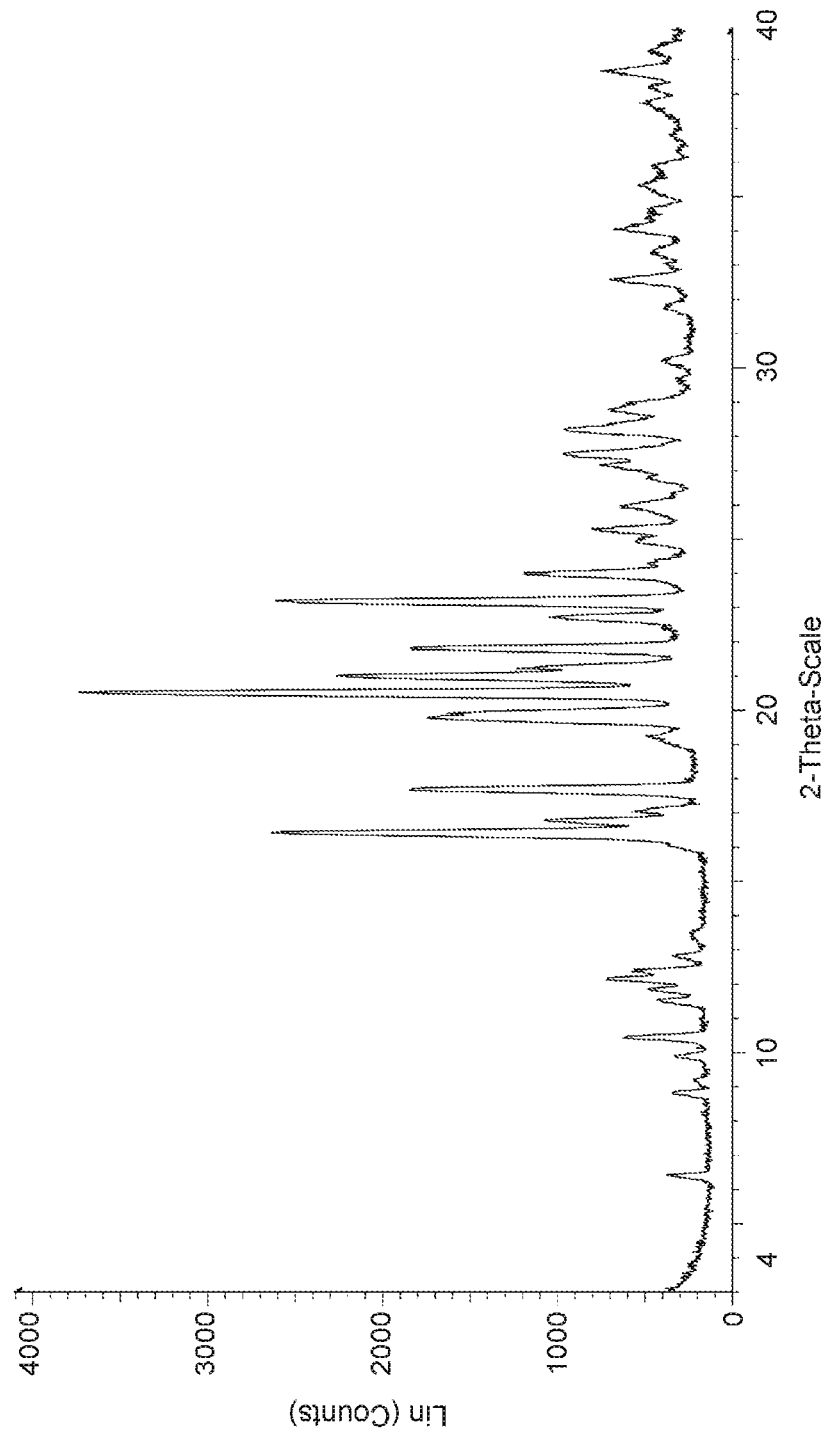
FIG. 6 is a characteristic x-ray powder diffraction pattern showing a crystalline form of Example 16 (Vertical Axis: Intensity (CPS); Horizontal Axis: Two theta (degrees)).

A powder X-ray diffraction of N-(3-chloropyridin-2-yl)-N-[(3R)-piperidin-3-yl]-4-(3H-[1,2,3]triazolo[4,5-b]pyridin-3-yl)benzamide is provided in FIG. 6.

Figure 7:
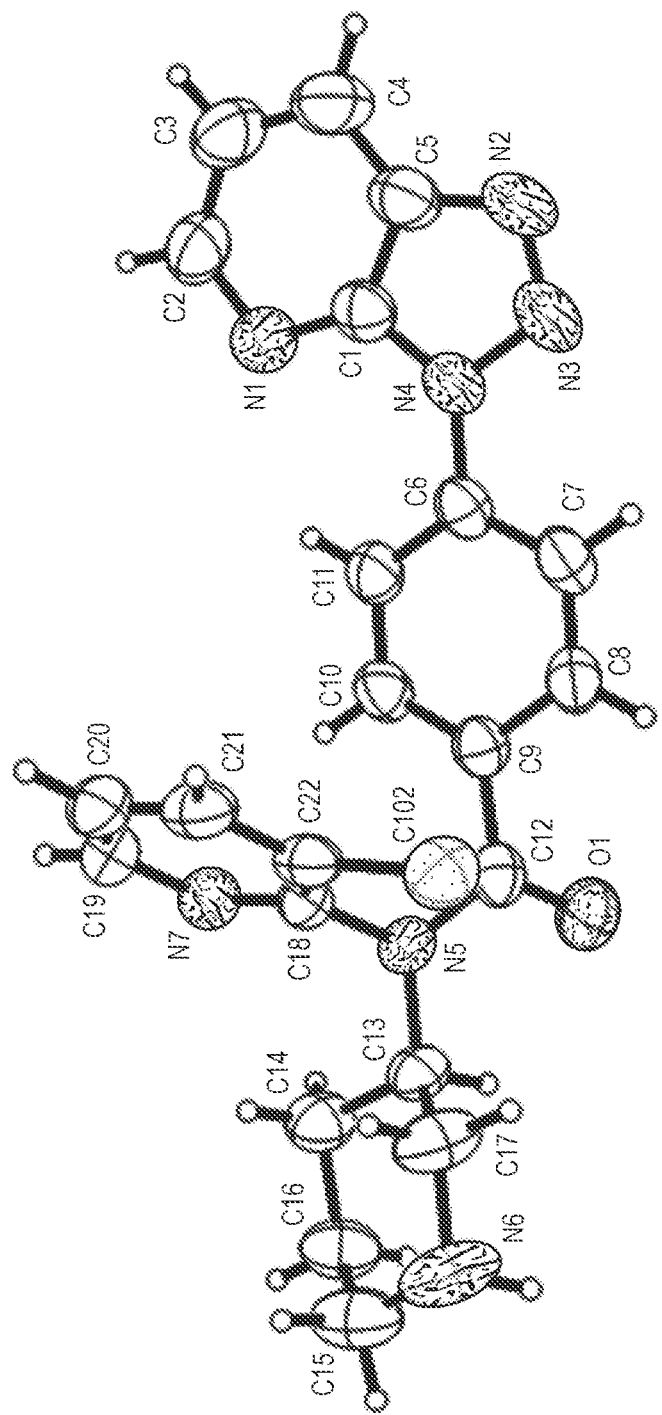
FIG. 7 is an X-ray crystal structure (ORTEP drawing) of Example 16.

FIG. 7 is an ORTEP drawing of N-(3-chloropyridin-2-yl)-N-[(3R)-piperidin-3-yl]-4-(3H-[1,2,3]triazolo[4,5-b]pyridin-3-yl)benzamide.

Single Crystal X-Ray Analysis for N-(3-chloropyridin-2-yl)-N-[(3R)-piperidin-3-yl]-4-(3H-[1,2,3]triazolo[4,5-b]pyridin-3-yl)benzamide: Data collection was performed on a Bruker APEX diffractometer at room temperature. Data collection consisted of 3 omega scans and low angle and three at high angle; each with 0.5 step. In addition, 2 phi scans were collected to improve the quality of the absorption correction.

The structure was solved by direct methods using SHELX software suite in the space group P1. The structure was subsequently refined by the full-matrix least squares method. All non-hydrogen atoms were found and refined using anisotropic displacement parameters.

Two molecules in the asymmetric unit, both with the same stereochemistry. Pseudo-symmetry (P-1).

All hydrogen atoms were placed in calculated positions and were allowed to ride on their carrier atoms. The final refinement included isotropic displacement parameters for all hydrogen atoms.

Analysis of the absolute structure using likelihood methods (Hooft 2008) was performed using PLATON (Spek 2010). The results indicate that the absolute structure has been correctly assigned. The method calculates that the probability that the structure is correct is 100.0. The Hooft parameter is reported as 0.06 with an esd of 0.019.

The final R-index was 3.8%. A final difference Fourier revealed no missing or misplaced electron density.

Pertinent crystal, data collection and refinement are summarized in Table 4.

TABLE 4

Crystal data and structure refinement for N-(3-chloropyridin-2-yl)-N-[(3R)-piperidin-3-yl]-4-(3H-[1,2,3]triazolo[4,5-b]pyridin-3-yl)benzamide

| | | |
|---|---|---|
| Empirical formula | C22 H20 Cl N7 O | |
| Formula weight | 433.90 | |
| Temperature | 273(2) K | |
| Wavelength | 1.54178 Å | |
| Crystal system | Triclinic | |
| Space group | P1 | |
| Unit cell dimensions | a = 8.9633(5) Å | α = 76.136(3)°. |
| | b = 9.4834(5) Å | β = 79.083(4)°. |
| | c = 13.9908(8) Å | γ = 66.929(3)°. |
| Volume | 1056.17(10) Å3 | |
| Z | 2 | |
| Density (calculated) | 1.364 Mg/m3 | |
| Absorption coefficient | 1.846 mm−1 | |
| F(000) | 452 | |
| Crystal size | 0.05 × 0.14 × 0.31 mm3 | |
| Theta range for data collection | 3.27 to 67.37°. | |
| Index ranges | −10 <= h <= 10, −11 <= k <= 11, −16 <= l <= 16 | |
| Reflections collected | 7107 | |
| Independent reflections | 4475 [R(int) = 0.0194] | |
| Completeness to theta = | 67.37° 88.0% | |
| Absorption correction | Empirical | |
| Refinement method | Full-matrix least-squares on F2 | |
| Data/restraints/parameters | 4475/5/567 | |
| Goodness-of-fit on F2 | 1.028 | |
| Final R indices [I > 2sigma(I)] | R1 = 0.0361, wR2 = 0.1009 | |
| R indices (all data) | R1 = 0.0379, wR2 = 0.1034 | |
| Absolute structure parameter | 0.004(13) | |
| Largest diff. peak and hole | 0.200 and −0.170 e.Å−3 | |

EXAMPLE 17

N-(3-methylpyridin-2-yl)-4-[1-methyl-5-(2H-tetrazol-5-yl)-1H-pyrazol-4-yl]-N-[(3R)-piperidin-3-yl]benzamide

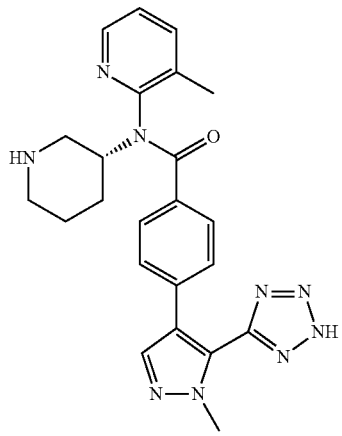 [SMILES: Cc1cccnc1N(C(=O)c1ccc(-c2cnn(C)c2-c2nn[nH]n2)cc1)[C@@H]1CCCNC1]

Preparation 25, tert-butyl (3R)-3-(4-(1-methyl-5-(2H-tetrazol-5-yl)-1H-pyrazol-4-yl)-N-(3-methylpyridin-2-yl)benzamido)piperidine-1-carboxylate (100 mg, 0.185 mmol) was dissolved in methanol (0.925 mL). To this was added HCl in dioxane (0.694 mL, 4M solution, 2.78 mmol) at room temperature. The reaction was stirred at room temperature. After 2 h, reaction was concentrated under reduced pressure, and then concentrated with toluene (3×10 mL). The crude material was triturated with EtOAc/MeOH (20:1) and filtered to afford N-(3-methylpyridin-2-yl)-4-[1-methyl-5-(2H-tetrazol-5-yl)-1H-pyrazol-4-yl]-N-[(3R)-piperidin-3-yl]benzamide (89.3 mg, 94%).

$^1$H NMR (MeOH-d$_4$) δ: 8.44 (d, 1H), 7.78 (s, 1H), 7.65-7.52 (m, 1H), 7.34 7.30 (m, 1H), 7.20-7.13 (m, 2H), 7.07-7.02 (m, 2H), 5.12-5.00 (m, 1H), 4.61-4.48 (m, 1H), 3.75-3.71 (m, 1H), 3.67 (s, 3H), 3.63-3.51 (m, 1H), 2.99-2.82 (m, 1H), 2.36-2.23 (m, 1H), 2.11-2.05 (m, 1H), 2.00 (s, 3H), 1.97-1.91 (m, 1H), 1.85-1.80 (m, 2H), 1.42-1.31 (m, 1H).

UPLC (UPLC-MS Method 1): $t_R$=0.48 min.
MS (ES+): 444.4 (M+H)$^+$.

EXAMPLE 18

4-[1-methyl-5-(5-oxo-4,5-dihydro-1,2,4-oxadiazol-3-yl)-1H-pyrazol-4-yl]-N-(3-methylpyridin-2-yl)-N-[(3R)-piperidin-3-yl]benzamide

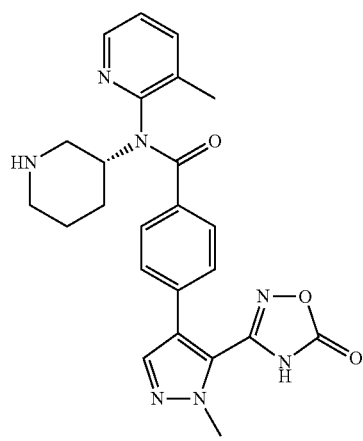 [SMILES: Cc1cccnc1N(C(=O)c1ccc(-c2cnn(C)c2-c2noc(=O)[nH]2)cc1)[C@@H]1CCCNC1]

Step 1

To a solution of Preparation 26, tert-butyl (3R)-3-{[4-(5-cyano-1-methyl-1H-pyrazol-4-yl)benzoyl](3-methylpyridin-2-yl)amino}piperidine-1-carboxylate (130 mg, 0.26 mmol) in EtOH (1.2 mL) was added NH$_2$OH (70 mg, 1.04 mmol, 50% (w/w)) at room temperature. The mixture was stirred at room temperature for 24 h. The mixture was then diluted with water (30 mL) and extracted with DCM (3×30 mL). The combined organic layers were washed with brine, dried over with sodium sulfate, filtered, and concentrated under reduced pressure to deliver a white solid (138 mg) which was used without further purification.

Step 2

To a solution of the white solid (138 mg) in THF (5 mL) was added 1,1'-carbonyldiimidazole (64 mg, 0.39 mmol) at room temperature. The reaction mixture was stirred at room temperature for 16 h and then concentrated under reduced pressure to give a residue. The resulting residue was dissolved in EtOAc (20 mL) and washed with 1 M NaOH (3×40 mL). The aqueous layer was diluted with DCM (40 mL), carefully acidified to pH 3 with 1M HCl at 0° C. The aqueous layer was then extracted with DCM (2×40 mL). The combined organic layers were washed with brine, dried over with sodium sulfate, filtered, and concentrated to give a yellow oil (138 mg) that was used without further purification.

Step 3

To a solution of the yellow oil (138 mg) in DCM (5 mL) was added HCl in EtOAc (5 mL) at room temperature. The reaction mixture was stirred for 1 h and then concentrated in vacuo. The residue was purified by prep-HPLC to afford the HCl salt of 4-[1-methyl-5-(5-oxo-4,5-dihydro-1,2,4-oxadiazol-3-yl)-1H-pyrazol-4-yl]-N-(3-methylpyridin-2-yl)-N-[(3R)-piperidin-3-yl]benzamide as a white solid (55 mg, 43%). (Prep-HPLC conditions: Column: Agela Durashell C18 (250×21.2 mm×5 μm); Mobile Phase: Gradient of 8% acetonitrile in H$_2$O (0.1% HCl) to 28% acetonitrile in H$_2$O (0.1% HCl).)

$^1$H NMR (DMSO-d$_6$) δ: 9.48 (br s, 1H), 9.14 (br s, 1H), 8.45 (br s, 0.8H), 8.40 (br s, 0.2H), 7.93 (s, 1H), 7.67-7.53 (m, 1H), 7.36-7.13 (m, 5H), 5.00-4.86 (m, 0.8H), 4.67-4.53 (m, 0.2H), 3.92 (s, 3H), 3.59-3.49 (m, 1H), 3.43-3.29 (m, 1H), 3.23-3.13 (m, 1H), 2.78-2.63 (m, 1H), 2.07 (s, 0.7H), 1.99 (s, 2.3H), 1.85-1.71 (m, 3H), 1.33-1.16 (m, 1H).

LC (LC-MS Method 4): $t_R$=1.02 min
MS (ES+): 460.1 (M+H)$^+$

EXAMPLE 19

N-(3-chloropyridin-2-yl)-4-[1-methyl-5-(5-oxo-4,5-dihydro-1,2,4-oxadiazol-3-yl)-1H-pyrazol-4-yl]-N-[(3R)-piperidin-3-yl]benzamide

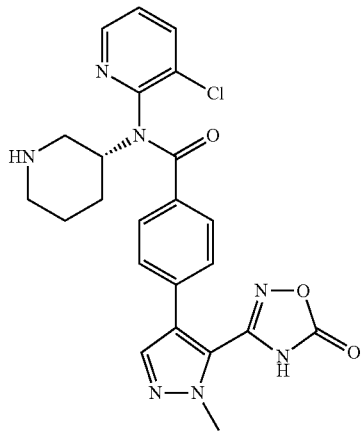 [SMILES: Cn1ncc(-c2ccc(C(=O)N(c3ncccc3Cl)[C@@H]3CCCNC3)cc2)c1-c1noc(=O)[nH]1]

The title compound was made in an analogous manner to EXAMPLE 18. (Prep-HPLC conditions: Column: Agela Durashell C18 (250×21.2 mm×5 µm); Mobile Phase: Gradient of 13% acetonitrile in $H_2O$ (0.1% HCl) to 33% acetonitrile in $H_2O$ (0.1% HCl).)

$^1$H NMR (MeOH-$d_4$) δ: 8.57 (br s, 0.7H), 8.53 (br s, 0.3H), 7.83-7.77 (m, 2H), 7.42-7.33 (m, 3H), 7.29-7.23 (m, 2H), 5.12-5.03 (m, 1H), 4.00 (s, 3H), 3.82-3.71 (m, 1H), 3.63-3.54 (m, 1H), 3.41-3.36 (m, 1H), 2.96-2.85 (m, 1H), 2.39-2.30 (m, 0.3H), 2.15-1.83 (m, 3H), 1.54-1.42 (m, 0.7H).

LC (LC-MS Method 4): $t_R$=1.01 min.

MS (ES+): 480.1 (M+H)$^+$.

EXAMPLE 20 ethyl 1-{3-[1-methyl-4-(4-{(3-methylpyridin-2-yl)[(3R)-piperidin-3-yl]carbamoyl}phenyl)-1H-pyrazol-5-yl]-5-oxo-1,2,4-oxadiazol-4(5H)-yl}ethyl carbonate

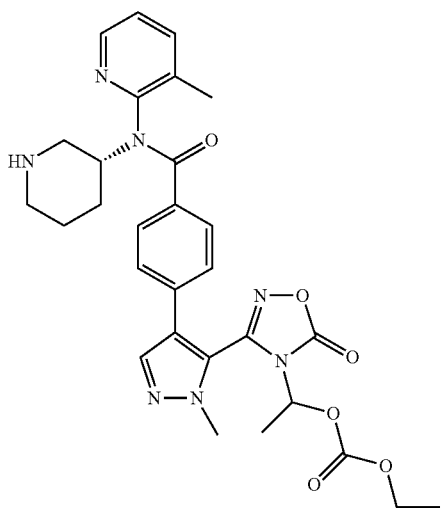 [SMILES: CCOC(=O)OC(C)n1c(-c2c(-c3ccc(C(=O)N(c4ncccc4C)[C@@H]4CCCNC4)cc3)cnn2C)noc1=O]

Step 1: tert-butyl (3R)-3-[{4-[5-(4-{1-[(ethoxycarbonyl)oxy]ethyl}-5-oxo-4,5-dihydro-1,2,4-oxadiazol-3-yl)-1-methyl-1H-pyrazol-4-yl]benzoyl}(3-methylpyridin-2-yl)amino]piperidine-1-carboxylate To a solution of the product of step 2 of EXAMPLE 18 (133 mg, 0.23 mmol) in THF (2 mL) was added 1-tert-butyl-2,2,4,4,4-pentakis(dimethylamino)-2λ5,4λ5-catenadi(phosphazene) (240 µL, 2M solution in THF, 0.48 mmol). The reaction mixture was stirred at room temperature for 1 h followed by the addition of 1-chloroethyl ethyl carbonate (105 µL, 0.78 mmol). The reaction was heated to 60° C. overnight. The reaction mixture was cooled to room temperature, diluted by saturated aqueous $NH_4Cl$ (30 mL), and extracted with ethyl acetate (3×50 mL). The combined organic phases were dried over $MgSO_4$ and concentrated in vacuo. The residue was purified by silica gel column chromatography eluting with a gradient of 0-100% EtOAc/heptane to afford tert-butyl (3R)-3-[{4-[5-(4-{1-[(ethoxycarbonyl)oxy]ethyl}-5-oxo-4,5-dihydro-1,2,4-oxadiazol-3-yl)-1-methyl-1H-pyrazol-4-yl]benzoyl}(3-methylpyridin-2-yl)amino]piperidine-1-carboxylate as a white solid (56 mg, 35%).

$^1$H NMR (CDCl$_3$) δ: 8.41 (br s, 1H), 7.68 (s, 1H), 7.46-7.28 (m, 3H), 7.19-6.96 (m, 3H), 5.24 (br s, 1H), 4.77-4.32 (m, 2H), 4.11 (q, 2H), 3.97 (s, 3H), 3.40 (d, 1H), 2.72-2.25 (m, 2H), 2.16 (d, 1H), 2.07 (s, 3H), 1.90-1.54 (m, 3H), 1.47-1.43 (m, 9H), 1.28-1.18 (m, 3H), 0.99-0.73 (m, 3H).

UPLC (UPLC-MS Method 1): $t_R$=1.00 min.

MS (ES+): 676.4 (M+H)$^+$.

Step 2 tert-butyl (3R)-3-[{4-[5-(4-{1-[(ethoxycarbonyl)oxy]ethyl}-5-oxo-4,5-dihydro-1,2,4-oxadiazol-3-yl)-1-methyl-1H-pyrazol-4-yl]benzoyl}(3-methylpyridin-2-yl)amino]piperidine-1-carboxylate (52 mg, 0.08 mmol) was dissolved in DCM (5 mL) and to the solution was added HCl in dioxane (0.5 mL, 4M solution, 2 mmol) and stirred at room temperature for 2 h. The reaction mixture was concentrated in vacuo. The resulting residue was triturated in diethyl ether to yield ethyl 1-{3-[1-methyl-4-(4-{(3-methylpyridin-2-yl)[(3R)-piperidin-3-yl]carbamoyl}phenyl)-1H-pyrazol-5-yl]-5-oxo-1,2,4-oxadiazol-4(5H)-yl}ethyl carbonate as a light yellow solid (40 mg, 80%).

$^1$H NMR (CD$_3$CN) δ: 9.87-9.59 (m, 1H), 9.52-9.33 (m, 1H), 9.33-9.02 (m, 1H), 8.40 (d, 1H), 7.99-7.75 (m, 2H), 7.41 (br s, 3H), 7.19 (br s, 2H), 5.52-5.09 (m, 1H), 5.12-4.46 (m, 1H), 4.01 (q, 2H), 3.90 (s, 3H), 3.71-3.55 (m, 1H), 3.31 (d, 1H), 2.82 (br s, 1H), 2.37-2.10 (m, 2H), 1.99-1.94 (m, 1H), 1.92 (s, 3H), 1.85-1.71 (m, 1H), 1.60-1.37 (m, 1H), 1.15 (t, 3H), 0.91-0.78 (m, 3H).

UPLC (UPLC-MS Method 1): $t_R$=0.65 min.

MS (ES+): 576.3 (M+H)$^+$.

EXAMPLE 21 ethyl 1-{3-[1-methyl-4-(4-{(3-methylpyridin-2-yl)[(3R)-piperidin-3-yl]carbamoyl}phenyl)-1H-pyrazol-5-yl]-5-oxo-1,2,4-oxadiazol-4(5H)-yl}ethyl carbonate

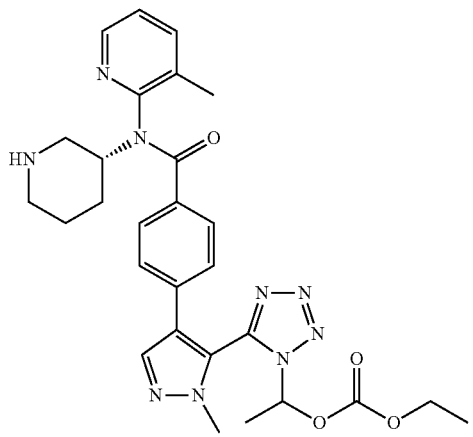 [SMILES: CCOC(=O)OC(C)n1nnnc1-c1c(-c2ccc(C(=O)N(c3ncccc3C)[C@@H]3CCCNC3)cc2)cnn1C]

To Preparation 25, tert-butyl (3R)-3-(4-(1-methyl-5-(2H-tetrazol-5-yl)-1H-pyrazol-4-yl)-N-(3-methylpyridin-2-yl)benzamido)piperidine-1-carboxylate (310 mg, 0.57 mmol) in DMF (1 mL) was added DIPEA (1 mL, 5.7 mmol) followed by 1-chloroethyl ethyl carbonate (0.46 mL, 3.4 mmol). The reaction mixture was heated at 60° C. for 16 h. The reaction mixture was quenched with saturated aqueous NH₄Cl solution (10 mL) and extracted with EtOAc (2×20 mL). The organic phases were combined and dried over sodium sulfate, filtered, and concentrated in vacuo to obtain the crude product which contains two regioisomers with the Boc-protected title compound as the minor component. The residue was purified by column chromatography on silica gel, eluting with a gradient of 0-80% EtOAc/heptanes to afford the Boc-protected title compound (24 mg, 6.4%). The Boc-protected title compound (45 mg, 0.068 mmol) was dissolved in DCM (1 mL). To the solution was added HCl in dioxane (0.5 mL. 4M solution) and the mixture was stirred at room temperature for 30 min, concentrated in vacuo to afford the HCl salt of ethyl 1-{3-[1-methyl-4-(4-{(3-methylpyridin-2-yl)[(3R)-piperidin-3-yl]carbamoyl}phenyl)-1H-pyrazol-5-yl]-5-oxo-1,2,4-oxadiazol-4(5H)-yl}ethyl carbonate (40 mg, 95%).

¹H NMR (DMSO-d₆) δ: 9.35-9.11 (m, 1H), 9.08-8.83 (m, 1H), 8.42 (s, 1H), 7.99 (d, 1H), 7.68-7.53 (m, 1H), 7.30 (d, 1H), 7.17 (d, 2H), 6.83 (d, 2H), 6.08-5.95 (m, 1H), 5.00-4.80 (m, 1H), 4.43-4.10 (m, 2H), 4.03-3.87 (m, 2H), 3.76 (s, 3H), 3.43-3.26 (m, 1H), 3.26-3.13 (m, 1H), 2.80-2.61 (m, 1H), 2.40-2.10 (m, 2H), 1.97 (d, 3H), 1.92-1.88 (m, 1H), 1.76 (d, 3H), 1.09 (t, 3H).

UPLC (UPLC-MS Method 1): $t_R$=0.61 min.

MS (ES+): 560.4 (M+H)⁺.

EXAMPLE 22

4-(4-{(3-chloropyridin-2-yl)[(3R)-piperidin-3-yl]carbamoyl}phenyl)-1-methyl-N-[(trifluoromethyl)sulfonyl]-1H-pyrazole-5-carboxamide

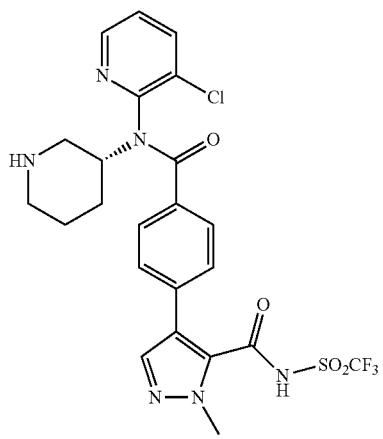

To a solution of the product of Step 1 of EXAMPLE 8 (0.15 g, 0.28 mmol) in DCM (2 mL) was added compound trifluoromethanesulfonamide (42 mg, 0.28 mmol), DMAP (34 mg, 0.28 mmol) and 1-(3-dimethylaminopropyl)-3-ethylcarbodiimide hydrochloride EDAP (57 mg, 0.30 mmol). The reaction was stirred at room temperature for 16 h. The solvent was concentrated under reduced pressure to give an oil that was used without further purification. To a solution of the oil in DCM (2 mL) was added trifluoroacetic acid (2 mL) at 0° C. The mixture was stirred at room temperature for 1 h. The mixture was concentrated in vacuo, and the resulting residue was purified by prep-HPLC to afford the trifluoroacetic acid salt of 4-(4-{(3-chloropyridin-2-yl)[(3R)-piperidin-3-yl]carbamoyl}phenyl)-1-methyl-N-[(trifluoromethyl)sulfonyl]-1H-pyrazole-5-carboxamide as a white solid (80 mg, 42%). (Prep-HPLC conditions: Column: Boston Symmetrix ODS-H (150×30 mm×5 μm); Mobile Phase: Gradient of 15% acetonitrile in H₂O (0.1% TFA) to 35% acetonitrile in H₂O (0.1% TFA).

¹H NMR (MeOH-d₄) δ: 8.53 (br s, 1H), 7.90-7.71 (m, 1H), 7.53 (s, 1H), 7.45-7.25 (m, 5H), 5.11-4.97 (m, 1H), 3.98 (s, 3H), 3.77-3.63 (m, 1H), 3.61-3.46 (m, 1H), 3.39-3.34 (m, 1H), 2.92-2.80 (m, 1H), 2.35-2.26 (m, 0.3H), 2.10-1.93 (m, 2H), 1.93-1.76 (m, 1H), 1.58-1.38 (m, 0.7H).

LC (LC-MS Method 4): $t_R$=0.89 min

MS (ES+): 571.0 (M+H)⁺.

EXAMPLE 23

1-methyl-4-(4-{(3-methylpyridin-2-yl)[(3R)-piperidin-3-yl]carbamoyl}phenyl)-N-[(trifluoromethyl)sulfonyl]-1H-pyrazole-5-carboxamide

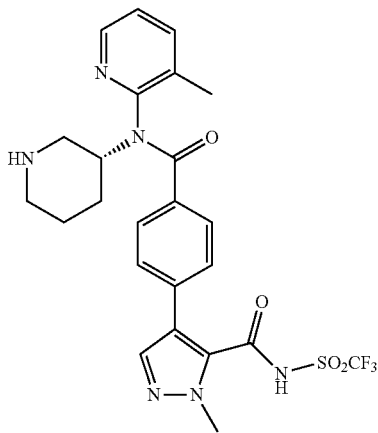

The title compound was made in an analogous manner to EXAMPLE 22 starting from Preparation 29.
HPLC (HPLC Method 5): $t_R$=1.96 min.
MS (ES+): 551.2 (M+H)$^+$.

EXAMPLE 24

4-(4-{(3-chloropyridin-2-yl)[(3R)-piperidin-3-yl]carbamoyl}phenyl)-1-methyl-N-(1H-tetrazol-5-yl)-1H-pyrazole-5-carboxamide

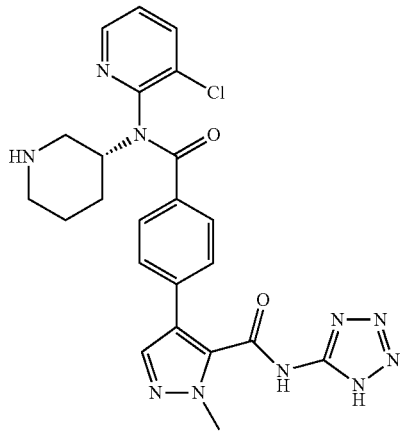 [SMILES: Cn1ncc(-c2ccc(C(=O)N(c3ncccc3Cl)[C@@H]3CCCNC3)cc2)c1C(=O)Nc1nnn[nH]1]

To a solution of the product of Step 1, EXAMPLE 8 (200 mg, 0.370 mmol) in DMF (2 mL) was added CDI (78 mg, 0.482 mmol) and DIPEA (72 mg, 0.556 mmol). The mixture was stirred at 80° C. for 30 min. 1H-tetrazol-5-amine (94 mg, 1.11 mmol) was added to the reaction mixture, and the resulting mixture was stirred at 80° C. for 16 h. The mixture was poured into water, acidified to pH 3 with 1N HCl and extracted with EtOAc (10 mL). The organic layer was dried over sodium sulfate and concentrated in vacuo to give an oil that was used without further purification. To the oil in DCM (5 mL) at 0° C. was added trifluoroacetic acid (1 mL) dropwise. The resulting mixture was stirred at room temperature for 30 min, and then the mixture was concentrated in vacuo. The resulting residue was purified by prep-HPLC to afford the trifluoroacetic acid salt of 4-(4-{(3-chloropyridin-2-yl)[(3R)-piperidin-3-yl]carbamoyl}phenyl)-1-methyl-N-(1H-tetrazol-5-yl)-1H-pyrazole-5-carboxamide as a white solid (45.1 mg, 20%). (Prep-HPLC conditions: Column: DIKMA Diamonsil (2) C18 (200×20 mm×5 μm); Mobile Phase: Gradient of 5% acetonitrile in H$_2$O (0.1% TFA) to 25% acetonitrile in H$_2$O (0.1% TFA).)
$^1$H NMR (MeOH-d$_4$) δ: 8.47 (br s, 0.7H), 8.43 (br s, 0.3H), 7.85-7.67 (m, 2H), 7.40-7.18 (m, 5H), 5.11-4.98 (m, 2H), 4.03 (s, 3H), 3.81-3.66 (m, 1H), 3.64-3.49 (m, 1H), 3.41-3.36 (m, 1H), 2.96-2.82 (m, 1H), 2.16-1.95 (m, 2H), 1.94-1.81 (m, 1H), 1.52-1.39 (m, 1H).
LC (LC-MS Method 4): $t_R$=0.91 min.
MS (ES+): 507.1 (M+H)$^+$.

EXAMPLE 25

4-(4-{(3-chloropyridin-2-yl)[(3R)-piperidin-3-yl]carbamoyl}phenyl)-N-hydroxy-1-methyl-1H-pyrazole-5-carboxamide

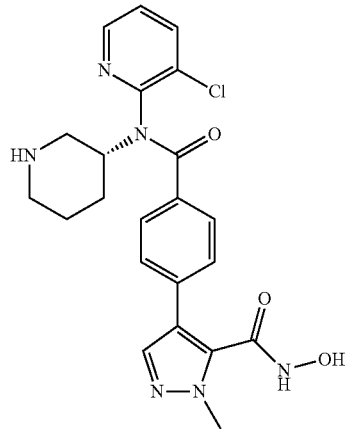 [SMILES: Cn1ncc(-c2ccc(C(=O)N(c3ncccc3Cl)[C@@H]3CCCNC3)cc2)c1C(=O)NO]

Sodium metal (0.55 g, 24.0 mmol) was added to MeOH (10 mL) followed by a solution of hydroxylamine hydrochloride (800 mg, 11.0 mmol) in MeOH (10 mL). The NaCl precipitate was then filtered off. To 2 mL of the free hydroxylamine solution thus prepared, was added Preparation 18, (R)-tert-Butyl 3-(N-(3-chloropyridin-2-yl)-4-(5-(ethoxycarbonyl)-1-methyl-1H-pyrazol-4-yl)benzamido)piperidine-1-carboxylate (200 mg, 0.352 mmol), and the reaction mixture was heated at reflux for 15 min. The solvent was removed in vacuo to give an oil, which was used without further purification. To the oil in DCM (5 mL) at 0° C. was added TFA (1 mL) dropwise. The resulting mixture was stirred at 30° C. for 5 min and then the mixture was concentrated in vacuo. The resulting residue was purified by prep-HPLC to afford the trifluoroacetic acid salt of 4-(4-{(3-chloropyridin-2-yl)[(3R)-piperidin-3-yl]carbamoyl}phenyl)-N-hydroxy-1-methyl-1H-pyrazole-5-carboxamide as an off-white solid (45 mg, 23%). (Prep-HPLC conditions: Column: YMC-Actus Triad C18 (150×30 mm); Mobile Phase: Gradient of 8% acetonitrile in H$_2$O (0.1% TFA) to 28% acetonitrile in H$_2$O (0.1% TFA).)

$^1$H NMR (DMSO-d$_6$) δ: 11.29 (br s, 1H), 8.91 (br s, 1H), 8.70 (br s, 1H), 8.61 (br s, 0.7H), 8.58 (br s, 0.3H), 8.01-7.81 (m, 2H), 7.48-7.41 (m, 1H), 7.38-7.29 (m, 2H), 7.29-7.17 (m, 2H), 4.98 (br s, 1H), 3.79 (s, 3H), 3.66-3.55 (m, 1H), 3.27-3.14 (m, 1H), 2.87-2.65 (m, 1H), 1.96-1.68 (m, 2H), 1.33-1.22 (m, 1H).

LC (LC-MS Method 4): $t_R$=0.87 min.

MS (ES+): 455.1 (M+H)$^+$.

EXAMPLE 26

N-(3-chloropyridin-2-yl)-4-[1-methyl-5-(2H-tetrazol-5-yl)-1H-pyrazol-4-yl]-N-[(3R)-piperidin-3-yl]benzamide

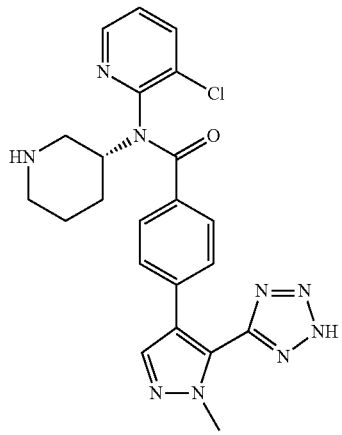 [SMILES: Cn1ncc(-c2ccc(C(=O)N(c3ncccc3Cl)[C@@H]3CCCNC3)cc2)c1-c1nn[nH]n1]

To a solution of (R)-tert-butyl 3-(N-(3-chloropyridin-2-yl)-4-(5-cyano-1-methyl-1H-pyrazol-4-yl)benzamido)piperidine-1-carboxylate (prepared in an analogous manner to Preparation 26 starting from Preparation 21 and Preparation 17) (300 mg, 0.58 mmol) in DMF (5 mL) was added sodium azide (142 mg, 2.19 mmol) and CuBr$_2$ (208 mg, 0.92 mmol). The reaction was then heated at 120° C. for 16 h. The reaction was diluted with H$_2$O and extracted with EtOAc, dried over sodium sulfate and concentrated to give a residue that was used without further purification. To the residue in DCM (3 mL) was added trifluoroacetic acid (3 mL) at 0° C. The mixture was stirred at room temperature for 1 h. The mixture was concentrated in vacuo, and the resulting residue was purified by prep-HPLC to afford the trifluoroacetic acid salt of N-(3-chloropyridin-2-yl)-4-[1-methyl-5-(2H-tetrazol-5-yl)-1H-pyrazol-4-yl]-N-[(3R)-piperidin-3-yl]benzamide as a white solid (162 mg, 49%). (Prep-HPLC conditions: Column: Boston Symmetrix ODS-H (150×30 mm×5 μm); Mobile Phase: Gradient of 15% acetonitrile in H$_2$O (0.1% TFA) to 35% acetonitrile in H$_2$O (0.1% TFA))

$^1$H NMR (DMSO-d$_6$) δ: 9.06 (br s, 1H), 8.78 (br s, 1H), 8.58 (br s, 0.7H), 8.54 (br s, 0.3H), 8.01-7.88 (m, 2H), 7.48-7.40 (m, 1H), 7.27-7.04 (m, 4H), 5.07-4.88 (m, 2H), 4.62 (br s, 1H), 3.68-2.95 (m, 4H), 2.84-2.67 (m, 1H), 2.19-2.09 (m, 0.3H), 1.99-1.65 (m, 3H), 1.34-1.19 (m, 0.7H).

LC (LC-MS Method 5): $t_R$=0.73 min.

MS (ES+): 464.1 (M+H)$^+$.

EXAMPLE 27

4-(4-{(3-chloropyridin-2-yl)[(3R)-piperidin-3-yl]carbamoyl}phenyl)-1-methyl-N-(methylsulfonyl)-1H-pyrazole-5-carboxamide

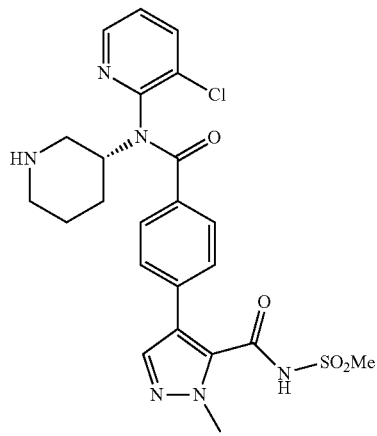 [SMILES: Cn1ncc(-c2ccc(C(=O)N(c3ncccc3Cl)[C@@H]3CCCNC3)cc2)c1C(=O)NS(C)(=O)=O]

Step 1

To a solution of the product of Step 1, EXAMPLE 8 (150 mg, 0.28 mmol) in DCM (2 mL) was added methanesulfonamide (26 mg, 0.28 mmol), DMAP (34 mg, 0.28 mmol) and EDAP (57 mg, 0.30 mmol). The reaction mixture was stirred at room temperature for 16 h. The reaction mixture was poured into EtOAc, washed with brine, dried over sodium sulfate, and concentrated in vacuo. The resulting residue was purified by silica gel chromatography eluting with a gradient of 5-10% MeOH/DCM to afford the Boc-protected title compound as a colorless oil (60 mg, 35%).

Step 2

To the Boc-protected title compound (60 mg, 0.098 mmol) in DCM (2 mL) was added TFA (2 mL) at 0° C. The mixture was stirred at room temperature for 1 h. The mixture was concentrated in vacuo, and the crude product was purified by prep-HPLC to afford the formic acid salt of 4-(4-{(3-chloropyridin-2-yl)[(3R)-piperidin-3-yl]carbamoyl}phenyl)-1-methyl-N-(methylsulfonyl)-1H-pyrazole-5-carboxamide as a brown gum (22 mg, 39%). (Prep-HPLC conditions: Column: YMC-Actus Triart C18 (150×30 mm); Mobile Phase: Gradient of 15% acetonitrile in H$_2$O (0.1% formic acid) to 35% acetonitrile in H$_2$O (0.1% formic acid).)

$^1$H NMR (DMSO-d$_6$) δ: 8.56 (d, 1H), 7.92-7.84 (m, 1H), 7.68 (s, 1H), 7.46-7.38 (m, 1H), 7.36-7.24 (m, 4H), 4.99-4.77 (m, 1H), 3.87 (s, 3H), 3.66-3.54 (m, 2H), 2.84-2.73 (m, 1H), 2.07-1.73 (m, 3H).

LC (LC-MS Method 4): $t_R$=0.98 min.

MS (ES+): 517.1 (M+H)$^+$.

EXAMPLE 28

1-methyl-4-(4-{(3-methylpyridin-2-yl)[(3R)-piperidin-3-yl]carbamoyl}phenyl)-N-(methylsulfonyl)-1H-pyrazole-5-carboxamide

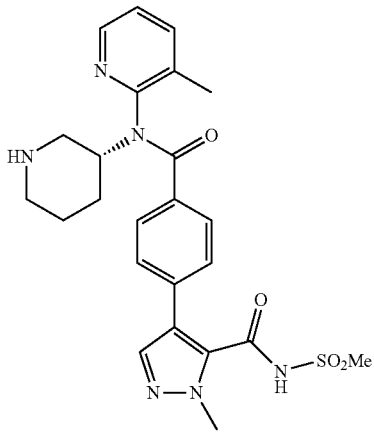

The title compound was made in an analogous manner to EXAMPLE 27 starting from Preparation 29.

$^1$H NMR (DMSO-d$_6$) δ: 9.41-9.19 (m, 1H), 9.11-8.85 (m, 1H), 8.46 (s, 1H), 7.77 (s, 1H), 7.68-7.53 (m, 1H), 7.35-7.27 (m, 1H), 7.24-7.20 (m, 4H), 5.05-4.88 (m, 2H), 3.88 (s, 3H), 3.25-3.14 (m, 1H), 2.72 (s, 3H), 2.74-2.68 (m, 2H), 2.22-2.01 (m, 2H), 1.98 (s, 3H), 1.83-1.75 (m, 2H).

UPLC (UPLC-MS Method 1): t$_R$=0.5 min.
MS (ES+): 497.2 (M+H)$^+$.

EXAMPLE 29 ethyl 1-[{[1-methyl-4-(4-{(3-methylpyridin-2-yl)[(3R)-piperidin-3-yl]carbamoyl}phenyl)-1H-pyrazol-5-yl]carbonyl}methylsulfonyl)amino]ethyl carbonate

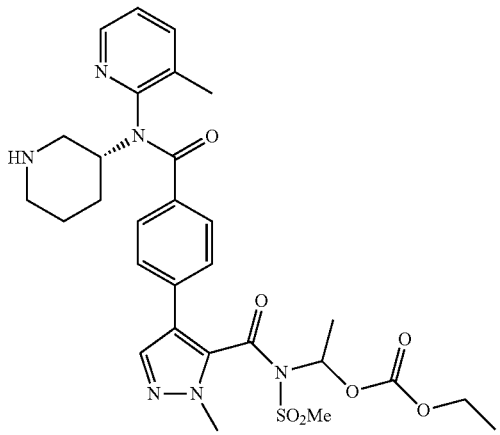 [SMILES: CCOC(=O)OC(C)N(C(=O)c1c(-c2ccc(C(=O)N(c3ncccc3C)[C@@H]3CCCNC3)cc2)cnn1C)S(C)(=O)=O]

The product of Step 1 of EXAMPLE 28 (81 mg, 0.14 mmol) was treated with KOH (0.14 mL, 1M in MeOH 0.14 mmol) in MeOH (1 mL), stirred for 1 h, and then concentrated. MeOH was removed completely by coevaporating with toluene to afford the potassium salt. The potassium salt was dissolved in acetonitrile (2 mL), 1-chloroethyl ethyl carbonate (63 mg, 0.42 mmol) was added and the mixture was heated at 50° C. for 2 d. The reaction mixture was directly purified, without concentration, by column chromatography on silica gel to afford the Boc-protected title compound (34 mg, 36%). The Boc-protected title compound (30 mg, 0.042 mmol) was dissolved in DCM (1 mL), treated with HCl in dioxane (0.5 mL, 4M solution) and stirred at room temperature for 30 min. The reaction mixture was concentrated in vacuo to afford the HCl salt of ethyl 1-[{[1-methyl-4-(4-{(3-methylpyridin-2-yl)[(3R)-piperidin-3-yl]carbamoyl}phenyl)-1H-pyrazol-5-yl]carbonyl}(methylsulfonyl)amino]ethyl carbonate (27 mg, 94%).

$^1$H NMR (DMSO-d$_6$) δ: 9.06 (br s, 1H), 8.86 (br s, 1H), 8.50-8.30 (m, 1H), 7.76 (s, 1H), 7.54-7.50 (m, 1H), 7.31-7.18 (m, 3H), 7.21-7.09 (m, 2H), 5.91-5.58 (m, 1H), 4.94 (br s, 1H), 4.60-4.20 (m, 1H), 4.11 (q, 2H), 3.91 (s, 3H) 3.59-3.55 (m, 1H), 3.28 (s, 3H), 3.18-3.16 (m, 1H), 2.95-2.60 (m, 2H), 2.05-2.01 (m, 2H), 1.97 (d, 3H), 1.77 (s, 3H), 1.45-1.30 (m, 1H), 1.24 (t, 3H).

UPLC (UPLC-MS Method 1): t$_R$=0.64 min.
MS (ES+): 613.2 (M+H)$^+$.

EXAMPLE 30 ethyl (1S)-1-{5-[1-methyl-4-(4-{(3-methylpyridin-2-yl)[(3R)-piperidin-3-yl]carbamoyl}phenyl)-1H-pyrazol-5-yl]-2H-tetrazol-2-yl}ethyl carbonate

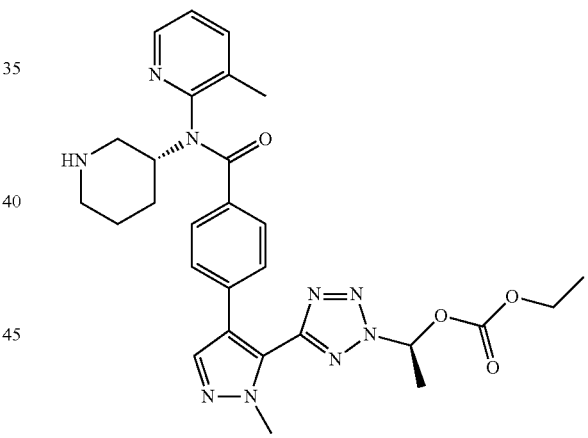

Preparation 27, tert-butyl (3R)-3-[{4-[5-(2-{(1S)-1-[(ethoxycarbonyl)oxy]ethyl}-2H-tetrazol-5-yl)-1-methyl-1H-pyrazol-4-yl]benzoyl}(3-methylpyridin-2-yl)amino]piperidine-1-carboxylate (438 mg, 0.664 mmol) was dissolved in acetonitrile (3.3 mL). To this was added HCl in dioxane (2.49 mL, 4M solution, 15 eq.) dropwise at room temperature. After 1 h, the reaction was concentrated in vacuo, and concentrated with toluene (3×15 mL). The crude material was suspended in EtOAc and heated to 80° C. for 16 h. Filtration of the material provided the hydrochloride salt of ethyl (1S)-1-{5-[1-methyl-4-(4-{(3-methylpyridin-2-yl)[(3R)-piperidin-3-yl]carbamoyl}phenyl)-1H-pyrazol-5-yl]-2H-tetrazol-2-yl}ethyl carbonate (242 mg, 65%).

$^1$H NMR (DMSO-d$_6$) δ: 9.46 (br s, 1H), 9.10 (br s, 1H), 8.44 (d, 1H), 7.86 (s, 1H), 7.59 (d, 1H), 7.33-7.25 (m, 2H), 7.17-7.10 (m, 4H), 4.96-4.89 (m, 1H), 4.61-4.58 (m, 1H), 4.20 (q, 2H), 3.95 (s, 3H), 3.55-3.52 (m, 1H), 3.19-3.16 (m,

1H), 2.79-2.63 (m, 1H), 2.19-1.97 (m, 1H), 1.97 (s, 3H), 1.89 (d, 3H), 1.84-1.72 (m, 3H), 1.24 (t, 3H).

UPLC (UPLC-MS Method 2): $t_R$=1.02 min.

MS (ES+): 560.4 (M+H)$^+$.

Elemental Analysis: Calc'd for $C_{28}H_{34}ClN_9O_4$ C, 56.42; H, 5.75; N, 21.15; Cl 5.95. Found C, 56.17; H, 5.81; N, 21.14; Cl 6.11.

A powder X-ray diffraction of Example 30 is provided in FIG. 9.

EXAMPLE 31 ethyl (1R)-1-{5-[1-methyl-4-(4-{(3-methylpyridin-2-yl)[(3R)-piperidin-3-yl]carbamoyl}phenyl)-1H-pyrazol-5-yl]-2H-tetrazol-2-yl}ethyl carbonate

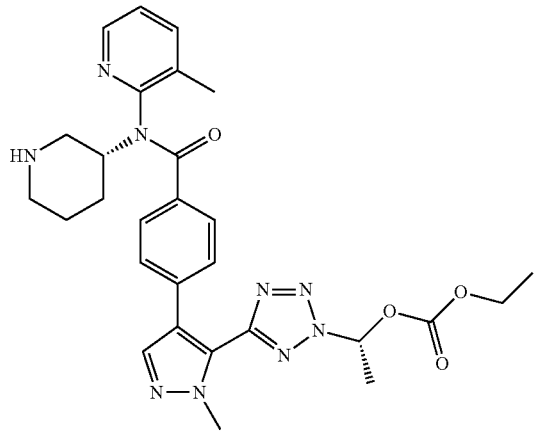 [SMILES: CCOC(=O)O[C@H](C)n1nnc(-c2c(-c3ccc(C(=O)N(c4ncccc4C)[C@@H]4CCCNC4)cc3)cnn2C)n1]

The title compound was made in an analogous manner to EXAMPLE 30 starting from Preparation 28, tert-butyl (3R)-3-[{4-[5-(2-{(1R)-1-[(ethoxycarbonyl)oxy]ethyl}-2H-tetrazol-5-yl)-1-methyl-1H-pyrazol-4-yl]benzoyl}(3-methylpyridin-2-yl)amino]piperidine-1-carboxylate.

$^1$H NMR (DMSO-d$_6$) δ: 9.46 (br s, 1H), 9.10 (br s, 1H), 8.44 (d, 1H), 7.86 (s, 1H), 7.59 (d, 1H), 7.33-7.23 (m, 2H), 7.23-7.05 (m, 4H), 5.03-4.83 (m, 1H), 4.61-4.58 (m, 1H), 4.20 (q, 2H), 3.95 (s, 3H), 3.61-3.47 (m, 1H), 3.24-3.12 (m, 1H), 2.75-2.62 (m, 1H), 2.20-2.03 (m, 1H), 1.97 (s, 3H), 1.90 (d, 3H), 1.85-1.69 (m, 3H), 1.24 (t, 3H).

UPLC (UPLC-MS Method 2): $t_R$=1.05 min.

MS (ES+): 560.3 (M+H)$^+$.

Elemental Analysis: Calc'd for $C_{28}H_{34}ClN_9O_4$ C, 56.42; H, 5.75; N, 21.15; Cl 5.95. Found C, 56.03; H, 5.70; N, 21.06; Cl 6.17.

A powder X-ray diffraction of EXAMPLE 31 is provided in FIG. 10.

The asterisks in Examples 32-55 denote unknown absolute configuration (R/S) at the chiral center where the asterisk is placed. Each Example, however, is a single diastereomer uniquely identified with analytical characteristics as shown by the chiral chromatography retention times of the specific Preparations from which the Examples were prepared and the uniqueness of $^1$H NMR spectrum of the individual examples.

EXAMPLE 32 ethyl 1-{5-[1-methyl-4-(4-{(3-methylpyridin-2-yl)[(3R)-piperidin-3-yl]carbamoyl}phenyl)-1H-pyrazol-5-yl]-2H-tetrazol-2-yl}propyl carbonate (Diastereomer A)

Diastereomer A

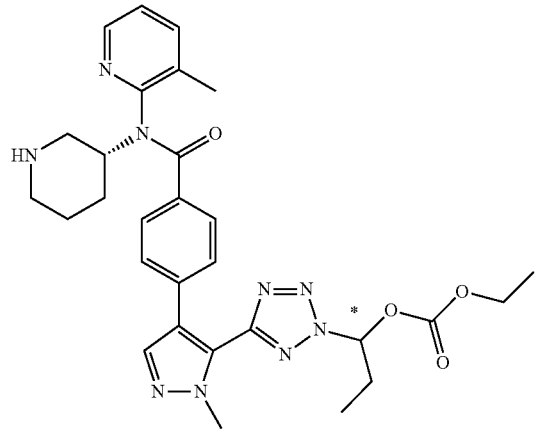

To a solution of Preparation 31 (123 mg, 0.183 mmol) in MeCN (2 mL) was added HCl (0.22 mL, 0.88 mmol, 4.0 M solution in dioxane). After 2 h, the reaction mixture was concentrated and dried in vacuo to afford the hydrochloride salt of title compound as a colorless solid in quantitative yield.

$^1$H NMR (CD$_3$CN) δ: 9.18 (br s, 1H), 8.94 (br s, 1H), 8.38-8.17 (m, 1H), 7.58 (s, 1H), 7.47-7.32 (m, 1H), 7.16-7.03 (m, 5H), 6.91 (t, 1H), 5.17-4.55 (m, 1H), 4.18-4.09 (m, 2H), 3.91 (s, 3H), 3.60-2.98 (m, 2H), 2.85-2.64 (m, 1H), 2.95-2.76 (m, 1H), 2.28-2,14 (m, 2H), 2.20-1.98 (m, 1H), 1.94 (br s, 3H), 1.82-1.74 (m, 1H), 1.59-1.63 (m, 1H), 1.34-1.24 (m, 1H), 1.19 (t, 3H), 0.83 (t, 3H).

UPLC (UPLC-MS Method 2): $t_R$=1.22 min.

MS (ES+): 574.3 (M+H)$^+$.

EXAMPLE 33 ethyl 1-{5-[1-methyl-4-(4-{(3-methylpyridin-2-yl)[(3R)-piperidin-3-yl]carbamoyl}phenyl)-1H-pyrazol-5-yl]-2H-tetrazol-2-yl}propyl carbonate (Diastereomer B)

Diastereomer B

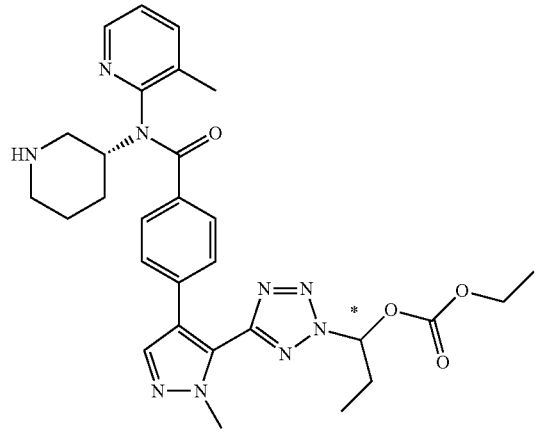

The title compound was made in an analogous manner to EXAMPLE 32 starting from Preparation 32.

¹H NMR (CDCl₃) δ: 9.99-9.73 (m, 2H), 8.42 (br s, 1H), 7.61 (s, 1H), 7.42 (br s, 1H), 7.25-7.12 (m, 4H), 6.98 (t, 1H), 5.05 (br s, 1H), 4.33-4.22 (m, 2H), 4.07 (s, 3H), 3.91-3.67 (m, 2H), 3.48 (br s, 1H), 2.91 (br s, 1H), 2.41-2.32 (m, 2H), 2.17-1.95 (m, 4H), 1.84-1.73 (m, 3H), 1.34 (t, 3H), 0.97 (t, 3H).

UPLC (UPLC-MS Method 2): $t_R$=1.17 min.

MS (ES+): 574.4 (M+H)⁺.

EXAMPLE 34 ethyl 2-methyl-1-{5-[1-methyl-4-(4-{(3-methylpyridin-2-yl)[(3R)-piperidin-3-yl]carbamoyl}phenyl)-1H-pyrazol-5-yl]-2H-tetrazol-2-yl}propyl carbonate (Diastereomer A)

Diastereomer A

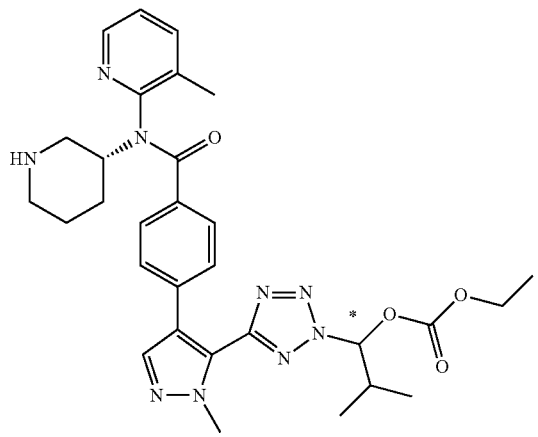

The title compound was made in an analogous manner to EXAMPLE 32 starting from Preparation 33a.

¹H NMR (CD₃CN) δ: 9.42 (br s, 1H), 8.96 (br s, 1H), 8.40 (d, 1H), 7.80-7.69 (m, 1H), 7.65 (s, 1H), 7.30-7.23 (m, 1H), 7.23-7.16 (m, 2H), 7.15-7.10 (m, 2H), 6.75 (d, 1H), 5.09-4.90 (m, 1H), 4.25-4.16 (m, 2H), 3.97 (s, 3H), 3.73-3.55 (m, 2H), 3.29-3.22 (m, 1H), 2.86-2.75 (m, 1H), 2.62-2.54 (m, 1H), 2.18-2.08 (m, 3H), 1.85-1.72 (m, 3H), 1.50-1.38 (m, 1H), 1.25 (t, 3H), 1.10 (d, 3H), 0.78 (d, 3H).

UPLC (UPLC-MS Method 2): $t_R$=1.26 min.

MS (ES+): 588.4 (M+H)⁺.

EXAMPLE 35 ethyl 2-methyl-1-{5-[1-methyl-4-(4-{(3-methylpyridin-2-yl)[(3R)-piperidin-3-yl]carbamoyl}phenyl)-1H-pyrazol-5-yl]-2H-tetrazol-2-yl}propyl carbonate (Diastereomer B)

Diastereomer B

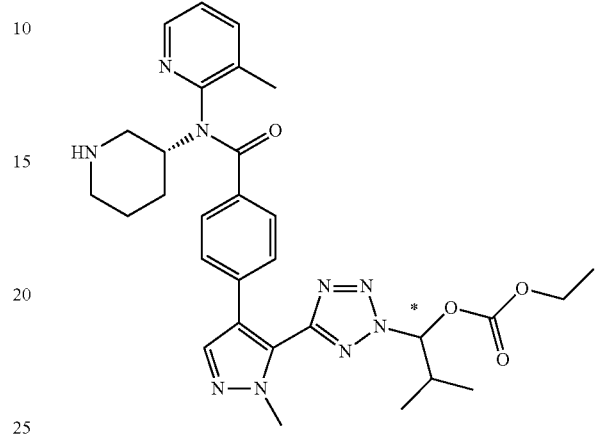

The title compound was made in an analogous manner to EXAMPLE 32 starting from Preparation 33b.

¹H NMR (CD₃CN) δ: 9.46 (br s, 1H), 9.17 (br s, 1H), 8.39 (d, 1H), 7.64 (s, 1H), 7.56-7.51 (m, 1H), 7.29-7.24 (m, 1H), 7.32-7.22 (m, 2H), 7.19-7.12 (m, 2H), 6.75 (d, 1H), 5.14-5.06 (m, 1H), 4.25-4.16 (m, 2H), 3.97 (s, 3H), 3.73-3.51 (m, 2H), 3.29-3.22 (m, 1H), 2.82-2.72 (m, 1H), 2.61-2.54 (m, 1H), 2.50-2.28 (m, 3H), 1.95-1.72 (m, 3H), 1.45-1.33 (m, 1H), 1.26 (t, 3H), 1.10 (d, 3H), 0.78 (d, 3H).

UPLC (UPLC-MS Method 2): $t_R$=1.26 min.

MS (ES+): 588.4 (M+H)⁺.

EXAMPLE 36

2,2-dimethyl-1-{5-[1-methyl-4-(4-{(3-methylpyridin-2-yl)[(3R)-piperidin-3-yl]carbamoyl}phenyl)-1H-pyrazol-5-yl]-2H-tetrazol-2-yl}propyl ethyl carbonate (Diastereomer A)

Diastereomer A

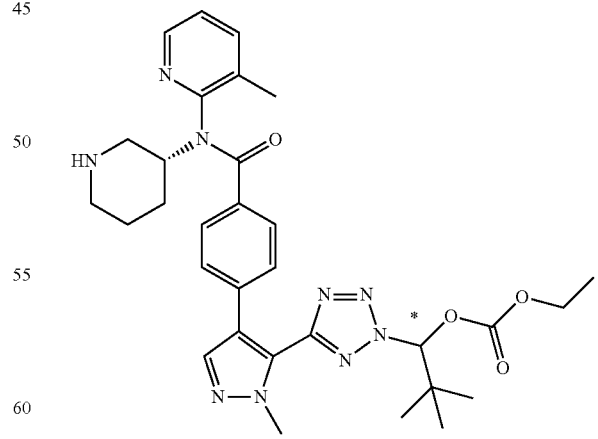

The title compound was made in an analogous manner to EXAMPLE 32 starting from Preparation 35.

¹H NMR (DMSO-d₆) δ: 9.31 (br s, 1H), 8.99 (br s, 1H), 8.49-8.34 (m, 1H), 7.87 (s, 1H), 7.58 (d, 1H), 7.32-7.26 (m, 1H), 7.11 (m, 4H), 6.90 (s, 1H), 5.02-4.81 (m, 1H), 4.23-4.11

(m, 2H), 3.91 (s, 3H), 3.61-3.48 (m, 1H), 3.44-3.28 (m, 1H), 3.25-3.11 (m, 1H), 2.76-2.59 (m, 1H), 2.18-1.90 (m, 3H), 1.85-1.69 (m, 4H), 1.21 (t, 3H), 1.00 (s, 9H).
UPLC (UPLC-MS Method 1): $t_R$=0.71 min.
MS (ES+): 602.4 (M+H)$^+$.

EXAMPLE 37

2,2-dimethyl-1-{5-[1-methyl-4-(4-{(3-methylpyridin-2-yl)[(3R)-piperidin-3-yl]carbamoyl}phenyl)-1H-pyrazol-5-yl]-2H-tetrazol-2-yl}propyl ethyl carbonate (Diastereomer B)

Diastereomer B

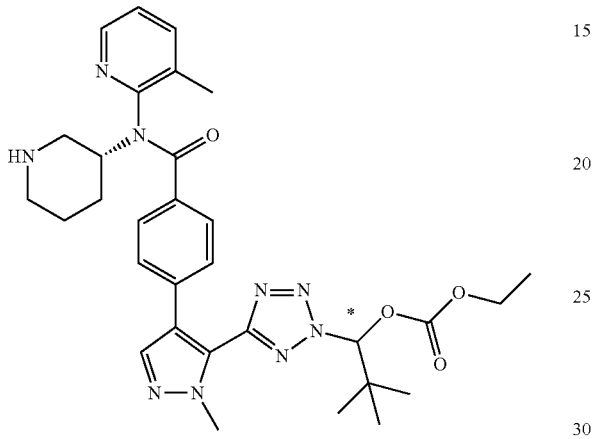

The title compound was made in an analogous manner to EXAMPLE 32 starting from Preparation 36.
$^1$H NMR (DMSO-$d_6$) δ: 9.15 (br s, 1H), 8.91 (br s, 1H), 8.48-8.35 (m, 1H), 7.87 (s, 1H), 7.66-7.52 (m, 1H), 7.32-7.27 (m, 1H), 7.18-7.07 (m, 4H), 6.91 (s, 1H), 5.02-4.84 (m, 1H), 4.29-4.09 (m, 2H), 3.91 (s, 3H), 3.58-3.51 (m, 1H), 3.45-3.26 (m, 1H), 3.25-3.12 (m, 1H), 2.79-2.59 (m, 1H), 2.18-1.95 (m, 3H), 1.83-1.68 (m, 4H), 1.21 (m, 3H), 1.00 (s, 9H).
UPLC (UPLC-MS Method 2): $t_R$=1.22 min.
MS (ES+): 602.4 (M+H)$^+$.

EXAMPLE 38

1-{5-[1-methyl-4-(4-{(3-methylpyridin-2-yl)[(3R)-piperidin-3-yl]carbamoyl}phenyl)-1H-pyrazol-5-yl]-2H-tetrazol-2-yl}propyl propanoate (Diastereomer A)

Diastereomer A

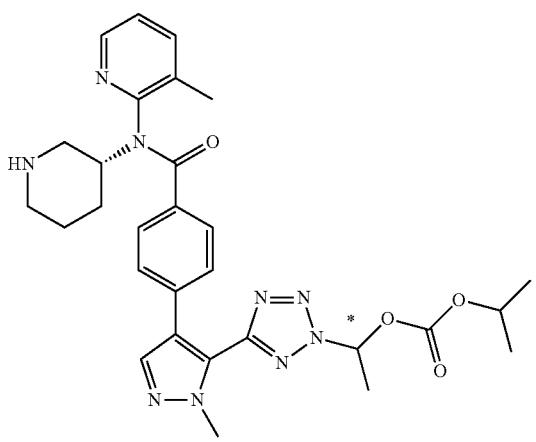

The title compound was made in an analogous manner to EXAMPLE 32 starting from Preparation 38.
$^1$H NMR (CD$_3$CN) δ: 9.71 (br s, 1H), 9.23 (br s, 1H), 8.41 (d, 1H), 8.03-7.73 (m, 1H), 7.64 (s, 1H), 7.56-7.39 (m, 1H), 7.35-7.25 (m, 2H), 7.22-7.05 (m, 3H), 5.18-4.94 (m, 1H), 4.88-4.83 (m, 1H), 3.98 (s, 3H), 3.89-3.54 (m, 2H), 3.30-3.26 (m, 1H), 2.88-2.73 (m, 1H), 2.15 (br. s., 3H), 2.03-1.95 (m, 2H), 1.90 (d, 3H), 1.86-1.74 (m, 1H), 1.59-1.42 (m, 1H), 1.29 (d, 3H), 1.23 (d, 3H).
UPLC (UPLC-MS Method 2): $t_R$=1.15 min.
MS (ES+): 574.3 (M+H)$^+$.

EXAMPLE 39

1-{5-[1-methyl-4-(4-{(3-methylpyridin-2-yl)[(3R)-piperidin-3-yl]carbamoyl}phenyl)-1H-pyrazol-5-yl]-2H-tetrazol-2-yl}ethyl propan-2-yl carbonate (Diastereomer B)

Diastereomer B

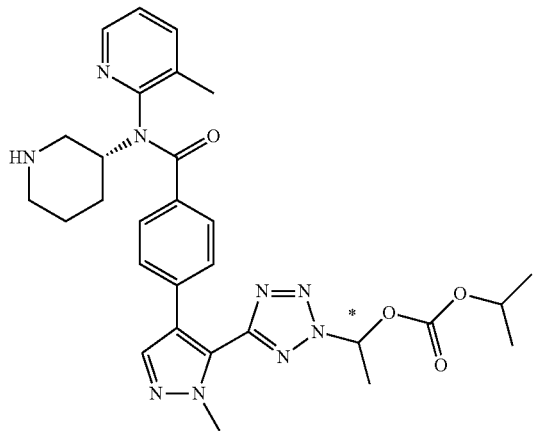

The title compound was made in an analogous manner to EXAMPLE 32 starting from Preparation 39.
$^1$H NMR (DMSO-$d_6$) δ: 8.83-8.53 (m, 2H), 8.45-8.35 (m, 1H), 7.84 (s, 1H), 7.63-7.52 (m, 1H), 7.33-7.20 (m, 2H), 7.20-7.03 (m, 4H), 4.99-4.87 (m, 1H), 4.80 (septet, 1H), 3.92 (s, 3H), 3.56 (d, 1H), 3.37-3.30 (m, 1H), 3.19 (d, 1H), 2.80-2.65 (m, 1H), 2.15-1.64 (m, 10H), 1.25 (d, 3H), 1.19 (d, 3H).
UPLC (UPLC-MS Method 2): $t_R$=1.21 min.
MS (ES+): 574.3 (M+H)$^+$.

EXAMPLE 40

1-{5-[1-methyl-4-(4-{(3-methylpyridin-2-yl)[(3R)-piperidin-3-yl]carbamoyl}phenyl)-1H-pyrazol-5-yl]-2H-tetrazol-2-yl}propyl propan-2-yl carbonate (Diastereomer A)

Diastereomer A

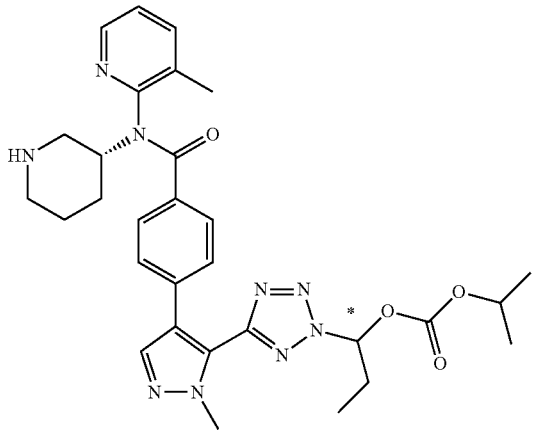

The title compound was made in an analogous manner to EXAMPLE 32 starting from Preparation 41.

$^1$H NMR (DMSO-d$_6$) δ: 9.20-9.17 (m, 1H), 8.96-8.86 (m, 1H), 8.44-8.39 (m, 1H), 7.86 (s, 1H), 7.66-7.55 (m, 1H), 7.30-7.27 (m, 1H), 7.14-7.09 (m, 3H), 4.95-4.91 (m, 1H), 4.82-4.78 (m, 2H), 4.60-4.53 (m, 1H), 3.92 (s, 3H), 3.54-3.50 (m, 2H), 3.38-3.32 (m, 1H), 3.19-3.17 (m, 1H), 2.81-2.65 (m, 1H), 2.28-2.20 (m, 2H), 2.14-2.03 (m, 1H), 1.95 (s, 3H), 1.78-1.71 (m, 2H), 1.27 (d, 3H), 1.20 (d, 3H), 0.86 (t, 3H).

UPLC (UPLC-MS Method 1): t$_R$=0.70 min.
MS (ES+): 588.4 (M+H)$^+$.

EXAMPLE 41

1-{5-[1-methyl-4-(4-{(3-methylpyridin-2-yl)[(3R)-piperidin-3-yl]carbamoyl}phenyl)-1H-pyrazol-5-yl]-2H-tetrazol-2-yl}propyl propan-2-yl carbonate (Diastereomer B)

Diastereomer B

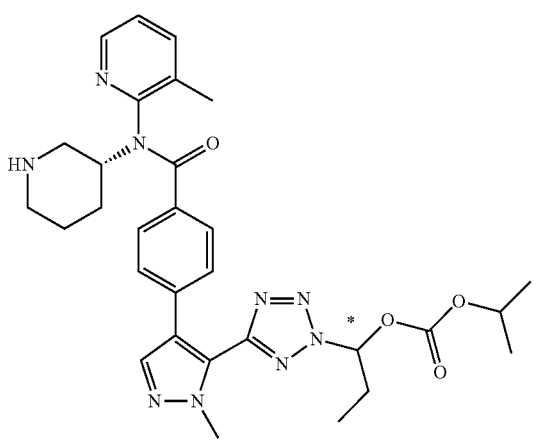

The title compound was made in an analogous manner to EXAMPLE 32 starting from Preparation 42.

$^1$H NMR (CDCl$_3$) δ: 9.93 (br s, 1H), 9.58 (br s, 1H), 8.45 (br s, 1H), 7.59 (s, 1H), 7.26-7.15 (m, 5H), 6.97 (t, 1H), 5.14-4.87 (m, 2H), 4.06 (s, 3H), 3.88 (br s, 1H), 3.51 (br s, 1H), 3.13-2.79 (m, 3H), 2.39-1.81 (m, 8H), 1.34 (d, 3H), 1.28 (d, 3H), 0.96 (t, 3H).

UPLC (UPLC-MS Method 1): t$_R$=0.67 min.
MS (ES+): 588.4 (M+H)$^+$.

EXAMPLE 42

2-methyl-1-{5-[1-methyl-4-(4-{(3-methylpyridin-2-yl)[(3R)-piperidin-3-yl]carbamoyl}phenyl)-1H-pyrazol-5-yl]-2H-tetrazol-2-yl}propyl propan-2-yl carbonate (Diastereomer A)

Diastereomer A

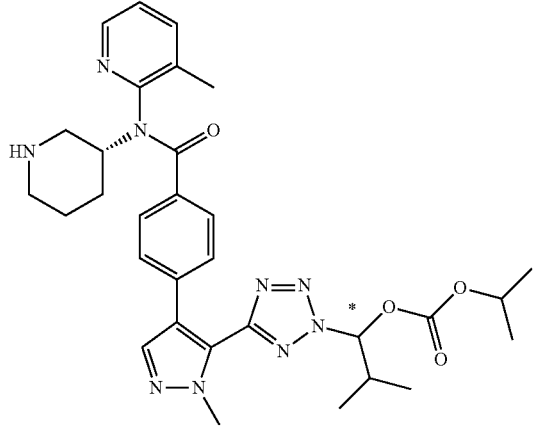

The title compound was made in an analogous manner to EXAMPLE 32 starting from Preparation 43a.

$^1$H NMR (CD$_3$CN) δ: 9.40 (br s, 1H), 9.03 (br s, 1H), 8.39 (d, 1H), 7.70-7.57 (m, 2H), 7.36-7.30 (m, 1H), 7.27-7.21 (m, 2H), 7.14-7.11 (m, 2H), 6.75 (d, 1H), 5.09-5.01 (m, 1H), 4.87-4.81 (m, 1H), 3.97 (s, 3H), 3.78-3.52 (m, 2H), 3.29-3.22 (m, 1H), 2.83-2.75 (m, 1H), 2.61-2.48 (m, 1H), 2.33-2.00 (m, 3H), 1.82-1.72 (m, 3H), 1.52-1.34 (m, 1H), 1.28 (d, 3H), 1.22 (d, 3H), 1.10 (d, 3H), 0.79 (d, 3H).

UPLC (UPLC-MS Method 2): t$_R$=1.33 min.
MS (ES+): 602.4 (M+H)$^+$.

EXAMPLE 43

2-methyl-1-{5-[1-methyl-4-(4-{(3-methylpyridin-2-yl)[(3R)-piperidin-3-yl]carbamoyl}phenyl)-1H-pyrazol-5-yl]-2H-tetrazol-2-yl}propyl propan-2-yl carbonate (Diastereomer B)

Diastereomer B

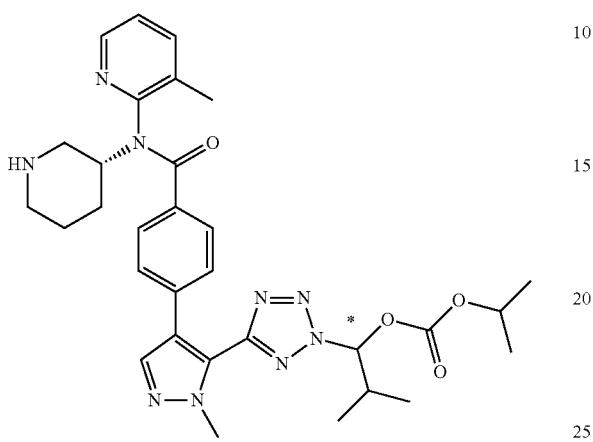

The title compound was made in an analogous manner to EXAMPLE 32 starting from Preparation 43b.

$^1$H NMR (CD$_3$CN) δ: 9.33 (br s, 1H), 8.95 (br s, 1H), 8.39 (d, 1H), 7.70-7.63 (m, 2H), 7.41-7.34 (m, 1H), 7.28-7.21 (m, 2H), 7.19-7.12 (m, 2H), 6.75 (d, 1H), 5.09-4.99 (m, 1H), 4.87-4.81 (m, 1H), 3.97 (s, 3H), 3.73-3.55 (m, 2H), 3.29-3.22 (m, 1H), 2.83-2.75 (m, 1H), 2.60-2.54 (m, 1H), 2.15-2.05 (m, 3H), 1.82-1.72 (m, 3H), 1.52-1.38 (m, 1H), 1.28 (d, 3H), 1.22 (d, 3H), 1.10 (d, 3H), 0.78 (d, 3H).

UPLC (UPLC-MS Method 2): t$_R$=1.33 min.
MS (ES+): 602.4 (M+H)$^+$.

EXAMPLE 44

1-{5-[1-methyl-4-(4-{(3-methylpyridin-2-yl)[(3R)-piperidin-3-yl]carbamoyl}phenyl)-1H-pyrazol-5-yl]-2H-tetrazol-2-yl}ethyl propanoate (Diastereomer A)

(Diastereomer A)

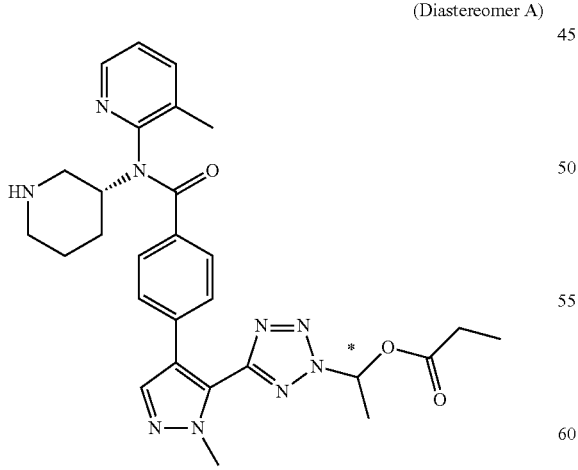

The title compound was made in an analogous manner to EXAMPLE 32 starting from Preparation 45.

$^1$H NMR (DMSO-d$_6$) δ: 9.41-9.21 (m, 1H), 9.13-8.92 (m, 1H), 8.49-8.35 (m, 1H), 7.87 (s, 1H), 7.70-7.52 (m, 1H), 7.45-7.34 (m, 1H), 7.34-7.22 (m, 1H), 7.22-7.09 (m, 4H), 5.04-4.84 (m, 1H), 3.94 (s, 3H), 3.61-3.48 (m, 1H), 3.44-3.31 (m, 1H), 3.27-3.11 (m, 1H), 2.79-2.60 (m, 1H), 2.48-2.32 (q, 2H), 2.20-2.02 (m, 1H), 2.02-1.94 (m, 3H), 1.87 (d, 3H), 1.83-1.72 (m, 3H), 1.04 (t, 3H).

UPLC (UPLC-MS Method 1): t$_R$=0.64 min.
MS (ES+): 544.3 (M+H)$^+$.

EXAMPLE 45

1-{5-[1-methyl-4-(4-{(3-methylpyridin-2-yl)[(3R)-piperidin-3-yl]carbamoyl}phenyl)-1H-pyrazol-5-yl]-2H-tetrazol-2-yl}ethyl propanoate (Diastereomer B)

Diastereomer B

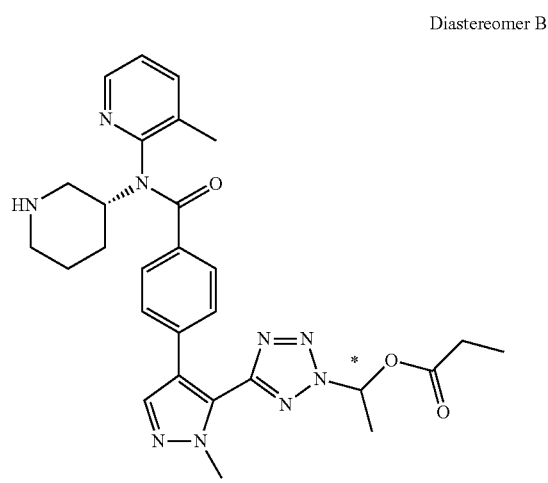

The title compound was made in an analogous manner to EXAMPLE 32 starting from

Preparation 46

$^1$H NMR (CDCl$_3$) δ: 9.87 (br s, 1H), 9.59 (br s, 1H), 8.41 (br s, 1H), 7.59 (s, 1H), 7.47-7.28 (m, 2H), 7.25-7.11 (m, 4H), 5.16-5.03 (m, 1H), 4.07 (s, 3H), 3.90-3.71 (m, 1H), 3.56-3.44 (m, 1H), 2.94-2.79 (m, 1H), 2.47-2.29 (m, 3H), 2.19-1.75 (m, 9H), 1.66-1.48 (m, 1H), 1.15 (t, 3H).

UPLC (UPLC-MS Method 1): t$_R$=0.63 min.
MS (ES+): 544.3 (M+H)$^+$.

EXAMPLE 46

1-{5-[1-methyl-4-(4-{(3-methylpyridin-2-yl)[(3R)-piperidin-3-yl]carbamoyl}phenyl)-1H-pyrazol-5-yl]-2H-tetrazol-2-yl}ethyl propan-2-yl carbonate (Diastereomer A)

Diastereomer A

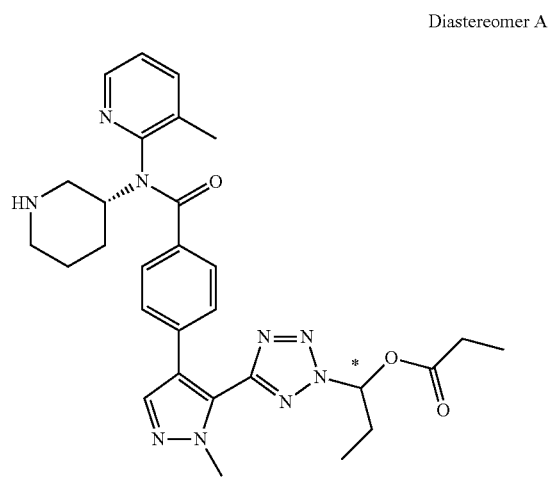 [SMILES: CCC(=O)OC(CC)n1nnc(-c2c(-c3ccc(C(=O)N(c4ncccc4C)[C@@H]4CCCNC4)cc3)cnn2C)n1]

The title compound was made in an analogous manner to EXAMPLE 32 starting from Preparation 48.

¹H NMR (CD₃CN) δ: 9.38 (br s, 1H), 8.94 (br s, 1H), 8.39 (d, 1H), 7.83-7.68 (m, 1H), 7.65 (s, 1H), 7.48-7.34 (m, 1H), 7.25 (br s, 2H), 7.20-7.05 (m, 3H), 5.18-4.47 (m, 1H), 3.97 (s, 3H), 3.79-3.51 (m, 2H), 3.36-3.15 (m, 1H), 2.95-2.76 (m, 1H), 2.46-2.31 (m, 4H), 2.27-2.21 (m, 2H), 1.94 (br. s., 3H), 1.89-1.72 (m, 1H), 1.58-1.36 (m, 1H), 1.07 (t, 3H), 0.90 (t, 3H).

UPLC (UPLC-MS Method 2): $t_R$=1.06 min.
MS (ES+): 558.9 (M+H)⁺.

EXAMPLE 47

1-{5-[1-methyl-4-(4-{(3-methylpyridin-2-yl)[(3R)-piperidin-3-yl]carbamoyl}phenyl)-1H-pyrazol-5-yl]-2H-tetrazol-2-yl}propyl propanoate (Diastereomer B)

(Diastereomer B)

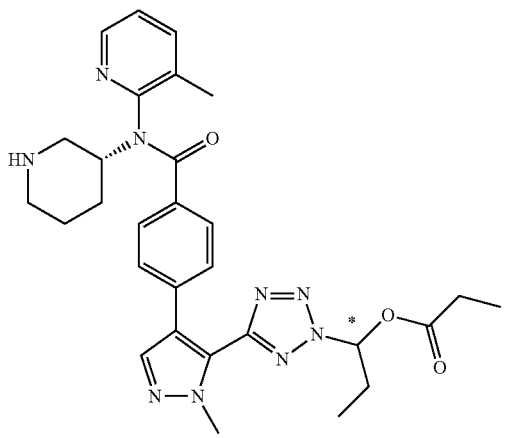

The title compound was made in an analogous manner to EXAMPLE 32 starting from Preparation 49.

¹H NMR (CDCl₃) δ: 9.91 (br s, 1H), 9.67 (br s, 1H), 8.41 (br s, 1H), 7.60 (s, 1H), 7.41 (br s, 1H), 7.25-1.09 (m, 4H), 5.13-5.10 (m, 1H), 4.06 (s, 3H), 3.88-3.75 (m, 1H), 3.54-3.45 (m, 1H), 2.95-2.81 (m, 1H), 2.49-1.56 (m, 13H), 1.15 (t, 3H), 0.96 (t, 3H).

UPLC (UPLC-MS Method 1): $t_R$=0.65 min.
MS (ES+): 559.0 (M+H)⁺.

EXAMPLE 48

2-methyl-1-{5-[1-methyl-4-(4-{(3-methylpyridin-2-yl)[(3R)-piperidin-3-yl]carbamoyl}phenyl)-1H-pyrazol-5-yl]-2H-tetrazol-2-yl}propyl propanoate (Diastereomer A)

(Diastereomer A)

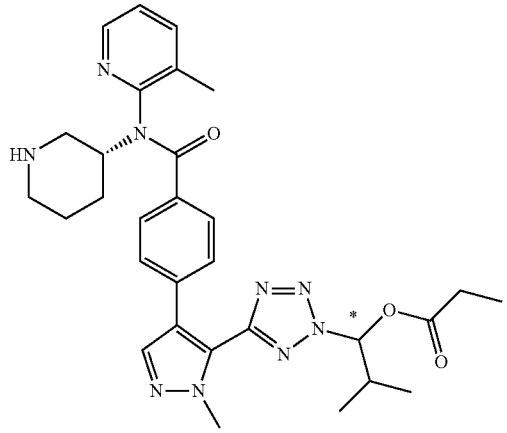

The title compound was made in an analogous manner to EXAMPLE 32 starting from Preparation 51.

¹H NMR (CD₃CN) δ: 9.63 (br s, 1H), 9.24 (br s, 1H), 8.43 (d, 1H), 7.75 (br s, 1H), 7.67 (s, 1H), 7.43 (br s, 1H), 7.28 (br s, 2H), 7.22-7.16 (br m, 2H), 6.94 (d, 1H), 5.06 (br s, 1H), 3.99 (s, 3H), 3.79 (br s, 1H), 3.64 (br s, 1H), 3.37-3.28 (br m, 1H), 2.89-2.80 (br m, 1H), 2.62-2.54 (m, 1H), 2.52-2.45 (m, 1H), 2.43-2.46 (m, 1H), 2.30-2.12 (br m, 4H), 2.04-1.99 (m, 1H), 1.85 (br s, 1H), 1.51 (br s, 1H), 1.12-1.09 (m, 6H), 0.82 (d, 3H).

UPLC (UPLC-MS Method 2): $t_R$=1.25 min.
MS (ES+): 572.4 (M+H)⁺.

EXAMPLE 49

2-methyl-1-{5-[1-methyl-4-(4-{(3-methylpyridin-2-yl)[(3R)-piperidin-3-yl]carbamoyl}phenyl)-1H-pyrazol-5-yl]-2H-tetrazol-2-yl}propyl propanoate (Diastereomer B)

Diastereomer B

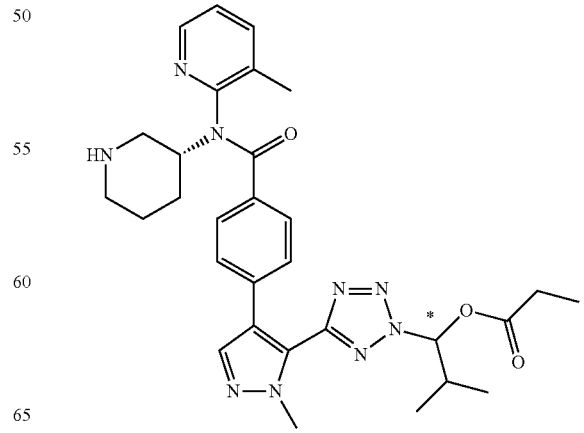

The title compound was made in an analogous manner to EXAMPLE 32 starting from Preparation 52.

¹H NMR (CDCl₃) δ: 9.09 (br s, 1H), 8.85 (br s, 1H), 8.46-8.42 (m, 1H), 7.84 (s, 1H), 7.56 (d, 1H), 7.28-7.26 (m, 1H), 7.10-7.08 (m, 3H), 6.99 (d, 1H), 4.97-4.81 (m, 1H), 4.01 (q, 2H), 3.90 (s, 3H), 3.54 (d, 1H), 3.28-3.42 (m, 1H), 3.17 (d, 2H), 2.32-2.44 (m, 2H), 1.94 (br s, 2H), 1.83-1.65 (m, 3H), 1.05-1.00 (m, 6H), 0.74 (d, 3H).

UPLC (UPLC-MS Method 2): $t_R$=1.21 min.
MS (ES+): 572.3 (M+H)⁺.

EXAMPLE 50

1-{5-[1-methyl-4-(4-{(3-methylpyridin-2-yl)[(3R)-piperidin-3-yl]carbamoyl}phenyl)-1H-pyrazol-5-yl]-2H-tetrazol-2-yl}ethyl 2-methylpropanoate (Diastereomer A)

Diastereomer A

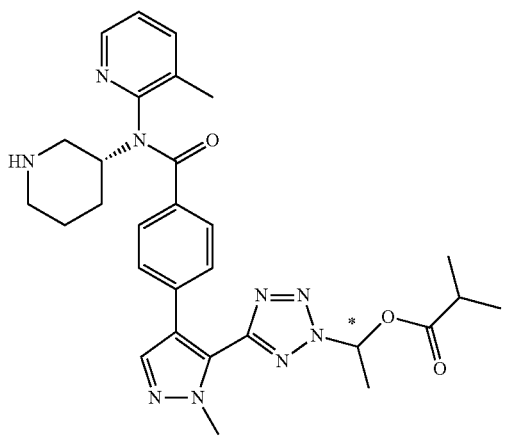

The title compound was made in an analogous manner to EXAMPLE 32 starting from Preparation 54.

¹H NMR (CD₃CN) δ: 9.58 (br s, 1H), 9.17 (br s, 1H), 8.44 (d, 1H), 7.78 (br s, 1H), 7.68 (s, 1H), 7.46 (br s, 1H), 7.36-7.29 (m, 3H), 7.22-7.18 (br m, 2H), 5.05 (br s, 1H), 3.99 (s, 3H), 3.80 (br s, 1H), 3.65 (br s, 1H), 3.32 (br d, 1H), 2.92-2.77 (br m, 1H), 2.67-2.57 (m, 1H), 2.18 (br s, 4H), 2.05-2.00 (br m, 1H), 1.92 (d, 3H), 1.87 (br s, 1H), 1.54 (br s, 1H), 1.17 (d, 3H), 1.11 (d, 3H).

UPLC (UPLC-MS Method 2): $t_R$=1.19 min.
MS (ES+): 558.4 (M+H)⁺.

EXAMPLE 51

1-{5-[1-methyl-4-(4-{(3-methylpyridin-2-yl)[(3R)-piperidin-3-yl]carbamoyl}phenyl)-1H-pyrazol-5-yl]-2H-tetrazol-2-yl}ethyl 2-methyl propanoate (Diastereomer B)

Diastereomer B

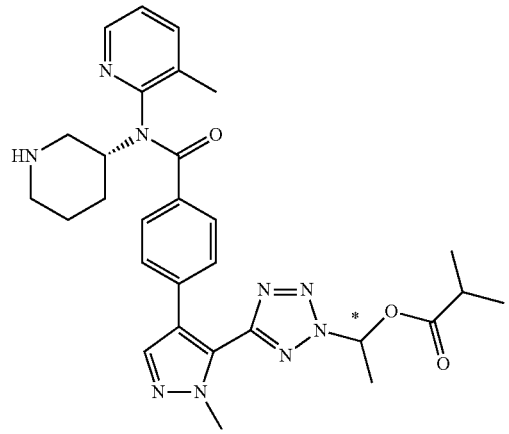

The title compound was made in an analogous manner to EXAMPLE 32 starting from Preparation 55.

¹H NMR (CD₃CN) δ: 9.75 (br s, 1H), 9.31 (br s, 1H), 8.47 (s, 1H), 7.98 (br s, 1H), 7.68 (s, 1H), 7.60 (br s, 1H), 7.38-7.32 (m, 3H), 7.24-7.20 (br m, 2H), 5.05 (br s, 1H), 3.99 (s, 3H), 3.87 (br s, 1H), 3.68 (br s, 1H), 3.33 (br s, 1H), 2.88 (br s, 1H), 2.64-2.59 (m, 1H), 2.26 (br s, 4H), 2.07-2.01 (m, 1H), 1.94-1.86 (m, 4H), 1.60 (br s, 1H), 1.17 (d, 3H), 1.10 (d, 3H).

UPLC (UPLC-MS Method 2): $t_R$=1.19 min.
MS (ES+): 558.4 (M+H)⁺.

EXAMPLE 52

1-{5-[1-methyl-4-(4-{(3-methylpyridin-2-yl)[(3R)-piperidin-3-yl]carbamoyl}phenyl)-1H-pyrazol-5-yl]-2H-tetrazol-2-yl}propyl 2-methylpropanoate (Diasteromer A)

Diastereomer A

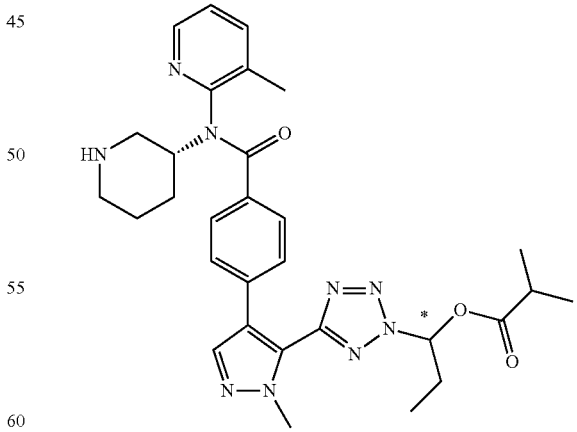

The title compound was made in an analogous manner to EXAMPLE 32 starting from Preparation 57.

¹H NMR (DMSO-d₆) δ: 9.08-9.03 (m, 1H), 8.90-8.75 (m, 1H), 8.49-8.39 (m, 1H), 7.88 (s, 1H), 7.66-7.57 (m, 1H), 7.32-7.27 (m, 1H), 7.24-7.21 (m, 1H), 7.15-7.10 (m, 3H), 5.0-4.98 (m, 1H), 3.92 (s, 3H), 3.60-3.52 (m, 1H), 3.44-3.32 (m, 1H), 3.23-3.15 (m, 1H), 2.78-2.59 (m, 1H), 2.34-2.20 (m,

2H), 2.17-2.04 (m, 1H), 1.96 (s, 3H), 1.83-1.68 (m, 2H), 1.28-1.24 (m, 1H), 1.20-1.16 (m, 1H), 1.13 (d, 3H), 1.05 (d, 3H), 0.90 (t, 3H).
UPLC (UPLC-MS Method 2): $t_R$=0.69 min.
MS (ES+): 572.4 (M+H)$^+$.

EXAMPLE 53

1-{5-[1-methyl-4-(4-{(3-methylpyridin-2-yl)[(3R)-piperidin-3-yl]carbamoyl}phenyl)-1H-pyrazol-5-yl]-2H-tetrazol-2-yl}propyl 2-methylpropanoate (Diastereomer B)

Diastereomer B

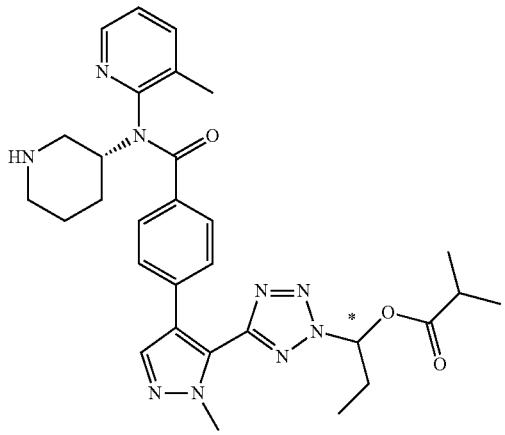

The title compound was made in an analogous manner to EXAMPLE 32 starting from Preparation 58.
$^1$H NMR (CDCl$_3$) δ: 9.84 (br s, 1H), 9.53 (br s, 1H), 8.43 (br s, 1H), 7.59 (s, 1H), 7.43 (br s, 1H), 7.23-7.07 (m, 5H), 5.14-4.98 (m, 1H), 4.04 (s, 3H), 3.92-3.74 (m, 2H), 3.57-3.25 (m, 1H), 2.94-2.78 (m, 1H), 2.68-2.54 (m, 1H), 2.35-2.25 (m, 2H), 2.21-1.78 (m, 5H), 1.67-1.49 (m, 1H), 1.19 (t, 3H), 1.13 (t, 3H), 0.95 (t, 3H).
UPLC (UPLC-MS Method 1): $t_R$=0.66 min.
MS (ES+): 572.4 (M+H)$^+$.

EXAMPLE 54

2-methyl-1-{5-[1-methyl-4-(4-{(3-methylpyridin-2-yl)[(3R)-piperidin-3-yl]carbamoyl}phenyl)-1H-pyrazol-5-yl]-2H-tetrazol-2-yl}propyl 2-methylpropanoate (Diastereomer A)

Diastereomer A

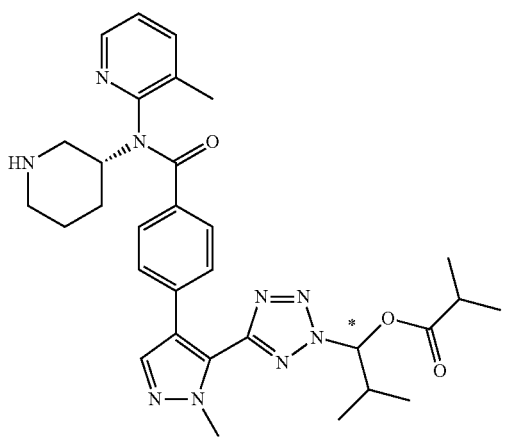

The title compound was made in an analogous manner to EXAMPLE 32 starting from Preparation 60.
$^1$H NMR (CD$_3$CN) δ: 9.61 (br s, 1H), 9.20 (br s, 1H), 8.43 (d, 1H), 7.75 (br s, 1H), 7.67 (s, 1H), 7.43 (br s, 1H), 7.28 (br s, 2H), 7.17 (br s, 2H), 6.93 (d, 1H), 5.05 (br s, 1H), 3.98 (s, 3H), 3.79 (br s, 1H), 3.64 (br s, 1H), 3.31 (br d, 1H), 2.83 (br s, 1H), 2.69-2.57 (m, 2H), 2.15 (br s, 4H), 2.02 (br s, 1H), 1.84 (br s, 1H), 1.50 (br s, 1H), 1.19 (d, 3H), 1.12-1.11 (m, 6H), 0.84 (d, 3H).
UPLC (UPLC-MS Method 2): $t_R$=1.34 min.
MS (ES+): 586.4 (M+H)$^+$.

EXAMPLE 55

2-methyl-1-{5-[1-methyl-4-(4-{(3-methylpyridin-2-yl)[(3R)-piperidin-3-yl]carbamoyl}phenyl)-1H-pyrazol-5-yl]-2H-tetrazol-2-yl}propyl 2-methylpropanoate (Diastereomer B)

Diastereomer B

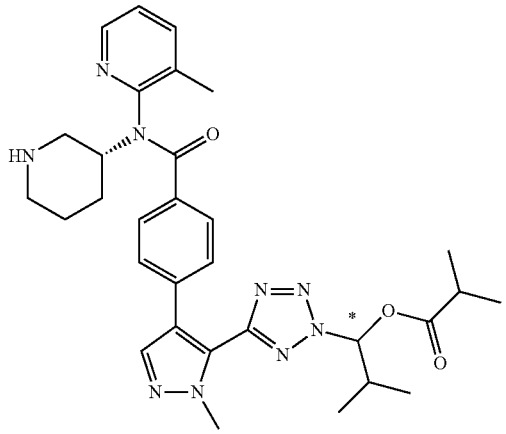

The title compound was made in an analogous manner to EXAMPLE 32 starting from Preparation 61.
$^1$H NMR (CDCl$_3$) δ: 9.94 (br s, 1H), 9.61 (br s, 1H), 8.78-8.44 (m, 1H), 7.94 (br s, 1H), 7.60 (s, 1H), 7.30 (br s, 1H), 7.18 (br s, 2H), 6.87 (d, 1H), 5.03-4.64 (m, 1H), 4.25 (br s, 1H), 4.04 (s, 3H), 3.90-3.72 (m, 2H), 3.54-3.45 (m, 1H), 2.98-2.88 (m, 1H), 2.70-2.61 (m, 2H), 2.50-2.06 (m, 4H), 1.31-1.23 (m, 2H), 1.21 (d, 3H), 1.15 (d, 3H), 1.10 (d, 3H), 0.85 (d, 3H).
UPLC (UPLC-MS Method 2): $t_R$=1.29 min.
MS (ES+): 586.4 (M+H)$^+$.

Throughout this application, various publications are referenced. The disclosures of these publications in their entireties are hereby incorporated by reference into this application for all purposes.

It will be apparent to those skilled in the art that various modifications and variations can be made in the present invention without departing from the scope or spirit of the invention. Other embodiments of the invention will be apparent to those skilled in the art from consideration of the specification and practice of the invention disclosed herein. It is

What is claimed is:

1. A compound having Formula I

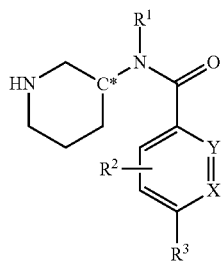

Formula I or a pharmaceutically acceptable salt thereof wherein
$R^1$ is pyrid-2-yl, isoquinolin-1-yl or 1H-pyrrolo[2,3-c]pyridin-7-yl;
$R^1$ is optionally mono- or di-substituted with chloro or $(C_1-C_4)$alkyl;
X and Y are independently either N or C(H), provided that at least one of X or Y is C(H);
$R^2$ is H, fluoro, hydroxyl or methyl; $R^3$ is

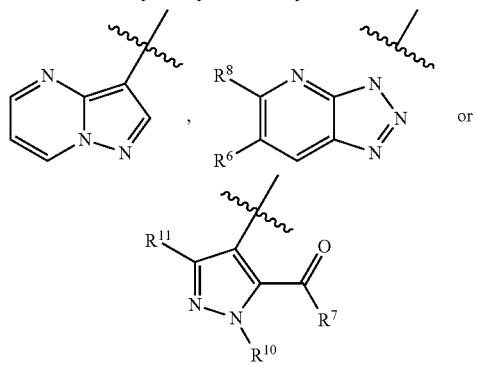 or wherein $R^6$ and $R^8$ are each independently H, methyl, halo or $(C_1-C_4)$alkyloxy, provided that only one of $R^6$ and $R^8$ is halo;
wherein $R^{10}$ and $R^{11}$ are each independently H, $(C_1-C_4)$alkyl or $(C_3-C_5)$cycloalkyl; and
wherein $R^7$ is hydroxyl, $(C_1-C_4)$alkyloxy, $(C_1-C_4)$alkoxycarbonyloxy$(C_1-C_4)$alkyloxy, or $(C_1-C_4)$alkylcarbonyloxy$(C_1-C_4)$alkoxy.

2. The compound of claim 1 wherein $R^1$ is pyrid-2-yl and the piperidinyl C* is the R configuration.

3. The compound of claim 2 wherein X and Y are both C(H), $R^2$ is H and $R^1$ is optionally mono-substituted with chloro or methyl.

4. The compound of claim 3 wherein $R^3$ is

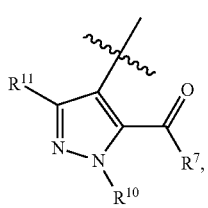

$R^7$ is hydroxyl, $(C_1-C_2)$alkyloxy or

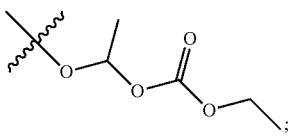 [SMILES: *OC(C)OC(=O)OCC]

$R^{10}$ is methyl; and
$R^{11}$ is H.

5. The compound of claim 3 wherein $R^3$ is

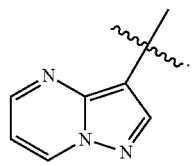 [SMILES: *c1cnn2cccnc12]

6. The compound of claim 3 wherein $R^3$ is

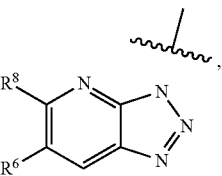

$R^6$ is H or methyl and $R^8$ is H.

7. The compound of claim 1 wherein $R^1$ isoquinolin-1-yl, and the piperidinyl C* is the R configuration.

8. The compound of claim 7 wherein X and Y are both C(H), $R^2$ is H, hydroxyl, or methyl and $R^1$ is optionally monosubstituted with chloro or methyl.

9. The compound of claim 8 wherein $R^3$ is

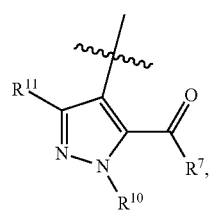

$R^7$ is hydroxyl, $(C_1-C_2)$alkyloxy or

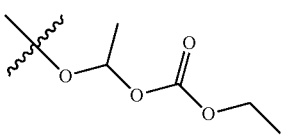 [SMILES: *OC(C)OC(=O)OCC]

$R^{10}$ is methyl; and
$R^{11}$ is H.

10. The compound of claim 8 wherein $R^3$ is

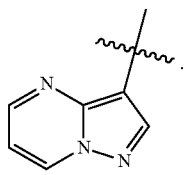 [SMILES: *c1cnn2cccnc12]

11. The compound of claim 8 wherein $R^3$ is

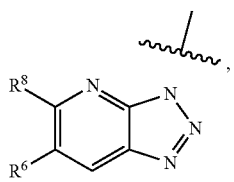

$R^6$ is H or methyl and $R^8$ is H.

12. The compound of claim 1 wherein $R^1$ is 1H-pyrrolo[2,3-c]pyridin-7-yl, and the piperidinyl C* is the R configuration.

13. The compound of claim 12 wherein X and Y are both C(H), $R^2$ is H, hydroxyl, or methyl and $R^1$ is optionally mono-substituted with chloro or methyl.

14. The compound of claim 13 wherein $R^3$ is

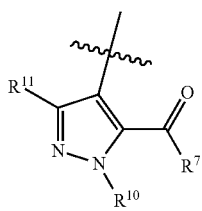

$R^7$ is hydroxyl, $(C_1-C_2)$alkyloxy or

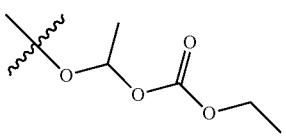 [SMILES: *OC(C)OC(=O)OCC]

$R^{10}$ is methyl; and
$R^{11}$ is H.

15. The compound of claim 13 wherein $R^3$ is

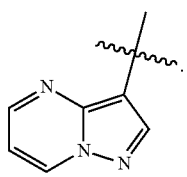 [SMILES: *c1cnn2cccnc12]

16. The compound of claim 13 wherein $R^3$ is

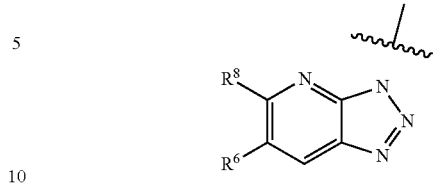

and $R^6$ is H or methyl and $R^8$ is H.

17. A compound, which is
N-(3-methylpyridin-2-yl)-N-[(3R)-piperidin-3-yl]-4-(pyrazolo[1,5-a]pyrimidin-3-yl)benzamide;
N-(3-chloropyridin-2-yl)-N-[(3R)-piperidin-3-yl]-4-(pyrazolo[1,5-a]pyrimidin-3-yl)benzamide;
N-(3-chloropyridin-2-yl)-4-(6-methyl-3H-[1,2,3]triazolo[4,5-b]pyridin-3-yl)-N-[(3R)-piperidin-3-yl]benzamide;
4-(4-{isoquinolin-1-yl[(3R)-piperidin-3-yl]carbamoyl}phenyl)-1-methyl-1H-pyrazole-5-carboxylic acid;
N-(3-chloropyridin-2-yl)-N-[(3R)-piperidin-3-yl]-5-(3H-[1,2,3]triazolo[4,5-b]pyridin-3-yl)pyridine-2-carboxamide;
ethyl 4-(4-{(3-chloropyridin-2-yl)[(3R)-piperidin-3-yl]carbamoyl}phenyl)-1-methyl-1H-pyrazole-5-carboxylate;
4-(4-{(3-chloropyridin-2-yl)[(3R)-piperidin-3-yl]carbamoyl}phenyl)-1-methyl-1H-pyrazole-5-carboxylic acid;
4-(4-{(3-chloropyridin-2-yl)[piperidin-3-yl]carbamoyl}phenyl)-1-methyl-1H-pyrazole-5-carboxylic acid;
1-[(ethoxycarbonyl)oxy]ethyl 4-(4-{(3-chloropyridin-2-yl)[piperidin-3-yl]carbamoyl}phenyl)-1-methyl-1H-pyrazole-5-carboxylate;
1-[(ethoxycarbonyl)oxy]ethyl 4-(4-{(3-chloropyridin-2-yl)[(3R)-piperidin-3-yl]carbamoyl}phenyl)-1-methyl-1H-pyrazole-5-carboxylate;
(1R)-1-[(ethoxycarbonyl)oxy]ethyl 4-(4-{(3-chloropyridin-2-yl)[(3R)-piperidin-3-yl]carbamoyl}phenyl)-1-methyl-1H-pyrazole-5-carboxylate;
(1 S)-1-[(ethoxycarbonyl)oxy]ethyl 4-(4-{(3-chloropyridin-2-yl)[(3R)-piperidin-3-yl]carbamoyl}phenyl)-1-methyl-1H-pyrazole-5-carboxylate; or
N-(3-chloropyridin-2-yl)-N-[(3R)-piperidin-3-yl]-4-(3H-[1,2,3]triazolo[4,5-b]pyridin-3-yl)benzamide;
or a pharmaceutically acceptable salt of any of said compounds.

18. A compound, which is
N-(3-chloropyridin-2-yl)-5-(6-methyl-3H-[1,2,3]triazolo[4,5-b]pyridin-3-yl)-N-[(3R)-piperidin-3-yl]pyridine-2-carboxamide;
methyl 4-(4-{(3-chloropyridin-2-yl)[(3R)-piperidin-3-yl]carbamoyl}phenyl)-1-methyl-1H-pyrazole-5-carboxylate;
1-[(ethoxycarbonyl)oxy]ethyl 4-(4-{isoquinolin-1-yl[(3R)-piperidin-3-yl]carbamoyl}phenyl)-1-methyl-1H-pyrazole-5-carboxylate;
1-methyl-4-(4-{(1-methyl-1H-pyrrolo[2,3-c]pyridin-7-yl)[(3R)-piperidin-3-yl]carbamoyl}phenyl)-1H-pyrazole-5-carboxylic acid;
methyl 1-methyl-4-(4-{(3-methylpyridin-2-yl)[(3R)-piperidin-3-yl]carbamoyl}phenyl)-1H-pyrazole-5-carboxylate; or 1-[(ethoxycarbonyl)oxy]ethyl 1-methyl-4-(4-{(1-methyl-1H-pyrrolo[2,3-c]pyridin-7-yl)[(3R)-piperidin-3-yl]carbamoyl}phenyl)-1H-pyrazole-5-carboxylate; or a pharmaceutically acceptable salt of any of said compounds.

19. A method for treating dyslipidemia, hypercholesterolemia, hypertriglyceridemia, hyperlipidemia, hypoalphalipoproteinemia, metabolic syndrome, diabetic complications, atherosclerosis, stroke, vascular dimensia, chronic kidney disease, coronary heart disease, coronary artery disease, retinopathy, inflammation, thrombosis, peripheral vascular disease or congestive heart failure in a mammal by administering to a mammal in need of such treatment a therapeutically effective amount of a compound of claim 1 or a pharmaceutically acceptable salt of said compound.

20. A pharmaceutical composition which comprises a therapeutically effective amount of a compound of claim 1 or a pharmaceutically acceptable salt of said compound and a pharmaceutically acceptable carrier, vehicle or diluent.

21. A pharmaceutical combination composition comprising: a therapeutically effective amount of a composition comprising a first compound, said first compound being a compound of claim 1 or a pharmaceutically acceptable salt of said compound;

a second compound, said second compound being a lipase inhibitor, an HMG-CoA reductase inhibitor, an HMG-CoA synthase inhibitor, an HMG-CoA reductase gene expression inhibitor, an HMG-CoA synthase gene expression inhibitor, an MTP/Apo B secretion inhibitor, a CETP inhibitor, a bile acid absorption inhibitor, a cholesterol absorption inhibitor, a cholesterol synthesis inhibitor, a squalene synthetase inhibitor, a squalene epoxidase inhibitor, a squalene cyclase inhibitor, a combined squalene epoxidase/squalene cyclase inhibitor, a fibrate, niacin, a combination of niacin and lovastatin, an ion-exchange resin, an antioxidant, an ACAT inhibitor or a bile acid sequestrant, or a pharmaceutically acceptable salt of said compound; and a pharmaceutically acceptable carrier, vehicle or diluents.

22. A compound having Formula II

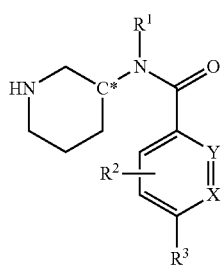

Formula II or a pharmaceutically acceptable salt thereof wherein $R^1$ is pyrid-2-yl, isoquinolin-1-yl or 1H-pyrrolo[2,3-c]pyridin-7-yl;

$R^1$ is optionally mono- or di-substituted with chloro or $(C_1-C_4)$alkyl;

X and Y are independently either N or C(H), provided that at least one of X or Y is C(H);

$R^2$ is H, fluoro, hydroxyl or methyl;

$R^3$ is

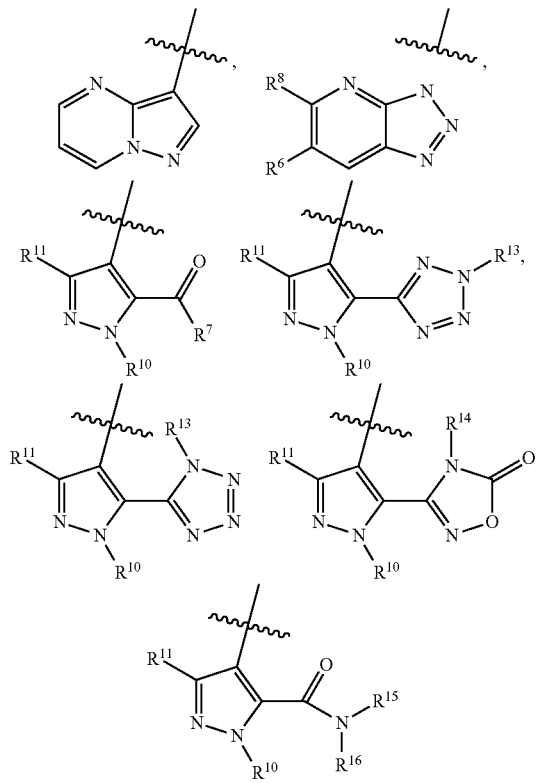

wherein $R^6$ and $R^8$ are each independently H, methyl, halo or $(C_1-C_4)$alkyloxy, provided that only one of $R^6$ and $R^8$ is halo;

wherein $R^{10}$ and $R^{11}$ are each independently H, $(C_1-C_4)$alkyl or $(C_3-C_5)$cycloalkyl; wherein $R^7$ is hydroxyl, $(C_1-C_4)$alkyloxy, $(C_1-C_4)$alkoxycarbonyloxy$(C_1-C_4)$alkyloxy, or $(C_1-C_4)$alkylcarbonyloxy$(C_1-C_4)$alkoxy;

$R^{13}$ is H, $(C_1-C_4)$alkyl, $(C_1-C_4)$alkylcarbonyloxy$(C_1-C_4)$alkyl or $(C_1-C_4)$alkoxycarbonyloxy$(C_1-C_4)$alkyl;

$R^{14}$ is H, $(C_1-C_4)$alkyl, $(C_1-C_4)$alkylcarbonyloxy$(C_1-C_4)$alkyl or $(C_1-C_4)$alkoxycarbonyloxy$(C_1-C_4)$alkyl;

$R^{15}$ is hydroxyl, tetrazolyl, $(C_1-C_2)$alkylsulfonyl or trifluoromethylsulfonyl, and $R^{16}$ is H, $(C_1-C_4)$alkyl, $(C_1-C_4)$alkylcarbonyloxy$(C_1-C_4)$alkyl or $(C_1-C_4)$alkoxycarbonyloxy$(C_1-C_4)$alkyl.

23. The compound of claim 22 wherein $R^1$ is pyrid-2-yl optionally mono-substituted with chloro or methyl;

the piperidinyl C* is the R configuration;

X and Y are both C(H);

$R^2$ is H;

$R^3$ is

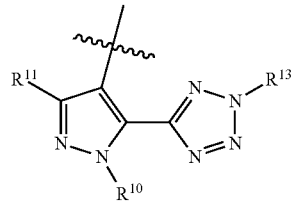

R¹⁰ is methyl;
R¹¹ is H; and
R¹³ is $(C_1-C_4)$alkylcarbonyloxy$(C_1-C_4)$alkyl.

24. The compound of 22 wherein
R¹ is pyrid-2-yl optionally mono-substituted with chloro or methyl;
the piperidinyl C* is the R configuration;
X and Y are both C(H);
R² is H; and
R³ is

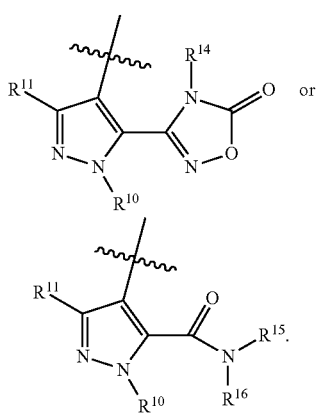

25. A compound, which is
4-(4-{(3-chloropyridin-2-yl)[(3R)-piperidin-3-yl]carbamoyl}phenyl)-1-methyl-N-[(trifluoromethyl)sulfonyl]-1H-pyrazole-5-carboxamide;
N-(3-chloropyridin-2-yl)-4-[1-methyl-5-(2H-tetrazol-5-yl)-1H-pyrazol-4-yl]-N-[(3R)-piperidin-3-yl]benzamide;
1-methyl-4-(4-{(3-methylpyridin-2-yl)[(3R)-piperidin-3-yl]carbamoyl}phenyl)-N-(methylsulfonyl)-1H-pyrazole-5-carboxamide;
N-(3-methylpyridin-2-yl)-4-[1-methyl-5-(2H-tetrazol-5-yl)-1H-pyrazol-4-yl]-N-[(3R)-piperidin-3-yl]benzamide; or
ethyl 1-[{[1-methyl-4-(4-{(3-methylpyridin-2-yl)[(3R)-piperidin-3-yl]carbamoyl}phenyl)-1H-pyrazol-5-yl]carbonyl}(methylsulfonyl)amino]ethyl carbonate;
or a pharmaceutically acceptable salt of any of said compounds.

26. A compound, which is
ethyl 1-{5-[1-methyl-4-(4-{(3-methylpyridin-2-yl)[(3R)-piperidin-3-yl]carbamoyl}phenyl)-1H-pyrazol-5-yl]-1H-tetrazol-1-yl}ethyl carbonate;
ethyl (1S)-1-{5-[1-methyl-4-(4-{(3-methylpyridin-2-yl)[(3R)-piperidin-3-yl]carbamoyl}phenyl)-1H-pyrazol-5-yl]-2H-tetrazol-2-yl}ethyl carbonate; or
ethyl (1R)-1-{5-[1-methyl-4-(4-{(3-methylpyridin-2-yl)[(3R)-piperidin-3-yl]carbamoyl}phenyl)-1H-pyrazol-5-yl]-2H-tetrazol-2-yl}ethyl carbonate;
or a pharmaceutically acceptable salt of any of said compounds.

27. A compound, which is
(1-{5-[1-methyl-4-(4-{(3-methylpyridin-2-yl)[(3R)-piperidin-3-yl]carbamoyl}phenyl)-1H-pyrazol-5-yl]-2H-tetrazol-2-yl}ethyl 2-methylpropanoate

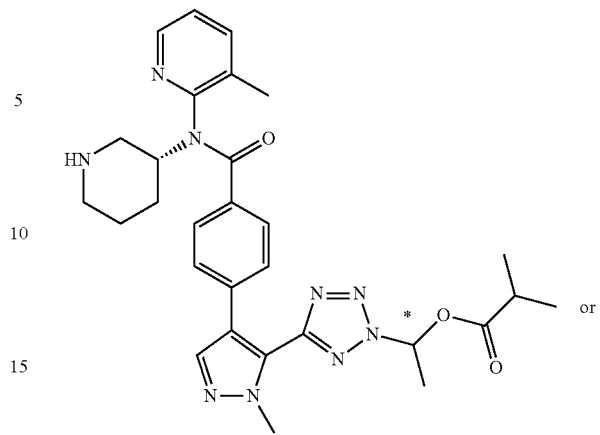

2-methyl-1-{5-[1-methyl-4-(4-{(3-methylpyridin-2-yl)[(3R)-piperidin-3-yl]carbamoyl}phenyl)-1H-pyrazol-5-yl]-2H-tetrazol-2-yl}propyl 2-methylpropanoate

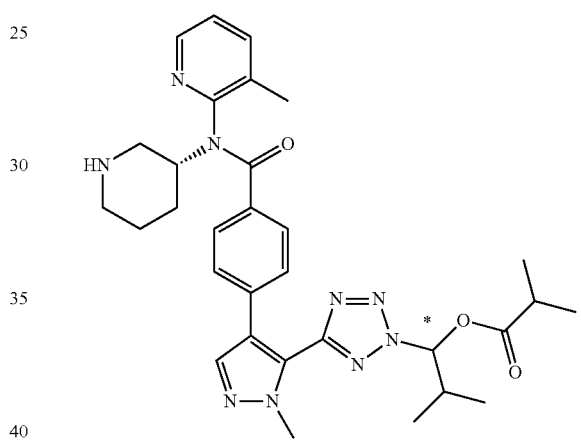

or a pharmaceutically acceptable salt of any of said compounds.

28. A method for treating dyslipidemia, hypercholesterolemia, hypertriglyceridemia, hyperlipidemia, hypoalphalipoproteinemia, metabolic syndrome, diabetic complications, atherosclerosis, stroke, vascular dimensia, chronic kidney disease, coronary heart disease, coronary artery disease, retinopathy, inflammation, thrombosis, peripheral vascular disease or congestive heart failure in a mammal by administering to a mammal in need of such treatment a therapeutically effective amount of a compound of claim 22 or a pharmaceutically acceptable salt of said compound.

29. A pharmaceutical composition which comprises a therapeutically effective amount of a compound of claim 22 or a pharmaceutically acceptable salt of said compound and a pharmaceutically acceptable carrier, vehicle or diluent.

30. A pharmaceutical combination composition comprising: a therapeutically effective amount of a composition comprising
a first compound, said first compound being a compound of claim 22 or a pharmaceutically acceptable salt of said compound;
a second compound, said second compound being a lipase inhibitor, an HMG-CoA reductase inhibitor, an HMG-CoA synthase inhibitor, an HMG-CoA reductase gene expression inhibitor, an HMG-CoA synthase gene expression inhibitor, an MTP/Apo B secretion inhibitor, a CETP inhibitor, a bile acid absorption inhibitor, a cholesterol absorption inhibitor, a cholesterol synthesis inhibitor, a squalene synthetase inhibitor, a squalene epoxidase inhibitor, a squalene cyclase inhibitor, a combined squalene epoxidase/squalene cyclase inhibitor, a fibrate, niacin, a combination of niacin and lovastatin, an ion-exchange resin, an antioxidant, an ACAT inhibitor or a bile acid sequestrant, or a pharmaceutically acceptable salt of said compound; and a pharmaceutically acceptable carrier, vehicle or diluents.

* * * * *